(12) United States Patent
Leusen et al.

(10) Patent No.: US 12,258,420 B2
(45) Date of Patent: *Mar. 25, 2025

(54) ENGINEERED IGA ANTIBODIES AND METHODS OF USE

(71) Applicant: Tiga TX, Inc., Westerly, RI (US)

(72) Inventors: Jeanette Henrica Wilhelmina Leusen, Utrecht (NL); Johannes Gerardus Maria Evers, Utrecht (NL); Geert Jan Van Tetering, Utrecht (NL)

(73) Assignee: TigaTX, Inc., Boston, MA (US)

( * ) Notice: Subject to any disclaimer, the term of this patent is extended or adjusted under 35 U.S.C. 154(b) by 626 days.

This patent is subject to a terminal disclaimer.

(21) Appl. No.: 17/343,249

(22) Filed: Jun. 9, 2021

(65) Prior Publication Data

US 2021/0380720 A1 Dec. 9, 2021

Related U.S. Application Data

(63) Continuation of application No. 17/091,897, filed on Nov. 6, 2020, now Pat. No. 11,059,909, which is a continuation of application No. PCT/NL2020/050217, filed on Mar. 27, 2020.

(60) Provisional application No. 62/824,864, filed on Mar. 27, 2019.

(51) Int. Cl.
*C07K 16/42* (2006.01)
*C07K 16/28* (2006.01)
*A61K 39/00* (2006.01)

(52) U.S. Cl.
CPC ........ *C07K 16/4283* (2013.01); *C07K 16/283* (2013.01); *C07K 16/2887* (2013.01); *A61K 2039/505* (2013.01); *C07K 2317/41* (2013.01); *C07K 2317/51* (2013.01); *C07K 2317/522* (2013.01); *C07K 2317/524* (2013.01); *C07K 2317/526* (2013.01); *C07K 2317/565* (2013.01); *C07K 2317/732* (2013.01); *C07K 2317/94* (2013.01)

(58) Field of Classification Search
CPC ............ C07K 2317/41; C07K 2317/51; C07K 2317/526
USPC ...................................... 424/133.1
See application file for complete search history.

(56) References Cited

U.S. PATENT DOCUMENTS

| | | |
|---|---|---|
| 3,270,960 A | 9/1966 | Phillips |
| 3,773,919 A | 11/1973 | Boswell |
| 4,179,337 A | 12/1979 | Davis |
| 4,301,144 A | 11/1981 | Iwashita |
| 4,485,045 A | 11/1984 | Regen |
| 4,495,285 A | 1/1985 | Shimizu |
| 4,496,689 A | 1/1985 | Mitra |
| 4,544,545 A | 10/1985 | Ryan |
| 4,609,546 A | 9/1986 | Hiratani |
| 4,640,835 A | 2/1987 | Shimizu |
| 4,766,106 A | 8/1988 | Katre |
| 4,791,192 A | 12/1988 | Nakagawa |
| 4,837,028 A | 6/1989 | Allen |
| 4,892,538 A | 1/1990 | Aebischer |
| 4,946,778 A | 8/1990 | Ladner |
| 5,019,369 A | 5/1991 | Presant |
| 5,057,313 A | 10/1991 | Shih |
| 5,223,409 A | 6/1993 | Ladner |
| 5,260,203 A | 11/1993 | Ladner |
| 5,283,187 A | 2/1994 | Aebischer |
| 5,443,953 A | 8/1995 | Hansen |
| 5,455,030 A | 10/1995 | Ladner |
| 5,747,654 A | 5/1998 | Pastan |
| 5,856,456 A | 1/1999 | Whitlow |
| 6,306,393 B1 | 10/2001 | Goldenberg |
| 8,236,561 B2 | 8/2012 | Jones |
| 8,313,730 B2 | 11/2012 | Simon |
| 9,334,331 B2 * | 5/2016 | Igawa ...................... A61P 7/04 |
| 9,505,848 B2 | 11/2016 | Davis |
| 9,522,184 B2 | 12/2016 | Von Gunten |
| 9,573,996 B2 | 2/2017 | Ariaans |
| 9,580,501 B2 | 2/2017 | Ariaans |
| 9,593,147 B2 | 3/2017 | Yuji |
| 9,828,418 B2 | 11/2017 | El Menyawi |
| 9,890,216 B2 | 2/2018 | Georgiou |
| 10,421,807 B2 * | 9/2019 | Gonzales ................ A61P 17/08 |
| 11,059,909 B2 * | 7/2021 | Leusen ............. C07K 16/2803 |
| 2003/0022243 A1 | 1/2003 | Kondejewski |
| 2017/0058018 A2 | 3/2017 | Brown |

(Continued)

FOREIGN PATENT DOCUMENTS

| | | |
|---|---|---|
| EP | B1708391 | 5/2017 |
| WO | 198705330 | 9/1987 |
| WO | 199206204 | 4/1992 |

(Continued)

OTHER PUBLICATIONS

Al Qaraghuli et al. (2020, Nature Scientific Reports 10:13969).*

(Continued)

*Primary Examiner* — Lynn A Bristol

(74) *Attorney, Agent, or Firm* — Greenberg Traurig, LLP

(57) ABSTRACT

Provided herein are engineered antibodies that comprise a modified IgA2 heavy chain constant region, pharmaceutical compositions, and methods of use. The engineered antibodies described herein comprise one or more amino acid substitutions or deletions in a constant region of an IgA2 domain that modify naturally occurring glycosylation site(s). Further provided herein are methods of treating disorders, including cancer, by administering an engineered IgA antibody described herein.

17 Claims, 34 Drawing Sheets

Specification includes a Sequence Listing.

(56) References Cited

U.S. PATENT DOCUMENTS

| | | | |
|---|---|---|---|
| 2019/0365717 | A1 | 12/2019 | Raaben |
| 2021/0395395 | A1* | 12/2021 | Leusen ............ C07K 16/2887 |

FOREIGN PATENT DOCUMENTS

| | | |
|---|---|---|
| WO | 199325673 | 12/1993 |
| WO | 199411026 | 5/1994 |
| WO | 1995017413 | 6/1995 |
| WO | 1995022625 | 8/1995 |
| WO | 0109186 | 2/2001 |
| WO | 200109186 | 2/2001 |
| WO | 20020518702 | 7/2002 |
| WO | 2003102018 | 12/2003 |
| WO | 2005035572 | 4/2005 |
| WO | 2005103081 | 11/2005 |
| WO | 20080496432 | 5/2008 |
| WO | 201003512 | 4/2010 |
| WO | 2013087911 | 6/2013 |
| WO | 20140659451 | 5/2014 |
| WO | 20140872482 | 6/2014 |
| WO | 20151386002 | 9/2015 |
| WO | 20180441721 | 3/2018 |
| WO | 2019059771 A2 | 3/2019 |
| WO | 2020154405 | 7/2020 |

OTHER PUBLICATIONS

Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Khan et al. (2014, J. Immunol. 192: 5398-5405).*
Poosarla et al. (2017, Biotechn. Bioeng. 114(6): 1331-1342).*
Stip et al(J Immunother Cancer Jul. 2023;11(7):e006948).*
Launay, P. et al. Fcα receptor (CD89) mediates the development of immunoglobulin a (IgA) nephropathy (Berger's disease): Evidence for pathogenic soluble receptor-IgA complexes in patients and CD89 transgenic mice. J. Exp. Med. 191, 1999-2009 (2000).
Lee, S. J. et al. Mannose receptor-mediated regulation of serum glycoprotein homeostasis. Science (80-. ). 295, 1898-1901 (2002).
Lefranc, M.P. et al. IMGT unique numbering for immunoglobulin and T cell receptor constant domains and Ig superfamily C-like domains." Dev Comp Immunol. 2005;29(3):185-203".
Lehmann CHK, et al. "DC subset specific induction of T cell responses upon antigen uptake via activating or inhibitory Fcγ receptors in vivo" J. Exp. Med 214:1509-1528. doi: 10.1084/jem.20160951. Epub Apr. 7, 2017 (11.2).
Leong, K. W. & Ding, J. L. The unexplored roles of human serum IgA. DNA Cell Biol. 33, 823 829 (2014).
Leusen, J.H.W. "Immunoreceptors: evolution, structure and therapeutic applications" EMBO Rep. 2012 12:1046-1048 (7.2).
Leusen, J.H.W., et al. "Disturbed interaction of p21-rac with mutated p67-phox causes chronic granulomatous disease" 1996. J. Exp. Med. 184:1243-1249. (13.9).
Leusen, J.H.W., et al., "A point mutation in gp91-phox of cytochrome b558 of the human NADPH oxidase leading to defective translocation of the cytosolic proteins p47-phox and p67-phox" 1994. J. Clin. Invest. 93:2120-2126 (13.8).
Leusen, J.H.W., et al., "Four novel mutations in the gene encoding gp91-phox of the human NADPH oxidase: consequences for oxidase assembly" 2000. Blood 95:666-673 (9.1).
Leusen, J.H.W., et al., "Interactions between the components of the human NADPH oxidase: a review about the Intrigues in the phox family" 1996. J. Lab Clin. Med. 128:461-476.
Leusen, J.H.W., et al., "Interactions between the cytosolic components p47-phox and p67-phox of the human NADPH oxidase that are not required for activation in the cell-free system" 1995. J. Biol. Chem. 270:11216-11221.(4.6).
Leusen, J.H.W., et al., "Pro→Gln substitution in the light chain of cytochrome b558 (p22-phox) of the human NADPH oxidase leads to defective translocation of the cytosolic proteins p47-phox and p67-phox" 1994. J. Exp. Med. 180:2329-2334 (13.9).
Leusen, J.W.H., IgA as therapeutic antibody, Molecular Immunology, vol. 68, Issue 1, 2015, pp. 35-39, ISSN 0161-5890.
Li, B. et al. CD89-mediated recruitment of macrophages via a bispecific antibody enhances anti-tumor efficacy. Oncoimmunology 7, 1-9 (2018).
Li, B. et al. Simultaneous exposure to FcγR and FcαR on monocytes and macrophages enhances antitumor activity in vivo. Oncotarget 8, 39356-39366 (2017).
Li, Cun et al. "Construction of a chimeric secretory IgA and its neutralization activity against avian influenza virus H5N1." Journal of immunology research vol. 2014 (2014): 394127. doi:10.1155/2014/394127.
Li, F. et al. Mouse strains influence clearance and efficacy of antibody and antibody-drug conjugate via Fc-FcGR Interaction. Mol. Cancer Ther. 18, 780-787 (2019).
Lindmark, R., et al., Binding of Immunoglobulins to Protein A and Immunoglobulin Levels in Mammalian Journal of Immunol. Meth. 62: 1-13 (1983).
Logtenberg, M. E. W. et al. Glutaminyl cyclase is an enzymatic modifier of the CD47-SIRPα axis and a target for cancer immunotherapy. Nat. Med. 25, 612-619 (2019).
Lohse et al., Effector mechanisms of IgA antibodies against CD20 include recruitment of myeloid 2 cells for antibody-dependent cell-mediated cytotoxicity (ADCC), 3 and complement dependent cytotoxicity(CDC), British Journal of Hematology. 2011 doi: 10.1111/bjh.14624.
Lohse, S. et al. "An Anti-EGFR IgA That Displays Improved Pharmacokinetics and Myeloid Effector Cell Engagement In Vivo" Cancer Res. Jan. 15, 2016;76(2):403-17. doi: 10.1158/0008-5472.CAN-15-1232. Epub Dec. 3, 2015. (9.3).
Lohse, S. et al. Characterization of a mutated IgA2 antibody of the m(1) allotype against the epidermal growth factor receptor for the recruitment of monocytes and macrophages. J. Biol. Chem. 287, 25139-25150 (2012).
Lohse, S., et al., "Recombinant Dimeric IgA Antibodies against the Epidermal Growth Factor Receptor Mediate Effective Tumor Cell Killing" J Immunol. 2011. 186(6):3770-8 doi: 10.4049/jimmunol.1003082. Epub Feb. 11, 2011.
Lombana, T. N. et al. Production, characterization, and in vivo half-life extension of polymeric IgA molecules in mice. MAbs 11, 1122-1138 (2019).
Lorin, V., et al., "Efficient generation of human IgA monoclonal antibodies" Journal of Immunological Methods, Elsevier Science Publishers V.B (2015) vol. 422, pp. 102-110.
Lowman, H.B., et al., Selecting High Affinity Binding Proteins by Monovalent Phage Display, 1991, Biochemistry 30: 10832-10837.
Maccallum, R.M., et al. Antibody-antigen interactions: contact analysis and binding site topography. J Mol Biol. Oct. 11, 1996;262(5):732-45. doi: 10.1006/jmbi.1996.0548. PMID: 8876650.
Macpherson, A. J. et al. A primitive T cell-independent mechanism of intestinal mucosal IgA responses to commensal bacteria. Science (80-. ). 288, 2222-2226 (2000).
Macpherson, A. J., et al. IgA Function in Relation to the Intestinal Microbiota. Annu. Rev. Immunol. 36, 359-381 (2018).
Macpherson, A. J., Geuking, M. B. & McCoy, K. D. Homeland Security: IgA immunity at the frontiers of the body. Trends Immunol. 33, 160-167 (2012).
Maliszewski, C.R., et al. "Expression Cloning of a Human Fc Receptor for IgA" (1990) J Exp. Med. 172:1665.
Matlung HL, et al. "Neutrophils kill antibody-opsonized cancer cells by trogoptosis" Cell Rep. Jun. 26, 2018;23(13):3946-3959.e6. doi: 10.1016/j.celrep.2018.05.082. (8.3).
Matlung, H., et al., "The CD47-SIRPα signaling axis as an innate immune checkpoint in caner", Immunological Reviews, (2017) vol. 276, No. 1, pp. 145-164.
Matthay et al., Treatment of High-Risk Neuroblastoma with Intensive Chemotherapy, Radiotherapy, Autologous Bone marrow Transplantation, and13-CIS-Retinoic Acid, 1999;New Engl. J. of Med vol. 341: pp. 1165-1173.

(56) References Cited

OTHER PUBLICATIONS

Mattu, T. S. et al. The glycosylation and structure of human serum IgA1, Fab, and Fc regions and the role of N-glycosylation on Fcα receptor interactions. J. Biol. Chem. 273, 2260-2272 (1998).

Mazur, Ni, et al., "Breast milk prefusion F IgG as a correlate of protection against respiratory syncytial virus acute respiratory illness" J Infect Dis. Jan. 1, 2019;219(1):59-67. doi: 10.1093/infdis/jiy477. (6.3).

Mccafferty, J. et al., "Phage Antibodies: Filamentous Phage Displaying Antibody Variable Doman" (1990) Nature 348:552-554).

Mcintosh, R.S., et al., "The importance of human FcgammaRI in mediating protection to malaria" 2007 PLOS Pathog. 3:e72 (8.1).

Mester, S, et al., ""Extended plasma half-life of albumin-binding domain fused human IgA upon pH-dependent albumin engagement of human FcRn in vitro and in vivo"" MAbs. Jan. 2021-Dec.;13(1):1893888. doi: 10.1080/19420862.2021.1893888. (4.6).

Meulenbroek, L.A.P.M., et al., "IgG antibodies in food allergy influence allergen-antibody complex formation and binding to B cells: a role for complement receptors" J Immunol. 2013 191:3526-3533. (5.6).

Meyer et al., 2016, Improved in vivo anti-tumor effects of IgA-Her2 antibodies through half-life extension and serum exposure enhancement by FcRn targeting, MAbsvol 8. pp. 87-98.

Meyer, S, et al. "New insights in Type I and II CD20 antibody mechanisms-of-action with a panel of novel CD20 antibodies" Br J Haematol. Mar. 2018;180(6):808-820. doi: 10.1111/bjh.15132. Epub Feb. 22, 2018. (5.7).

Meyer, S., et al. "Regulation of complement and modulation of its activity in monoclonal antibody therapy of cancer" MAbs. Jul. 1, 2014;6(5). [Epub ahead of print] Review. (5.3).

Mora, J, Dinutuximab for the treatment of pediatric patients with high-risk neuroblastoma, Expert review of clinical pharmacology, pp. 1-7; http://dx.doi.org/10.1586/17512433.2016.1160775.

Morgan, R.A. and Anderson, W.F. "Human Gene Therapy" 1993, Ann. Rev. Biochem. 62:191-217; May 1993.

Morrell, A. et al, Metabolic Properties of Human IgA Subclasses, 1973, Clin Exp Immunol 13(4): 521-528.

Muda, M. et al. Therapeutic assessment of SEED: A new engineered antibody platform designed to generate mono-and bispecific antibodies. Protein Eng. Des. Sel. 24, 447-454 (2011).

Mulligan, R.C., "The Basic Science of Gene Therapy" 1993, Science 260:926-932.

Muyldermans, S. et al., "Recognition of Antigens by Single-Domain Antibody Fragments: the Superfluous Luxury of Paired Domains" Trend Biochemical Science (2001) 26: 230-235.

Nassin et al 2018, Immune Reconstitution Following Autologous Stem Cell Transplantation in Patients with High-Risk Neuroblastoma at the Time of Immunotherapy, Biol Blood Marrow Transplant 24(3): 452-459).

Navid et al 2014, Phase I Trial of a Novelanti-GD2 Monoclonal Antibody, Hu14.18K322A, Designed to Decrease Toxicity inChildren With Refractory or Recurrent Neuroblastoma, J Clin Oncol 32(14): 1445-1452.

Nederend, M, et al., "Bovine IgG Prevents Experimental Infection With RSV and Facilitates Human T Cell Responses to RSV" Front Immunol. Aug. 6, 2020;11:1701. doi: 10.3389/fimmu.2020.01701. eCollection 2020.PMID:32849597 (5.1).

Ner, et al., Laboratory Methods A Simple & Efficient Procedure for Generating Random Point Mutations and for Codon Replacements 1988, DNA 7: 127.

Ness et al., "DNA Shuffling of Subgenomic Sequences of Subtilisin" 1999, Nature Biotechnology 17: 893-896.

Nilson B. H., et al.. Protein L from Peptostreptococcus magnus binds to the K light chain variable domain. J. Biol. Chem. 267, 2234-2239 (1992).

Olde Nordkamp, M.J.M., et al. "Inhibition of the Classical and Lectin Pathway of the Complement System by Recombinant LAIR-2" J Innate Immun. 2014 6:284-292.

Osbourn et al., Directed Selection of MIP-1α neutralizing CCR5 Antibodies from a Phage Display Human Antibody Library Nat. Biotechnol., 16: 778 (1998)).

Otten, M.A., et al., "FcR γ-chain dependent signaling in immature neutrophils is mediated by FcαRI, but not by FcgRI" 2007 J. Immuno !. 179:2918-24 (5.6).

Overdijk, M.B., "Crosstalk between Human IgG Isotypes and Murine Effector Cells" J Immunol. 2012 189:3430-3438. (5,6).

Overdijk,M.B., et al. "The Therapeutic CD38 Monoclonal Antibody Daratumumab Induces Programmed Cell Death via Fcγ Receptor-Mediated Cross-Linking" J Immunol. Jun. 17, 2016. pii: 1501351. [Epub ahead of print] (5.6).

Padlan, E A et al. "Structure of an antibody-antigen complex: crystal structure of the HyHEL-10 Fab-lysozyme complex." Proceedings of the National Academy of Sciences of the United States of America vol. 86, 15 (1989): 5938-42.

Parren, P.W., et al., "Antibody-catalyzed water oxidation: state-of-the-art immunity or ancient history?" 2003. Trends Immunol. 24:467-469 (10.4).

Pascal, Virginie et al., (2012) Anti-CD20 IgA Can Protect Mice Against Lymphoma Development: Evaluation of the Direct Impact of IgA and Cytotoxic Effector Recruitment on CD20 Target Cells, Haematologica, pp. 1686-1694 DOI: 10.3324/haematol.2011.061408.

Pasquier, B. et al. Identification of FcαRI as an inhibitory receptor that controls inflammation: Dual role of FcRγ ITAM. Immunity 22, 31-42 (2005).

Pfaffenbach et al., Activation of the Guinea Pig Alternative Complement Pathway by Mouse IgA Immune Complexes, The Journal of Experimental medicine. 1982;155(1):231-47.

Pleass, et al., Identification of Residues in the CH2/CH3 Domain Interface of IgA Essential for Interaction with the Human Fcα Receptor (FcαR) CD89*) The Journal of Biological Chemistry (1999) vol. 274, No. 33, pp. 23508-23514.

Plomp, R. et al. Comparative glycomics of immunoglobulin A and G from saliva and plasma reveals biomarker potential. Front. Immunol. 9, 1-12 (2018).

Posgai, et al., "FcαRI binding at the IgA1 Ch2-Ch3 interface induces long-range conformational changes that are transmitted to the hinge region" PNAS (2018) vol. 115, No. 38.

Presta, L.G., et al., "Humanization of an Anti-Vascular Endothelial Growth Factor Monoclonal Antibody for the Therapy of Solid Tumors and other Disorders", Cancer Res. 57:4593-4599 (1997).

Raaz, D., et al., "FcγRIIa genotype is associated with acute coronary syndromes as first manifestation of coronary artery disease" Atherosclerosis. 2009 205:512-6 (4.0).

Raaz-Schrauder, D., et al., "Patients with unstable angina pectoris show an increased frequency of the Fc gamma RIIa R131 allele" Autoimmunity. 2012 45:556-564 (2.5).

Raffaghello et al., Anti-GD2 monoclonal antibody immunotherapy: a promising strategy in the prevention of neuroblastoma relapse, 2003 Cancer Lett, vol. 197(1-2): p. 205-209.

Rajasekaranet al., 2015, Enhancement of antibody-dependent cell mediated cytotoxicity: a new era in cancer treatment, ImmunoTargets and Therapy vol. 4: 91.

Randall, et al., "Immunoglobulin isotype knowledge and application to Fc engineering" Current Opinion in Immunology, Elsevier vol. 40, pp. 62-69.

Reidhaar-Olson and Sauer, "Combinatorial Cassette Mutagenesis as a Probe of the Informational Content of Protein Sequences" 1988, Science 241: 53-57.

Reineke, U. "Antibody Epitope Mapping Using Arrays of Synthetic Peptides" 2004, Methods Mol Biol 248:443-463.

Rifai, A., et al. The N-glycans determine the differential blood clearance and hepatic uptake of human immunoglobulin (Ig)A1 and IgA2 isotypes. J. Exp. Med. 191, 2171-2181 (2000).

Robinson, C., "Gene Therapy—Proceeding from Laboratory to Clinic" Trends in Biotechnology, vol. 11, Issue 5, 155.

Rodriguez, M.E., et al., "Fc receptor-mediated immunity against Bordetella pertussis" 2001 J. Immunol. 167:6545-6451 (5.6).

Roos et al., 2001, Human IgA Activates the Complement System Via the Mannan-Binding Lectin Pathway. J Immunol 167(5): 2861-2868.

(56) References Cited

OTHER PUBLICATIONS

Rösner T, et al., "Immune effector functions of human IgG2 antibodies against EGFR" Mol Cancer Ther. Jan. 2019;18(1):75-88. doi: 10.1158/1535-7163.MCT-18-0341 (5,4).

Rossato, E. et al. Reversal of arthritis by human monomeric IgA through the receptor-mediated SH2 domain-containing phosphatase 1 inhibitory pathway. Arthritis Rheumatol. 67, 1766-1777 (2015).

Roth, Z., et al., "Identification and Quantification of Protein Glycosylation" International Journal of Carbohydrate Chemistry, vol. 2012, Article ID 640923.

Rouwendal, G. J. A. et al. A comparison of anti-HER2 IgA and IgG1 in vivo efficacy is facilitated by high N-glycan sialylation of the IgA. MAbs 8, 74-86 (2016).

Roux et al. Comparisons of the ability of human IgG3 hinge mutants, IgM, IgE, and IgA2, to form small immune complexes: a role for flexibility and geometry. J Immunol. Oct. 15, 1998;161(8):4083-90. PMID: 9780179.

Rudikoff, S et al. "Single amino acid substitution altering antigen-binding specificity." Proceedings of the National Academy of Sciences of the United States of America vol. 79,6 (1982): 1979-83. doi:10.1073/pnas.79.6.1979.

Running Deer, J. et al., "High-Level Expression of Proteins in Mammalian Cells Using Transcription Regulatory Sequences from the Chinese Hamster EF1a Gene" Biotechnol. Prog.20:880-889 (2004).

Saeland, E., et al., "Central role of complement in passive protection by human IgG1 and IgG2 anti-pneumococcal antibodies in mice" 2003. J Immunol. 170:6158-6164 (5,6).

Saeland, E., et al., "Role of leukocyte immunoglobuin G receptors in vaccine-induced immunity to *Streptococcus pneumoniae*" 2003. J Infect Dis. 187:1686-1693 (5.8).

Schneider, M.P., et al. "The Fcγ receptor IIA R131H gene polymorphism is associated with endothelial function in patients with hypercholesterolaemia" Atherosclerosis. Jul. 20, 2011. (4.0).

Sharma, S. K. et al. Fc-mediated anomalous biodistribution of therapeutic antibodies in immunodeficient mouse models. Cancer Res. 78, 1820-1832 (2018).

Shields, R.L., et al., Hi Resolution Mapping of the Binding Site on Human IgG1 for FcγRI, FcγRII, FcγRIII, and FcRN and Design of IgG1 Variants with Improved Bidning to the FcγR (2001) J. Biol. Chem., 276:6591-6604.

Sillevis Smitt, J.H., et al. "Chronic bullous disease of childhood and a paecilomyces lung infection in chronic granulomatous disease" 1997. Arch. Dis. Child. 77:150-152.

Sitaraman, K, et al., High-Throughput Protein Expression Using Cell-Free System Methods Mol. Biol. 498: 229-44 (2009).

Smit, J.J, et al., Contribution of classic and alternative effector pathways in peanut-induced anaphylactic responses. PLoS One. 2011;6(12):e28917. doi: 10.1371/journal.pone.0028917. Epub Dec. 14, 2011. PMID: 22194949; PMCID: PMC3237567.

Snoeck, V., et al. The IgA system: a comparison of structure and function in different species. Vet. Res. 37, 455-467 (2006).

Sorkin et al., Anti-GD2 with an FC point mutation reduces complement fixation and decreases antibody-induced allodynia, 2010, Pain 149(1): 135-142.

Spirin, A.S. et al., "High-Throughput Cell-Free Systems for Synthesis of Funcationally Active Proteins" Trends Biotechnol. 22: 538-45 (2004).

Sprong, H., et al. Aberrant receptor-mediated endocytosis of Schistosoma mansoni glycoproteins on host lipoproteins. PLoS Med. 2006;3(8):e253. doi:10.1371/journal.pmed.0030253.

Steeghs, L., et al., "Teasing apart structural determinants of "toxicity" and "adjuvanticity": implications for meningococcal vaccine development" 2004 J Endotoxin Res. 10:113-119.

Åhlin, M., et al., "Prevalence, clinical presentation and genetics of chronic granulomatous disease in Sweden" 1995. Acta Pediatrica 84:1386-1394.

Yu et al., "Anti-GD2 Antibody with GM-CSF, Interleukin-2,and Isotretinoin for Neuroblastoma" (2010) N Engl J Med 363(14): 1324-1334.

Zhang, W. et al. Advances in Anti-Tumor Treatments Targeting the CD47/SIRPα Axis. Front. Immunol. 11, 1-15 (2020).

Zhao, X.W., et al., "CD47-signal regulatory protein-alpha (SIRPalpha) interactions form a barrier for antibody-mediated tumor cell destruction", Proceedings of the National Academy of Sciences, vol. 108, No. 45, Nov. 8, 2011 (Nov. 8, 2011), p. 18342-18347.

Zhong, X. et al. Transient CHO expression platform for robust antibody production and its enhanced N-glycan sialylation on therapeutic glycoproteins. Biotechnol. Prog. 35, 1-12 (2019).

Zhu, X. et al. MHC Class I-Related Neonatal Fc Receptor for IgG Is Functionally Expressed in Monocytes, Intestinal Macrophages, and Dendritic Cells. J. Immunol. 166, 3266-3276 (2001).

Zoller, M.J., et al., "Oligonucleotide-directed Mutagenesis using M13-dervied Vectors: an Efficient and general Procedure for the Production of Point Mutations in Any Fragment of DNA" Nucl. Acids Res. 10:6487 (1982).

Klein, Christian, et al., "Epitope interactions of Monoclonal Antibodies Targeting CD20 and Their Relationship to Functional Properties", MABS, col. 5, No. 1, Jan. 1, 2013, pp. 22-33.

A. Jamal, et al., "Biological Validation of Plant-Derived Anti-Human Colorectal Cancer Monoclonal Antibody CO17-1A" 2009. Hybridoma. 28:7-12.

A.B. van Spriel, et al., "Mac-1 (CD11b/CD18) is essential for Fc receptor-mediated neutrophil cytotoxicity and Immunologic synapse formation" 2001. Blood 97:2478-2486 (11.8).

Ahmed, M., et al., Engineering anti-GD2 Monoclonal Antibodies for Cancer Immunotherapy, 2014; FEBS letters588: 288-297.

Albanesi, M., et al., "FcγRIII (CD16) and FcγRI (CD64) are responsible for anti-glycoprotein 75 monoclonal antibody TA99 therapy for experimental metastatic B16 melanoma" J. Immunol Cutting Edge, 2012 189:5513-5517. (5.6).

Allazikani et al, "Standard Conformations for the Canonical Structures of Immunoglobulins" J. Molec. Biol. (1997) 273:927-948.

Allesandri-Haber, Nicole et al., A Transient Receptor Potential Vanilloid-4-Dependent Mechanism of Hyperalgesia Is Engaged by Concerted Action of Inflammatory Mediators, The Journal of Neuroscience, Apr. 5, 2006, 26(14):3864-3784.

Almagro, JC, & Fransson, J., "Humanization of antibodies" Front Biosci. Jan. 1, 2008;13:1619-33. doi: 10.2741/2786. PMID: 17981654.

Andersen, J. T. et al. "Anti-carcinoembryonic antigen single-chain variable fragment antibody variants bind mouse and human neonatal Fc receptor with different affinities that reveal distinct cross-species differences in serum half-life." J. Biol. Chem. 287, 22927-22937 (2012).

Armour et al. "Recombinant human IgG molecules lacking Fcgamma receptor I binding and monocyte triggering activities." Eur J Immunol 29(8):2613-2624 (1999).

Atkin, J. D., et al., "Mutagenesis of the human IgA1 heavy chain tailpiece that prevents dimer assembly" J. Immunol. 157, 156-9 (1996).

Baars, P.A., et al., "Cytolytic mechanisms and expression of activation-regulating receptors on effector-type, CD8+CD45RA+CD27-human T cells" 2000. J Immunol. 165:1910-1917. (5.6).

Bakema, J. E. & Van Egmond, M., "Immunoglobulin A: a next generation of therapeutic antibodies?" MAbs 3, 352-361 (2011).

Bakema, J.E., et al., "c-Jun activating binding protein 1 binds to the IgA receptor and modulates protein levels of FcalphaRI and FcRgamma-chain" Eur. J. Immunol. 2010. 40:2035-2040 (4.5).

Bakema, J.E., et al., "Inside-out regulation of FcaRI (CD89) depends on Protein Phosphatase 2A" 2008. J. Immuno! 181:4080-4088 (5.6).

Bakema, J.E., et al., "Signaling through mutants of the IgA receptor, CD89, and consequences for FcR γ-chain Interaction" 2006. J. Immunol. 176:3603-10. (5.6).

Barker, Edward et al., Effect of a Chimeric Anti-Ganglioside GD2 Antibody on Cell-mediated Lysis of Human Neuroblastoma Cells, Cancer Res, vol. 51: p. 144-149.

Bate-Eya, Laurel et al., (2014), Newly-derived neuroblastoma cell lines propagated inserum-fre media recapitulate the genotype and phenotype of primary neuroblastoma tumours, European Journal of Cancer 50.3: 628-637.

(56) References Cited

OTHER PUBLICATIONS

Batova, Ayse et al., TheCh14.18-GM-CSF Fusion Protein Is Effective at Mediating Antibody-dependent Cellular Cytotoxicity and Complement-dependent Cytotoxicity inVitro, (1999) ClinCancer Res vol. 5: p. 4259-4263.
Beekman, J.M., et al., "Direct interaction between periplakin and FcγRI controls receptor endocytosis and ligand binding capacity" 2004. Proc Natl Acad Sci U S A. 101:10392-10397. (9.8).
Beekman, J.M., et al., "FcgRI (CD64) resides constitutively in lipid rafts" 2008 Immuno!. Lett. 116:149-155.
Beekman, J.M., et al., "Filamin A stabilizes FcγRI surface expression and prevents its lysosomal routing" 2008. J. Immunol 180:3938-45 (5.6).
Beekman, J.M., et al., "Modulation of FcγRI (CD64) ligand binding capacity by periplakin peptides" 2004. J. Biol. Chem. 279:33875-33881. (4.6).
Beekman, J.M., et al., "Protein 4.1G binds to a unique motif within the FcγRI cytoplasmic tail" 2008 Mo !. Imm. 45:2069-2075 (3.0).
Better, M et al. "Potent anti-CD5 ricin A chain immunoconjugates from bacterially produced Fab' and F(ab')2." Proc. Natl. Acad. Sci. USA 90: 457-461 (1993).
Bevaart, L., et al., "CpG oligodeoxynucleotides enhance FcgammaRI-mediated cross presentation by dendritic cells" 2004. Int Immunol. 16:1091-1098.
Bevaart, L., et al., "Direct targeting of genetically modified tumour cells to FcγRI triggers potent tumour cytotoxicity" 2006. Br J Haematol, 132:317-25. (5.0).
Bevaart, L., et al., "The high-affinity IgG receptor, FcγRI, plays a central role in antibody therapy of experimental melanoma" 2006. Cancer Res. 66: 1261-1264. (9.3).
Beyer, T. et al. "Serum-free production and purification of chimeric IgA antibodies" J. Immunol. Methods 346, 26-37 (2009).
Bird, et al., "Single-Chain Antigen-Binding Proteins" (1988) Science 242(4877):423-426.
Blaese, R. M., et al. "Hypercatabolismof IgG, IgA, IgM, and albumin in the Wiskott-Aldrich syndrome. A unique disorder of serum protein metabolism" J. Clin. Invest. 50, 2331-2338 (1971).
Bogdanovich, S., et al. "Human IgG1 antibodies suppress angiogenesis in a target-independent manner" Signal Transduct Target Ther. 2016;1. pii: 15001. Epub Jan. 28, 2016.
Bogenmann, E. "A Metastatic Neuroblastoma Model in SCID Mice" Int. J. Cancer vol. 67:379.
Bondza, S., et al. ""Bivalent binding on cells varies between anti-CD20 antibodies and is dose-dependent"" MAbs. Jan. 2020-Dec. 12(1):1792673. doi: 10.1080/19420862.2020.1792673. PMID: 32744151 (4.6).
Boross et al. IgA EGFR antibodies mediate tumour killing in vivo. EMBO Mol Med 5:1213-1226 (2013).
Boross et al. The in vivo mechanism of action of CD20 monoclonal antibodies depends on local tumor burden. Haematologica 96:1822-1830 (2011).
Boross, P., et al. "Anti-tumor activity of human IgG1 anti-gp75 TA99 mAb against B16F10 melanoma in human FcgammaRI transgenic mice" Immunol Lett. 2014 160:151-157. (2.5).
Boross, P., et al. "FcRγ-chain ITAM signaling is critically required for cross-presentation of soluble antibody-antigen complexes by dendritic cells" J Immunol. Dec. 1, 2014;193(11):5506-14. doi: 10.4049/jimmunol. 1302012. Epub Oct. 29, 2014.
Boross, P., et al., "Boosting antibody therapy with complement" Blood. Jun. 21, 2012;119(25):5945-7. (11.8).
Boross, P., et al., "Both activating and inhibitory Fc gamma receptors mediate rituximab-induced trogocytosis of CD20 in mice" Immunol. Lett. 2011 upon invitation.
Boross, P., et al., "Fc receptors" 2008 Encyclopedia of Life Sciences (ELS). Review, chapter, online Wiley's editor.
Boross, Peter et al., Mechanisms of action of CD20 antibodies, Am JCancer Res. 2012; 2(6): 676-690. Published online Nov. 20, 2012.
Borrok, M.J., et al. Enhancement of antibody-dependent cell-mediated cytotoxicity by endowing igG with FcαRI (CD89) binding. MAbs 7, 743-751 (2015).

Bowie and Sauer, 1989, Proc. Natl. Acad. Sci. USA 86: 2152-2156.
Braekeveldt, Noemie et al., Neuroblastoma patient-derived orthotopic xenografts reflect the microenvironmental hallmarks of aggressive patient tumors, Cancer Lett. 2016 vol. 1;375(2):384-9. doi: 10.1016/j.canlet.2016.02.046.
Brandsma A.M., "Fc receptor inside-out signaling and possible impact on antibody therapy" Immunol Rev. Nov. 2015;268(1):74-87. doi: 10.1111/imr.12332. Review. (12.2).
Brandsma AM, et al. "Single nucleotide polymorphisms of the high affinity IgG receptor FcγRI reduce IC binding and downstream effector functions" J Immunol. Aug. 16, 2017. pii: ji1601929. doi: 10.4049/jimmunol.1601929. [Epub ahead of print] (5.6).
Brandsma, A. M. et al. Potent Fc receptor signaling by IgA leads to superior killing of cancer cells by neutrophils compared to IgG. Front. Immunol. 10, (2019).
Brandsma, A. M. et al. Simultaneous targeting of FcgRs and FcaRI enhances tumor cell killing. Cancer Immunol. Res. 3, 1316-1324 (2015).
Brandsma, A.M., et al. Clarifying the Confusion between Cytokine and Fc Receptor "Common Gamma Chain" Immunity. Aug. 16, 2016;45(2):225-6. doi: 10.1016/j.immuni.2016.07.006. (IF=24.1).
Bronner, I.M., et al., "Association of the leukocyte immunoglobulin G (Fcgamma) receptor IIIa-158V/F polymorphism with inflammatory myopathies in Dutch patients" Tissue Antigens. 2009 73:586-589 (2.4).
Steffen, U. et al. IgA subclasses have different effector functions associated with distinct glycosylation profiles. Nat. Commun. 11, (2020).
Stemerding, A.M., et al. "*Staphylococcus aureus* Formyl Peptide Receptor-like 1 Inhibitor (FLIPr) and Its Homologue FLIPr-like Are Potent FcγR Antagonists That Inhibit IgG-Mediated Effector Functions" J Immunol. 2013 191:353-362 (5.6).
Steurer, W. et al., Ex Vivo Coating of Islet Cell Allografts With Murine CTLA4/Fc Promotes Graft Tolerance, 1995. J Immunol. 155(3):1165-74.
Stockmeyer, B. et al. Triggering FCα-Receptor I (CD89) Recruits Neutrophils as Effector Cells for CD20-Directed Antibody Therapy. J. Immunol. 165, 5954-5961 (2000).
Stork, A.C., et al. "Fcγ receptor IIIA genotype is associated with rituximab response in antimyelin-associated glycoprotein neuropathy" J Neurol Neurosurg Psychiatry. 2014 85:918-920. (4.9).
Story, C. M., et al., A major histocompatibility complex class I-like Fc receptor cloned from human placenta: Possible role in transfer of immunoglobulin G from mother to fetus. J. Exp. Med. 180, 2377-2381 (1994).
Sturtevant, J.N., Biochemical Applications of Differential Scanning Calorimetry 1987, Annual Review of Physical Chemistry 38: 463-488.
Suzuki and Cheung, Disialoganglioside GD2 as a therapeutic target for human diseases, 2015, Expert Opinionon Therapeutic Targets vol. 19: p. 349-362.
Terme et al., Chimeric Antibody c.8B6 to O-acetyl-GD2 Mediates the Same Efficient Anti-Neuroblastoma Effects as Therapeutic ch14.18 Antibody to GD2 Without Antibody Induced Allodynia, 2014, PLoS One 9(2): e87210.
Thotakura, et al., "Enzymatic Deglycosylation of Glycoproteins" Meth. Enzymol. 138: 350-359 (1987).
Tian, J., et al., "Accurate Multiplex Gene Synthesis from Programmable DNA Microchips" (2004), Nature 432: 1050-1054.
Tolstoshev, P., "Gene Therapy, Concepts Current Trials and Future Predictions" 1993, Ann. Rev. Pharmacol. Toxicol. 32:573-596.
Tomic, M., et al., A rapid and simple method for introducing specific mutations into any position of DNA leaving all other positions unaltered, Nucleic Acids Research (1990) 18(6):1656.
Tramontano, A., et al., "Framework Residue 71 is a Major Determinant of the Position and Conformation of the Second Hypervariable Region in the Hb Domains of Immunoglobulins" 71 IS J. Mol. Biol, 215: 175-182 (1990).
Treffers, L. W. et al., "IgA-Mediated Killing of Tumor Cells by Neutrophils is Enhanced by CD47-SIRP[alpha] Checkpoint Inhibition", Cancer Immunology Research, vol. 8, No. 1, Nov. 5, 2019 (Nov. 5, 2019), p. 120-130.

(56) References Cited

OTHER PUBLICATIONS

Treffers, L. W. et al., FcγRIIIb restricts antibody-dependent destruction of cancer cells by human neutrophils. Front. Immunol. 10, 1-13 (2019).
Ulfman, L.H., et al. "Effects of bovine immunoglobulins on immune function, allergy and infection" Front Nutr. Jun. 22, 2018;5:52. doi: 10.3389/fnut.2018.00052. eCollection 2018. Review. (4.5).
UNITUXIN (dinutuximab) Highlights of Prescribing Information United Therapeutics Corp., Silver Spring, MD 20910, US License No. 1993, p. 19, Copyright 2015.
Vajdos, F.F., et al., Comprehensive functional maps of the antigen-binding site of an anti-ErbB2 antibody obtained with shotgun scanning mutagenesis. J Mol Biol. Jul. 5, 2002;320(2):415-28.
Valerius, T, et al., CD47 Blockade and Rituximab in Non-Hodgkin's Lymphoma. N Engl J Med. Jan. 31, 2019;380(5):496-7. doi: 10.1056/NEJMc1816156. (79.3).
Valerius, T. et al. FcalphaRI (CD89) as a novel trigger molecule for bispecific antibody therapy. Blood 90, 4485-4492 (1997).
Van Bommel, et al., "CD20-Selective Inhibition of CD47-SIRP-alpha 'Don't Eat Me' Signaling With A Bispecific Antibody-Derivative Enhances The Anticancer Activity of Daratumumab, Alemtuzumab and Obinutuzumab Oncoimmunology" (2018) vol. 7, No. 2.
Van De Walle, I., et al. "ARGX-117, a therapeutic complement inhibiting antibody targeting C2" J Allergy Clin Immunol. Sep. 11, 2020:S0091-6749(20)31239-2. doi: 10.1016/j.jaci.2020.08.028. (14.9).
Van Der Poel, C.E., et al., "Cytokine-induced immune complex binding to the high affinity IgG receptor, FcgRI, in the presence of monomeric IgG" Blood 2010 116:5327-33 (11.8).
Van Der Poel, C.E., et al., "Functional characteristics of the high affinity IgG receptor, FcγRI" J. Immunol, 2011. 186:2699-704. (5.6).
Van Der Schoot, JMS, et al., "Functional diversification of hybridoma-produced antibodies by CRISPR/HDR genomic engineering." Science advances vol. 5,8 eaaq1822. Aug. 28, 2019, doi:10.1126/sciadv.aaw1822.
Van Egmond, M. et al. FcαRI-positive live Kupffer cells: Reappraisal of the function of immunoglobulin A in immunity. Nat. Med. 6, 680-685 (2000).
Van Egmond, M. et al. Human immunoglobulin A receptor (FcαRI, CD89) function in transgenic mice requires both FCR γ chain and CR3 (CD11b/CD18). Blood 93, 4387-4394 (1999).
Van Egmond, M. et al., IgA and the IgA Fc receptor. Trends Immunol. 22, 205-211 (2001).
Van Royen-Kerkhof, A., et al., "a novel human CD32 mAb blocks experimental immune haemolytic anaemia in FcgammaRIIA transgenic mice" 2005. Br J Haematol. 130:130-7. (5.0).
Van Royen-Kerkhof, A., et al., "Expression of CD64 (FcgRI) in skin of patients with acute graft-versus-host disease" Bone marrow transplant. Jan. 17, 2011. (2.9).
Van Royen-Kerkhof, A., et al., "Flow cytometric determination of FcgRIIa (CD32)" 2004. polymorphism. J. Immunol. Methods. 294:135-144.
Van Sorge, N.M., et al., "Anti-GM1 IgG antibodies induce leukocyte effector functions via Fcgamma receptirs" 2003. Ann Neurol. 53:570-579 (11.9).
Van Spriel, A. B., et al. Mac-1 (CD11b/CD18) as Accessory Molecule for FcαR (CD89) Binding of IgA. J. Immunol. 169, 3831-3836 (2002).
Van Tetering, G, et al. "Fc Engineering Strategies to Advance IgA Antibodies as Therapeutic Agents" Antibodies (Basel). Dec. 15, 2020;9(4):70.
Van Vugt, M.J. , "The FcγRIa (CD64) ligand binding chain triggers MHC class II antigen presentation independently of its associated FcR g-chain" 1999. Blood 94:808-817.
Van Vugt, M.J., et al. "The alternatively spliced CD64 transcript FcγRIb2 does not specify a surface expressed isoform" 1999 Eur J Immunol 29:143-149.
Verhoeven, A.J., et al., "Inhibition of neutrophil NADPH oxidase assembly by a myristoylated pseudosubstrate of protein kinase C" 1993. J. Biol. Chem. 268:18593-18598 (4.6).
Vikström, I.B., et al. "MCL-1 is required throughout B-cell development and its loss sensitizes specific B-cell subsets to inhibition of BCL-2 or BCL-XL" Cell Death Dis. Aug. 25, 2016;7(8):e2345. doi: 10.1038/cddis.2016.237. (IF=5.0).
Vyborova A, et al. "γ9δ2T cell diversity and the receptor interface with tumor cells" J Clin Invest. Jun. 2, 2020:132489. doi: 10.1172/JCI132489. Online ahead of print.J Clin Invest. 2020. PMID: 32484803 (12.3).
Walbaum, S, et al. " Complement receptor 3 mediates both sinking phagocytosis and phagocytic cup formation via distinct mechanisms" J Biol Chem. Jan. 4, 2021:jbc.RA120.015346. doi: 10.1074/jbc.RA120.015346. (4.2).
Ward, E. S., et al., Targeting FcRn to Generate Antibody-Based Therapeutics. Trends Pharmacol. Sci. 39, 892-904 (2018).
Ward, E.S., et al., "Binding Activities of a Repertoire of Single Immunoglobulin Variable Domains Secreted from *Escherichia coli*" Nature (1989) 341: 544-546.
Widjaja, I., et al. "Recombinant Soluble Respiratory Syncytial Virus F Protein That Lacks Heptad Repeat B, Contains a GCN4 Trimerization Motif and is Not Cleaved Displays Prefusion-Like Characteristics" PLoS One. Jun. 24, 2015;10 (6):e0130829 (3.5).
Wines, B. D., "The Interaction of FcαRI with IgA and Its Implications for Ligand Binding by Immunoreceptors of the Leukocyte Receptor Cluster" J. Immunol. 166, 1781-1789 (2001).
Winiarska, M., et al. "Inhibitors of SRC kinases impair antitumor activity of anti-CD20 monoclonal antibodies" MAbs. 2014 6:1300-1313.
Woof, et al., "Structure and function relationships in IgA" Nature (2011, vol. 4, No. 6 p. 590-597.
Wu, H., et al., Humanization of a murine monoclonal antibody by simultaneous optimization of framework and CDR residues. J Mol Biol. Nov. 19, 1999;294(1): 151-62.
Xiao, et al., 1997, Electrophysiological Characteristics of Primary Afferent Fibers After Systemic Administration of Anti-GC2 Ganglioside Antibody, Pain69: 145-151.
Yasuma, R., et al. Intravenous immune globulin suppresses angiogenesis in mice and humans. Sig Transduct Target Ther 1, 15002 (2016). https://doi.org/10.1038/sigtrans.2015.2.
Evers, M, et al., "The Latest Development with Anti-CD20 Monoclonal Antibodies in Chronic Lymphocytic Leukemia" Expert Opin Biol Ther. Sep. 2018;18(9):973-982. doi: 10.1080/14712598.2018. 1508444. Epub Aug. 10, 2018. (4.0).
Firan, M. et al. The MHC class I-related receptor, FcRn, plays an essential role in the maternofetal transfer of γ-globulin in humans. Int. Immunol. 13, 993-1002 (2001).
Flinsenberg, T.W., et al. "A novel FcγRIIa Q27W gene variant is associated with common variable immune deficiency through defective FcγRIIa downstream signaling" Clin Immunol. 2014 155:108-117. (4.0).
Galluzi, Lorenzo et al, Trial Watch: Monoclonal Antibodies in Cancer Therapy, Jan./Feb. 2012, Oncolmmunology, vol. 1, Issue 1, pp. 28-37.
Gazzano-Santoro, H., et al., A non-radioactive complement-dependent cytotoxicity assay for anti-CD20 monoclonal antibody. J Immunol Methods. Mar. 28, 1997;202(2):163-71. doi: 10.1016/s0022-1759(97)00002-1. PMID: 9107305.
Geissmann, F. et al. A Subset of Human Dendritic Cells Expresses IgA Fc Receptor (CD89), Which Mediates Internalization and Activation Upon Cross-Linking by IgA Complexes. J. Immunol. 166, 346-352 (2001).
Geller, A. & Yan, J. The role of membrane bound complement regulatory proteins in tumor development and cancer immunotherapy. Front. Immunol. 10, 1-13 (2019).
Ghetie, V. et al. Abnormally short serum half-lives of IgG in β2-microglobulin-deficient mice. Eur. J. Immunol. 26, 690-696 (1996).
Gillies et al., 1989, High-level expression of chimeric antibodies using adapted cDNA variableregion cassettes, J Immunol Methods, 125, p. 191-202.

(56) References Cited

OTHER PUBLICATIONS

Gilman et al 2009, Phase I Study of ch14.18 With Granulocyte-Macrophage Colony-Stimulating Factor and Interleukin-2 in Children With Neuroblastoma After Autologous Bone Marrow Transplantation or Stem-Cell Rescue: A Report From the Children's Oncology Group, J Clin Oncol 27(1): 85-91.
Goebl, N. A. et al. Neonatal Fc receptor mediates internalization of Fc in transfected human endothelial cells. Mol. Biol. Cell 19, 5490-5505 (2008).
Golay, Josee et al., Glycoengineered CD20 antibody obinutuzumab activates neutrophils and mediatesphagocytosis through CD16B more efficiently than rituximab, Immunobiology, Nov. 14, 2013, Blood (2013) 122 (20): 3482-3491, https://doi.org/10.1182/blood-2013-05-504043.
Gomes, M. M. et al. Analysis of IgA1 N-glycosylation and its contribution to FcαRI binding. Biochemistry 47, 11285-11299 (2008).
Göritzer, et al., "Exploring Site-Specific N-Glycosylation of HEK293 and Plant-Produced Human IgA Isotypes" J. Proteome Res. (2017), 16, 2560-2570.
Göritzer, K. et al. Distinct Fcα receptor N-glycans modulate the binding affinity to immunoglobulin A (IgA) antibodies. J. Biol. Chem. 294, 13995-14008 (2019).
Graziano, et al., "Antibody-dependent Cell-mediated Cytotoxicity (ADCC)" (2006) Encyclopedia of Life Sciences p. 1-5.
Gregory, R. L., et al., Separation of human IgA1 and IgA2 using jacalin-agarose chromatography. J. Immunol. Methods 99, 101-106 (1987).
Guss, et al., "Structure of the IgG-binding Regions of Streptococcal Protein G" The EMBO Journal 5(7):1567-1575 (1986).
Hakimuddin, T., et al. A Chemical Method for the Deglycosylation of Proteins Arch. Biochem. Biophys. 259: 52 (1987).
Heystek, H. C., et al., Human Immature Dendritic Cells Efficiently Bind and Take up Secretory IgA Without the Induction of Maturation. J. Immunol. 168, 102-107 (2002).
Hidalgo, A., et al., The Neutrophil Life Cycle. Trends Immunol. 40, 584-597 (2019).
Hiemstra, Peter S. et al., Activation of the alternative pathway of complement by humanserum IgA European journal of immunology. 1987;17(3):321-6.
Hochleitner, E.O., et al., "Characterization of a discontinuous epitope of the human immunodeficiency virus (HIV) core protein p24 by epitope excision and differential chemical modification followed by mass spectrometric peptide mapping analysis" Protein Science. 2000;9(3):487-496.
Holliger, P., et al., Engineered Antibody Fragments and the Rise of Single Domains Nat. Biotech., 23(9):1126-1129 (2005).
Holt, A.J., et al. "Domain Antibodies: Proteins for Therapy" Trends Biotechnol (2003): 21: 484-490.
Huls, G. et al. Antitumor immune effector mechanisms recruited by phage display-derived fully human IgG1 and IgA1 monoclonal antibodies. Cancer Res. 59, 5778-5784 (1999).
Huston, J.S., et al., Protein Engineering of Antibody Binding Sites: Recovery of Specific Activity in an Anti-Digoxin Single-Chain Fc Analogue Produced in *Escherichia coli*(1988) Proc. Natl. Acad. Sci. USA 85:5879-5883.
Idosogie et al., Mapping of the C1q Binding Site on Rituxan, aChimeric Antibody with a Human IgG1 Fc, 2000. UImmunol. 164(8):4178-84.
Idusogie, et al. Engineered antibodies with increased activity to recruit complement. J Immunol. Feb. 15, 2001;166(4):2571-5.
International Search Report and Written Opinion for corresponding PCT Application No. PCT/2020014617 issued Aug. 17, 2020.
International Search Report and Written Opinion for corresponding PCT Application No. PCT/NL2019/050712 issued Mar. 30, 2020.
International Search Report and Written Opinion for corresponding PCT Application No. PCT/US2019/058648 issued Apr. 9, 2020.
Israel, E. J., et al. Increased clearance of IgG in mice that lack β2-microglobulin: Possible protective role of FcRn. Immunology 89, 573-578 (1996).

Jacobino, Sr, et al. "Reformatting palivizumab and motavizumab from IgG to human IgA impairs their efficacy against RSV infection in vitro and in vivo" MAbs. Apr. 2018;10(3):453-462. doi: 10.1080/19420862.2018.1433974. Epub Mar. 19, 2018. (5.3).
Jansen, B., et al., "Os9 interacts with DC-stamp and modulates its intracellular localization in response to TLR igation" 2009. Mol. Imm 46:505-515 (3.0).
Jarvis, G.A., et al., Human IgA1 initiates Compliment Mediated Killing of Neisseria Meningitis, J Immunol. 1989;143(5):1703-9.
Jefferis, R. Recombinant antibody therapeutics: the impact of glycosylation on mechanisms of action. Trends Pharmacol Sci. Jul. 2009;30(7):356-62. doi:10.1016/j.tips.2009.04.007. Epub Jun. 22, 2009. Review. PubMed PMID: 19552968.
Johansen, F. E. et al., Regulation of the polymeric immunoglobulin receptor and IgA transport: New advances in environmental factors that stimulate pIgR expression and its role in mucosal immunity. Mucosal Immunol. 4, 598-602 (2011).
Johansen, F., et al., "Recombinant expression of polymeric IgA: incorporation of J chain and secretory component of human origin" European Journal of Immunology (1999) vol. 29, No. 5.
Junghans, R. P., et al., The protection receptor for IgG catabolismis the β2-microglobulin-containing neonatal Intestinal transport receptor. Proc. Natl. Acad. Sci. U. S. A. 93, 5512-5516 (1996).
Keler, T. et al. Differential Effect of Cytokine Treatment on Fcα Receptor I-and Fcγ Receptor I-Mediated Tumor Cytotoxicity by Monocyte-Derived Macrophages. J. Immunol. 164, 5746-5752 (2000).
Kelton, C. et al. Anti-EGFR biparatopic-SEED antibody has enhanced combination-activity in a single molecule. Arch. Biochem. Biophys. 526, 219-225 (2012).
Kelton, W. et al. IgGA: A 'cross-isotype' engineered human Fc antibody domain that displays both IgG-like and IgA-like effector functions. Chem. Biol. 21, 1603-1609 (2014).
Kierkels GJJ, et al. "Identification of a tumor-specific allo-HLA-restricted γδTCR" Blood Adv. Oct. 8, 2019;3(19):2870-2882. doi: 10.1182/bloodadvances.2019032409.
Kim, Jin-Kyoo et al., Identifying amino acid residues that influence plasma clearance of murine IgG1 fragments by site-directed mutagenesis Eur. J. Immunol. (1994) 24:542-548.
Kruijsen, D., et al., "Serum antibodies critically affect virus specific CD4+/CD8+ T cell balance during RSV Infections" J. Immunol, 2010, 185:6489-98 (5.6).
Kunkel, T.A., et al., Rapid and Efficient Site-Specific Mutagenesis without Phenotypic Selection, Methods Enzymol,, 154:367-82, 1987.
Kuribayashi, F., et al., "A novel polymorphism in the coding region of CYBB, the human gp91-phox gene" 1996. Human Genetics 97:611-613.
Ladenstein et al.2013, Ch14.18 antibody produced in CHO cells in relapsed or refractory Stage 4 neuroblastoma patients A SIOPEN phase 1 study, MAbs 5(5): 801-809.
Lamminmaki, U., et al., Crystal Structure of a Recombinant Anti-estradiol Fab Fragment in Complex with 17β-Estradiol, JBC 2001, 276:36687-36694.
Brandsma, Arianne M., et al. "Mechanisms of inside-out signaling of the high-affinity IgG receptor FcγRI." Science signaling vol. 11,540 eaaq0891. Jul. 24, 2018, doi:10.1126/scisignal.aaq0891.
Brandtzaeg, P. & Prydz, H. Direct evidence for an integrated function of J chain and secretory component in epithelial transport of immunoglobulins. Nature 311, 71-73 (1984).
Bras AE, et al. "CD123 expression levels in 846 acute leukemia patients based on standardized immunophenotyping" Cytometry B Clin Cytom. Mar. 2019;96(2): 134-142. doi: 10.1002/cyto.b. 21745 (2.8).
Brezski, Randall et al., Immunoglobulin isotype Knowledge and Application to FC Engineering, Current Opinions in Immunology, 2016, 40:62-69.
Brodzik, R., et al., "Plant-derived anti-Lewis Y mAb exhibits biological activities for efficient immunotherapy against human cancer cells" Proc Nat! Acad Sci U S A. 2006. 103:8804-8809 (9.8).
Broeke Ten T., "Meeting report on immunoreceptors 2014" FASEB J. Mar. 2015;29(3):740-4 (5.5).

(56) References Cited

OTHER PUBLICATIONS

Broeke Ten, T, et al. "FcαRI Dynamics Are Regulated by GSK-3 and PKCZ During Cytokine Mediated Inside-Out Signaling" Front Immunol. Jan. 31, 2019;9:3191. doi: 10.3389/fimmu.2018.03191. (6.4).
Bruchelt et al (1989); Lysis of neuroblastoma cells by the ADCC-reaction: granulocytes of patients with chronic granulomatous disease are more effective than those of healthy donors, Immunol Lett 22(3): 217-220.
Bruhns et al. Specificity and Affinity of Human Fc Receptors and Their Polymorphic Variants for Human IgG Subclasses. Blood 113(16):3716-3725 (2009).
Brunke, C. et al. Effect of a tail piece cysteine deletion on biochemical and functional properties of an epidermal growth factor receptor-directed IgA2 min(1) antibody. MAbs 5, 936-945 (2013).
Büll, C. et al. "Targeted Delivery of a Sialic Acid-Blocking Glycomimetic to Cancer Cells Inhibits Metastatic Spread" ACS Nano. Jan. 27, 2015;9(1):733-45. Epub Jan. 14, 2015 (12.0).
Carayannopoulos, L., et al. Localization of the binding site for the monocyte immunoglobulin (Ig) A-Fc receptor (CD89) to the domain boundary between Cα2 and Cα3 in human IgA1. J. Exp. Med. 183, 1579-1586 (1996).
Carter, P., et al., "High Level *Escherichia Coli Escherichia Coli* Expression and Production of a Bivalent Humanized Antibody Fragment" Biotechnology (1992) 10:163-167.
Casset, F., et al., A peptide mimetic of an anti-CD4 monoclonal antibody by rational design, Biochem Biophys Res Commun. Jul. 18, 2003;307(1):198-205.
Challacombe, S. J., et al., Estimation of the intravascular half-lives of normal rhesus monkey IgG, IgA and IgM. Immunology 36, 331-338 (1979).
Chao et al. Anti-CD47 antibody synergizes with rituximab to promote phagocytosis and eradicate non-Hodgkin lymphoma. Cell 142:699-713 (2010).
Chao Mark P et al, "Anti-CD47 antibody synergizes with rituximab to promote phagocytosis and eradicate non-Hodgkin lymphoma", 20100903, vol. 142, No. 5, Sep. 3, 2010 (Sep. 3, 2010), p. 699-713.
Chaplan et al. Quantitative assessment of tactile allodynia in the rat paw. J Neurosci Methods 53:55-63 (1994).
Chen et al., "Selection and analysis of an optimized anti-VEGF antibody: crystal structure of an affinity-matured Fab in complex with antigen" J. Mol. Biol. 293:865-881 (1999).
Chen, Y., et al., Selection and analysis of an optimized anti-VEGF antibody: crystal structure of an affinity-matured Fab in complex with antigen. J Mol Biol. Nov. 5, 1999;293(4):865-81.
Cheung, Irene et al., Activation of Peripheral-Blood Granulocytes Is Strongly Correlated With Patient Outcome After Immunotherapy With Anti-GD2 Monoclonal Antibody and Granulocyte-Macrophage Colony-Stimulating Factor,2012, J Clin Oncol, vol. 30: p. 426-432.
Cheung, Nai-Kong V. at al (2014), Key Role for Myeloid Cells: Phase II Results of Anti-GD2 Antibody3F8 Plus Granulocyte-Macrophage Colony-Stimulating Factor for Chemoresistant Osteomedullary Neuroblastoma, Int J Cancer 135(9): 2199-2205).
Cheung, Nai-Kong V. et al., 2012, Humanizing murine IgG3 anti-GD2 antibody m3F8 substantially improves antibody-dependent cell-mediated cytotoxicity while retaining targeting in vivo, Oncoimmunology 1.4: 477-486.
Chintalacharuvu, K. R., et al., Divergence of human alpha-chain constant region gene sequences. A novel recombinant alpha 2 gene. J. Immunol. 152, 5299-304 (1994).
Chintalacharuvu, K.R., et al., Hybrid IgA2/IgG1 antibodies with tailor-made effector functions. Clin. Immunol. 101, 21-31 (2001).
Choa, et al., "Anti-CD47 antibody synergizes with rituximab to promote phagocytosis and eradicate non-Hodgkin lymphoma", J. Cell (2010) vol. 142, No. 5 pp. 699-713.
Chothia, C., et al., Structural repertoire of the human VH segments. J Mol Biol. Oct. 5, 1992;227(3):799-817. doi: 10.1016/0022-2836(92)90224-8. PMID: 1404389.

Chothia, et al., Canonical structures for the hypervariable regions of immunoglobulins. J Mol Biol. Aug. 20, 1987;196(4):901-17. doi: 10.1016/0022-2836(87)90412-8. PMID: 3681981.
Clarkson, T., et al., "Making Antibody Fragments Using Phage Display Libraries" Nature 352:624-628 (1991).
Daha, M.R., et al., "Isolation from purulent sputum of an antigen with Wegener's granulomatosis" 1990. Neth. J. Med., 36:117-120.
Davies J, et al. 'Camelising' human antibody fragments: NMR studies on VH domains. FEBS Lett. Feb. 21, 1994;339(3):285-90. doi: 10.1016/0014-5793(94)80432-x. PMID: 8112468.
Davis, J. H. et al., SEEDbodies: Fusion proteins based on strand-exchange engineered domain (SEED) CH3 heterodimers in an Fc analogue platform for asymmetric binders or immunofusions and bispecific antibodies. Protein Eng. Des. Sel. 23, 195-202 (2010).
De Haij, S., et al.., "In vivo cytotoxicity of type I CD20 antibodies critically depends on FcR ITAM signaling" 2010. Cancer Research 2010 70:3209-17 (9.3).
De Pascalis, R., et al., Grafting of "Abbreviated" Complementarity-Determining Regions Containing Specificity-Determining Residues Essential for Ligand Contact to Engineer a Less Immunogenic Humanized Monoclonal Antibody, J Immunol 2002; 169:3076-3084.
Dechant, M. et al. Chimeric IgA antibodies against HLA class II effectively trigger lymphoma cell killing. Blood 100, 4574-4580 (2002).
Dechant, M. et al. Effector Mechanisms of Recombinant IgA Antibodies against Epidermal Growth Factor Receptor. J. Immunol. 179, 2936-2943 (2007).
Delacroix, D. L., Elkon, et al. Changes in size, subclass, and metabolic properties of serum immunoglobulin A in liver diseases and in other diseases with high serum immunoglobulin A. J. Clin. Invest. 71, 358-367 (1983).
Den Hartog, G, et al. "Specificity and Effector Functions of Human RSV-Specific IgG from Bovine Milk" PLoS One. Nov. 6, 2014;9(11):e112047 (3.5).
Deo, Y. M., et al., Bispecific molecules directed to the Fc receptor for IgA (Fc alpha RI, CD89) and tumor antigens efficiently promote cell-mediated cytotoxicity of tumor targets in whole blood. J. Immunol. 160, 1677-86 (1998).
Derbyshire, et al., A simple and efficient procedure for saturation mutagenesis using mixed oligodeoxynucleotides. Gene. 1986;46(2-3):145-52. doi: 10.1016/0378-1119(86)90398-7. PMID: 3803923.
Dickinson, B. L. et al. Bidirectional FcRn-dependent IgG transport in a polarized human intestinal epithelial cell line. J. Clin. Invest. 104, 903-911 (1999).
Dooley, H. et al. Antibody repertoire development in cartilaginous fish. Dev Comp Immunol. 2006;30(1-2):43-56. doi: 10.1016/j.dci. 2005.06.022. PMID: 16146649.
Edge, A.S., et al. Deglycosylation of glycoproteins by trifluoromethanesulfonic acid. Anal Biochem. Nov. 15, 1981;118(1):131-7. doi: 10.1016/0003-2697(81)90168-8. PMID: 6175244.
Ehring, Hanno, Hydrogen Exchange/Electrospray Ionization Mass Spectrometry Studies of Structural Features of Proteins and Protein/Protein Interactions, Analytical Biochemistry, vol. 267, Issue 2, 1999, pp. 252-259, ISSN 0003-2697, https://doi.org/10.1006/abio. 1998.3000.
Eijkelkamp et al., GRK2: A Novel Cell-Specific Regulator of Severity andDuration of Inflammatory Pain, J. Neuroscience, Feb. 20, 2010, pp. 2138-2149.
Eijkelkamp, et al., "IL4-10 Fusion Protein is a Novel Drug to Treat Persistent Inflammatory Pain" The Journal of Neuroscience, Jul. 13, 2016; 36(28):7353-7363.
Endo, Y, et al., High-throughput, genome-scale protein production method based on the wheat germ cell-free expression system. Biotechnol Adv. Nov. 2003;21(8):695-713. doi: 10.1016/s0734-9750(03)00105-8. PMID: 14563476.
Engen, J.R., & Smith, D.L., Peer Reviewed: Investigating Protein Structure and Dynamics by Hydrogen Exchange MS Anal. Chem. (2001) 73:256A-265A.
Evers M, et al, "Novel chimerized IgA CD20 antibodies: Improving neutrophil activation against CD20-positive malignancies" MAbs. Jan. 2020-Dec.;12(1):1795505. doi: 10.1080/19420862.2020. 1795505. PMID: 32744145 (4.6).

(56) References Cited

OTHER PUBLICATIONS

Evers M, et al. "Type I CD20 Antibodies Recruit the B Cell Receptor for Complement-Dependent Lysis of Malignant B Cells". J Immunol. Apr. 15, 2018;200(8):2515-2516. (5.6).

* cited by examiner

>tr|A0A0G2JMB2|A0A0G2JMB2_HUMAN Immunoglobulin heavy
constant alpha 2 (Fragment) OS=Homo sapiens OX=9606
GN=IGHA2 PE=1 SV=1

ASPTSPKVFPLSLDSTPQDGNVVVACLVQGFFPQEPLSVTWSESGQNVTARNFPPSQ
DASGDLYTTSSQLTLPATQCPDGKSVTCHVKHYTNPSQDVTVPCPVPPPCCHPRL
SLHRPALEDLLLGSEANLTCTLTGLRDASGATFTWTPSSGKSAVQGPPERDLCGCYS
VSSVLPGCAQPWNHGETFTCTAAHPELKTPLTANITKSGNTFRPEVHLLPPPSEELA
LNELVTLTCLARGFSPKDVLVRWLQGSQELPREKYLTWASRQEPSQGTTTFAVTSIL
RVAAEDWKKGDTFSCMVGHEALPLAFTQKTIDRLAGK<u>PTHVNVSVVMAEVDGTCY</u>

SEQ ID NO: 1

FIG. 1

>sp|P01877|IGHA2_HUMAN Immunoglobulin heavy constant alpha 2 OS=Homo sapiens OX=9606 GN=IGHA2 PE=1 SV=4

ASPTSPKVFPLSLDSTPQDGNVVVACLVQGFFPQEPLSVTWSESGQNVTARNF
PPSQDASGDLYTTSSQLTLPATQCPDGKSVTCHVKHYTNSSQDVTVPCRVPPP
PPCCHPRLSLHRPALEDLLLGSEANLTCTLTGLRDASGATFTWTPSSGKSAVQ
GPPERDLCGCYSVSSVLPGCAQPWNHGETFTCTAAHPELKTPLTANITKSGNT
FRPEVHLLPPPSEELALNELVLTCLARGFSPKDVLVRWLQGSQELPREKYLT
WASRQEPSQGTTTYAVTSILRVAAEDWKKGETFSCMVGHEALPLAFTQKTIDR
MAGKPTHINVSVVMAEADGTCY

SEQ ID NO: 2

FIG. 2

>tr|A0A286YEY5|A0A286YEY5_HUMAN Immunoglobulin heavy constant alpha 2 (Fragment) OS=Homo sapiens OX=9606 GN=IGHA2 PE=1 SV=1

ASPTSPKVFPLSLDSTPQDGNVVVACLVQGFFPQEPLSVTWSESGQNVTARNFPPSQDASG
DLYTTSSQLTLPATQCPDGKSVTCHVKHYTNSSQDVTVPCRVPPPPCCHPRLSLHRPALE
DLLLGSEANLTCTLTGLRDASGATFTWTPSSGKSAVQGPPERDLCGCYSSSVLPGCAQPW
NHGETFTCTAAHPELKTPLTANITKSGNTFRPEVHLLPPSEELALNELVTLTCLARGFSP
KDVLVRWLQGSQELPREKYLTWASRQEPSQGTTTYAVTSILRVAAEDWKKGETFSCMVGHE
ALPLAFTQKTIDRMAGSCCVADWQMPPPYVVLDLPQETLEEETPGANLWPTTITFLTLFLL
SLFYSTALTVTSVRGPSGKREGPQY

SEQ ID NO: 3

FIG. 3

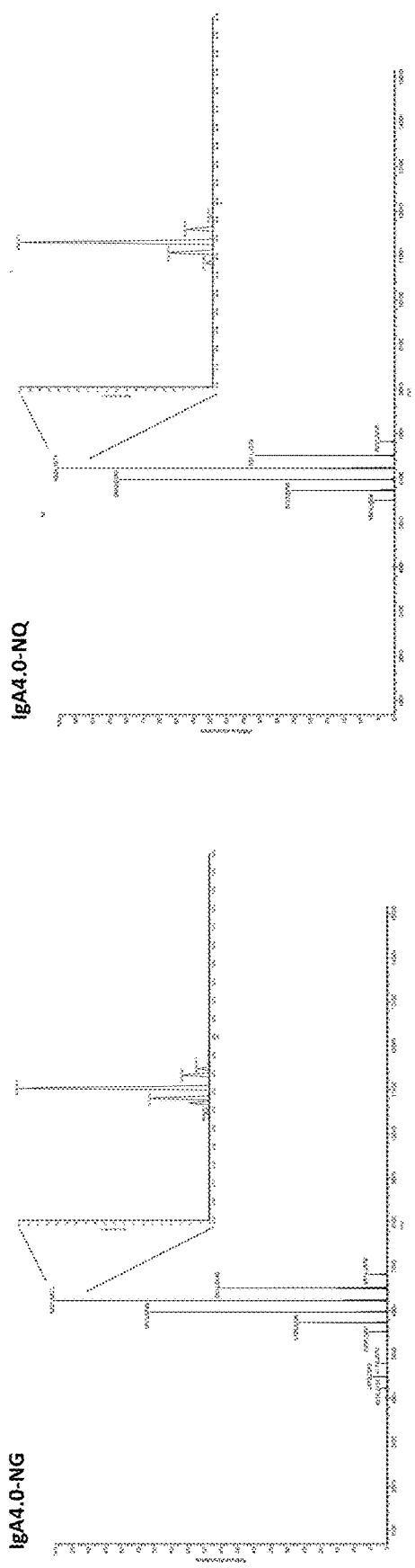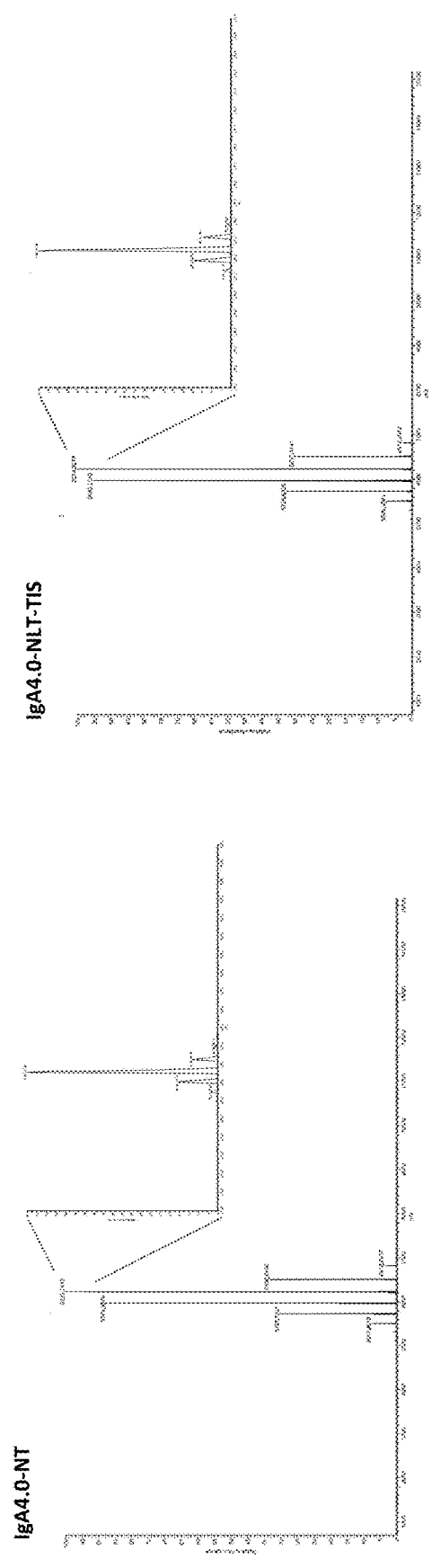
FIG. 19D  FIG. 19E  FIG. 19F  FIG. 19G

SEQUENCE LISTING

```
<160> NUMBER OF SEQ ID NOS: 123

<210> SEQ ID NO 1
<211> LENGTH: 340
<212> TYPE: PRT
<213> ORGANISM: Artificial Sequence
<220> FEATURE:
<223> OTHER INFORMATION: IgA2m1

<400> SEQUENCE: 1

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
        275                 280                 285

Ala Glu Asp Trp Lys Lys Gly Asp Thr Phe Ser Cys Met Val Gly His
    290                 295                 300

Glu Ala Leu Pro Leu Ala Phe Thr Gln Lys Thr Ile Asp Arg Leu Ala
```

```
                305                 310                 315                 320
Gly Lys Pro Thr His Val Asn Val Ser Val Val Met Ala Glu Val Asp
                    325                 330                 335
Gly Thr Cys Tyr
            340

<210> SEQ ID NO 2
<211> LENGTH: 340
<212> TYPE: PRT
<213> ORGANISM: Artificial Sequence
<220> FEATURE:
<223> OTHER INFORMATION: IgA2m2

<400> SEQUENCE: 2

Ala Ser Pro Thr Ser Pro Lys Val Phe Pro Leu Ser Leu Asp Ser Thr
1               5                   10                  15

Pro Gln Asp Gly Asn Val Val Ala Cys Leu Val Gln Gly Phe Phe
            20                  25                  30

Pro Gln Glu Pro Leu Ser Val Thr Trp Ser Glu Ser Gly Gln Asn Val
            35                  40                  45

Thr Ala Arg Asn Phe Pro Pro Ser Gln Asp Ala Ser Gly Asp Leu Tyr
50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Ser Ser Gln Asp
                85                  90                  95

Val Thr Val Pro Cys Arg Val Pro Pro Pro Pro Cys Cys His Pro
                100                 105                 110

Arg Leu Ser Leu His Arg Pro Ala Leu Glu Asp Leu Leu Leu Gly Ser
            115                 120                 125

Glu Ala Asn Leu Thr Cys Thr Leu Thr Gly Leu Arg Asp Ala Ser Gly
            130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
            195                 200                 205

Ser Gly Asn Thr Phe Arg Pro Glu Val His Leu Leu Pro Pro Pro Ser
210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Tyr Ala Val Thr Ser Ile Leu Arg Val Ala
            275                 280                 285

Ala Glu Asp Trp Lys Lys Gly Glu Thr Phe Ser Cys Met Val Gly His
            290                 295                 300

Glu Ala Leu Pro Leu Ala Phe Thr Gln Lys Thr Ile Asp Arg Met Ala
305                 310                 315                 320

Gly Lys Pro Thr His Ile Asn Val Ser Val Val Met Ala Glu Ala Asp
```

Gly Thr Cys Tyr
            340

<210> SEQ ID NO 3
<211> LENGTH: 391
<212> TYPE: PRT
<213> ORGANISM: Artificial Sequence
<220> FEATURE:
<223> OTHER INFORMATION: IgA2_A0A286YEY5

<400> SEQUENCE: 3

Ala Ser Pro Thr Ser Pro Lys Val Phe Pro Leu Ser Leu Asp Ser Thr
1               5                   10                  15

Pro Gln Asp Gly Asn Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Ser Ser Gln Asp
                85                  90                  95

Val Thr Val Pro Cys Arg Val Pro Pro Pro Pro Cys Cys His Pro
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Tyr Ala Val Thr Ser Ile Leu Arg Val Ala
        275                 280                 285

Ala Glu Asp Trp Lys Lys Gly Glu Thr Phe Ser Cys Met Val Gly His
    290                 295                 300

Glu Ala Leu Pro Leu Ala Phe Thr Gln Lys Thr Ile Asp Arg Met Ala
305                 310                 315                 320

Gly Ser Cys Cys Val Ala Asp Trp Gln Met Pro Pro Pro Tyr Val Val
                325                 330                 335

Leu Asp Leu Pro Gln Glu Thr Leu Glu Glu Glu Thr Pro Gly Ala Asn

```
                340                 345                 350
Leu Trp Pro Thr Thr Ile Thr Phe Leu Thr Leu Phe Leu Leu Ser Leu
            355                 360                 365

Phe Tyr Ser Thr Ala Leu Thr Val Thr Ser Val Arg Gly Pro Ser Gly
            370                 375                 380

Lys Arg Glu Gly Pro Gln Tyr
385                 390

<210> SEQ ID NO 4
<211> LENGTH: 113
<212> TYPE: PRT
<213> ORGANISM: Artificial Sequence
<220> FEATURE:
<223> OTHER INFORMATION: Dinutuximab (also called Ch14.18 or Unituxin)

<400> SEQUENCE: 4

Glu Val Gln Leu Leu Gln Ser Gly Pro Glu Leu Glu Lys Pro Gly Ala
1               5                   10                  15

Ser Val Met Ile Ser Cys Lys Ala Ser Gly Ser Ser Phe Thr Gly Tyr
            20                  25                  30

Asn Met Asn Trp Val Arg Gln Asn Ile Gly Lys Ser Leu Glu Trp Ile
        35                  40                  45

Gly Ala Ile Asp Pro Tyr Tyr Gly Gly Thr Ser Tyr Asn Gln Lys Phe
    50                  55                  60

Lys Gly Arg Ala Thr Leu Thr Val Asp Lys Ser Ser Ser Thr Ala Tyr
65                  70                  75                  80

Met His Leu Lys Ser Leu Thr Ser Glu Asp Ser Ala Val Tyr Tyr Cys
                85                  90                  95

Val Ser Gly Met Glu Tyr Trp Gly Gln Gly Thr Ser Val Thr Val Ser
            100                 105                 110

Ser

<210> SEQ ID NO 5
<211> LENGTH: 113
<212> TYPE: PRT
<213> ORGANISM: Artificial Sequence
<220> FEATURE:
<223> OTHER INFORMATION: Dinutuximab (also called Ch14.18 or Unituxin)

<400> SEQUENCE: 5

Glu Ile Val Met Thr Gln Ser Pro Ala Thr Leu Ser Val Ser Pro Gly
1               5                   10                  15

Glu Arg Ala Thr Leu Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Leu Thr Phe Gly Ala Gly Thr Lys Leu Glu Leu
            100                 105                 110

Lys

<210> SEQ ID NO 6
```

```
<211> LENGTH: 21
<212> TYPE: PRT
<213> ORGANISM: Artificial Sequence
<220> FEATURE:
<223> OTHER INFORMATION: CD20 epitope

<400> SEQUENCE: 6

Tyr Asn Cys Glu Pro Ala Asn Pro Ser Glu Lys Asn Ser Pro Ser Thr
1               5                   10                  15

Gln Tyr Cys Tyr Ser
            20

<210> SEQ ID NO 7
<211> LENGTH: 122
<212> TYPE: PRT
<213> ORGANISM: Artificial Sequence
<220> FEATURE:
<223> OTHER INFORMATION: UMAB10

<400> SEQUENCE: 7

Gln Ala Tyr Leu Gln Gln Ser Gly Ala Asp Leu Val Arg Pro Gly Ala
1               5                   10                  15

Ser Val Lys Met Ser Cys Lys Ala Ser Gly Phe Thr Phe Pro Ser Tyr
            20                  25                  30

Asn Leu His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ser Ala Tyr Tyr Gly Ser Asn Val Trp Phe Phe Asp Val Trp
            100                 105                 110

Gly Thr Gly Thr Thr Val Thr Val Ser Ser
        115                 120

<210> SEQ ID NO 8
<211> LENGTH: 106
<212> TYPE: PRT
<213> ORGANISM: Artificial Sequence
<220> FEATURE:
<223> OTHER INFORMATION: UMAB10

<400> SEQUENCE: 8

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

Asp Trp Tyr Gln Gln Lys Pro Gly Ser Ser Pro Lys Pro Trp Ile Tyr
        35                  40                  45

Ala Thr Ser Asn Leu Ala Ser Gly Val Pro Thr Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ile Ser Asn Pro Pro Thr
                85                  90                  95

Phe Gly Ala Gly Thr Lys Leu Asp Leu Lys
            100                 105
```

```
<210> SEQ ID NO 9
<211> LENGTH: 18
<212> TYPE: PRT
<213> ORGANISM: Artificial Sequence
<220> FEATURE:
<223> OTHER INFORMATION: tail piece

<400> SEQUENCE: 9

Pro Thr His Ile Asn Val Ser Val Val Met Ala Glu Ala Asp Gly Thr
1               5                   10                  15

Cys Tyr

<210> SEQ ID NO 10
<211> LENGTH: 8
<212> TYPE: PRT
<213> ORGANISM: Artificial Sequence
<220> FEATURE:
<223> OTHER INFORMATION: CDR1

<400> SEQUENCE: 10

Glu Phe Thr Phe Thr Asp Tyr Tyr
1               5

<210> SEQ ID NO 11
<211> LENGTH: 10
<212> TYPE: PRT
<213> ORGANISM: Artificial Sequence
<220> FEATURE:
<223> OTHER INFORMATION: CDR2

<400> SEQUENCE: 11

Ile Arg Asn Arg Ala Asn Gly Tyr Thr Thr
1               5                   10

<210> SEQ ID NO 12
<211> LENGTH: 10
<212> TYPE: PRT
<213> ORGANISM: Artificial Sequence
<220> FEATURE:
<223> OTHER INFORMATION: CDR3

<400> SEQUENCE: 12

Ala Arg Val Ser Asn Trp Ala Phe Asp Tyr
1               5                   10

<210> SEQ ID NO 13
<211> LENGTH: 12
<212> TYPE: PRT
<213> ORGANISM: Artificial Sequence
<220> FEATURE:
<223> OTHER INFORMATION: CDR1

<400> SEQUENCE: 13

Gln Ser Leu Leu Lys Asn Asn Gly Asn Thr Phe Leu
1               5                   10

<210> SEQ ID NO 14
<211> LENGTH: 3
<212> TYPE: PRT
<213> ORGANISM: Artificial Sequence
<220> FEATURE:
<223> OTHER INFORMATION: CDR2

<400> SEQUENCE: 14

Lys Val Ser
1
```

<210> SEQ ID NO 15
<211> LENGTH: 9
<212> TYPE: PRT
<213> ORGANISM: Artificial Sequence
<220> FEATURE:
<223> OTHER INFORMATION: CDR3

<400> SEQUENCE: 15

Ser Gln Ser Thr His Ile Pro Tyr Thr
1               5

<210> SEQ ID NO 16
<211> LENGTH: 338
<212> TYPE: PRT
<213> ORGANISM: Artificial Sequence
<220> FEATURE:
<223> OTHER INFORMATION: IgA3.0+

<400> SEQUENCE: 16

Ala Ser Pro Thr Ser Pro Lys Val Phe Pro Leu Ser Leu Asp Ser Thr
1               5                   10                  15

Pro Gln Asp Gly Asn Val Val Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Arg Val Pro Pro Pro Pro Cys Cys His Pro
            100                 105                 110

Arg Leu Ser Leu His Arg Pro Ala Leu Glu Asp Leu Leu Leu Gly Ser
            115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Ser Ala Gln Pro Trp Asn His Gly Glu Thr Phe Thr Cys Thr
            180                 185                 190

Ala Ala His Pro Glu Leu Lys Thr Pro Leu Thr Ala Thr Leu Ser Lys
            195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
            275                 280                 285

Ala Glu Asp Trp Lys Lys Gly Asp Thr Phe Ser Cys Met Val Gly His

```
                290                 295                 300

Glu Ala Leu Pro Leu Ala Phe Thr Gln Lys Thr Ile Asp Arg Leu Ala
305                 310                 315                 320

Gly Lys Pro Thr His Val Gln Val Ser Val Val Met Ala Glu Val Asp
                325                 330                 335

Gly Thr

<210> SEQ ID NO 17
<211> LENGTH: 322
<212> TYPE: PRT
<213> ORGANISM: Artificial Sequence
<220> FEATURE:
<223> OTHER INFORMATION: IgA3.0min

<400> SEQUENCE: 17

Ala Ser Pro Thr Ser Pro Lys Val Phe Pro Leu Ser Leu Asp Ser Thr
1               5                   10                  15

Pro Gln Asp Gly Asn Val Val Ala Cys Leu Val Gln Gly Phe Phe
                20                  25                  30

Pro Gln Glu Pro Leu Ser Val Thr Trp Ser Glu Ser Gly Gln Gly Val
                35                  40                  45

Thr Ala Arg Asn Phe Pro Pro Ser Gln Asp Ala Ser Gly Asp Leu Tyr
50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Arg Val Pro Pro Pro Pro Cys Cys His Pro
                100                 105                 110

Arg Leu Ser Leu His Arg Pro Ala Leu Glu Asp Leu Leu Leu Gly Ser
                115                 120                 125

Glu Ala Asn Leu Thr Cys Thr Leu Thr Gly Leu Arg Asp Ala Ser Gly
130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Ser Ala Gln Pro Trp Asn His Gly Glu Thr Phe Thr Cys Thr
                180                 185                 190

Ala Ala His Pro Glu Leu Lys Thr Pro Leu Thr Ala Thr Leu Ser Lys
                195                 200                 205

Ser Gly Asn Thr Phe Arg Pro Glu Val His Leu Leu Pro Pro Pro Ser
210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
                260                 265                 270

Ser Gln Gly Thr Thr Thr Phe Ala Val Thr Ser Ile Leu Arg Val Ala
                275                 280                 285

Ala Glu Asp Trp Lys Lys Gly Asp Thr Phe Ser Cys Met Val Gly His
                290                 295                 300

Glu Ala Leu Pro Leu Ala Phe Thr Gln Lys Thr Ile Asp Arg Leu Ala
305                 310                 315                 320
```

Gly Lys

```
<210> SEQ ID NO 18
<211> LENGTH: 322
<212> TYPE: PRT
<213> ORGANISM: Artificial Sequence
<220> FEATURE:
<223> OTHER INFORMATION: IgA4.0_NG

<400> SEQUENCE: 18
```

| | | | | | | | | | | | | | | | |
|---|---|---|---|---|---|---|---|---|---|---|---|---|---|---|---|
| Ala | Ser | Pro | Thr | Ser | Pro | Lys | Val | Phe | Pro | Leu | Ser | Leu | Asp | Ser | Thr |
| 1 | | | | 5 | | | | | 10 | | | | | 15 | |
| Pro | Gln | Asp | Gly | Asn | Val | Val | Ala | Cys | Leu | Val | Gln | Gly | Phe | Phe | |
| | | | 20 | | | | | 25 | | | | | 30 | | |
| Pro | Gln | Glu | Pro | Leu | Ser | Val | Thr | Trp | Ser | Glu | Ser | Gly | Gln | Gly | Val |
| | | | 35 | | | | | 40 | | | | | 45 | | |
| Thr | Ala | Arg | Asn | Phe | Pro | Pro | Ser | Gln | Asp | Ala | Ser | Gly | Asp | Leu | Tyr |
| | 50 | | | | | 55 | | | | | 60 | | | | |
| Thr | Thr | Ser | Ser | Gln | Leu | Thr | Leu | Pro | Ala | Thr | Gln | Cys | Pro | Asp | Gly |
| 65 | | | | | 70 | | | | | 75 | | | | | 80 |
| Lys | Ser | Val | Thr | Cys | His | Val | Lys | His | Tyr | Thr | Asn | Pro | Ser | Gln | Asp |
| | | | | 85 | | | | | 90 | | | | | 95 | |
| Val | Thr | Val | Pro | Cys | Arg | Val | Pro | Pro | Pro | Pro | Cys | Cys | His | Pro | |
| | | | 100 | | | | | 105 | | | | | 110 | | |
| Arg | Leu | Ser | Leu | His | Arg | Pro | Ala | Leu | Glu | Asp | Leu | Leu | Leu | Gly | Ser |
| | | | 115 | | | | | 120 | | | | | 125 | | |
| Glu | Ala | Gly | Leu | Thr | Cys | Thr | Leu | Thr | Gly | Leu | Arg | Asp | Ala | Ser | Gly |
| | 130 | | | | | 135 | | | | | 140 | | | | |
| Ala | Thr | Phe | Thr | Trp | Thr | Pro | Ser | Ser | Gly | Lys | Ser | Ala | Val | Gln | Gly |
| 145 | | | | | 150 | | | | | 155 | | | | | 160 |
| Pro | Pro | Glu | Arg | Asp | Leu | Cys | Gly | Cys | Tyr | Ser | Val | Ser | Ser | Val | Leu |
| | | | | 165 | | | | | 170 | | | | | 175 | |
| Pro | Gly | Ser | Ala | Gln | Pro | Trp | Asn | His | Gly | Glu | Thr | Phe | Thr | Cys | Thr |
| | | | 180 | | | | | 185 | | | | | 190 | | |
| Ala | Ala | His | Pro | Glu | Leu | Lys | Thr | Pro | Leu | Thr | Ala | Thr | Leu | Ser | Lys |
| | | | 195 | | | | | 200 | | | | | 205 | | |
| Ser | Gly | Asn | Thr | Phe | Arg | Pro | Glu | Val | His | Leu | Leu | Pro | Pro | Pro | Ser |
| | 210 | | | | | 215 | | | | | 220 | | | | |
| Glu | Glu | Leu | Ala | Leu | Asn | Glu | Leu | Val | Thr | Leu | Thr | Cys | Leu | Ala | Arg |
| 225 | | | | | 230 | | | | | 235 | | | | | 240 |
| Gly | Phe | Ser | Pro | Lys | Asp | Val | Leu | Val | Arg | Trp | Leu | Gln | Gly | Ser | Gln |
| | | | | 245 | | | | | 250 | | | | | 255 | |
| Glu | Leu | Pro | Arg | Glu | Lys | Tyr | Leu | Thr | Trp | Ala | Ser | Arg | Gln | Glu | Pro |
| | | | 260 | | | | | 265 | | | | | 270 | | |
| Ser | Gln | Gly | Thr | Thr | Thr | Phe | Ala | Val | Thr | Ser | Ile | Leu | Arg | Val | Ala |
| | | | 275 | | | | | 280 | | | | | 285 | | |
| Ala | Glu | Asp | Trp | Lys | Lys | Gly | Asp | Thr | Phe | Ser | Cys | Met | Val | Gly | His |
| | 290 | | | | | 295 | | | | | 300 | | | | |
| Glu | Ala | Leu | Pro | Leu | Ala | Phe | Thr | Gln | Lys | Thr | Ile | Asp | Arg | Leu | Ala |
| 305 | | | | | 310 | | | | | 315 | | | | | 320 |
| Gly | Lys | | | | | | | | | | | | | | |

```
<210> SEQ ID NO 19
<211> LENGTH: 322
<212> TYPE: PRT
```

```
<213> ORGANISM: Artificial Sequence
<220> FEATURE:
<223> OTHER INFORMATION: IgA4.0_NQ

<400> SEQUENCE: 19

Ala Ser Pro Thr Ser Pro Lys Val Phe Pro Leu Ser Leu Asp Ser Thr
1               5                   10                  15

Pro Gln Asp Gly Asn Val Val Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Arg Val Pro Pro Pro Pro Cys Cys His Pro
                100                 105                 110

Arg Leu Ser Leu His Arg Pro Ala Leu Glu Asp Leu Leu Leu Gly Ser
        115                 120                 125

Glu Ala Gln Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Ser Ala Gln Pro Trp Asn His Gly Glu Thr Phe Thr Cys Thr
            180                 185                 190

Ala Ala His Pro Glu Leu Lys Thr Pro Leu Thr Ala Thr Leu Ser Lys
        195                 200                 205

Ser Gly Asn Thr Phe Arg Pro Glu Val His Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
        275                 280                 285

Ala Glu Asp Trp Lys Lys Gly Asp Thr Phe Ser Cys Met Val Gly His
    290                 295                 300

Glu Ala Leu Pro Leu Ala Phe Thr Gln Lys Thr Ile Asp Arg Leu Ala
305                 310                 315                 320

Gly Lys

<210> SEQ ID NO 20
<211> LENGTH: 322
<212> TYPE: PRT
<213> ORGANISM: Artificial Sequence
<220> FEATURE:
<223> OTHER INFORMATION: IgA4.0_NT

<400> SEQUENCE: 20

Ala Ser Pro Thr Ser Pro Lys Val Phe Pro Leu Ser Leu Asp Ser Thr
```

```
                1               5                   10                  15
            Pro Gln Asp Gly Asn Val Val Ala Cys Leu Val Gln Gly Phe Phe
                            20                  25                  30
            Pro Gln Glu Pro Leu Ser Val Thr Trp Ser Glu Ser Gly Gln Gly Val
                            35                  40                  45
            Thr Ala Arg Asn Phe Pro Ser Gln Asp Ala Ser Gly Asp Leu Tyr
            50                          55                  60
            Thr Thr Ser Ser Gln Leu Thr Leu Pro Ala Thr Gln Cys Pro Asp Gly
            65                          70                  75                  80
            Lys Ser Val Thr Cys His Val Lys His Tyr Thr Asn Pro Ser Gln Asp
                                85                  90                  95
            Val Thr Val Pro Cys Arg Val Pro Pro Pro Pro Cys Cys His Pro
                            100                 105                 110
            Arg Leu Ser Leu His Arg Pro Ala Leu Glu Asp Leu Leu Leu Gly Ser
                            115                 120                 125
            Glu Ala Thr Leu Thr Cys Thr Leu Thr Gly Leu Arg Asp Ala Ser Gly
                    130                 135                 140
            Ala Thr Phe Thr Trp Thr Pro Ser Ser Gly Lys Ser Ala Val Gln Gly
            145                         150                 155                 160
            Pro Pro Glu Arg Asp Leu Cys Gly Cys Tyr Ser Val Ser Ser Val Leu
                                165                 170                 175
            Pro Gly Ser Ala Gln Pro Trp Asn His Gly Glu Thr Phe Thr Cys Thr
                            180                 185                 190
            Ala Ala His Pro Glu Leu Lys Thr Pro Leu Thr Ala Thr Leu Ser Lys
                            195                 200                 205
            Ser Gly Asn Thr Phe Arg Pro Glu Val His Leu Leu Pro Pro Pro Ser
                    210                 215                 220
            Glu Glu Leu Ala Leu Asn Glu Leu Val Thr Leu Thr Cys Leu Ala Arg
            225                         230                 235                 240
            Gly Phe Ser Pro Lys Asp Val Leu Val Arg Trp Leu Gln Gly Ser Gln
                                245                 250                 255
            Glu Leu Pro Arg Glu Lys Tyr Leu Thr Trp Ala Ser Arg Gln Glu Pro
                            260                 265                 270
            Ser Gln Gly Thr Thr Thr Phe Ala Val Thr Ser Ile Leu Arg Val Ala
                            275                 280                 285
            Ala Glu Asp Trp Lys Lys Gly Asp Thr Phe Ser Cys Met Val Gly His
                    290                 295                 300
            Glu Ala Leu Pro Leu Ala Phe Thr Gln Lys Thr Ile Asp Arg Leu Ala
            305                         310                 315                 320
            Gly Lys

<210> SEQ ID NO 21
<211> LENGTH: 322
<212> TYPE: PRT
<213> ORGANISM: Artificial Sequence
<220> FEATURE:
<223> OTHER INFORMATION: IgA4.0_NLT-TIS

<400> SEQUENCE: 21

Ala Ser Pro Thr Ser Pro Lys Val Phe Pro Leu Ser Leu Asp Ser Thr
            1               5                   10                  15
            Pro Gln Asp Gly Asn Val Val Ala Cys Leu Val Gln Gly Phe Phe
                            20                  25                  30
            Pro Gln Glu Pro Leu Ser Val Thr Trp Ser Glu Ser Gly Gln Gly Val
                            35                  40                  45
```

```
Thr Ala Arg Asn Phe Pro Pro Ser Gln Asp Ala Ser Gly Asp Leu Tyr
         50                  55                  60

Thr Thr Ser Ser Gln Leu Thr Leu Pro Ala Thr Gln Cys Pro Asp Gly
 65                  70                  75                  80

Lys Ser Val Thr Cys His Val Lys His Tyr Thr Asn Pro Ser Gln Asp
                 85                  90                  95

Val Thr Val Pro Cys Arg Val Pro Pro Pro Pro Cys Cys His Pro
             100                 105                 110

Arg Leu Ser Leu His Arg Pro Ala Leu Glu Asp Leu Leu Leu Gly Ser
             115                 120                 125

Glu Ala Thr Ile Ser Cys Thr Leu Thr Gly Leu Arg Asp Ala Ser Gly
         130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                 165                 170                 175

Pro Gly Ser Ala Gln Pro Trp Asn His Gly Glu Thr Phe Thr Cys Thr
             180                 185                 190

Ala Ala His Pro Glu Leu Lys Thr Pro Leu Thr Ala Thr Leu Ser Lys
             195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                 245                 250                 255

Glu Leu Pro Arg Glu Lys Tyr Leu Thr Trp Ala Ser Arg Gln Glu Pro
             260                 265                 270

Ser Gln Gly Thr Thr Thr Phe Ala Val Thr Ser Ile Leu Arg Val Ala
    275                 280                 285

Ala Glu Asp Trp Lys Lys Gly Asp Thr Phe Ser Cys Met Val Gly His
290                 295                 300

Glu Ala Leu Pro Leu Ala Phe Thr Gln Lys Thr Ile Asp Arg Leu Ala
305                 310                 315                 320

Gly Lys

<210> SEQ ID NO 22
<211> LENGTH: 1020
<212> TYPE: DNA
<213> ORGANISM: Artificial Sequence
<220> FEATURE:
<223> OTHER INFORMATION: IgA2m1

<400> SEQUENCE: 22
gccagcccca ccagccccaa ggtgttcccc ctgagcctgg acagcacccc ccaggacggc      60
aacgtggtgg tggcctgcct ggtgcagggc ttcttccccc aggagcccct gagcgtgacc     120
tggagcgaga gcggccagaa cgtgaccgcc aggaacttcc cccccagcca ggacgccagc     180
ggcgacctgt acaccaccag cagccagctg accctgcccg ccacccagtg ccccgacggc     240
aagagcgtga cctgccacgt gaagcactac accaacccca gccaggacgt gaccgtgccc     300
tgccccgtgc cccccccccc ccctgctgc cacccccagg ctgagcctgca caggcccgcc     360 ctggaggacc tgctgctggg cagcgaggcc aacctgacct gcaccctgac cggcctgagg     420
gacgccagcg gcgccacctt cacctggacc cccagcagcg gcaagagcgc cgtgcagggc     480
```

| | |
|---|---|
| cccccccgaga gggacctgtg cggctgctac agcgtgagca gcgtgctgcc cggctgcgcc | 540 |
| cagccctgga accacggcga gaccttcacc tgcaccgccg cccacccga gctgaagacc | 600 |
| cccctgaccg ccaacatcac caagagcggc aacaccttca ggcccgaggt gcacctgctg | 660 |
| cccccccca gcgaggagct ggccctgaac gagctggtga ccctgacctg cctggccagg | 720 |
| ggcttcagcc ccaaggacgt gctggtgagg tggctgcagg gcagccagga gctgcccagg | 780 |
| gagaagtacc tgacctgggc cagcaggcag gagcccagcc agggcaccac caccttcgcc | 840 |
| gtgaccagca tcctgagggt ggccgccgag gactggaaga agggcgacac cttcagctgc | 900 |
| atggtgggcc acgaggccct gccctggcc ttcacccaga gaccatcga caggctggcc | 960 |
| ggcaagccca cccacgtgaa cgtgagcgtg gtgatggccg aggtggacgg cacctgctac | 1020 |

<210> SEQ ID NO 23
<211> LENGTH: 1020
<212> TYPE: DNA
<213> ORGANISM: Artificial Sequence
<220> FEATURE:
<223> OTHER INFORMATION: IgA2m2

<400> SEQUENCE: 23

| | |
|---|---|
| gccagcccca ccagccccaa ggtgttcccc ctgagcctgg acagcacccc ccaggacggc | 60 |
| aacgtggtgg tggcctgcct ggtgcagggc ttcttccccc aggagcccct gagcgtgacc | 120 |
| tggagcgaga gcggccagaa cgtgaccgcc aggaacttcc cccccagcca ggacgccagc | 180 |
| ggcgacctgt acaccaccag cagccagctg accctgcccg ccacccagtg ccccgacggc | 240 |
| aagagcgtga cctgccacgt gaagcactac accaacagca gccaggacgt gaccgtgccc | 300 |
| tgcagggtgc ccccccccc cccctgctgc caccccaggc tgagcctgca caggcccgcc | 360 |
| ctggaggacc tgctgctggg cagcgaggcc aacctgacct gcaccctgac cggcctgagg | 420 |
| gacgccagcg gcgccacctt cacctggacc cccagcagcg gcaagagcgc cgtgcagggc | 480 |
| cccccccgaga gggacctgtg cggctgctac agcgtgagca gcgtgctgcc cggctgcgcc | 540 |
| cagccctgga accacggcga gaccttcacc tgcaccgccg cccacccga gctgaagacc | 600 |
| cccctgaccg ccaacatcac caagagcggc aacaccttca ggcccgaggt gcacctgctg | 660 |
| cccccccca gcgaggagct ggccctgaac gagctggtga ccctgacctg cctggccagg | 720 |
| ggcttcagcc ccaaggacgt gctggtgagg tggctgcagg gcagccagga gctgcccagg | 780 |
| gagaagtacc tgacctgggc cagcaggcag gagcccagcc agggcaccac cacctacgcc | 840 |
| gtgaccagca tcctgagggt ggccgccgag gactggaaga agggcgagac cttcagctgc | 900 |
| atggtgggcc acgaggccct gccctggcc ttcacccaga gaccatcga caggatggcc | 960 |
| ggcaagccca cccacatcaa cgtgagcgtg gtgatggccg aggccgacgg cacctgctac | 1020 |

<210> SEQ ID NO 24
<211> LENGTH: 1173
<212> TYPE: DNA
<213> ORGANISM: Artificial Sequence
<220> FEATURE:
<223> OTHER INFORMATION: IgA2_A0A286YEY5

<400> SEQUENCE: 24

| | |
|---|---|
| gccagcccca ccagccccaa ggtgttcccc ctgagcctgg acagcacccc ccaggacggc | 60 |
| aacgtggtgg tggcctgcct ggtgcagggc ttcttccccc aggagcccct gagcgtgacc | 120 |
| tggagcgaga gcggccagaa cgtgaccgcc aggaacttcc cccccagcca ggacgccagc | 180 |

```
ggcgacctgt acaccaccag cagccagctg accctgcccg ccacccagtg ccccgacggc      240
aagagcgtga cctgccacgt gaagcactac accaacagca gccaggacgt gaccgtgccc      300
tgcagggtgc ccccccccc ccctgctgc caccccaggc tgagcctgca caggcccgcc        360
ctggaggacc tgctgctggg cagcgaggcc aacctgacct gcaccctgac cggcctgagg      420
gacgccagcg cgccaccttt cacctggacc cccagcagcg caagagcgc cgtgcagggc      480 cccccccgaga gggacctgtg cggctgctac agcgtgagca gcgtgctgcc cggctgcgcc    540
cagccctgga accacggcga gaccttcacc tgcaccgccg cccaccccga gctgaagacc      600
cccctgaccg ccaacatcac caagagcggc aacaccttca ggcccgaggt gcacctgctg      660 cccccccccca gcgaggagct ggccctgaac gagctggtga ccctgacctg cctggccagg    720
ggcttcagcc ccaaggacgt gctggtgagg tggctgcagg gcagccagga gctgcccagg      780
gagaagtacc tgacctgggc cagcaggcag gagcccagcc agggcaccac cacctacgcc      840
gtgaccagca tcctgagggt ggccgccgag gactggaaga agggcgagac cttcagctgc      900
atggtgggcc acgaggccct gcccctggcc ttcacccaga gaccatcga caggatggc       960 ggcagctgct gcgtggccga ctggcagatg cccccccct acgtggtgct ggacctgccc      1020
caggagaccc tggaggagga ccccccggc gccaacctgt ggcccaccac catcaccttc      1080
ctgaccctgt tcctgctgag cctgttctac agcaccgccc tgaccgtgac cagcgtgagg    1140
ggccccagcg gcaagaggga gggcccccag tac                                  1173

<210> SEQ ID NO 25
<211> LENGTH: 1014
<212> TYPE: DNA
<213> ORGANISM: Artificial Sequence
<220> FEATURE:
<223> OTHER INFORMATION: IgA3.0+

<400> SEQUENCE: 25
gctagcccaa cctctcctaa ggtgttccct ctgagcctgg acagcacccc tcaggatgga       60
aatgtggtgg tggcctgtct ggtgcaggga ttcttcccac aagagcccct gtccgtgact      120
tggagcgaat ctggacaggg cgtgaccgcc agaaacttcc caccttctca ggacgccctct    180 ggcgacctgt acaccacctc ttctcagctg accctgcctg ccacacagtg ccctgatggc      240
aagtctgtga cctgccacgt gaagcactac accaatccta gccaggacgt gaccgtgcct      300
tgcagagttc ctcctcctcc accttgctgt caccctcggc tgtctctgca cagacccgct      360
ctggaagatc tgctgctggg ctctgaggcc aacctgacat gtaccctgac cggcctgaga      420
gatgcttctg cgccaccttt acctggaca ccttccagcg gaaagtccgc tgttcaggga       480
cctcctgaga gggacctgtg cggctgttac tctgtgtcta gtgtgctgcc tggcagcgcc      540
cagccttgga atcatggcga gacattcacc tgtaccgctg ctcaccccga gctgaaaacc      600
cctctgaccg ccacactgtc caagtccggc aacaccttcc ggcctgaagt gcatctgctg      660
cctccaccta gcgaggaact ggccctgaat gagctggtca ccctgacctg tctggccagg      720
ggctttagcc ctaaggacgt gctcgttaga tggctgcagg gctcccaaga gctgcccaga      780
gagaagtatc tgacctgggc ctctcggcaa gagccatctc agggcaccac aacctttgcc      840
gtgaccagca tcctgagagt ggccgccgaa gattggaaga agggcgacac cttcagctgc      900
atggtcggac atgaagccct gcctctggct ttcacccaga aaaccatcga cagactggcc      960
ggcaagccca cccatgtcca gtgtctgtt gtcatggcgg aggtggacgg cacc            1014
```

```
<210> SEQ ID NO 26
<211> LENGTH: 966
<212> TYPE: DNA
<213> ORGANISM: Artificial Sequence
<220> FEATURE:
<223> OTHER INFORMATION: IgA3.0min

<400> SEQUENCE: 26
gctagcccaa cctctcctaa ggtgttccct ctgagcctgg acagcacccc tcaggatgga      60
aatgtggtgg tggcctgtct ggtgcaggga ttcttcccac aagagcccct gtccgtgact     120
tggagcgaat ctggacaggg cgtgaccgcc agaaacttcc caccttctca ggacgcctct     180
ggcgacctgt acaccacctc ttctcagctg accctgcctg ccacacagtg ccctgatggc     240
aagtctgtga cctgccacgt gaagcactac accaatccta gccaggacgt gaccgtgcct     300
tgcagagttc ctcctcctcc accttgctgt caccctcggc tgtctctgca cagacccgct     360
ctggaagatc tgctgctggg ctctgaggcc aacctgacat gtaccctgac cggcctgaga     420
gatgcttctg gcgccacctt tacctggaca ccttccagcg aaagtccgc tgttcaggga      480 cctcctgaga gggacctgtg cggctgttac tctgtgtcta gtgtgctgcc tggcagcgcc     540
cagccttgga atcatggcga gacattcacc tgtaccgctg ctcaccccga gctgaaaacc     600
cctctgaccg ccacactgtc caagtccggc aacaccttcc ggcctgaagt gcatctgctg     660
cctccaccta gcgaggaact ggccctgaat gagctggtca ccctgacctg tctggccagg     720
ggctttagcc ctaaggacgt gctcgttaga tggctgcagg gctcccaaga gctgcccaga     780
gagaagtatc tgacctgggc ctctcggcaa gagccatctc agggcaccac aacctttgcc     840
gtgaccagca tcctgagagt ggccgccgaa gattggaaga agggcgacac cttcagctgc     900
atggtcggac atgaagccct gcctctggct ttcacccaga aaccatcga cagactggcc      960 ggcaag                                                                966

<210> SEQ ID NO 27
<211> LENGTH: 966
<212> TYPE: DNA
<213> ORGANISM: Artificial Sequence
<220> FEATURE:
<223> OTHER INFORMATION: IgA4.0_NG

<400> SEQUENCE: 27
gctagcccaa cctctcctaa ggtgttccct ctgagcctgg acagcacccc tcaggatgga      60
aatgtggtgg tggcctgtct ggtgcaggga ttcttcccac aagagcccct gtccgtgact     120
tggagcgaat ctggacaggg cgtgaccgcc agaaacttcc caccttctca ggacgcctct     180
ggcgacctgt acaccacctc ttctcagctg accctgcctg ccacacagtg ccctgatggc     240
aagtctgtga cctgccacgt gaagcactac accaatccta gccaggacgt gaccgtgcct     300
tgcagagttc ctcctcctcc accttgctgt caccctcggc tgtctctgca cagacccgct     360
ctggaagatc tgctgctggg ctctgaggcc ggcctgacat gtaccctgac cggcctgaga     420
gatgcttctg gcgccacctt tacctggaca ccttccagcg aaagtccgc tgttcaggga      480 cctcctgaga gggacctgtg cggctgttac tctgtgtcta gtgtgctgcc tggcagcgcc     540
cagccttgga atcatggcga gacattcacc tgtaccgctg ctcaccccga gctgaaaacc     600
cctctgaccg ccacactgtc caagtccggc aacaccttcc ggcctgaagt gcatctgctg     660
cctccaccta gcgaggaact ggccctgaat gagctggtca ccctgacctg tctggccagg     720
ggctttagcc ctaaggacgt gctcgttaga tggctgcagg gctcccaaga gctgcccaga     780
```

```
gagaagtatc tgacctgggc ctctcggcaa gagccatctc agggcaccac aacctttgcc    840
gtgaccagca tcctgagagt ggccgccgaa gattggaaga agggcgacac cttcagctgc    900
atggtcggac atgaagccct gcctctggct ttcacccaga aaaccatcga cagactggcc    960
ggcaag                                                               966
```

<210> SEQ ID NO 28
<211> LENGTH: 966
<212> TYPE: DNA
<213> ORGANISM: Artificial Sequence
<220> FEATURE:
<223> OTHER INFORMATION: IgA4.0_NQ

<400> SEQUENCE: 28

```
gctagcccaa cctctcctaa ggtgttccct ctgagcctgg acagcacccc tcaggatgga     60
aatgtggtgg tggcctgtct ggtgcaggga ttcttcccac aagagcccct gtccgtgact    120
tggagcgaat ctggacaggg cgtgaccgcc agaaacttcc caccttctca ggacgcctct    180
ggcgacctgt acaccacctc ttctcagctg acctgcctg ccacacagtg ccctgatggc    240
aagtctgtga cctgccacgt gaagcactac accaatccta gccaggacgt gaccgtgcct    300
tgcagagttc ctcctcctcc accttgctgt caccctcggc tgtctctgca cagacccgct    360
ctggaagatc tgctgctggg ctctgaggcc cagctgacat gtaccctgac cggcctgaga    420
gatgcttctg cgccaccttt tacctggaca ccttccagcg aaagtccgc tgttcaggga    480 cctcctgaga gggacctgtg cggctgttac tctgtgtcta gtgtgctgcc tggcagcgcc    540
cagccttgga atcatggcga acattcacc tgtaccgctg ctcaccccga gctgaaaacc    600
cctctgaccg ccacactgtc caagtccggc aacaccttcc ggcctgaagt gcatctgctg    660
cctccaccta gcgaggaact ggccctgaat gagctggtca ccctgacctg tctggccagg    720
ggctttagcc ctaaggacgt gctcgttaga tggctgcagg ctcccaaga gctgcccaga    780 gagaagtatc tgacctgggc ctctcggcaa gagccatctc agggcaccac aacctttgcc    840
gtgaccagca tcctgagagt ggccgccgaa gattggaaga agggcgacac cttcagctgc    900
atggtcggac atgaagccct gcctctggct ttcacccaga aaaccatcga cagactggcc    960
ggcaag                                                               966
```

<210> SEQ ID NO 29
<211> LENGTH: 966
<212> TYPE: DNA
<213> ORGANISM: Artificial Sequence
<220> FEATURE:
<223> OTHER INFORMATION: IgA4.0_NT

<400> SEQUENCE: 29

```
gctagcccaa cctctcctaa ggtgttccct ctgagcctgg acagcacccc tcaggatgga     60
aatgtggtgg tggcctgtct ggtgcaggga ttcttcccac aagagcccct gtccgtgact    120
tggagcgaat ctggacaggg cgtgaccgcc agaaacttcc caccttctca ggacgcctct    180
ggcgacctgt acaccacctc ttctcagctg acctgcctg ccacacagtg ccctgatggc    240
aagtctgtga cctgccacgt gaagcactac accaatccta gccaggacgt gaccgtgcct    300
tgcagagttc ctcctcctcc accttgctgt caccctcggc tgtctctgca cagacccgct    360
ctggaagatc tgctgctggg ctctgaggcc accctgacat gtaccctgac cggcctgaga    420
gatgcttctg cgccaccttt tacctggaca ccttccagcg aaagtccgc tgttcaggga    480 cctcctgaga gggacctgtg cggctgttac tctgtgtcta gtgtgctgcc tggcagcgcc    540
```

```
cagccttgga atcatggcga cattcacc   tgtaccgctg ctcaccccga gctgaaaacc      600
cctctgaccg ccacactgtc caagtccggc aacaccttcc ggcctgaagt gcatctgctg      660
cctccaccta gcgaggaact ggccctgaat gagctggtca ccctgacctg tctggccagg      720
ggctttagcc ctaaggacgt gctcgttaga tggctgcagg gctcccaaga gctgccaga      780 gagaagtatc tgacctgggc ctctcggcaa gagccatctc agggcaccac aacctttgcc      840
gtgaccagca tcctgagagt ggccgccgaa gattggaaga agggcgacac cttcagctgc      900
atggtcggac atgaagccct gcctctggct ttcacccaga aaaccatcga cagactggcc      960
ggcaag                                                                  966

<210> SEQ ID NO 30
<211> LENGTH: 966
<212> TYPE: DNA
<213> ORGANISM: Artificial Sequence
<220> FEATURE:
<223> OTHER INFORMATION: IgA4.0_NLT-TIS

<400> SEQUENCE: 30
gctagcccaa cctctcctaa ggtgttccct ctgagcctgg acagcacccc tcaggatgga       60
aatgtggtgg tggcctgtct ggtgcaggga ttcttcccac aagagcccct gtccgtgact      120
tggagcgaat ctggacaggg cgtgaccgcc agaaacttcc caccttctca ggacgcctct      180
ggcgacctgt acaccacctc ttctcagctg accctgcctg ccacacagtg ccctgatggc      240
aagtctgtga cctgccacgt gaagcactac accaatccta gccaggacgt gaccgtgcct      300
tgcagagttc ctcctcctcc accttgctgt caccctcggc tgtctctgca cagacccgct      360
ctggaagatc tgctgctggg ctctgaggcc accatcagct gtaccctgac cggcctgaga      420
gatgcttctg gcgccacctt tacctggaca ccttccagcg gaaagtccgc tgttcaggga      480
cctcctgaga gggaccctgtg cggctgttac tctgtgtcta gtgtgctgcc tggcagcgcc      540
cagccttgga atcatggcga cattcacc   tgtaccgctg ctcaccccga gctgaaaacc      600
cctctgaccg ccacactgtc caagtccggc aacaccttcc ggcctgaagt gcatctgctg      660
cctccaccta gcgaggaact ggccctgaat gagctggtca ccctgacctg tctggccagg      720
ggctttagcc ctaaggacgt gctcgttaga tggctgcagg gctcccaaga gctgccaga      780 gagaagtatc tgacctgggc ctctcggcaa gagccatctc agggcaccac aacctttgcc      840
gtgaccagca tcctgagagt ggccgccgaa gattggaaga agggcgacac cttcagctgc      900
atggtcggac atgaagccct gcctctggct ttcacccaga aaaccatcga cagactggcc      960
ggcaag                                                                  966

<210> SEQ ID NO 31
<211> LENGTH: 107
<212> TYPE: PRT
<213> ORGANISM: Artificial Sequence
<220> FEATURE:
<223> OTHER INFORMATION: kappa light chain constant domain

<400> SEQUENCE: 31

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45
```

```
Ser Gly Asn Ser Gln Glu Ser Val Thr Glu Gln Asp Ser Lys Asp Ser
        50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105
```

```
<210> SEQ ID NO 32
<211> LENGTH: 321
<212> TYPE: DNA
<213> ORGANISM: Artificial Sequence
<220> FEATURE:
<223> OTHER INFORMATION: kappa light chain constant domain

<400> SEQUENCE: 32
cggacagtgg ccgctccttc cgtgttcatc ttcccacctt ccgacgagca gctgaagtcc      60
ggcacagcta gcgtggtctg cctgctgaac aacttctacc ctcgggaagc caaggtgcag     120
tggaaggtgg acaatgccct gcagtccggc aactcccaag agtctgtgac cgagcaggac     180
tccaaggaca gcacctacag cctgtcctcc acactgaccc tgtccaaggc cgactacgag     240
aagcacaagg tgtacgcctg cgaagtgacc catcagggcc tgtctagccc tgtgaccaag     300
tctttcaacc ggggcgagtg t                                               321
```

```
<210> SEQ ID NO 33
<211> LENGTH: 10
<212> TYPE: PRT
<213> ORGANISM: Artificial Sequence
<220> FEATURE:
<223> OTHER INFORMATION: CDR1 Obinutuzumab

<400> SEQUENCE: 33

Gly Tyr Ala Phe Ser Tyr Ser Trp Ile Asn
1               5                   10
```

```
<210> SEQ ID NO 34
<211> LENGTH: 10
<212> TYPE: PRT
<213> ORGANISM: Artificial Sequence
<220> FEATURE:
<223> OTHER INFORMATION: CDR1 Dinutuximab (also called Ch14.18 or
      Unituxin)

<400> SEQUENCE: 34

Gly Ser Ser Phe Thr Gly Tyr Asn Met Asn
1               5                   10
```

```
<210> SEQ ID NO 35
<211> LENGTH: 10
<212> TYPE: PRT
<213> ORGANISM: Artificial Sequence
<220> FEATURE:
<223> OTHER INFORMATION: CDR1 Trastuzumab

<400> SEQUENCE: 35

Gly Phe Asn Ile Lys Asp Thr Tyr Ile His
1               5                   10
```

```
<210> SEQ ID NO 36
<211> LENGTH: 10
<212> TYPE: PRT
```

```
<213> ORGANISM: Artificial Sequence
<220> FEATURE:
<223> OTHER INFORMATION: CDR1 TA99

<400> SEQUENCE: 36

Gly Phe Asn Ile Lys Asp Tyr Phe Leu His
1               5                   10

<210> SEQ ID NO 37
<211> LENGTH: 11
<212> TYPE: PRT
<213> ORGANISM: Artificial Sequence
<220> FEATURE:
<223> OTHER INFORMATION: CDR1

<400> SEQUENCE: 37

Gly Tyr Ser Ile Thr Ser Gly Tyr Gly Trp Asn
1               5                   10

<210> SEQ ID NO 38
<211> LENGTH: 12
<212> TYPE: PRT
<213> ORGANISM: Artificial Sequence
<220> FEATURE:
<223> OTHER INFORMATION: CDR1 2.3D11

<400> SEQUENCE: 38

Ser Gly Val Ser Ile Arg Ser Ile Asn Trp Trp Asn
1               5                   10

<210> SEQ ID NO 39
<211> LENGTH: 11
<212> TYPE: PRT
<213> ORGANISM: Artificial Sequence
<220> FEATURE:
<223> OTHER INFORMATION: CDR1 C47A8-CQ

<400> SEQUENCE: 39

Ser Gly Tyr Thr Phe Thr Ser Tyr Tyr Met His
1               5                   10

<210> SEQ ID NO 40
<211> LENGTH: 10
<212> TYPE: PRT
<213> ORGANISM: Artificial Sequence
<220> FEATURE:
<223> OTHER INFORMATION: CDR1 UMAB10

<400> SEQUENCE: 40

Gly Phe Thr Phe Pro Ser Tyr Asn Leu His
1               5                   10

<210> SEQ ID NO 41
<211> LENGTH: 17
<212> TYPE: PRT
<213> ORGANISM: Artificial Sequence
<220> FEATURE:
<223> OTHER INFORMATION: CDR2 Obinutuzumab

<400> SEQUENCE: 41

Arg Ile Phe Pro Gly Asp Gly Asp Thr Asp Tyr Asn Gly Lys Phe Lys
1               5                   10                  15

Gly

<210> SEQ ID NO 42
<211> LENGTH: 17
```

```
<212> TYPE: PRT
<213> ORGANISM: Artificial Sequence
<220> FEATURE:
<223> OTHER INFORMATION: CDR2 Dinutuximab (also called Ch14.18 or
      Unituxin)

<400> SEQUENCE: 42

Ala Ile Asp Pro Tyr Tyr Gly Gly Thr Ser Tyr Asn Gln Lys Phe Lys
1               5                   10                  15

Gly

<210> SEQ ID NO 43
<211> LENGTH: 17
<212> TYPE: PRT
<213> ORGANISM: Artificial Sequence
<220> FEATURE:
<223> OTHER INFORMATION: CDR2 Trastuzumab

<400> SEQUENCE: 43

Arg Ile Tyr Pro Thr Asn Gly Tyr Thr Arg Tyr Ala Asp Ser Val Lys
1               5                   10                  15

Gly

<210> SEQ ID NO 44
<211> LENGTH: 17
<212> TYPE: PRT
<213> ORGANISM: Artificial Sequence
<220> FEATURE:
<223> OTHER INFORMATION: CDR2 TA99

<400> SEQUENCE: 44

Trp Ile Asn Pro Asp Asn Gly Asn Thr Val Tyr Asp Pro Lys Phe Gln
1               5                   10                  15

Gly

<210> SEQ ID NO 45
<211> LENGTH: 16
<212> TYPE: PRT
<213> ORGANISM: Artificial Sequence
<220> FEATURE:
<223> OTHER INFORMATION: CDR2

<400> SEQUENCE: 45

Phe Ile Tyr Tyr Glu Gly Ser Thr Tyr Tyr Asn Pro Ser Ile Lys Ser
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: CDR2 2.3D11

<400> SEQUENCE: 46

Glu Ile Tyr His Ser Gly Ser Thr Asn Tyr Asn Pro Ser Leu Lys Ser
1               5                   10                  15

<210> SEQ ID NO 47
<211> LENGTH: 17
<212> TYPE: PRT
<213> ORGANISM: Artificial Sequence
<220> FEATURE:
<223> OTHER INFORMATION: CDR2 C47A8-CQ

<400> SEQUENCE: 47
```

Ile Ile Asn Pro Ser Gly Gly Ser Thr Ser Tyr Ala Gln Lys Phe Gln
1               5                   10                  15
Gly

<210> SEQ ID NO 48
<211> LENGTH: 17
<212> TYPE: PRT
<213> ORGANISM: Artificial Sequence
<220> FEATURE:
<223> OTHER INFORMATION: CDR2 UMAB10

<400> SEQUENCE: 48

Ala Ile Tyr Pro Gly Asn Gly Asp Thr Ser Tyr Asn Gln Lys Phe Lys
1               5                   10                  15
Gly

<210> SEQ ID NO 49
<211> LENGTH: 10
<212> TYPE: PRT
<213> ORGANISM: Artificial Sequence
<220> FEATURE:
<223> OTHER INFORMATION: CDR3 Obinutuzumab

<400> SEQUENCE: 49

Asn Val Phe Asp Gly Tyr Trp Leu Val Tyr
1               5                   10

<210> SEQ ID NO 50
<211> LENGTH: 4
<212> TYPE: PRT
<213> ORGANISM: Artificial Sequence
<220> FEATURE:
<223> OTHER INFORMATION: CDR3 Dinutuximab (also called Ch14.18 or
      Unituxin)

<400> SEQUENCE: 50

Gly Met Glu Tyr
1

<210> SEQ ID NO 51
<211> LENGTH: 11
<212> TYPE: PRT
<213> ORGANISM: Artificial Sequence
<220> FEATURE:
<223> OTHER INFORMATION: CDR3 Trastuzumab

<400> SEQUENCE: 51

Trp Gly Gly Asp Gly Phe Tyr Ala Met Asp Tyr
1               5                   10

<210> SEQ ID NO 52
<211> LENGTH: 12
<212> TYPE: PRT
<213> ORGANISM: Artificial Sequence
<220> FEATURE:
<223> OTHER INFORMATION: CDR3 TA99

<400> SEQUENCE: 52

Arg Asp Tyr Thr Tyr Glu Lys Ala Ala Leu Asp Tyr
1               5                   10

<210> SEQ ID NO 53
<211> LENGTH: 7
<212> TYPE: PRT
<213> ORGANISM: Artificial Sequence
<220> FEATURE:

```
<223> OTHER INFORMATION: CDR3

<400> SEQUENCE: 53

Gln Thr Gly Tyr Phe Asp Tyr
1               5

<210> SEQ ID NO 54
<211> LENGTH: 16
<212> TYPE: PRT
<213> ORGANISM: Artificial Sequence
<220> FEATURE:
<223> OTHER INFORMATION: CDR3 2.3D11

<400> SEQUENCE: 54

Asp Gly Gly Ile Ala Val Thr Asp Tyr Tyr Tyr Gly Leu Asp Val
1               5                   10                  15

<210> SEQ ID NO 55
<211> LENGTH: 10
<212> TYPE: PRT
<213> ORGANISM: Artificial Sequence
<220> FEATURE:
<223> OTHER INFORMATION: CDR3 C47A8-CQ

<400> SEQUENCE: 55

Ser Thr Leu Trp Phe Ser Glu Phe Asp Tyr
1               5                   10

<210> SEQ ID NO 56
<211> LENGTH: 13
<212> TYPE: PRT
<213> ORGANISM: Artificial Sequence
<220> FEATURE:
<223> OTHER INFORMATION: CDR3 UMAB10

<400> SEQUENCE: 56

Ser Ala Tyr Tyr Gly Ser Asn Val Trp Phe Phe Asp Val
1               5                   10

<210> SEQ ID NO 57
<211> LENGTH: 16
<212> TYPE: PRT
<213> ORGANISM: Artificial Sequence
<220> FEATURE:
<223> OTHER INFORMATION: LC CDR1 Obinutuzumab

<400> SEQUENCE: 57

Arg Ser Ser Lys Ser Leu Leu His Ser Asn Gly Ile Thr Tyr Leu Tyr
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: LC CDR1 Dinutuximab (also called Ch14.18 or
      Unituxin)

<400> SEQUENCE: 58

Arg Ser Ser Gln Ser Leu Val His Arg Asn Gly Asn Thr Tyr Leu His
1               5                   10                  15

<210> SEQ ID NO 59
<211> LENGTH: 11
<212> TYPE: PRT
<213> ORGANISM: Artificial Sequence
<220> FEATURE:
```

<223> OTHER INFORMATION: LC CDR1 Trastuzumab

<400> SEQUENCE: 59

Arg Ala Ser Gln Asp Val Asn Thr Ala Val Ala
1               5                   10

<210> SEQ ID NO 60
<211> LENGTH: 11
<212> TYPE: PRT
<213> ORGANISM: Artificial Sequence
<220> FEATURE:
<223> OTHER INFORMATION: LC CDR1 TA99

<400> SEQUENCE: 60

Arg Ala Ser Gly Asn Ile Tyr Asn Tyr Leu Ala
1               5                   10

<210> SEQ ID NO 61
<211> LENGTH: 17
<212> TYPE: PRT
<213> ORGANISM: Artificial Sequence
<220> FEATURE:
<223> OTHER INFORMATION: LC CDR1

<400> SEQUENCE: 61

Lys Ser Ser Gln Ser Leu Phe Asn Ser Asn Ala Lys Thr Asn Tyr Leu
1               5                   10                  15

Asn

<210> SEQ ID NO 62
<211> LENGTH: 11
<212> TYPE: PRT
<213> ORGANISM: Artificial Sequence
<220> FEATURE:
<223> OTHER INFORMATION: LC CDR1 2.3D11

<400> SEQUENCE: 62

Arg Ala Ser Glu Ser Val Ser Ser Asn Leu Ala
1               5                   10

<210> SEQ ID NO 63
<211> LENGTH: 14
<212> TYPE: PRT
<213> ORGANISM: Artificial Sequence
<220> FEATURE:
<223> OTHER INFORMATION: LC CDR1 C47A8-CQ

<400> SEQUENCE: 63

Ser Gly Thr Ser Ser Asp Val Gly Gly His Asn Tyr Val Ser
1               5                   10

<210> SEQ ID NO 64
<211> LENGTH: 10
<212> TYPE: PRT
<213> ORGANISM: Artificial Sequence
<220> FEATURE:
<223> OTHER INFORMATION: LC CDR1 UMAB10

<400> SEQUENCE: 64

Arg Ala Ser Ser Ser Val Ser Tyr Met Asp
1               5                   10

<210> SEQ ID NO 65
<211> LENGTH: 7
<212> TYPE: PRT
<213> ORGANISM: Artificial Sequence

```
<220> FEATURE:
<223> OTHER INFORMATION: LC CDR2 Obinutuzumab

<400> SEQUENCE: 65

Gln Met Ser Asn Leu Val Ser
1               5

<210> SEQ ID NO 66
<211> LENGTH: 7
<212> TYPE: PRT
<213> ORGANISM: Artificial Sequence
<220> FEATURE:
<223> OTHER INFORMATION: LC CDR2 Dinutuximab (also called Ch14.18 or
      Unituxin)

<400> SEQUENCE: 66

Lys Val Ser Asn Arg Phe Ser
1               5

<210> SEQ ID NO 67
<211> LENGTH: 7
<212> TYPE: PRT
<213> ORGANISM: Artificial Sequence
<220> FEATURE:
<223> OTHER INFORMATION: LC CDR2 Trastuzumab

<400> SEQUENCE: 67

Ser Ala Ser Phe Leu Tyr Ser
1               5

<210> SEQ ID NO 68
<211> LENGTH: 7
<212> TYPE: PRT
<213> ORGANISM: Artificial Sequence
<220> FEATURE:
<223> OTHER INFORMATION: LC CDR2 TA99

<400> SEQUENCE: 68

Asp Ala Lys Thr Leu Ala Asp
1               5

<210> SEQ ID NO 69
<211> LENGTH: 7
<212> TYPE: PRT
<213> ORGANISM: Artificial Sequence
<220> FEATURE:
<223> OTHER INFORMATION: LC CDR2

<400> SEQUENCE: 69

Tyr Ala Ser Thr Arg His Thr
1               5

<210> SEQ ID NO 70
<211> LENGTH: 7
<212> TYPE: PRT
<213> ORGANISM: Artificial Sequence
<220> FEATURE:
<223> OTHER INFORMATION: LC CDR2 2.3D11

<400> SEQUENCE: 70

Gly Ala Phe Asn Arg Ala Thr
1               5

<210> SEQ ID NO 71
<211> LENGTH: 7
<212> TYPE: PRT
<213> ORGANISM: Artificial Sequence
```

```
<220> FEATURE:
<223> OTHER INFORMATION: LC CDR2 C47A8-CQ

<400> SEQUENCE: 71

Asp Val Thr Lys Arg Pro Ser
1               5

<210> SEQ ID NO 72
<211> LENGTH: 7
<212> TYPE: PRT
<213> ORGANISM: Artificial Sequence
<220> FEATURE:
<223> OTHER INFORMATION: LC CDR2 UMAB10

<400> SEQUENCE: 72

Ala Thr Ser Asn Leu Ala Ser
1               5

<210> SEQ ID NO 73
<211> LENGTH: 9
<212> TYPE: PRT
<213> ORGANISM: Artificial Sequence
<220> FEATURE:
<223> OTHER INFORMATION: LC CDR3 Obinutuzumab

<400> SEQUENCE: 73

Ala Gln Asn Leu Glu Leu Pro Tyr Thr
1               5

<210> SEQ ID NO 74
<211> LENGTH: 10
<212> TYPE: PRT
<213> ORGANISM: Artificial Sequence
<220> FEATURE:
<223> OTHER INFORMATION: LC CDR3 Dinutuximab (also called Ch14.18 or
      Unituxin)

<400> SEQUENCE: 74

Ser Gln Ser Thr His Val Pro Pro Leu Thr
1               5                   10

<210> SEQ ID NO 75
<211> LENGTH: 9
<212> TYPE: PRT
<213> ORGANISM: Artificial Sequence
<220> FEATURE:
<223> OTHER INFORMATION: LC CDR3 Trastuzumab

<400> SEQUENCE: 75

Gln Gln His Tyr Thr Thr Pro Pro Thr
1               5

<210> SEQ ID NO 76
<211> LENGTH: 7
<212> TYPE: PRT
<213> ORGANISM: Artificial Sequence
<220> FEATURE:
<223> OTHER INFORMATION: LC CDR3 TA99

<400> SEQUENCE: 76

Gln His Phe Trp Ser Leu Pro
1               5

<210> SEQ ID NO 77
<211> LENGTH: 9
<212> TYPE: PRT
<213> ORGANISM: Artificial Sequence
```

```
<220> FEATURE:
<223> OTHER INFORMATION: LC CDR3

<400> SEQUENCE: 77

Gln Gln Trp Tyr Asp Tyr Pro Tyr Thr
1               5

<210> SEQ ID NO 78
<211> LENGTH: 8
<212> TYPE: PRT
<213> ORGANISM: Artificial Sequence
<220> FEATURE:
<223> OTHER INFORMATION: LC CDR3 2.3D11

<400> SEQUENCE: 78

Gln Gln Arg Ser Asp Trp Phe Thr
1               5

<210> SEQ ID NO 79
<211> LENGTH: 10
<212> TYPE: PRT
<213> ORGANISM: Artificial Sequence
<220> FEATURE:
<223> OTHER INFORMATION: LC CDR3 C47A8-CQ

<400> SEQUENCE: 79

Gln Ser Tyr Ala Gly Ser Arg Val Tyr Val
1               5                   10

<210> SEQ ID NO 80
<211> LENGTH: 9
<212> TYPE: PRT
<213> ORGANISM: Artificial Sequence
<220> FEATURE:
<223> OTHER INFORMATION: LC CDR3 UMAB10

<400> SEQUENCE: 80

Gln Gln Trp Ile Ser Asn Pro Pro Thr
1               5

<210> SEQ ID NO 81
<211> LENGTH: 119
<212> TYPE: PRT
<213> ORGANISM: Artificial Sequence
<220> FEATURE:
<223> OTHER INFORMATION: Obinutuzu-mab

<400> SEQUENCE: 81

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
```

<210> SEQ ID NO 82
<211> LENGTH: 120
<212> TYPE: PRT
<213> ORGANISM: Artificial Sequence
<220> FEATURE:
<223> OTHER INFORMATION: Trastuzumab

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 83
<211> LENGTH: 121
<212> TYPE: PRT
<213> ORGANISM: Artificial Sequence
<220> FEATURE:
<223> OTHER INFORMATION: TA99

<400> SEQUENCE: 83

Glu Val Gln Leu Gln Gln Ser Gly Ala Glu Leu Val Arg Pro Gly Ala
1               5                   10                  15

Leu Val Lys Leu Ser Cys Lys Thr Ser Gly Phe Asn Ile Lys Asp Tyr
            20                  25                  30

Phe Leu His Trp Val Arg Gln Arg Pro Asp Gln Gly Leu Glu Trp Ile
        35                  40                  45

Gly Trp Ile Asn Pro Asp Asn Gly Asn Thr Val Tyr Asp Pro Lys Phe
    50                  55                  60

Gln Gly Thr Ala Ser Leu Thr Ala Asp Thr Ser Ser Asn Thr Val Tyr
65                  70                  75                  80

Leu Gln Leu Ser Gly Leu Thr Ser Glu Asp Thr Ala Val Tyr Phe Cys
                85                  90                  95

Thr Arg Arg Asp Tyr Thr Tyr Glu Lys Ala Ala Leu Asp Tyr Trp Gly
            100                 105                 110

Gln Gly Thr Thr Val Thr Val Ser Thr
        115                 120

<210> SEQ ID NO 84
<211> LENGTH: 116
<212> TYPE: PRT
<213> ORGANISM: Artificial Sequence
<220> FEATURE:
<223> OTHER INFORMATION: Ab

<400> SEQUENCE: 84

```
Gln Val Lys Leu Glu Glu Ser Gly Pro Gly Leu Val Asn Pro Ser Gln
1               5                   10                  15

Ser Leu Ser Leu Ser Cys Ser Val Thr Gly Tyr Ser Ile Thr Ser Gly
                20                  25                  30

Tyr Gly Trp Asn Trp Ile Arg Gln Phe Pro Gly Gln Lys Val Glu Trp
            35                  40                  45

Met Gly Phe Ile Tyr Tyr Glu Gly Ser Thr Tyr Asn Pro Ser Ile
        50                  55                  60

Lys Ser Arg Ile Ser Ile Thr Arg Asp Thr Ser Lys Asn Gln Phe Phe
65                  70                  75                  80

Leu Gln Val Asn Ser Val Thr Thr Glu Asp Thr Ala Thr Tyr Tyr Cys
                85                  90                  95

Ala Arg Gln Thr Gly Tyr Phe Asp Tyr Trp Gly Gln Gly Thr Met Val
            100                 105                 110

Thr Val Ser Ser
        115

<210> SEQ ID NO 85
<211> LENGTH: 125
<212> TYPE: PRT
<213> ORGANISM: Artificial Sequence
<220> FEATURE:
<223> OTHER INFORMATION: 2.3D11

<400> SEQUENCE: 85

Gln Val Gln Leu Gln Glu Ser Gly Pro Gly Leu Val Lys Pro Ser Gly
1               5                   10                  15

Thr Leu Ser Leu Thr Cys Ala Val Ser Gly Val Ser Ile Arg Ser Ile
                20                  25                  30

Asn Trp Trp Asn Trp Val Arg Gln Pro Pro Gly Lys Gly Leu Glu Trp
            35                  40                  45

Ile Gly Glu Ile Tyr His Ser Gly Ser Thr Asn Tyr Asn Pro Ser Leu
        50                  55                  60

Lys Ser Arg Val Thr Ile Ser Val Asp Lys Ser Lys Asn Gln Phe Ser
65                  70                  75                  80

Leu Lys Leu Asn Ser Val Thr Ala Ala Asp Thr Ala Val Tyr Tyr Cys
                85                  90                  95

Ala Arg Asp Gly Gly Ile Ala Val Thr Asp Tyr Tyr Tyr Gly Leu
            100                 105                 110

Asp Val Trp Gly Gln Gly Thr Thr Val Thr Val Ser Ser
        115                 120                 125

<210> SEQ ID NO 86
<211> LENGTH: 119
<212> TYPE: PRT
<213> ORGANISM: Artificial Sequence
<220> FEATURE:
<223> OTHER INFORMATION: C47A8-CQ

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
```

```
            50                  55                  60
Gln Gly Arg Val Thr Met Thr Arg Asp Thr Ser Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Thr Leu Trp Phe Ser Glu Phe Asp Tyr Trp Gly Gln Gly
            100                 105                 110

Thr Leu Val Thr Val Ser Ser
        115

<210> SEQ ID NO 87
<211> LENGTH: 357
<212> TYPE: DNA
<213> ORGANISM: Artificial Sequence
<220> FEATURE:
<223> OTHER INFORMATION: Obinutuzumab

<400> SEQUENCE: 87
caggtgcaat tggtgcagtc tggcgctgaa gttaagaagc tgggagttc agtgaaggtc    60 tcctgcaagg cttccggata cgccttcagc tattcttgga tcaattgggt gcggcaggcg   120
cctggacaag ggctcgagtg gatgggacgg atctttcccg cgatgggga tactgactac   180 aatgggaaat tcaagggcag agtcacaatt accgccgaca aatccactag cacagcctat   240
atggagctga gcagcctgag atctgaggac acggccgtgt attactgtgc aagaaatgtc   300
tttgatggtt actggcttgt ttactggggc agggaaccc tggtcaccgt ctcgaca     357

<210> SEQ ID NO 88
<211> LENGTH: 339
<212> TYPE: DNA
<213> ORGANISM: Artificial Sequence
<220> FEATURE:
<223> OTHER INFORMATION: Dinutuximab (also called Ch14.18 or Unituxin)

<400> SEQUENCE: 88
gaagtgcagc tggtgcagag cggcgcggaa gtggaaaaac cgggcgcgag cgtgaaaatt    60
agctgcaaag cgagcggcag cagctttacc ggctataaca tgaactgggt gcgccagaac   120
attggcaaaa gcctggaatg gattggcgcg attgatccgt attatggcgg caccagctat   180
aaccagaaat ttaaaggccg cgcgacccctg accgtggata aaagcaccag caccgcgtat   240
atgcatctga aaagcctgcg cagcgaagat accgcggtgt attattgcgt gagcggcatg   300
gaatattggg ccagggcac cagcgtgacc gtgagcagc                         339

<210> SEQ ID NO 89
<211> LENGTH: 360
<212> TYPE: DNA
<213> ORGANISM: Artificial Sequence
<220> FEATURE:
<223> OTHER INFORMATION: Trastuzumab

<400> SEQUENCE: 89
gaggtgcagc tggtcgagag cggcggaggg ctggtgcagc caggcggcag cctgaggctg    60
tcctgcgccg ccagcggctt caacatcaag gacacctaca tccactgggt gcggcaggcc   120
ccaggcaagg gcctggagtg ggtggccagg atctaccccca ccaacggcta caccagatac   180
gccgacagcg tgaagggcag gttcaccatc agcgccgaca ccagcaagaa caccgcctac   240
ctgcagatga acagcctgag ggccgaggac accgccgtgt actactgcag cagatggggc   300
ggggacggct tctacgctat ggactactgg ggccagggca ccctggtgac cgtgagcagc   360
```

<210> SEQ ID NO 90
<211> LENGTH: 363
<212> TYPE: DNA
<213> ORGANISM: Artificial Sequence
<220> FEATURE:
<223> OTHER INFORMATION: TA99

<400> SEQUENCE: 90

```
gaggttcagt tgcagcagtc tggcgccgaa ctcgttagac ctggcgctct ggttaagctg      60
tcctgcaaga cctccggctt caatatcaag gactacttcc tgcactgggt ccgacagagg     120
cctgaccaag gactggaatg gatcggctgg atcaacccog acaacggcaa caccgtgtac     180
gaccctaagt tccagggcac cgcttctctg accgccgaca cctcttccaa taccgtgtac     240
ctgcagctgt ccggcctgac ctctgaggat accgccgtgt acttctgcac cagacgggac     300
tacacctacg agaaggccgc tctggattat tggggccagg gcacaaccgt gaccgtgtct     360
aca                                                                   363
```

<210> SEQ ID NO 91
<211> LENGTH: 357
<212> TYPE: DNA
<213> ORGANISM: Artificial Sequence
<220> FEATURE:
<223> OTHER INFORMATION: ab

<400> SEQUENCE: 91

```
caggtgaaac tggaagaaag cggcccgggc ctggtgaacc cgagccagag cctgagcctg      60
agctgcagcg tgaccggcta tagcattacc agcggctatg gctggaactg gattcgccag     120
tttccgggcc agaaagtgga atggatgggc tttatttatt atgaaggcag cacctattat     180
aacccgagca ttaaaagccg cattagcatt accgcgata ccagcaaaaa ccagttttttt     240
ctgcaggtga acagcgtgac caccgaagat accgcgacct attattgcgc gcgccagacc     300
ggctattttg attattgggg ccagggcacc atggtgaccg tgagcagcgg tgagtgc       357
```

<210> SEQ ID NO 92
<211> LENGTH: 375
<212> TYPE: DNA
<213> ORGANISM: Artificial Sequence
<220> FEATURE:
<223> OTHER INFORMATION: 2.3D11

<400> SEQUENCE: 92

```
caggtgcagc tgcaggaaag cggcccgggc ctggtgaaac cgagcggcac cctgagcctg      60
acctgcgcgg tgagcggcgt gagcattcgc agcattaact ggtggaactg ggtgcgccag     120
ccgccgggca aaggcctgga atggattggc gaaatttatc atagcggcag caccaactat     180
aacccgagcc tgaaaagccg cgtgaccatt agcgtggata aaagcaaaaa ccagtttagc     240
ctgaaactga acagcgtgac cgcggcggat accgcggtgt attattgcgc gcgcgatggc     300
ggcattgcgg tgaccgatta ttattattat ggcctggatg tgtggggcca gggcaccacc     360
gtgaccgtga gcagc                                                     375
```

<210> SEQ ID NO 93
<211> LENGTH: 357
<212> TYPE: DNA
<213> ORGANISM: Artificial Sequence
<220> FEATURE:
<223> OTHER INFORMATION: C47A8-CQ

<400> SEQUENCE: 93

```
caggtgcagc tggtgcagag cggcgcggaa gtgaaaaaac cgggcgcgag cgtgaaagtg    60
agctgcaaag cgagcggcta cctttacc  agctattata tgcattgggt gcgccaggcg   120
ccgggccagg gcctggaatg gatgggcatt attaacccga gcggcggcag caccagctat   180
gcgcagaaat tcagggccg cgtgaccatg acccgcgata ccagcaccag caccgtgtat    240
atggaactga gcagcctgcg cagcgaagat accgcggtgt attattgcgc gcgcagcacc   300
ctgtggttta gcgaatttga ttattggggc cagggcaccc tggtgaccgt gagcagc     357
```

<210> SEQ ID NO 94
<211> LENGTH: 366
<212> TYPE: DNA
<213> ORGANISM: Artificial Sequence
<220> FEATURE:
<223> OTHER INFORMATION: UMAB10

<400> SEQUENCE: 94

```
caagcctacc tgcagcagtc tggcgccgat ctcgtgcggc ctggcgcctc tgtgaagatg    60
agctgtaaag ccagcggctt caccttcccc agctacaacc tgcactgggt caagcagacc   120
cccagacagg gcctggaatg gatcggagcc atctaccccg gcaacggcga cacctcctac   180
aaccagaagt tcaagggcaa ggccaccctg accgtggaca agagcagcag caccgcctac   240
atgcagctga gcagcctgac cagcgaggac agcgccgtgt acttctgtgc cagaagcgcc   300
tactacggca gcaacgtgtg gttcttcgac gtgtggggca ccggcaccac cgtgacagtg   360
tcatct                                                              366
```

<210> SEQ ID NO 95
<211> LENGTH: 112
<212> TYPE: PRT
<213> ORGANISM: Artificial Sequence
<220> FEATURE:
<223> OTHER INFORMATION: Obinutuzu-mab

<400> SEQUENCE: 95

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110
```

<210> SEQ ID NO 96
<211> LENGTH: 107
<212> TYPE: PRT
<213> ORGANISM: Artificial Sequence
<220> FEATURE:
<223> OTHER INFORMATION: Trastuzumab

<400> SEQUENCE: 96

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 97
<211> LENGTH: 106
<212> TYPE: PRT
<213> ORGANISM: Artificial Sequence
<220> FEATURE:
<223> OTHER INFORMATION: TA99

<400> SEQUENCE: 97

```
Ile Gln Met Ser Gln Ser Pro Ala Ser Leu Ser Ala Ser Val Gly Glu
1               5                   10                  15

Thr Val Thr Ile Thr Cys Arg Ala Ser Gly Asn Ile Tyr Asn Tyr Leu
            20                  25                  30

Ala Trp Tyr Gln Gln Lys Gln Gly Lys Ser Pro His Leu Leu Val Tyr
        35                  40                  45

Asp Ala Lys Thr Leu Ala Asp Gly Val Pro Ser Arg Phe Ser Gly Ser
    50                  55                  60

Gly Ser Gly Thr Gln Tyr Ser Leu Lys Ile Ser Ser Leu Gln Thr Glu
65                  70                  75                  80

Asp Ser Gly Asn Tyr Tyr Cys Gln His Phe Trp Ser Leu Pro Phe Thr
                85                  90                  95

Phe Gly Ser Gly Thr Lys Leu Glu Ile Lys
            100                 105
```

<210> SEQ ID NO 98
<211> LENGTH: 113
<212> TYPE: PRT
<213> ORGANISM: Artificial Sequence
<220> FEATURE:
<223> OTHER INFORMATION: Ab

<400> SEQUENCE: 98

```
Asp Val Met Met Thr Gln Ser Pro Ser Ser Met Ser Val Ser Ala Gly
1               5                   10                  15

Glu Lys Ala Thr Ile Ser Cys Lys Ser Ser Gln Ser Leu Phe Asn Ser
            20                  25                  30

Asn Ala Lys Thr Asn Tyr Leu Asn Trp Tyr Met Gln Lys Pro Gly Gln
        35                  40                  45

Ser Pro Lys Leu Leu Thr Tyr Tyr Ala Ser Thr Arg His Thr Gly Val
    50                  55                  60

Pro Asp Arg Phe Arg Gly Ser Gly Ser Gly Thr Asp Phe Thr Leu Thr
65                  70                  75                  80

Ile Ser Ser Val Gln Asp Glu Asp Gln Ala Phe Tyr Tyr Cys Gln Gln
                85                  90                  95
```

Trp Tyr Asp Tyr Pro Tyr Thr Phe Gly Ala Gly Thr Lys Leu Glu Ile
            100                 105                 110

Lys

<210> SEQ ID NO 99
<211> LENGTH: 106
<212> TYPE: PRT
<213> ORGANISM: Artificial Sequence
<220> FEATURE:
<223> OTHER INFORMATION: 2.3D11

<400> SEQUENCE: 99

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Phe Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asp Trp Phe Thr
                85                  90                  95

Phe Gly Gly Gly Thr Lys Val Glu Ile Lys
            100                 105

<210> SEQ ID NO 100
<211> LENGTH: 110
<212> TYPE: PRT
<213> ORGANISM: Artificial Sequence
<220> FEATURE:
<223> OTHER INFORMATION: C47A8-CQ

<400> SEQUENCE: 100

Gln Ser Val Leu Thr Gln Pro Ser Ser Val Ser Ala Ser Pro Gly Gln
1               5                   10                  15

Ser Ile Thr Ile Ser Cys Ser Gly Thr Ser Ser Asp Val Gly Gly His
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Tyr Ala Gly Ser
                85                  90                  95

Arg Val Tyr Val Phe Gly Thr Gly Thr Lys Leu Thr Val Leu
            100                 105                 110

<210> SEQ ID NO 101
<211> LENGTH: 336
<212> TYPE: DNA
<213> ORGANISM: Artificial Sequence
<220> FEATURE:
<223> OTHER INFORMATION: Obinutuzumab

<400> SEQUENCE: 101
gatatcgtga tgacccagac acctctgagc ctgcctgtga cacctggcga gcctgcttcc     60

```
atctcctgcc ggtcctctaa gtccctgctg cactctaacg gcatcaccta cctgtactgg    120
tatctgcaga agcccggcca gtctcctcag ctgctgatct accagatgtc caacctggtg    180
tctggcgtgc ccgacagatt ttccggctct ggctctggca ccgacttcac cctgaagatc    240
tccagagtgg aagccgagga cgtgggcgtg tactattgtg cccagaacct ggaactgccc    300
tacacctttg gcggaggcac caaggtggaa atcaag                             336
```

<210> SEQ ID NO 102
<211> LENGTH: 339
<212> TYPE: DNA
<213> ORGANISM: Artificial Sequence
<220> FEATURE:
<223> OTHER INFORMATION: Dinutuximab (also called Ch14.18 or Unituxin)

<400> SEQUENCE: 102

```
gaaattgtga tgacccagag cccggcgacc ctgagcgtga gcccgggcga acgcgcgacc    60
ctgagctgcc gcagcagcca gagcctggtg catcgcaacg gcaacaccta tctgcattgg    120
tatctgcaga aaccgggcca gagcccgaaa ctgctgattc ataaagtgag caaccgcttt    180
agcggcgtgc cggatcgctt tagcggcagc ggcagcggca ccgattttac cctgaaaatt    240
agccgcgtgg aagcggaaga tctgggcgtg tattttttgca gccagagcac ccatgtgccg    300
ccgctgacct ttggcgcggg caccaaactg gaactgaaa                          339
```

<210> SEQ ID NO 103
<211> LENGTH: 321
<212> TYPE: DNA
<213> ORGANISM: Artificial Sequence
<220> FEATURE:
<223> OTHER INFORMATION: Trastuzumab

<400> SEQUENCE: 103

```
gacatccaga tgacccagtc tccatcctct ctgtccgcct ctgtgggcga cagagtgacc    60
atcacctgta gagccagcca ggacgtgaac accgccgtgg cttggtatca gcagaagcct    120
ggcaaggccc ctaagctgct gatctactcc gcctccttcc tgtactctgg cgtgccctcc    180
agattctccg gcagcagatc tggcaccgac tttaccctga catctccag cctgcagcct    240 gaggacttcg ccacctacta ctgccagcag cactacacca cacctccaac ctttggccag    300
ggcaccaagg tggaaatcaa g                                             321
```

<210> SEQ ID NO 104
<211> LENGTH: 318
<212> TYPE: DNA
<213> ORGANISM: Artificial Sequence
<220> FEATURE:
<223> OTHER INFORMATION: TA99

<400> SEQUENCE: 104

```
atccagatga gtcagtctcc ggcctcccta tctgcatctg tgggagaaac tgtcaccatc    60
acatgtcgag caagtggaaa tatttacaat tatttagcat ggtatcagca gaaacaggga    120
aaatctcctc acctcctggt ctatgatgca aaaaccttag cagatggtgt gccatcaagg    180
ttcagtggca gtggctcagg gacacaatat tctctcaaga ttagcagcct tcagactgaa    240
gattctggga attattactg tcaacatttt tggagtcttc cattcacgtt cggctcgggg    300
accaagctgg aaataaaa                                                 318
```

<210> SEQ ID NO 105

```
<211> LENGTH: 339
<212> TYPE: DNA
<213> ORGANISM: Artificial Sequence
<220> FEATURE:
<223> OTHER INFORMATION: ab

<400> SEQUENCE: 105
gatgtgatga tgacccagag cccgagcagc atgagcgtga gcgcgggcga aaaagcgacc    60
attagctgca aaagcagcca gagcctgttt aacagcaacg cgaaaaccaa ctatctgaac   120
tggtatatgc agaaaccggg ccagagcccg aaactgctga cctattatgc gagcacccgc   180
cataccggcg tgccggatcg ctttcgcggc agcggcagcg gcaccgattt taccctgacc   240
attagcagcg tgcaggatga agatcaggcg ttttattatt gccagcagtg gtatgattat   300 ccgtataccct tggcgcgggg caccaaactg gaaattaaa                        339

<210> SEQ ID NO 106
<211> LENGTH: 318
<212> TYPE: DNA
<213> ORGANISM: Artificial Sequence
<220> FEATURE:
<223> OTHER INFORMATION: 2.3D11

<400> SEQUENCE: 106
gaaattgtgc tgacccagag cccggcgacc ctgagcctga gcccgggcga acgcgcgacc    60
ctgagctgcc gcgcgagcga aagcgtgagc agcaacctgg cgtggtatca gcagaaaccg   120
ggccaggcgc cgcgcctgct gatttatggc gcgtttaacc gcgcgaccgg cattccggcg   180
cgctttagcg gcagcggcag cggcaccgat tttaccctga ccattagcag cctggaaccg   240
gaagattttg cggtgtatta ttgccagcag cgcagcgatt ggtttacctt tggcggcggc   300
accaaagtgg aaattaaa                                                318

<210> SEQ ID NO 107
<211> LENGTH: 330
<212> TYPE: DNA
<213> ORGANISM: Artificial Sequence
<220> FEATURE:
<223> OTHER INFORMATION: C47A8-CQ

<400> SEQUENCE: 107
cagagcgtgc tgacccagcc gagcagcgtg agcgcgagcc cgggccagag cattaccatt    60
agctgcagcg gcaccagcag cgatgtgggc ggccataact atgtgagctg gtatcagcag   120
catccgggca aagcgccgaa actgatgatt tatgatgtga ccaaacgccc gagcggcgtg   180
ccggatcgct ttagcggcag caaaagcggc aacaccgcga gcctgaccgt gagcggcctg   240
caggcggaag atgaagcgga ttattattgc cagagctatg cgggcagccg cgtgtatgtg   300
tttggcaccg gcaccaaact gaccgtgctg                                   330

<210> SEQ ID NO 108
<211> LENGTH: 318
<212> TYPE: DNA
<213> ORGANISM: Artificial Sequence
<220> FEATURE:
<223> OTHER INFORMATION: UMAB10

<400> SEQUENCE: 108
cagatcgtgc tgagccagag ccccgccatc ctgagtgcta gccctggcga gaaagtgacc    60
atgacctgca gagccagcag cagcgtgtcc tacatggact ggtatcagca gaagcccggc   120
agcagcccca gccctggat ctacgccaca agcaatctgg ccagcggcgt gcccacaaga   180
```

```
tttccggca gcggctctgg caccagctac agcctgacca tcagccgggt ggaagccgaa    240
gatgccgcca cctactactg ccagcagtgg atcagcaacc ccccaccttt tggagccggc    300
accaagctgg atctgaag                                                  318
```

```
<210> SEQ ID NO 109
<211> LENGTH: 102
<212> TYPE: PRT
<213> ORGANISM: Artificial Sequence
<220> FEATURE:
<223> OTHER INFORMATION: CH1 domain of WT IgA2 heavy chain constant
      region

<400> SEQUENCE: 109

Ala Ser Pro Thr Ser Pro Lys Val Phe Pro Leu Ser Leu Asp Ser Thr
1               5                   10                  15

Pro Gln Asp Gly Asn Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro
            100

<210> SEQ ID NO 110
<211> LENGTH: 101
<212> TYPE: PRT
<213> ORGANISM: Artificial Sequence
<220> FEATURE:
<223> OTHER INFORMATION: CH2 domain of WT IgA2 heavy chain constant
      region

<400> SEQUENCE: 110

Cys Cys His Pro Arg Leu Ser Leu His Arg Pro Ala Leu Glu Asp Leu
1               5                   10                  15

Leu Leu Gly Ser Glu Ala Asn Leu Thr Cys Thr Leu Thr Gly Leu Arg
            20                  25                  30

Asp Ala Ser Gly Ala Thr Phe Thr Trp Thr Pro Ser Ser Gly Lys Ser
        35                  40                  45

Ala Val Gln Gly Pro Pro Glu Arg Asp Leu Cys Gly Cys Tyr Ser Val
    50                  55                  60

Ser Ser Val Leu Pro Gly Cys Ala Gln Pro Trp Asn His Gly Glu Thr
65                  70                  75                  80

Phe Thr Cys Thr Ala Ala His Pro Glu Leu Lys Thr Pro Leu Thr Ala
                85                  90                  95

Asn Ile Thr Lys Ser
            100

<210> SEQ ID NO 111
<211> LENGTH: 131
<212> TYPE: PRT
<213> ORGANISM: Artificial Sequence
<220> FEATURE:
<223> OTHER INFORMATION: CH3 domain of WT IgA2 heavy chain constant
      region including C-terminal Tail-piece
```

<400> SEQUENCE: 111

Gly Asn Thr Phe Arg Pro Glu Val His Leu Leu Pro Pro Ser Glu
1               5                   10                  15

Glu Leu Ala Leu Asn Glu Leu Val Thr Leu Thr Cys Leu Ala Arg Gly
            20                  25                  30

Phe Ser Pro Lys Asp Val Leu Val Arg Trp Leu Gln Gly Ser Gln Glu
            35                  40                  45

Leu Pro Arg Glu Lys Tyr Leu Thr Trp Ala Ser Arg Gln Glu Pro Ser
        50                  55                  60

Gln Gly Thr Thr Thr Phe Ala Val Thr Ser Ile Leu Arg Val Ala Ala
65                  70                  75                  80

Glu Asp Trp Lys Lys Gly Asp Thr Phe Ser Cys Met Val Gly His Glu
                85                  90                  95

Ala Leu Pro Leu Ala Phe Thr Gln Lys Thr Ile Asp Arg Leu Ala Gly
            100                 105                 110

Lys Pro Thr His Val Asn Val Ser Val Val Met Ala Glu Val Asp Gly
            115                 120                 125

Thr Cys Tyr
    130

<210> SEQ ID NO 112
<211> LENGTH: 9
<212> TYPE: PRT
<213> ORGANISM: Artificial Sequence
<220> FEATURE:
<223> OTHER INFORMATION: integrin-binding peptide

<400> SEQUENCE: 112

Cys Tyr Gly Gly Arg Gly Asp Thr Pro
1               5

<210> SEQ ID NO 113
<211> LENGTH: 102
<212> TYPE: PRT
<213> ORGANISM: Artificial Sequence
<220> FEATURE:
<223> OTHER INFORMATION: IGHA2*01 F CH1 gDNA

<400> SEQUENCE: 113

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
            20                  25                  30

Pro Gln Glu Pro Leu Ser Val Thr Trp Ser Glu Ser Gly Gln Asn Val
            35                  40                  45

Thr Ala Arg Asn Phe Pro Pro Ser Gln Asp Ala Ser Gly Asp Leu Tyr
        50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro
            100

<210> SEQ ID NO 114
<211> LENGTH: 307
<212> TYPE: DNA
<213> ORGANISM: Artificial Sequence
<220> FEATURE:
<223> OTHER INFORMATION: IgHA2*01 F CH1 gDNA

<400> SEQUENCE: 114

```
gcatccccga ccagccccaa ggtcttcccg ctgagcctcg acagcacccc ccaagatggg    60
aacgtggtcg tcgcatgcct ggtccagggc ttcttccccc aggagccac tcagtgtgac   120 ctggagcgaa agcggacaga acgtgaccgc cagaaacttc ccacctagcc aggatgcctc   180
cggggacctg tacaccacga gcagccagct gaccctgccg gccacacagt gcccagacgg   240
caagtccgtg acatgccacg tgaagcacta cacgaatccc agccaggatg tgactgtgcc   300
ctgccca                                                           307
```

<210> SEQ ID NO 115
<211> LENGTH: 6
<212> TYPE: PRT
<213> ORGANISM: Artificial Sequence
<220> FEATURE:
<223> OTHER INFORMATION: IGHA2*01 F H gDNA

<400> SEQUENCE: 115

Val Pro Pro Pro Pro Pro
1               5

<210> SEQ ID NO 116
<211> LENGTH: 18
<212> TYPE: DNA
<213> ORGANISM: Artificial Sequence
<220> FEATURE:
<223> OTHER INFORMATION: IGHA2*01 F H gDNA

<400> SEQUENCE: 116

```
gttcccccac ctccccca                                                 18
```

<210> SEQ ID NO 117
<211> LENGTH: 101
<212> TYPE: PRT
<213> ORGANISM: Artificial Sequence
<220> FEATURE:
<223> OTHER INFORMATION: IGHA2*01 F CH2 gDNA

<400> SEQUENCE: 117

Cys Cys His Pro Arg Leu Ser Leu His Arg Pro Ala Leu Glu Asp Leu
1               5                   10                  15

Leu Leu Gly Ser Glu Ala Asn Leu Thr Cys Thr Leu Thr Gly Leu Arg
            20                  25                  30

Asp Ala Ser Gly Ala Thr Phe Thr Trp Thr Pro Ser Ser Gly Lys Ser
        35                  40                  45

Ala Val Gln Gly Pro Pro Glu Arg Asp Leu Cys Gly Cys Tyr Ser Val
    50                  55                  60

Ser Ser Val Leu Pro Gly Cys Ala Gln Pro Trp Asn His Gly Glu Thr
65                  70                  75                  80

Phe Thr Cys Thr Ala Ala His Pro Glu Leu Lys Thr Pro Leu Thr Ala
                85                  90                  95

Asn Ile Thr Lys Ser
            100

<210> SEQ ID NO 118
<211> LENGTH: 303
<212> TYPE: DNA
<213> ORGANISM: Artificial Sequence
<220> FEATURE:

<223> OTHER INFORMATION: IGHA2*01 F CH2 gDNA

<400> SEQUENCE: 118

```
tgctgccacc cccgactgtc gctgcaccga ccggccctcg aggacctgct cttaggttca    60
gaagcgaacc tcacgtgcac actgaccggc ctgagagatg cctctggtgc caccttcacc   120
tggacgccct caagtgggaa gagcgctgtt caaggaccac ctgagcgtga cctctgtggc   180
tgctacagcg tgtccagtgt cctgcctggc tgtgcccagc catggaacca tggggagacc   240
ttcacctgca ctgctgccca ccccgagttg aagacccac taaccgccaa catcacaaaa    300
tcc                                                                 303
```

<210> SEQ ID NO 119
<211> LENGTH: 131
<212> TYPE: PRT
<213> ORGANISM: Artificial Sequence
<220> FEATURE:
<223> OTHER INFORMATION: IGHA2*01 F CH3-CH3 gDNA

<400> SEQUENCE: 119

```
Gly Asn Thr Phe Arg Pro Glu Val His Leu Leu Pro Pro Ser Glu
1               5                   10                  15

Glu Leu Ala Leu Asn Glu Leu Val Thr Leu Thr Cys Leu Ala Arg Gly
            20                  25                  30

Phe Ser Pro Lys Asp Val Leu Val Arg Trp Leu Gln Gly Ser Gln Glu
        35                  40                  45

Leu Pro Arg Glu Lys Tyr Leu Thr Trp Ala Ser Arg Gln Glu Pro Ser
    50                  55                  60

Gln Gly Thr Thr Thr Phe Ala Val Thr Ser Ile Leu Arg Val Ala Ala
65                  70                  75                  80

Glu Asp Trp Lys Lys Gly Asp Thr Phe Ser Cys Met Val Gly His Glu
                85                  90                  95

Ala Leu Pro Leu Ala Phe Thr Gln Lys Thr Ile Asp Arg Leu Ala Gly
            100                 105                 110

Lys Pro Thr His Val Asn Val Ser Val Val Met Ala Glu Val Asp Gly
        115                 120                 125

Thr Cys Tyr
    130
```

<210> SEQ ID NO 120
<211> LENGTH: 394
<212> TYPE: DNA
<213> ORGANISM: Artificial Sequence
<220> FEATURE:
<223> OTHER INFORMATION: IGHA2*01 F CH3-CHS gDNA

<400> SEQUENCE: 120

```
ggaaacacat tccggcccga ggtccacctg ctgccgccgc cgtcggagga gctggccctg    60
aacgagctgg tgacgctgac gtgcctggca cgtggcttca gccccaagga tgtgctggtt   120
cgctggctgc agggtcaca ggagctgccc cgcgagaagt acctgacttg gcatcccgg    180
caggagcccc agccaggca ccaccacctt cgctgtgacc agcatactgc gcgtggcagc   240
cgaggactgg aagaaggggg acaccttctc ctgcatggtg ggccacgagg ccctgccgct   300
ggccttcaca cagaagacca tcgaccgctt ggcgggtaaa cccacccatg tcaatgtgtc   360
tgtttgcatg gcggaggtgg acggcacctg ctac                               394
```

<210> SEQ ID NO 121

```
<211> LENGTH: 121
<212> TYPE: PRT
<213> ORGANISM: Artificial Sequence
<220> FEATURE:
<223> OTHER INFORMATION: light chain variable region

<400> SEQUENCE: 121

Gln Ile Val Leu Ser Gln Ser Pro Ala Val Leu Phe Ala Ser Pro Gly
1               5                   10                  15

Glu Lys Val Thr Met Thr Cys Arg Ala Arg Ser Ser Val Ser Tyr Met
            20                  25                  30

Asp Trp Tyr Gln Gln Lys Pro Arg Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Ser Gly Thr Lys Leu Glu Ile Lys Arg Ala Asp Ala Ala Pro
            100                 105                 110

Thr Val Ser Ile Phe Pro Pro Ser Ser
            115                 120

<210> SEQ ID NO 122
<211> LENGTH: 15
<212> TYPE: PRT
<213> ORGANISM: Artificial Sequence
<220> FEATURE:
<223> OTHER INFORMATION: (Gly-4-Ser)3

<400> SEQUENCE: 122

Gly Ser Ser Ser Ser Gly Ser Ser Ser Ser Gly Ser Ser Ser Ser
1               5                   10                  15

<210> SEQ ID NO 123
<211> LENGTH: 9
<212> TYPE: PRT
<213> ORGANISM: Artificial Sequence
<220> FEATURE:
<223> OTHER INFORMATION: integrin binding peptide

<400> SEQUENCE: 123

Cys Tyr Gly Gly Arg Gly Asp Thr Pro
1               5
```

ENGINEERED IGA ANTIBODIES AND METHODS OF USE

CROSS-REFERENCE

This application is a Continuation of U.S. patent application Ser. No. 17/091,897, filed Nov. 6, 2020, which is a Continuation Application of International Patent Application PCT/NL2020/050217, filed Mar. 27, 2020, which claims the benefit of U.S. Provisional Application No. 62/824,864, filed Mar. 27, 2019; each of which application is incorporated herein by reference in their entirety.

SEQUENCE LISTING

The instant application contains a Sequence Listing which has been filed electronically in ASCII format and is hereby incorporated by reference in its entirety. Said ASCII copy, created on Apr. 8, 2024, is named 55207_706_302_SequenceListing.txt and is 90,761 bytes in size.

BACKGROUND OF THE DISCLOSURE

Monoclonal antibodies of IgG isotype targeting tumor antigens have proven to be an effective treatment of various cancers. Over the years an increasing number of monoclonal antibodies targeting different tumor antigens have been approved for use in cancer therapies. However, their clinical efficacy and side effects, especially as a monotherapy, are still insufficient. Therefore, it is of interest to develop new antibody therapies with increased clinical efficacy, novel targeting modalities or modes of action and/or decreased number and severity of side effects.

SUMMARY OF THE DISCLOSURE

Provided herein is an antibody or a functional fragment thereof that comprises: an antigen binding domain; and a constant domain, wherein the constant domain comprises an immunoglobulin A (IgA) heavy chain constant region, wherein the IgA heavy chain constant region comprises an IgA CH2 region and an IgA CH3 region, wherein the IgA heavy chain constant region comprises a modification of at least two naturally occurring glycosylation sites, as compared to a corresponding wild type (WT) IgA heavy chain constant region, and wherein each of the at least two naturally occurring glycosylation sites is in the IgA CH2 region or in the IgA CH3 region.

In some embodiments, the at least two naturally occurring glycosylation sites are two naturally occurring N-linked glycosylation sites. In some embodiments, one or more of the at least two naturally occurring glycosylation sites comprise a naturally occurring asparagine (N) amino acid residue which are modified in the engineered antibodies disclosed herein as compared to a corresponding wild type IgA. In some embodiments, the modification comprises an amino acid substitution, or an amino acid deletion of one, or both of the at least two naturally occurring glycosylation sites. In some embodiments, the amino acid substitution is a non-conservative amino acid substitution. In some embodiments, the IgA heavy chain constant region comprises an amino acid substitution at: i.N114 and N135, ii. N114 and N15.2, or iii. N135 and N15.2, relative to a corresponding WT IgA heavy chain constant region comprising an amino acid sequence of SEQ ID NO: 1, numbering according to IMGT® scheme. In some embodiments, the IgA heavy chain constant region comprises: i. a N114T amino acid substitution and a N135Q amino acid substitution, ii. a N114T amino acid substitution and an amino acid substitution selected from the group consisting of N15.2G, N15.2Q, and N15.2T, or iii. a N135Q amino acid substitution and an amino acid substitution from the group consisting of N15.2G, N15.2Q, and N15.2T, relative to a corresponding WT IgA heavy chain constant region comprising an amino acid sequence of SEQ ID NO: 1, numbering according to IMGT® scheme.

In some embodiments, the IgA heavy chain constant region comprises a modification of at least three naturally occurring glycosylation sites, as compared to a corresponding wild type IgA. In some embodiments, the at least three naturally occurring glycosylation sites are three N-linked glycosylation sites. In some embodiments, the three naturally occurring glycosylation sites each comprise an asparagine (N) amino acid residue which is modified in the antibodies described herein.

In some embodiments, the modification is an amino acid substitution or an amino acid deletion. In some embodiments, the amino acid substitution is a non-conservative substitution. In some embodiments, the IgA heavy chain constant region comprises an amino acid substitution at: N114, N135, and N15.2, relative to the WT IgA heavy chain constant region comprising an amino acid sequence of SEQ ID NO: 1, numbering according to IMGT® scheme. In some embodiments, the IgA heavy chain constant region comprises: i. a N114T amino acid substitution, ii. a N135Q amino acid substitution, and iii. an amino acid substitution selected from the group consisting of N15.2G, N15.2Q, and N15.2T, relative to a WT IgA heavy chain constant region comprising an amino acid sequence of SEQ ID NO: 1, numbering according to the IMGT® scheme.

In some embodiments, an IgA heavy chain constant region of an antibody described herein further comprises an IgA CH1 region. In some embodiments, the heavy chain constant region comprises a modification of at least one naturally occurring N-linked glycosylation site in the IgA CH2 region, at least one naturally occurring glycosylation site in the IgA CH3 regions, and at least one naturally occurring glycosylation site within the IgA CH1 region, as compared to a corresponding wild type IgA. In some embodiments, the IgA heavy chain constant region comprises an amino acid substitution at: i. N45.2, N114, and N135, or ii. N45.2, N15.2, and N135, relative to a WT IgA heavy chain constant region comprising an amino acid sequence of SEQ ID NO: 1, numbering according to IMGT® scheme.

In some embodiments, the IgA heavy chain constant region comprises: i. a N45.2G amino acid substitution, a N114T amino acid substitution, and a N135Q amino acid substitution; or ii. the N45.2G amino acid substitution, the N135Q amino acid substitution, and an amino acid substitution selected from a group consisting of N15.2G, N15.2Q, and N15.2T, relative to a WT IgA heavy chain constant region comprising an amino acid sequence of SEQ ID NO: 1, numbering according to IMGT® scheme.

In some embodiments, the heavy chain constant region of an antibody described herein comprises a modification of at least two naturally occurring N-linked glycosylation site in the IgA CH2 region, and at least one naturally occurring glycosylation site within the IgA CH1 region, as compared to a corresponding wild type IgA. In some embodiments, the IgA heavy chain constant region comprises an amino acid substitution at: i. N45.2, N114, and N15.2G, numbering according to IMGT® scheme. In some embodiments, described herein the IgA heavy chain constant region comprises: i. a N45.2G amino acid substitution, ii. a N114T amino acid substitution, and iii. an amino acid substitution selected from the group consisting of N15.2G, N15.2Q, and N15.2T, relative to the WT IgA heavy chain constant region comprising an amino acid sequence of SEQ ID NO: 1, numbering according to IMGT® scheme In some embodiments, an antibody described herein or functional fragment thereof exhibits a greater circulating half-life compared to a corresponding WT IgA antibody. In some embodiments, the antibody or the functional fragment thereof exhibits decreased aggregation compared to a corresponding WT IgA antibody. In some embodiments, the antibody or the functional fragment thereof exhibits decreased aggregation with serum proteins, compared to a corresponding WT IgA antibody. In some embodiments, the antibody or the functional fragment thereof induces increased antibody dependent cell mediated cytotoxicity (ADCC), compared to a comparable antibody comprising an IgG heavy chain constant region. In some embodiments, the antibody or the functional fragment thereof exhibits increased thermostability, compared to a corresponding WT IgA antibody. In some embodiments, the antibody or the functional fragment thereof exhibits decreased glycosylation, compared to a corresponding WT IgA antibody.

In some embodiments, the IgA heavy chain constant region exhibits binding to a FcαR expressed on an immune effector cell with increased affinity, compared to a corresponding WT IgA antibody. In some embodiments, the IgA heavy chain constant region comprises a modification of at least four naturally occurring glycosylation sites, as compared to a corresponding wild type IgA. In some embodiments, the at least four naturally occurring glycosylation sites are four naturally occurring N-linked glycosylation sites. In some embodiments, the at least four naturally occurring glycosylation sites each comprise a naturally occurring asparagine (N) amino acid residue. In some embodiments, the heavy chain constant region comprises a modification of at least two naturally occurring N-linked glycosylation sites within the IgA CH2 region, at least one naturally occurring N-linked glycosylation sites within the IgA CH3 region, and at least one naturally occurring N-linked glycosylation site within the IgA CH1 region, as compared to a corresponding wild type IgA. In some embodiments, the IgA heavy chain constant region comprises an amino acid substitution at amino acid residues: N45.2, N114, N135, and N15.2, relative to a WT IgA heavy chain constant region comprising an amino acid sequence of SEQ ID NO: 1, numbering according to IMGT® scheme.

In some embodiments, the IgA heavy chain constant region of an antibody described herein comprises a non-conservative amino acid substitution at amino acid residues: N45.2, N114, N135, and N15.2, numbering according to IMGT® scheme.

In some embodiments, the IgA heavy chain constant region comprises: i. a N45.2G amino acid substitution, ii. a N114T amino acid substitution, iii. a N135Q amino acid substitution, and iv an amino acid substitution selected from the group consisting of N15.2G, N15.2Q, and N15.2T, relative to the WT IgA heavy chain constant region comprising an amino acid sequence of SEQ ID NO: 1, numbering according to IMGT® scheme. In some embodiments, the antibody or the functional fragment thereof exhibits a greater circulating half-life compared to a corresponding IgA antibody comprising at least one naturally occurring N-linked glycosylation site. In some embodiments, the antibody or the functional fragment thereof induces increased antibody dependent cell mediated cytotoxicity (ADCC), compared to a corresponding comparable antibody comprising an IgG CH2 domain and an IgG CH3 domain. In some embodiments, the antibody or the functional fragment thereof exhibits increased thermostability, compared to a corresponding IgA antibody comprising at least one naturally occurring N-linked glycosylation site. In some embodiments, the antibody or the functional fragment thereof exhibits decreased glycosylation, compared to a corresponding IgA antibody comprising at least one naturally occurring N-linked glycosylation site. In some embodiments, the IgA heavy chain constant region exhibits binding to a FcαR expressed on an immune effector cell with increased affinity, compared to a corresponding IgA antibody comprising at least one naturally occurring N-linked glycosylation site.

In some embodiments, the IgA heavy chain constant region of an antibody described herein comprises a modification of at least one naturally occurring cysteine (C) amino acid residue, as compared to a corresponding wild type IgA. In some embodiments, the modification is an amino acid substitution or an amino acid deletion of the at least one naturally occurring cysteine (C) amino acid residue. In some embodiments, the amino acid substitution is a non-conservative amino acid substitution of the at least one naturally occurring cysteine (C) amino acid residue. In some embodiments, the at least one naturally occurring cysteine amino acid residue is C147 or C86, relative to a WT IgA heavy chain constant region comprising an amino acid sequence of SEQ ID NO: 1, numbering according to IMGT® scheme. In some embodiments, the IgA heavy chain constant region comprises a C86S amino acid substitution, relative to the WT IgA heavy chain constant region comprising an amino acid sequence of SEQ ID NO: 1, numbering according to IMGT® scheme. In some embodiments, the IgA heavy chain constant region comprises a deletion of C147, relative to the WT IgA heavy chain constant region comprising an amino acid sequence of SEQ ID NO: 1, numbering according to the IMGT® scheme. In some embodiments, the antibody or the functional fragment thereof exhibits decreased aggregation compared to a corresponding WT IgA antibody or the functional fragment thereof. In some embodiments, the antibody or the functional fragment thereof exhibits decreased aggregation with serum proteins compared to a corresponding WT IgA construct.

In some embodiments, the IgA heavy chain constant region of an antibody described herein comprises a modification of at least two naturally occurring cysteine (C) amino acid residues, as compared to a corresponding wild type IgA. In some embodiments, the modification comprises an amino acid substitution of one, or both of the at least two naturally occurring cysteine (C) amino acid residues. In some embodiments, the modification comprises a deletion of one, or both of the at least two naturally occurring cysteine (C) amino acid residues.

In some embodiments, the IgA heavy chain constant region comprises an amino acid substitution one of the at least two naturally occurring cysteine (C) amino acid residues, and a deletion of one of the at least two naturally occurring cysteine (C) amino acid residues. In some embodiments, the at least two naturally occurring cysteine amino acid residue are C147 and C86, relative to the WT IgA heavy chain constant region comprising an amino acid sequence of SEQ ID NO: 1, numbering according to IMGT® scheme. In some embodiments, the IgA heavy chain constant region comprises a deletion of C147, relative to the WT IgA heavy chain constant region comprising an amino acid sequence of SEQ ID NO: 1, numbering according to IMGT® scheme. In some embodiments, the IgA heavy chain constant region comprises an amino acid substitution of C86, relative to the WT IgA heavy chain constant region comprising an amino acid sequence of SEQ ID NOs: 1, numbering according to IMGT® scheme.

In some embodiments, the IgA heavy chain constant region of an antibody described herein comprises an amino acid substitution of the naturally occurring C86 amino acid residue, and a deletion of the naturally occurring C147 amino acid residue, relative to a WT IgA heavy chain constant region comprising an amino acid sequence of SEQ ID NO: 1, numbering according to IMGT® scheme. In some embodiments, the IgA heavy chain constant region comprises an C86S amino acid substitution, relative to the WT IgA heavy chain constant region comprising an amino acid sequence of SEQ ID NO: 1, numbering according to IMGT® scheme. In some embodiments, the antibody or the functional fragment thereof exhibits decreased aggregation compared to a corresponding WT IgA antibody. In some embodiments, the antibody or the functional fragment thereof exhibits decreased aggregation with serum proteins compared to a corresponding WT IgA antibody.

In some embodiments, the IgA heavy chain constant region of an antibody described herein comprises a modification of at least one naturally occurring tyrosine (Y) amino acid residue, as compared to a corresponding wild type IgA. In some embodiments, the modification is an amino acid substitution or a deletion of the at least one naturally occurring tyrosine (Y) amino acid residue. In some embodiments, the amino acid substitution is a non-conservative amino acid mutation of the at least one naturally occurring tyrosine (Y) amino acid residue, as compared to a WT IgA antibody. In some embodiments, the at least one tyrosine residue is Y148, relative to a WT IgA heavy chain constant region comprising an amino acid sequence of SEQ ID NO: 1, numbering according to IMGT® scheme. In some embodiments, the amino acid Y148 is deleted, relative to the WT IgA heavy chain constant region comprising an amino acid sequence of SEQ ID NO: 1, numbering according to IMGT® scheme. In some embodiments, the antibody or the functional fragment thereof exhibits decreased aggregation compared to a corresponding WT IgA antibody. In some embodiments, the antibody or the functional fragment thereof exhibits decreased aggregation with serum proteins compared to a corresponding WT IgA antibody.

In some embodiments, the IgA heavy chain constant region of an antibody described herein comprises a modification of at least one naturally occurring threonine (T) amino acid residue, as compared to a corresponding wild type IgA antibody. In some embodiments, the modification comprises an amino acid substitution or deletion of the at least one naturally occurring threonine (T) amino acid residue, as compared to a corresponding wild type IgA antibody. In some embodiments, the amino acid substitution is a non-conservative amino acid substitution of the at least one naturally occurring threonine (T) amino acid residue. In some embodiments, the at least one naturally occurring threonine amino acid residue is T116 or T16, relative to the WT IgA heavy chain constant region comprising an amino acid sequence of SEQ ID NO: 1, numbering according to IMGT® scheme. In some embodiments, the antibody or the functional fragment thereof exhibits decreased aggregation compared to a corresponding WT IgA antibody. In some embodiments, the antibody or the functional fragment thereof exhibits decreased aggregation with serum proteins compared to a corresponding WT IgA antibody. In some embodiments, the IgA heavy chain constant region comprises a modification of at least two naturally occurring threonine (T) amino acid residues, as compared to a corresponding wild type IgA. In some embodiments, the modification comprises an amino acid substitution or a deletion of one, or both the at least two naturally occurring threonine (T) amino acid residues. In some embodiments, the amino acid substitution is a non-conservative amino acid substitution of one, or both of the at least two naturally occurring threonine (T) amino acid residues. In some embodiments, the at least two naturally occurring threonine (T) amino acid residue are T116 or T16, relative to a WT IgA heavy chain constant region comprising an amino acid sequence of SEQ ID NO: 1, numbering according to IMGT® scheme. In some embodiments, the IgA heavy chain constant region comprises a T116S amino acid substitution, relative to a WT IgA heavy chain constant region comprising an amino acid sequence of SEQ ID NO: 1, numbering according to IMGT® scheme. In some embodiments, the IgA heavy chain constant region comprises a T16S amino acid substitution, relative to the WT IgA heavy chain constant region comprising an amino acid sequence of SEQ ID NO: 1, numbering according to IMGT® scheme.

In some embodiments, the IgA heavy chain constant region of an antibody described herein comprises a modification of at least one naturally occurring isoleucine (I) amino acid residue, as compared to a corresponding wild type IgA. In some embodiments, the modification comprises an amino acid substitution or a deletion of the at least one naturally occurring isoleucine (I) amino acid residue. In some embodiments, the amino acid substitution comprises a non-conservative amino acid substitution of the at least one naturally occurring isoleucine (I) amino acid residue. In some embodiments, the at least one naturally occurring isoleucine (I) residue is I115, relative to the WT IgA heavy chain constant region comprising an amino acid sequence of SEQ ID NO: 1, numbering according to IMGT® scheme. In some embodiments, the IgA heavy chain constant region comprises a I115L amino acid substitution, relative to a WT IgA heavy chain constant region comprising an amino acid sequence of SEQ ID NO: 1, numbering according to IMGT® scheme. In some embodiments, the IgA heavy chain constant region comprises a modification of at least one naturally occurring leucine (L) amino acid residue, as compared to a corresponding wild type IgA. In some embodiments, the modification comprises an amino acid substitution or a deletion of the at least one naturally occurring leucine (L) amino acid residue. In some embodiments, the amino acid substitution is a non-conservative amino acid substitution of the at least one naturally occurring leucine (L) amino acid residue. In some embodiments, the at least one naturally occurring leucine (L) residue is L15.3, relative to the WT IgA heavy chain constant region comprising an amino acid sequence of SEQ ID NO: 1, numbering according to IMGT® scheme. In some embodiments, the IgA heavy chain constant region comprises a L15.3I amino acid substitution, relative to a WT IgA heavy chain constant region comprising an amino acid sequence of SEQ ID NO: 1, numbering according to IMGT® scheme.

In some embodiments, the IgA heavy chain constant region of an antibody described herein comprises a modification of at least one naturally occurring proline (P) amino acid residue, as compared to a corresponding wild type IgA. In some embodiments, the IgA heavy chain constant region comprises an amino acid substitution or a deletion of the at least one naturally occurring proline (P) amino acid residue. In some embodiments, the amino acid substitution is a non-conservative amino acid substitution of the at least one naturally occurring proline (P) amino acid residue. In some embodiments, the at least one naturally occurring proline (P) residue is P124, relative to a WT IgA heavy chain constant region comprising an amino acid sequence of SEQ ID NO: 1, numbering according to IMGT® scheme. In some embodiments, the IgA heavy chain constant region comprises a P124R amino acid substitution, relative to the WT IgA heavy chain constant region comprising an amino acid sequence of SEQ ID NO: 1, numbering according to IMGT® scheme. In some embodiments, the antibody or functional fragment thereof exhibits greater stability, compared to a corresponding WT IgA antibody. In some embodiments, the antibody or the functional fragment thereof exhibits greater stability between a heavy chain and a light chain, compared to a corresponding WT IgA antibody. In some embodiments, the antibody or functional fragment thereof has a covalent linkage between the heavy chain and the light chain. In some embodiments, the antibody or the functional fragment thereof comprises a disulfide bond between a cysteine (C) amino acid residue of the heavy chain and a cysteine (C) amino acid residue of the light chain. In some embodiments, the IgA heavy chain constant region comprises an amino acid sequence selected from any one of SEQ ID NOs: 16-21.

In some embodiments, antibody described herein comprises a heavy chain region of a modified IgA of an allotype IgA2m(1) antibody or IgA2m(2). In some embodiments, the antibody is an allotype Caucasian IgA2m(1) antibody. In some embodiments, the IgA heavy chain constant region comprises a modification of a C-terminal IgA tail piece, as compared to a corresponding wild type IgA. In some embodiments, the modification comprises a deletion of the C-terminal 25, 24, 23, 22, 21, 20, 19, 18, 17, 16, 15, 12, 10, 8, 6, 4, or 2 amino acids. In some embodiments, the modification comprises a deletion of the C-terminal 18 amino acids. In some embodiments, the modification comprises a deletion of C-terminal amino acid residues 131-148, relative to the WT IgA heavy chain constant region comprising an amino acid sequence of SEQ ID NO: 1, numbering according to IMGT® scheme. In some embodiments, the IgA heavy chain constant region comprises a deletion of the C-terminal amino acid residues P131-Y148 relative to the WT IgA heavy chain constant region comprising an amino acid sequence of SEQ ID NO: 1, numbering according to IMGT® scheme.

In some embodiments, the IgA heavy chain constant region of an antibody described herein comprises an IgA1 constant region comprising an IgA1 CH2 region and an IgA1 CH3 region. In some embodiments, the IgA1 constant region further comprises an IgA1 CH1 region. In some embodiments, the IgA heavy chain constant region comprises an IgA2 constant region comprising an IgA2 CH2 region and an IgA2 CH3 region. In some embodiments, the IgA2 constant region further comprises an IgA2 CH1 region. In some embodiments, the antibody or the functional fragment thereof exhibits a circulating half-life within 1/a, 5%, 10%, 20%, or 30% of the circulating half-life of a corresponding antibody comprising the antigen binding domain and an IgA heavy chain constant region comprising an IgG CH2 region and an IgG CH3 region.

Provided herein is an antibody or a functional fragment thereof comprising: an antigen binding domain; and a constant domain, wherein the constant domain comprises an IgA2 heavy chain constant region comprising an IgA2 CH1 region, IgA2 CH2 region and an IgA2 CH3 region; wherein the IgA2 heavy chain constant region comprises a N135Q amino acid substitution, numbering according to IMGT® scheme, as compared to a corresponding relative to a WT IgA heavy chain constant region comprising an amino acid sequence of SEQ ID NO: 1.

In some embodiments, the heavy chain constant region further comprises: a N45.2G amino acid substitution, a N114T amino acid substitution, a I115L amino acid substitution, a T116S amino acid substitution, and an amino acid substitution selected from the group consisting of N15.2G, N15.2Q, and N15.2T, relative to a WT IgA2 heavy chain constant region comprising an amino acid sequence of SEQ ID NO: 1, numbering according to IMGT® scheme. In some embodiments, the heavy chain constant region further comprises: a C86S amino acid substitution, a P124R amino acid substitution, a deletion of C147, a deletion of Y148, a L15.3I amino acid substitution, a T16S amino acid substitution, or a combination thereof, relative to the WT IgA2 heavy chain constant region comprising an amino acid sequence of SEQ ID NO: 1, numbering according to IMGT® scheme.

Provided herein is an antibody or a functional fragment thereof comprising: an antigen binding domain; and a constant domain, wherein the constant domain comprises an IgA2 heavy chain constant region comprising an IgA2 CH2 region and an IgA2 CH3 region, and wherein the IgA2 heavy chain constant region comprises: a C86S amino acid substitution, a N114T amino acid substitution, a I115L amino acid substitution, a T116S amino acid substitution, and a N135Q amino acid substitution, relative to WT IgA2 heavy chain constant region comprising an amino acid sequence of SEQ ID NO: 1, numbering according to IMGT® scheme.

Provided herein is an antibody or a functional fragment thereof comprising: an antigen binding domain; and a constant domain, wherein the constant domain comprises an IgA2 heavy chain constant region comprising an IgA2 CH1 region, an IgA2 CH2 region, and an IgA CH3 region, and wherein the IgA2 heavy chain constant region comprises: a N45.2G amino acid substitution, a C86S amino acid substitution, a N114T amino acid substitution, a I115L amino acid substitution, a T116S amino acid substitution, a N135Q amino acid substitution, a deletion of C147, and a deletion of Y148, relative to the WT IgA2 heavy chain constant region comprising an amino acid sequence of SEQ ID NO: 1, numbering according to IMGT® scheme. In some embodiments, the IgA2 heavy chain constant region comprises an amino acid sequence that is at least 95% identical to SEQ ID NO: 16.

Provided herein is an antibody or a functional fragment thereof comprising: an antigen binding domain; and a constant domain, wherein the constant domain comprises an IgA2 heavy chain constant region comprising an IgA2 CH1 region, an IgA2 CH2 region, and an IgA2 CH3 region, and wherein the IgA2 heavy chain constant region comprises: a N45.2G amino acid substitution, a C86S amino acid substitution, a N114T amino acid substitution, a I115L amino acid substitution, a T116S amino acid substitution, and a deletion of C-terminal tail piece, relative to the WT IgA2 heavy chain constant region comprising an amino acid sequence of SEQ ID NO: 1, numbering according to IMGT® scheme.

In some embodiments, the deletion of C-terminal tail piece comprises a deletion of C-terminal amino acid residues P131-Y148, relative to the WT IgA heavy chain constant region comprising an amino acid sequence of SEQ ID NO: 1, numbering according to the IMGT® scheme.

In some embodiments, an IgA2 heavy chain constant region of an antibody described herein comprises an amino acid sequence that is at least 75%, 80%, 85%, 90%, 95%, 96%, 97%, 98%, 99%, 99.1%, 99.2%, 99.3%, 99.4%, 99.5%, 99.6, 99.7%, 99.8%, 99.9% or 100% identical to SEQ ID NO: 17.

Provided herein is an antibody or a functional fragment thereof comprising: an antigen binding domain; and a constant domain, wherein the constant domain comprises an IgA2 heavy chain constant region comprising an IgA2 CH1 region, an IgA2 CH2 region, and an IgA2 CH3 region; wherein the IgA2 heavy chain constant region comprises: a N45.2G amino acid substitution, a N114T amino acid substitution, a I115L amino acid substitution, a T116S amino acid substitution, a N135Q amino acid substitution, an amino acid substitution selected from the group consisting of N15.2G, N15.2Q, and N15.2T, a L15.3I amino acid substitution, and a T16S amino acid substitution, relative to the WT IgA2 heavy chain constant region comprising an amino acid sequence of SEQ ID NO: 1, numbering according to the IMGT® scheme.

Provided herein is an antibody or a functional fragment thereof comprising: an antigen binding domain; and a constant domain, wherein the constant domain comprises an IgA2 heavy chain constant region comprising an IgA2 CH1 region, an IgA2 CH2 region, and an IgA2 CH3 region, and wherein the IgA2 heavy chain constant region comprises: a N45.2G amino acid substitution, a N114T amino acid substitution, a I115L amino acid substitution, a T116S amino acid substitution, an amino acid substitution selected from the group consisting of N15.2G, N15.2Q, and N15.2T, a L15.3I amino acid substitution, a T16S amino acid substitution, and a deletion of C-terminal amino acids P131-Y148, relative to the WT IgA2 heavy chain constant region comprising an amino acid sequence of SEQ ID NO: 1, numbering according to the IMGT® scheme.

In some embodiments, an antibody or the functional fragment thereof disclosed herein comprising: a C86S amino acid substitution, a P124R amino acid substitution, a deletion of C147, a deletion of Y148, or a combination thereof, relative to the WT IgA2 heavy chain constant region comprising an amino acid sequence of SEQ ID NO: 1, numbering according to IMGT® scheme. In some embodiments, the IgA2 heavy chain constant region comprises an amino acid sequence that is at least 95% identical to a sequence selected from any one of SEQ ID NOs: 18-21. In some embodiments, the antibody or the functional fragment thereof is aglycosylated. In some embodiments, the antibody or the functional fragment thereof has increased circulatory half life than a corresponding IgA comprising one or more of wild type amino acid residues N45.2, N114, I115, T116, N15.2, L15.3, T16, or a C-terminal amino acid residues P131-Y148, numbering according to the IMGT® scheme.

In some embodiments, an antibody or functional fragment thereof described herein induces increased antibody dependent cell mediated cytotoxicity (ADCC), compared to a corresponding antibody comprising an IgG heavy chain constant domain. In some embodiments, the antibody or the functional fragment thereof exhibits increased thermostability, compared to a corresponding IgA comprising one or more of wild type amino acid residues N45.2, N114, I115, T116, N15.2, L15.3, T16, or a C-terminal amino acid residues P131-Y148, numbering according to the IMGT® scheme. In some embodiments, the antibody or the functional fragment thereof exhibits decreased glycosylation, compared to a corresponding IgA comprising one or more of wild type amino acid residues N45.2, N114, I115, T116, N15.2, L15.3, T16, or a C-terminal amino acid residues P131-Y148, numbering according to the IMGT® scheme. In some embodiments, the IgA heavy chain constant region exhibits binding to FcαR expressed on an immune effector cell with increased affinity, compared to a comprising one or more of wild type amino acid residues N45.2, N114, I115, T116, N15.2, L15.3, T16, or a C-terminal amino acid residues P131-Y148, numbering according to the IMGT® scheme. In some embodiments, the IgA heavy chain constant region further comprises a hinge region. In some embodiments, the hinge region comprises an IgA hinge amino acid sequence or a variant or a fragment thereof. In some embodiments, the hinge region comprises a human IgA hinge amino acid sequence or a variant or a fragment thereof. In some embodiments, the hinge is an IgA1 hinge or an IgA2 hinge, or a variant or a fragment thereof. In some embodiments, the constant domain further comprises a light chain constant region. In some embodiments, the light chain constant region is a kappa light chain constant region, wherein the kappa light chain constant region comprises a sequence of SEQ ID NO: 31 In some embodiments, the IgA heavy chain constant region further comprises one or more albumin binding regions. In some embodiments, the one or more albumin binding domains are fused to the C-terminus of the CH3 region. In some embodiments, the constant region comprises the light chain constant region and the one or more albumin binding domain is fused to the light chain constant region. In some embodiments, the antibody or the functional fragment thereof has a greater circulating half-life compared to a corresponding IgA antibody that does not comprise the one or more albumin binding domains. In some embodiments, the antibody or the functional fragment thereof exhibits decreased complement-dependent cytotoxicity (CDC) compared to a corresponding antibody comprising an IgG heavy chain constant domain when measured in a suitable in vitro CDC assay.

In some embodiments, an antibody or functional fragment thereof described herein exhibits increased antibody-dependent cell-mediated cytotoxicity (ADCC) compared to a corresponding WT IgA antibody when measured in a suitable in vitro ADCC assay. In some embodiments, the antigen binding domain comprises a heavy chain variable region and a light chain variable region. In some embodiments, the heavy chain variable region of an antibody described herein comprises at least one of complementarity determining regions (CDRs): HC-CDR1 comprising an amino acid sequence selected from any one of SEQ ID NOs: 33-40, HC-CDR2 comprising an amino acid sequence selected from any one of SEQ ID NOs: 41-48; and HC-CDR3 comprising an amino acid sequence selected from any one of SEQ ID NOs: 49-56.

In some embodiments, the light chain variable region of an antibody described herein comprises at least one of complementarity determining regions (CDRs): LC-CDR1 comprising an amino acid sequence selected from any one of SEQ ID NOs: 57-64;LC-CDR2 comprising an amino acid sequence selected from any one of SEQ ID NOs: 65-72; and LC-CDR3 comprising an amino acid sequence selected from any one of SEQ ID NOs: 73-80.

In some embodiments, the heavy chain variable region of an antibody described comprises a sequence having at least 75%, 80%, 85%, 90%, 95%, 96%, 97%, 98%, 99%, 99.1%, 99.2%, 99.3%, 99.4%, 99.5%, 99.6%, 99.7%, 99.8%, 99.9% or 100% identity to an amino acid sequence selected from any one of SEQ ID NOs: 4, 7, 81-86. In some embodiments, the light chain variable region comprises a sequence having at least 75%, 80%, 85%, 90%, 95%, 96%, 97%, 98%, 99%, 99.1%, 99.2%, 99.3%, 99.4%, 99.5%, 99.6%, 99.7%, 99.8%, 99.9% or 100% identity to an amino acid sequence selected from any one of SEQ ID NOs: 5, 8, 95-100. In some embodiments, each of the heavy chain and light chain CDRs are derived from an IgG antibody.

In some embodiments, the heavy chain variable region further comprises four framework regions (FWs): HC—FW1, HC—FW2, HC—FW3, and HC—FW4. In some embodiments, the light chain variable region further comprises four framework regions (FWs): LC-FW1, LC-FW2, LC-FW3, and LC-FW4.

In some embodiments, each the heavy chain and light chain FW regions are derived from an IgG antibody. In some embodiments, each the heavy chain and light chain FW regions are derived from an IgA antibody.

In some embodiments, an antibody described herein or the functional fragment thereof is a chimeric antibody, a heavy chain antibody, a single chain antibody, a humanized antibody, a human antibody, a monoclonal antibody, a deimmunized antibody, a bispecific antibody, a multispecific antibody, a multivalent antibody, or a combination thereof.

In some embodiments, the antigen-binding fragment of an antibody described herein comprises a Fab, Fab', Fab'-SH, Fv, scFv, F(ab')2, a diabody, a linear antibody, a single domain antibodies (sdAb), a VHH domain, or a multispecific antibody formed from antibody fragments, In some embodiments, the variable domain specifically binds to GD2, CD20, CD47, CD38, CD19, EGFR, HER2, PD-L1, or CD25. In some embodiments, the antibody or the functional fragment thereof further comprises an enzyme, a substrate, cofactor, a fluorescent marker, a chemiluminescent marker, a peptide tag, a magnetic particle, a drug, a toxin, a radionuclide, a binding site for secondary antibodies, a metal binding domain, or a combination thereof.

Provided herein is a pharmaceutical composition of comprising the antibody or the functional fragment thereof of any one of aspects above and a pharmaceutically acceptable carrier.

Provided herein is a method of treating or a composition for use in treating a subject in need thereof, comprising administering to the subject a therapeutic dose of the antibody or the functional fragment thereof of any one of aspects above or the pharmaceutical composition disclosed above.

In some embodiments, the antibody or the functional fragment thereof or the pharmaceutical composition is cytolytic to a target cell. In some embodiments, the target cell is a cancer cell. In some embodiments, the antibody or the functional fragment thereof or the pharmaceutical composition inhibits tumor growth. In some embodiments, the antibody or the functional fragment thereof or the pharmaceutical composition is administered subcutaneously, intravenously, intradermally, intraperitoneally, orally, intramuscularly or intracranially. In some embodiments, the antibody or the functional fragment thereof or the pharmaceutical composition is administered to the subject in combination with a second therapeutic agent.

In some embodiments, the second therapeutic agent comprises an anti-cancer agent, a chemotherapeutic agent, radiation therapy, a cytotoxic agent, a NSAID, a corticosteroid, a dietary supplement such as an antioxidant, or a combination thereof. In some embodiments, the second therapeutic agent is administered prior to, concurrently, or after administering the antibody or the functional fragment thereof or the pharmaceutical composition.

Provided herein is an isolated nucleic acid encoding the antibody or the functional fragment thereof of any one of aspects above.

Provided herein is an isolated nucleic acid molecule encoding a heavy chain polypeptide, the isolated nucleic acid molecule comprising a first nucleic acid sequence encoding a IgA heavy chain constant region, wherein the first nucleic acid sequence is selected from any one of SEQ ID NOs: 25-32. In some embodiments, the isolated nucleic acid molecule aspect above, further comprises a second nucleic acid sequence encoding a variable heavy chain region, wherein the second nucleic acid sequence is selected from any one of SEQ ID NOs:87-84.

Provided herein is a vector comprising the isolated nucleic acid molecule of any one of aspects above.

Provided herein is a host cell comprising the isolated nucleic acid molecule of any one of aspects above. In some embodiments, the host cell of any one of aspects above, further comprises an isolated nucleic acid molecule encoding a light chain polypeptide, wherein the isolated nucleic acid molecule encoding the light chain polypeptide comprises a nucleic acid sequence encoding a variable light chain region, wherein the nucleic acid sequence is selected from any one of SEQ ID NOs:101-108. In some embodiments, the isolated nucleic acid molecule encoding the light chain polypeptide further comprises a nucleic acid sequence encoding a kappa light chain constant region, wherein the nucleic acid sequence comprises a sequence of SEQ ID NO:32.

Provided herein is a host cell expressing the antibody or the functional fragment thereof of any one of aspects above. In some embodiments, the host cell is a bacterial cell or a mammalian cell. In some embodiments, the host cell is a CHO cell, or a HEK293 cell.

Provided herein is a method of producing an antibody or the functional fragment thereof, the method comprising: (a) culturing the host cell of any one of aspects above in a medium under conditions permitting expression of a polypeptide encoded by the isolated nucleic acid molecule and assembling of the antibody or the functional fragment thereof; and (b) purifying the antibody or the functional fragment thereof from the cultured host cell or the medium of the host cell. In some embodiments, the purifying is by size exclusion chromatography.

Provided herein is an antibody or a functional fragment thereof that selectively binds to a CD20 polypeptide or a variant thereof, comprising: (a) an IgA heavy chain constant region, wherein the IgA heavy chain constant region comprises an amino acid sequence selected from any one of SEQ ID NOs:16-21; and (b) a variable heavy chain region, wherein the variable heavy chain region comprises at least one of a complementarity-determining region heavy chain 1 (HC-CDR1) of SEQ ID NO: 33, HC-CDR2 of SEQ ID NO: 41, and HC-CDR3 of SEQ ID NO: 49; (c) a variable light chain region, wherein the variable light chain region comprises at least one of a complementarity-determining region light chain 1 (LC-CDR1) of SEQ ID NO:57, LC-CDR2 of SEQ ID NO:65, and LC-CDR3 of SEQ ID NO:73; or (d) the variable heavy chain of (b) and the variable light chain of (c). In some embodiments, the variable heavy chain comprises a polypeptide sequence having at least 95% sequence identity to the amino acid sequence of SEQ ID NO: 81, and the variable light chain comprises a polypeptide sequence having at least 95% sequence identity to the amino acid sequence of SEQ ID NO: 95.

Provided herein is an antibody or a functional fragment thereof that selectively binds to a GD2 protein or a variant thereof, comprising: (a) an IgA heavy chain constant region, wherein the IgA heavy chain constant region comprises an amino acid sequence selected from any one of SEQ ID NOs: 16-21; and (b) a variable heavy chain region, wherein the variable heavy chain region comprises at least one of a complementarity-determining region heavy chain 1 (HC- CDR1) of SEQ ID NO: 34, HC-CDR2 of SEQ ID NO: 42, and HC-CDR3 of SEQ ID NO: 50; (c) a variable light chain region, wherein the variable light chain region comprises at least one of a complementarity-determining region light chain 1 (LC-CDR1) of SEQ ID NO: 58, LC-CDR2 of SEQ ID NO: 66, and LC-CDR3 of SEQ ID NO: 74; or (d) the variable heavy chain of (b) and the variable light chain of (c). In some embodiments, the variable heavy chain comprises a polypeptide sequence having at least 95% sequence identity to the amino acid sequence of SEQ ID NO: 4, and the variable light chain comprises a polypeptide sequence having at least 95% sequence identity to the amino acid sequence of SEQ ID NO: 5.

Provided herein is an antibody or a functional fragment thereof that selectively binds to a Her2 protein or a variant thereof, comprising: (a) an IgA heavy chain constant region, wherein the IgA heavy chain constant region comprises an amino acid sequence selected from SEQ ID NOs: 16-21; and (b) a variable heavy chain region, wherein the variable heavy chain region comprises at least one of a complementarity-determining region heavy chain 1 (HC-CDR1) of SEQ ID NO: 35, HC-CDR2 of SEQ ID NO: 43, and HC-CDR3 of SEQ ID NO: 51; (c) a variable light chain region, wherein the variable light chain region comprises at least one of a complementarity-determining region light chain 1 (LC-CDR1) of SEQ ID NO: 59, LC-CDR2 of SEQ ID NO: 67, and LC-CDR3 of SEQ ID NO: 75; or (d) the variable heavy chain of (b) and the variable light chain of (c). In some embodiments, the variable heavy chain comprises a polypeptide sequence having at least 95% sequence identity to the amino acid sequence of SEQ ID NO: 82, and the variable light chain comprises a polypeptide sequence having at least 95% sequence identity to the amino acid sequence of SEQ ID NO: 96.

Provided herein is an antibody or a functional fragment thereof that selectively binds to a gp75 protein or a variant thereof, comprising: (a) an IgA heavy chain constant region, wherein the IgA heavy chain constant region comprises an amino acid sequence selected from SEQ ID NOs: 16-21; and (b) a variable heavy chain region, wherein the variable heavy chain region comprises at least one of a complementarity-determining region heavy chain 1 (HC-CDR1) of SEQ ID NO: 36, HC-CDR2 of SEQ ID NO: 44, and HC-CDR3 of SEQ ID NO: 52; (c) a variable light chain region, wherein the variable light chain region comprises at least one of a complementarity-determining region light chain 1 (LC-CDR1) of SEQ ID NO: 60, LC-CDR2 of SEQ ID NO: 68, and LC-CDR3 of SEQ ID NO: 76; or (d) the variable heavy chain of (b) and the variable light chain of (c). In some embodiments, the variable heavy chain comprises a polypeptide sequence having at least 95% sequence identity to the amino acid sequence of SEQ ID NO: 83, and the variable light chain comprises a polypeptide sequence having at least 95% sequence identity to the amino acid sequence of SEQ ID NO: 97.

Provided herein is an antibody or a functional fragment thereof that selectively binds to a CTLA4 protein or a variant thereof, comprising: (a) an IgA heavy chain constant region, wherein the IgA heavy chain constant region comprises an amino acid sequence selected from SEQ ID NOs: 16-21; and (b) a variable heavy chain region, wherein the variable heavy chain region comprises at least one of a complementarity-determining region heavy chain 1 (HC-CDR1) of SEQ ID NO: 37, HC-CDR2 of SEQ ID NO: 45, and HC-CDR3 of SEQ ID NO: 53; (c) a variable light chain region, wherein the variable light chain region comprises at least one of a complementarity-determining region light chain 1 (LC-CDR1) of SEQ ID NO: 61, LC-CDR2 of SEQ ID NO: 69, and LC-CDR3 of SEQ ID NO: 77; or (d) the variable heavy chain of (b) and the variable light chain of (c). In some embodiments, the variable heavy chain comprises a polypeptide sequence having at least 95% sequence identity to the amino acid sequence of SEQ ID NO: 84, and the variable light chain comprises a polypeptide sequence having at least 95% sequence identity to the amino acid sequence of SEQ ID NO:98.

Provided herein is an antibody or a functional fragment thereof that selectively binds to a CD47 protein or a variant thereof, comprising: (a) an IgA heavy chain constant region, wherein the IgA heavy chain constant region comprises an amino acid sequence selected from SEQ ID NOs:16-21; and (b) a variable heavy chain region, wherein the variable heavy chain region comprises at least one of a complementarity-determining region heavy chain 1 (HC-CDR1) of SEQ ID NO: 38, HC-CDR2 of SEQ ID NO: 46, and HC-CDR3 of SEQ ID NO: 54; (c) a variable light chain region, wherein the variable light chain region comprises at least one of a complementarity-determining region light chain 1 (LC-CDR1) of SEQ ID NO: 62, LC-CDR2 of SEQ ID NO: 70, and LC-CDR3 of SEQ ID NO: 78; or (d) the variable heavy chain of (b) and the variable light chain of (c). In some embodiments, the variable heavy chain comprises a polypeptide sequence having at least 95% sequence identity to the amino acid sequence of SEQ ID NO: 85, and the variable light chain comprises a polypeptide sequence having at least 95% sequence identity to the amino acid sequence of SEQ ID NO: 99.

Provided herein is an antibody or a functional fragment thereof comprising: an antigen binding domain; and a constant domain, wherein the constant domain comprises an IgA2 heavy chain constant region comprising an IgA2 CH1 region, an IgA2 CH2 region, and an IgA2 CH3 region, and wherein the IgA2 heavy chain constant region comprises: a N45.2G amino acid substitution, a N135Q amino acid substitution, a deletion of C147, and a deletion of Y148, relative to the WT IgA2 heavy chain constant region comprising an amino acid sequence of SEQ ID NO: 1, numbering according to IMGT® scheme.

Provided herein is an antibody or a functional fragment thereof comprising: an antigen binding domain; and a constant domain, wherein the constant domain comprises an IgA2 heavy chain constant region comprising an IgA2 CH1 region, an IgA2 CH2 region, and an IgA2 CH3 region, and wherein the IgA2 heavy chain constant region comprises: a N45.2G amino acid substitution, a N114T amino acid substitution, a I115L amino acid substitution, a T116S amino acid substitution, an amino acid substitution selected from the group consisting of N15.2G, N15.2Q, and N15.2T, and a deletion of C-terminal amino acids P131-Y148, relative to the WT IgA heavy chain constant region comprising an amino acid sequence of SEQ ID NO: 1, numbering according to the IMGT® scheme.

In some embodiments, the antibody or the functional fragment thereof of aspect above, further comprises: a C86S amino acid substitution, a P124R amino acid substitution, a deletion of C147, a deletion of Y148, a L15.3I amino acid substitution, a T16S amino acid substitution or a combination thereof,
    relative to the WT IgA heavy chain constant region comprising an amino acid sequence of SEQ ID NO: 1, numbering according to IMGT® scheme. In some embodiments, the IgA2 heavy chain constant region comprises an amino acid sequence that is at least 95% identical to a sequence selected from any one of SEQ ID NOs: 18-21. In some embodiments the antibody or the functional fragment thereof is aglycosylated.

In some embodiments the antibody or the functional fragment thereof has increased circulatory half-life than a corresponding IgA comprising one or more of wild type amino acid residues N45.2, N114, I115, T116, N15.2, or a C-terminal amino acid residues P131-Y148, numbering according to the IMGT® scheme.

In some embodiments the antibody or the functional fragment thereof induces increased antibody dependent cell mediated cytotoxicity (ADCC), compared to a corresponding antibody comprising an IgG heavy chain constant domain. In some embodiments the antibody or the functional fragment thereof exhibits increased thermostability, compared to a corresponding IgA comprising one or more of wild type amino acid residues N45.2, N114, I115, T116, N15.2, or a C-terminal amino acid residues P131-Y148, numbering according to the IMGT® scheme, numbering according to the IMGT® scheme. In some embodiments the antibody or the functional fragment thereof exhibits decreased glycosylation, compared to a corresponding IgA comprising one or more of wild type amino acid residues N45.2, N114, I115, T116, N15.2, or a C-terminal amino acid residues P131-Y148, numbering according to the IMGT® scheme.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1 is an illustration showing the amino acid sequence of IgA2 heavy chain (UniProt Reference No.: A0A0G2JMB2) (SEQ ID NO: 1). The highlighted amino acids depict the amino acids subject to substitution in some embodiments described herein. The underlined sequence indicates the tail piece, which all or part of can be deleted in some embodiments described herein.

FIG. 2 is an illustration showing the amino acid sequence of IgA2 heavy chain (UniProt Reference No.: P01877) (SEQ ID NO: 2). The highlighted amino acids depict the amino acids subject to substitution in some embodiments described herein. The underlined sequence indicates the tail piece, which all or part of can be deleted in some embodiments described herein.

FIG. 3 is an illustration showing the amino acid sequence of a representative IgA2 heavy chain (UniProt Reference No.: A0A286YEY5) (SEQ ID NO: 3). The highlighted amino acids depict the amino acids subject to substitution or deletion in some embodiments described herein. In some further embodiments, a corresponding amino acid can be deleted in a comparable IgA antibody or a comparable chimeric antibody with an IgA2 constant region.

FIG. 4A shows representation of wild type (WT) IgA; IgA2m1 antibody. The wild type (WT) IgA; IgA2 ml contains three N-glycosylation sites in its CH domains and 1 glycosylation site in its tailpiece.

FIG. 4B shows representation of an engineered IgA3.0+ (plus) variant. The engineered IgA3.0+ variant is generated by engineering IgA2 ml antibody to contain a stabilized heavy and light chain linkage via a CH1-P124R mutation, removal of two free cysteines of which 1 is mutated to serine (CH2-C86S) and the second (CH3-CHS-C147del) is removed by deletion of two final amino acids of the tailpiece. In addition, three N-linked glycosylation sites have been removed by substituting critical amino acids in three N-glycosylation motifs. Mutation in the three N-glycosylation motifs include CH1-N45.2G; CH2-N114T-I115L-T116S; CH3-CHS-N135Q.

FIG. 4C shows representation of an engineered IgA3.0– or IgA3.0min variant contains deletion of the entire tailpiece (CH3-CHS-P131-Y148del). The IgA3.0min variant contains a stabilized heavy and light chain linkage (CH1-P124R mutation), deletion of entire tailpiece (CH3-CHS-P131-Y148del), lacks two free cysteines of which 1 is mutated to serine (CH2-C86S) and the second (CH3-CHS-C147del) is deletion of the tailpiece. In addition, three N-linked glycosylation sites have been removed by substituting critical amino acids in 2 N-glycosylation motifs i.e., CH1-N45.2G and CH2-N114T-I115L-T116S and deletion of CH3-CHS-N135Qdel by deletion of tailpiece.

FIG. 4D shows representation of an engineered IgA4.0 variant that contains all the features of the IgA3.0min and further contains a mutation in the final N-linked glycosylation motif CH2-N15.2. Therefore, IgA4.0 variant contains a stabilized heavy and light chain linkage (CH1-P124R mutation), deletion of entire tailpiece (CH3-CHS-P131-Y148del), lacks two free cysteines of which 1 is mutated to serine (CH2-C86S) and the second (CH3-CHS-C147del) is deletion of the tailpiece. In addition, four N-linked glycosylation sites have been removed by substituting critical amino acids in four N-glycosylation motifs (CH1-N45.2G; CH2-N114T-I115L-T116S; CH3-CHS-N135Q; and one of CH2-N15.2G; CH2-N15.2Q; CH2-N15.2T; or CH2-N15.2T-L15.3I-T16S). IgA4.0 variant is an aglycosylated IgA.

FIG. 5A shows concentration of anti-Her2 IgA antibody i.e., IgA2-Her2 as determined by ELISA on supernatants of HEK293F cells transfected with different heavy chain (HC): light chain (LC):pAdvantage™ ratios.

FIG. 5B shows concentration of anti-CD47 IgA3.0min antibody i.e., IgA3.0min antibody containing anti-CD47 variable domains (IgA3.0min-C47A8-CQ) as determined by ELISA on supernatants of HEK293F cells transfected with different heavy chain (HC):light chain (LC):pAdvantage™ ratios. The variable domains are obtained from C47A8-CQ antibody.

FIG. 6A shows comparison of production rate in HEK293F cells versus CHO cells of anti-CD20 IgA3.0min-Obi antibody. IgA3.0min-Obi antibody contains IgA3.0min with Obinutuzumab (Obi) variable domains.

FIG. 6B shows comparison of production rate in HEK293F cells versus CHO cells of anti-Her2 IgA3.0min-Her2 antibody. IgA3.0min-Her2 antibody contains IgA3.0min with anti-Her2 variable domains.

FIG. 6C shows comparison of production rate in HEK293F cells versus CHO cells of anti-mCTLA4 IgA3.0min-mCTLA4 antibody. IgA3.0min-mCTLA4 contains IgA3.0min with anti-mCTLA4 variable domains.

FIG. 7A shows concentration of anti-GD2 IgA3.0min-ch14.18 antibody. IgA3.0min-ch14.18 antibody contains IgA3.0min with ch14.18 variable domains.

FIG. 7B shows concentration of anti-gp75 IgA3.0min-TA99 antibody. IgA3.0min-TA99 antibody contains IgA3.0min with TA99 variable domains.

FIG. 7C shows concentration of anti-Her2 IgA3.0min-Her2 antibody. IgA3.0min-Her2 antibody contains IgA3.0min with anti-Her2 variable domains (anti-Her2 variable domains were derived from anti-Her2 antibody Trastuzumab).

FIG. 7D shows concentration of anti-CD20 IgA3.0min-Obi antibody. IgA3.0min-Obi antibody contains IgA3.0min with Obinutuzumab (Obi) variable domains.

FIG. 8A shows production of anti-CD20 IgA4.0_NG-Obi variant. IgA4.0_NG-Obi variant contains IgA4.0 with CH2-N15.2G mutation in glycosylation site and variable domains from Obi.

FIG. 8B shows production of anti-CD20 IgA4.0_NT-Obi variant. IgA4.0_NT-Obi variant contains IgA4.0 with CH2-N15.2T mutation in glycosylation site and variable domains from Obi.

FIG. 8C shows production of anti-CD20 IgA4.0_NQ-Obi variant. IgA4.0 NQ-Obi variant contains IgA4.0 with CH2-N15.2Q mutation in glycosylation site and variable domains from Obi FIG. 8D shows production of anti-CD20 IgA4.0_NLT-TIS-Obi variant. IgA4.0_NLT-TIS-Obi variant contains IgA4.0 with N15.2T-L15.3I-T16S mutation in glycosylation site and variable domains from Obi.

FIG. 12A shows unstained CD20+Daudi cells control.

FIG. 12B shows Daudi cells stained with secondary antibody only negative control.

FIG. 12C shows stained with anti-CD20 IgA Obi (5 ug/mL) positive control.

FIG. 12D shows Daudi cells stained with IgA3.0+-Obi (supernatant). FIG. 12E shows Daudi cells stained with IgA3.0min-Obi (supernatant). FIGS. 12D-12E shows Daudi cells stained with supernatants from HEK293F cells transfected with IgA3.0min-Obi or IgA3.0+-Obi. Both variants IgA3.0+-Obi (FIG. 12D) and IgA3.0min-Obi (FIG. 12E) bind to CD20 positive Daudi to the same extent as IgA Obi (FIG. 12C).

FIG. 16A shows IgA3.0min-Her2 antibody induces ADCC to a similar or better extent than IgA2-Her2 of SKBR3 cells as determined by chromium release assay.

FIGS. 16B-16C show IgA3.0min-Obi antibody produced by HEK293F cells or CHO-S cells (ExpiCHO-S™ cells) induce similar level of ADCC of Ramos cells (FIG. 16B) and Daudi cells (FIG. 16C) as assessed by chromium release assay.

FIG. 16D shows induction of ADCC by IgA variants against Daudi cells. Purified IgA3.0min-Obi, supernatant from cells transfected with IgA3.0min-Obi, IgA4.0_NG-Obi, IgA4.0_NQ-Obi, IgA4.0_NT-Obi, and IgA4.0_NLT-TIS-Obi show increased ADCC compared to purified IgG1-Obi. IgA4.0-obi variants; IgA4.0_NG-Obi, IgA4.0_NQ-Obi, IgA4.0_NT-Obi, and IgA4.0_NLT-TIS-Obi show similar levels of ADCC induction compared to Purified IgA3.0min-Obi, supernatant from cells transfected with IgA-3.0min-Obi.

FIG. 17A demonstrates the engineered IgA3.0min variants; IgA3.0min with Obi variable domains and IgA3.0min with 2.3D11 variable domains showed increased thermostability compared to wild type IgA2(m1), i.e., IgA2 with ch14.18 variable domains and IgA2 with Her2 variable domains.

FIG. 17A also demonstrates the engineered IgA4.0 min variants; IgA4.0 NQ, IgA4.0 NT, IgA4.0 NLT-TIS, and IgA4.0 NG all with Obi variable domains showed increased thermostability compared to wild type IgA2(m1), i.e., IgA2 with ch14.18 variable domains and IgA2 with Her2 variable domains. The increased thermostability of engineered IgA3.0min variants and engineered IgA4.0 variants relative wild type IgA2(m1) is indicated by the shift to the higher temperatures.

FIG. 17B shows a plot of average Tm values of analysed engineered IgA3.0min variants and engineered IgA4.0 variants relative to wild type IgA2(m1). The plot shows engineered IgA3.0min variants and engineered IgA4.0 variants are more thermostable compared to wild type IgA2.

FIG. 17C shows antibodies exposed to increasing temperatures tested for their functionality in a PMN-ADCC against CD20 expressing Raji cells. Wild type IgA2(m1) shows a decremental efficacy from 47° C. on, while both IgA3.0min-Obi and IgA4.0 NT-Obi are still effective. At 71° C. both IgA3.0min-Obi as well as IgA4.0 NT-Obi give more than 50% killing efficacy while IgA2(m1) is dysfunctional at this temperature.

FIGS. 19A-19G show total glycosylation profile of wild type IgA2 and engineered IgA variants as determined with MALDI-TOF-MS.

FIG. 19A shows total glycosylation profile of HEK293 cells produced wild type IgA2; IgA2-Her2.

FIG. 19B shows total glycosylation profile of HEK293 cells produced engineered IgA3.0min variant; IgA3.0min-Her2. The profile shows all signals from a single glycosylation site present in engineered IgA3.0min variant.

FIG. 19C shows glycosylation site specific analysis of engineered IgA3.0min variant; IgA3.0min-Obi produced in HEK293F and CHO-S (ExpiCHO-S™). IgA3.0min-Obi produced in CHO-S (ExpiCHO-S™) shows less free galactoses implying to be less susceptible to ASGPR-dependent clearance in the liver.

FIGS. 19D-19G show native MS analysis of four IgA4.0 variants; IgA4.0_NG-Obi (FIG. 19D), IgA4.0_NQ-Obi (FIG. 19E), IgA4.0_NT-Obi (FIG. 19F), and IgA4.0_NLT-TIS-Obi (FIG. 19G) Large plot displays broad mass range of antibody, inset zooms in on highest peak. Observed mass is virtually equal to theoretical mass, excluding presence of bulky N-glycans, indicating absence of glycosylation in IgA4.0 variants.

FIG. 20A shows that IgA3.0min variant; IgA3.0min-dinutuximab showed extended half-life as compared to its wild type IgA2 counterpart.

FIG. 20B shows comparison between IgA3.0min and IgA4.0 in an Obinituzumab format. Engineered IgA4.0 variant; IgA4.0-obinutuzumab showed a better half-life profile than engineered IgA3.0min variant; IgA3.0min-Obinutuzumab. Obinutuzumab IgA4.0 can still be detected after 120 hours.

DETAILED DESCRIPTION OF THE DISCLOSURE

Figures 4A, 4B, 4C, 4D:
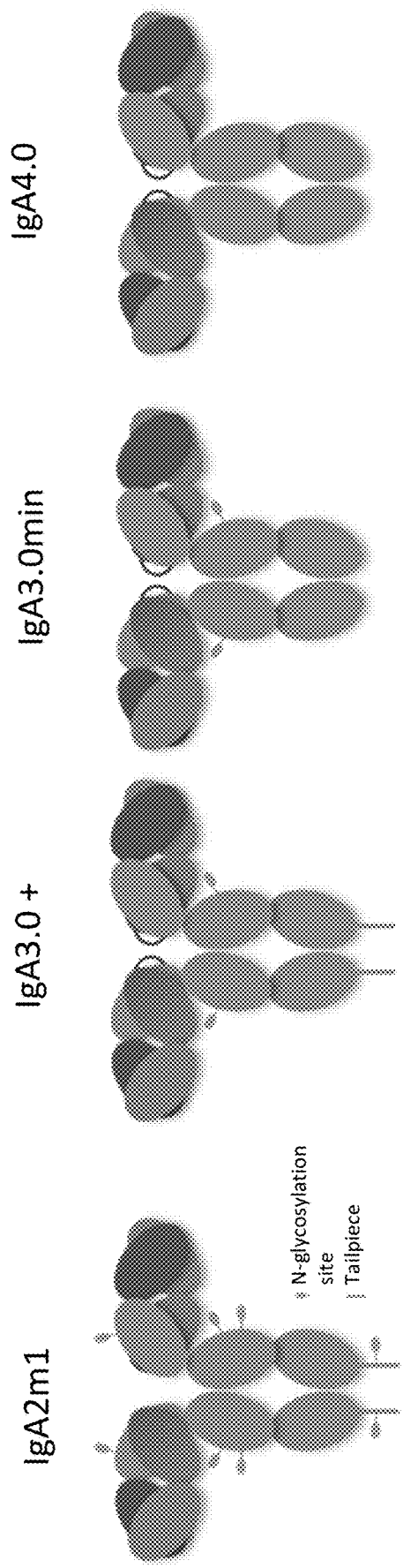
FIGS. 4A-4D show a schematic representation of engineered IgA variants relative to a wild type IgA (IgA2(m1)).

The following description and examples illustrate embodiments of the present disclosure in detail. It is to be understood that this disclosure is not limited to the particular embodiments described herein and as such can vary. Those of skill in the art will recognize that there are numerous variations and modifications of this disclosure, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the present disclosure may be described in the context of a single embodiment, the features can also be provided separately or in any suitable combination. Conversely, although the present disclosure may be described herein in the context of separate embodiments for clarity, the present disclosure can also be implemented in a single embodiment.

Definitions

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosure.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps. It is contemplated that any embodiment discussed in this specification can be implemented with respect to any method or composition of the present disclosure, and vice versa. Furthermore, compositions of the present disclosure can be used to achieve methods of the present disclosure.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. In another example, the amount "about 10" includes 10 and any amounts from 9 to 11.

In yet another example, the term "about" in relation to a reference numerical value can also include a range of values plus or minus 10%, 9%, 8%, 7%, 6%, 5%, 4%, 3%, 2%, or 1% from that value. Alternatively, particularly with respect to biological systems or processes, the term "about" can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "antibody" refers to an immunoglobulin (Ig) whether natural or partly or wholly synthetically produced. The term also covers any polypeptide or protein having a binding domain which is, or is homologous to, an antigen-binding domain. The term further includes "antigen-binding fragments" or "functional fragment thereof", or "fragment of an antibody", "antibody fragment", "functional fragment of an antibody" and other interchangeable terms for similar binding fragments such as described below.

An antibody includes, for example, monoclonal antibodies, chimeric antibodies, humanized antibodies, human antibodies, recombinant antibodies, chemically engineered antibodies, deimmunized antibodies, affinity-matured antibodies, multispecific antibodies (for example, bispecific antibodies and polyreactive antibodies), heteroconjugate antibodies, antibody fragments, and combinations thereof (e.g., a monoclonal antibody that is also deimmunized, a humanized antibody that is also deimmunized, etc.).

An antibody can be, for example, murine, chimeric, humanized, heteroconjugate, bispecific, diabody, triabody, or tetrabody. The antigen binding fragment can include, for example, Fab', F(ab')2, Fab, Fv, rIgG, scFv, hcAbs (heavy chain antibodies), a single domain antibody, VHH, VNAR, sdAbs, or nanobody.

The term "monoclonal antibodies," as used herein, refers to antibodies that are produced by a single clone of B-cells and bind to the same epitope. In contrast, "polyclonal antibodies" refer to a population of antibodies that are produced by different B-cells and bind to different epitopes of the same antigen. A whole antibody typically consists of four polypeptides: two identical copies of a heavy (H) chain polypeptide and two identical copies of a light (L) chain polypeptide. Each of the heavy chains contains one N-terminal variable (VH) region and three C-terminal constant (CH1, CH2 and CH3) regions, and each light chain contains one N-terminal variable (VL) region and one C-terminal constant (CL) region. The variable regions of each pair of light and heavy chains form the antigen binding site of an antibody. The VH and VL regions have a similar general structure, with each region comprising four framework regions, whose sequences are relatively conserved. The framework regions are connected by three complementarity determining regions (CDRs). The three CDRs, known as CDR1, CDR2, and CDR3, form the "hypervariable region" of an antibody, which is responsible for antigen binding.

As used herein a "chimeric antibody" is an antibody that comprises an amino acid sequence derived from two different species or, or two different sources, and includes synthetic molecules. By way of non-limiting example, an antibody that comprises a non-human CDR and a human variable region framework or constant or Fc region, an antibody with binding domains from two different monoclonal antibodies, or an antibody comprising a mutation of one or more amino acid residues to increase or decrease biological activity or binding of a part of the antibody. In certain embodiments, recombinant antibodies are produced from a recombinant DNA molecule or synthesized. In certain embodiments, the antibodies described herein are a polypeptide(s) encoded by one or more polynucleotides.

As used herein, "recognize" refers to the association or binding between an antigen binding domain and an antigen. As used herein, an "antigen" refers to an antigenic substance that can trigger an immune response in a host. An antigenic substance can be a molecule, such as a costimulatory molecule that can trigger an immune response in a host.

As used herein, an "antibody construct" refers to a construct that contains an antigen binding domain and an Fc domain.

As used herein, a "binding domain" refers to an antibody or non-antibody domain.

As used herein, an "antigen binding domain" refers to a binding domain from an antibody or from a non-antibody that can bind to an antigen. An antigen binding domain can be a tumor antigen binding domain or a binding domain that can bind to an antigen (such as a molecule) on an antigen presenting cell. Antigen binding domains can be numbered when there is more than one antigen binding domain in a given conjugate or antibody construct (e.g., first antigen binding domain, second antigen binding domain, third antigen binding domain, etc.). Different antigen binding domains in the same conjugate or construct can target the same antigen or different antigens (e.g., first antigen binding domain that can bind to a tumor antigen, second antigen binding domain that can bind to a molecule on an antigen presenting cell (APC antigen), and third antigen binding domain that can bind to an APC antigen). The term "antigen binding domain" refers to a fragment of an antibody that comprises the area which specifically binds to an epitope, and is complementary to part or all of an antigen. An antigen binding domain may be provided by, for example, one or more antibody variable domains (also called antibody variable regions). Particularly, an antigen binding domain comprises an antibody light chain variable region (VL) and an antibody heavy chain variable region (VH).

As used herein, the term "antigen" means a molecule or portion of a molecule that can react with a recognition site on an antibody. The term "antigen" also includes a molecule or a portion of a molecule that can, either by itself or in conjunction with an adjuvant or carrier, elicit an immune response (also called an "immunogen"). The term "antigen" as used herein includes molecules or portions of molecules (epitopes) that can elicit production of antibodies or that can bind to antibodies. The term includes materials that react strongly and with high specificity, and also includes materials that react weakly and/or with low affinity to an antibody.

The term "epitope," as used herein, refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen. Various techniques known to persons of ordinary skill in the art can be used to determine whether an antigen-binding domain of an antibody "interacts with one or more amino acids" within a polypeptide or protein. Exemplary techniques include, e.g., routine cross-blocking assay such as that described Antibodies, Harlow and Lane (Cold Spring Harbor Press, Cold Spring Harb., NY), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antigen-binding domain of an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues, which correspond to the specific amino acids with which the antibody interacts. See, e.g., Ehring (1999) Analytical Biochemistry 267(2):252-259; Engen and Smith (2001) Anal. Chem. 73:256A-265A. X-ray crystallography of the antigen/antibody complex may also be used for epitope mapping purposes.

As used herein, an "antibody antigen binding domain" refers to a binding domain from an antibody that can bind to an antigen.

As used herein, an "Fc domain" refers to an Fc domain from an antibody or from a non-antibody that can bind to an Fc receptor. As used herein, an "Fc domain" and an "Fc comprising domain" can be used interchangeably.

As used herein, a "target binding domain" refers to a construct that contains an antigen binding domain from an antibody or from a non-antibody that can bind to an antigen.

As used herein, the abbreviations for the natural 1—enantiomeric amino acids are conventional and can be as follows: alanine (A, Ala); arginine (R, Arg); asparagine (N, Asn); aspartic acid (D, Asp); cysteine (C, Cys); glutamic acid (E, Glu); glutamine (Q, Gin); glycine (G, Gly); histidine (H, His); isoleucine (I, He); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); valine (V, Val). Unless otherwise specified, X can indicate any amino acid. In some aspects, X can be asparagine (N), glutamine (Q), histidine (H), lysine (K), or arginine (R).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "cancer," "tumor," "proliferative disease," "malignancy," or "malignant disease" relate to the physiological condition in mammals characterized by deregulated cell growth. Cancer is a class of diseases in which a group of cells display uncontrolled growth or unwanted growth. Cancer cells can also spread to other locations, which can lead to the formation of metastases. Spreading of cancer cells in the body can, for example, occur via lymph or blood. Uncontrolled growth, intrusion and metastasis formation are also termed malignant properties of cancers. These malignant properties differentiate cancers from benign tumors, which typically do not invade or metastasize.

"Antigen recognition moiety" or "antibody recognition domain" refers to a molecule or portion of a molecule that specifically binds to an antigen. In one embodiment, the antigen recognition moiety is an antibody, antibody like molecule or fragment thereof and the antigen is a tumor antigen or an infectious disease antigen.

The terms "fragment of an antibody," "antibody fragment," "functional fragment of an antibody," "antigen-binding portion" or their grammatical equivalents are used interchangeably herein to mean one or more fragments or portions of an antibody that retain the ability to specifically bind to an antigen (see, generally, Holliger et al., Nat. Biotech., 23(9):1126-1129 (2005)). The antibody fragment desirably comprises, for example, one or more CDRs, the variable region (or portions thereof), the constant region (or portions thereof), or combinations thereof. Examples of antibody fragments include, but are not limited to, (i) a Fab fragment, which is a monovalent fragment consisting of the VL, VH, CL, and CH1 domains; (ii) a F(ab')2 fragment, which is a bivalent fragment comprising two Fab fragments linked by a disulfide bridge at the stalk region; (iii) a Fv fragment consisting of the VL and VH domains of a single arm of an antibody; (iv) a single chain Fv (scFv), which is a monovalent molecule consisting of the two domains of the Fv fragment (i.e., VL and VH) joined by a synthetic linker which enables the two domains to be synthesized as a single polypeptide chain (see, e.g., Bird et al., Science, 242: 423-426 (1988); Huston et al., Proc. Natl. Acad. Sci. USA, 85: 5879-5883 (1988); and Osbourn et al., Nat. Biotechnol., 16: 778 (1998)) and (v) a diabody, which is a dimer of polypeptide chains, wherein each polypeptide chain comprises a VH connected to a VL by a peptide linker that is too short to allow pairing between the VH and VL on the same polypeptide chain, thereby driving the pairing between the complementary domains on different VH-VL polypeptide chains to generate a dimeric molecule having two functional antigen binding sites. Antibody fragments are known in the art and are described in more detail in, e.g., U.S. Pat. No. 8,603,950. Other antibody fragments can include variable fragments of heavy chain antibodies (VHH).

The term "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and Schirmer, R. H., Principles of Protein Structure, Springer-Verlag, New York (1979)). According to such analyses, groups of amino acids may be defined where amino acids within a group exchange preferentially with each other, and therefore resemble each other most in their impact on the overall protein structure (Schulz, G. E. and Schirmer, R. H., supra). Examples of conservative mutations include amino acid substitutions of amino acids within the sub-groups above, for example, lysine for arginine and vice versa such that a positive charge may be maintained; glutamic acid for aspartic acid and vice versa such that a negative charge may be maintained; serine for threonine such that a free —OH can be maintained; and glutamine for asparagine such that a free —NH2 can be maintained. Alternatively or additionally, the therapeutic IgA antibodies can comprise the amino acid sequence of the reference protein with at least one non-conservative amino acid substitution.

The terms "non-conservative mutation" or "non-conservative amino acid substitution" involve amino acid substitutions between different groups, for example, lysine for tryptophan, or phenylalanine for serine, etc. In this case, it is preferable for the non-conservative amino acid substitution to not interfere with, or inhibit the biological activity of the therapeutic IgA antibody. The non-conservative amino acid substitution may enhance the biological activity of the therapeutic IgA antibody, such that the biological activity of the therapeutic IgA antibody is increased as compared to the wild type therapeutic IgA antibody.

As used herein, "humanized" antibodies refer to forms of non-human (e.g. murine) antibodies that are specific chimeric immunoglobulins, immunoglobulin chains, or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Other forms of humanized antibodies have one or more CDRs (one, two, three, four, five, six) which are altered with respect to the original antibody, which are also termed one or more CDRs "derived from" one or more CDRs from the original antibody.

As used herein, an "isolated antibody" is one that has been separated and/or recovered from a component of its natural environment. Contaminant components of its natural environment are materials that would interfere with diagnostic or therapeutic uses of the antibody, and may include enzymes, hormones, and other proteinaceous or non-proteinaceous components. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity as shown by SDS-PAGE under reducing or non-reducing conditions and using Coomassie blue or, preferably, silver staining. Isolated antibody includes the antibody in situ within recombinant cells since at least one component of the antibody's natural environment will not be present. Ordinarily, however, isolated antibody will be prepared by at least one purification step.

By "substantially purified" is meant that the antibody, or the functional fragment thereof is substantially free of cellular material or other contaminating proteins from the cell or tissue source from which it is derived, or is substantially free from chemical precursors or other chemicals when chemically synthesized. The language includes preparations of an antibody, which is separated from cellular components of the cells from which it is isolated or recombinantly produced. Thus, an antibody, that is substantially free of cellular material includes preparations having less than about 30%, 20%, 10% or 5% (by dry weight) of contaminating protein and culture medium. In some embodiments, the antibody can be purified by chromatography, for example, size exclusion chromatography or ion exchange chromatography.

As used herein, the term "Complementarity Determining Regions" (CDRs, i.e., CDR1, CDR2, and CDR3) refers to the amino acid residues of an antibody variable domain the presence of which are necessary for antigen binding. Each variable domain typically has three CDR regions identified as CDR1, CDR2 and CDR3. The CDRs of variable heavy chain can be CDR-H1, CDR-H2 and CDR-H3. The CDRs of variable light chain can be CDR-L1, CDR-L2 and CDR-L3. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987)). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3 (Kabat et al., Sequences of Proteins of Immunological Interest, 5th ed. (1991)). Tus, the HVs may be comprised within the corresponding CDRs and references herein to the "hypervariable loops" of VH and VL domains should be interpreted as also encompassing the corresponding CDRs, and vice versa, unless otherwise indicated. The more highly conserved regions of variable domains are called the framework region (FR), as defined below. The variable domains of native heavy and light chains each comprise four FRs (FR1, FR2, FR3 and FR4, respectively), largely adopting a [beta]-sheet configuration, connected by the three hypervariable loops. The hypervariable loops in each chain are held together in close proximity by the FRs and, with the hypervariable loops from the other chain, contribute to the formation of the antigen-binding site of antibodies. Structural analysis of antibodies revealed the relationship between the sequence and the shape of the binding site formed by the complementarity determining regions (Chothia et al., J. Mol. Biol. 227: 799-817 (1992)); Tramontano et al., J. Mol. Biol, 215: 175-182 (1990)). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Allazikani et al (1997) J. Molec. Biol. 273:927-948)). A CDR may refer to CDRs defined by either approach or by a combination of both approaches.

A "constant region" of an antibody refers to the constant region of the antibody light chain, i.e, a light chain constant region or the constant region of the antibody heavy chain, i.e., a heavy chain constant region either alone or in combination. The constant region does not vary with respect to antigen specificity.

As used herein, the term "heavy chain region" includes amino acid sequences derived from the constant domains of an immunoglobulin heavy chain. A polypeptide comprising a heavy chain region comprises at least one of: a CH1 domain, a hinge (e.g., upper, middle, and/or lower hinge region) domain, a CH2 domain, a CH3 domain, or a variant or fragment thereof. In an embodiment, an antibody or an antigen-binding fragment thereof may comprise the Fc region of an immunoglobulin heavy chain (e.g., a hinge portion, a CH2 domain, and a CH3 domain). In another embodiment, an antibody or an antigen-binding fragment thereof lacks at least a region of a constant domain (e.g., all or part of a CH2 domain). In certain embodiments, at least one, and preferably all, of the constant domains are derived from a human immunoglobulin heavy chain. For example, in one preferred embodiment, the heavy chain region comprises a fully human hinge domain. In other preferred embodiments, the heavy chain region comprising a fully human Fc region (e.g., hinge, CH2 and CH3 domain sequences from a human immunoglobulin). In certain embodiments, the constituent constant domains of the heavy chain region are from different immunoglobulin molecules. For example, a heavy chain region of a polypeptide may comprise a domain derived from an IgA molecule and a hinge region derived from an IgA1 or IgA2 molecule. In other embodiments, the constant domains are chimeric domains comprising regions of different immunoglobulin molecules. For example, a hinge may comprise a first region from an IgA1 molecule and a second region from an IgA2 molecule. As set forth above, it will be understood by one of ordinary skill in the art that the constant domains of the heavy chain region may be modified such that they vary in amino acid sequence from the naturally occurring (wild-type) immunoglobulin molecule. That is, the polypeptides of the invention disclosed herein may comprise alterations or modifications to one or more of the heavy chain constant domains (CH1, hinge, CH2 or CH3) and/or to the light chain constant domain (CL). Exemplary modifications include additions, deletions or substitutions of one or more amino acids in one or more domains. In some embodiments, the modifications are selected from modifications in Table 2.

The antibodies or antigen-binding fragment thereof of the present disclosure can comprise a CDR3 region that is a length of at least about 10, 11, 12, 13, 14, 15, 16, 17, 18, 19, 20, 21, 22, 23, 24, 25, 26, 27, 28, 29, or 30 amino acids in length. The antibodies or antigen-binding fragment thereof of the present disclosure can comprise a CDR3 region that is at least about 18 amino acids in length.

As used herein, the term "hinge region" includes the region of a heavy chain molecule that joins the CH1 domain to the CH2 domain. The hinge region can comprise approximately 25 residues and is flexible, thus allowing the two N-terminal antigen binding regions to move independently. Hinge regions can be subdivided into three distinct domains: upper, middle, and lower hinge domains (Roux et al. J. Immunol. 1998 161:4083).

As used herein, the term "Fv" is the minimum antibody fragment that contains a complete antigen-recognition and -binding site. This fragment consists of a dimer of one heavy- and one light-chain variable region domain in tight, non-covalent association.

From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Heavy chain variable region" or "VH" with regard to an antibody refers to the fragment of the heavy chain that contains three CDRs interposed between flanking stretches known as framework regions, these framework regions are generally more highly conserved than the CDRs and form a scaffold to support the CDRs.

"light chain variable region" or "VL" with regard to an antibody refers to the fragment of the light heavy chain that contains three CDRs interposed between flanking stretches known as framework regions, these framework regions are generally more highly conserved than the CDRs and form a scaffold to support the CDRs.

Six hypervariable loops (three loops each from the Heavy and Light chain) contribute the amino acid residues for antigen-binding and confer antigen-binding specificity to the antibody. However, even a single variable domain (or half of an Fv comprising only three CDRs specific for an antigen) has the ability to recognize and bind antigen, although at a lower affinity than the entire binding site.

"Framework" or FR residues are those variable domain residues other than the hypervariable region residues.

It is understood in the art that an antibody is a glycoprotein having at least two heavy (H) chains and two light (L) chains interconnected by disulfide bonds, or an antigen-binding portion thereof. A heavy chain is comprised of a heavy chain variable region (VH) and a heavy chain constant region (CH1, CH2 and CH3). A light chain is comprised of a light chain variable region (VL) and a light chain constant region (CL). The variable regions of both the heavy and light chains comprise framework regions (FRs or FWRs) and hypervariable regions (HVRs). The HVRs are the amino acid residues of an antibody that are responsible for antigen binding. The hypervariable region generally comprises amino acid residues from a complementarity determining region (CDR), which have the highest sequence variability and/or involved in antigen recognition. With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or α-CDRs. Exemplary α-CDRs (a-CDR-L1, α-CDR-L2, α-CDR-L3, α-CDR-H1, α-CDR-H2, and α-CDR-H3) occur at amino acid residues 31-34 of L1, 50-55 of L2, 89-96 of L3, 31-35B of H1, 50-58 of H2, and 95-102 of H3. (See, e.g., Fransson, Front. Biosci. 13:1619-1633 (2008))

Unless otherwise indicated, HVR residues and other residues in the variable domain (e.g., FR residues) are numbered herein according to Kabat et al., supra. A variable region is a domain of an antibody heavy or light chain that is involved in binding the antibody to antigen. (See, e.g., Kindt et al. Kuby Immunology, 6th ed., W.H. Freeman and Co., p. 91 (2007)). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. (See, e.g., Portolano et al., J. Immunol. 150:880-887 (1993); Clarkson et al., Nature 352:624-628 (1991)). The four FWR regions are typically more conserved while CDR regions (CDR1, CDR2 and CDR3) represent hypervariable regions and are arranged from NH2 terminus to the COOH terminus as follows: FWR1, CDR1, FWR2, CDR2, FWR3, CDR3, and FWR4. The variable regions of the heavy and light chains contain a binding domain that interacts with an antigen while, depending of the isotype, the constant region(s) may mediate the binding of the immunoglobulin to host tissues or factors. An antibody also includes chimeric antibodies, humanized antibodies, and recombinant antibodies, human antibodies generated from a transgenic non-human animal, as well as antibodies selected from libraries using enrichment technologies available to the artisan.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa ("u") and lambda (" ") light chains refer to the two major antibody light chain isotypes.

An antibody or antigen-binding fragment thereof "specifically binds" or "preferentially binds" to a target if it binds with greater affinity and/or avidity than it binds to epitopes on unrelated polypeptides. The specificity of an antibody or antigen-binding fragment or portion thereof can be determined based on affinity and/or avidity. Methods to determine such specific binding are also well known in the art. According to certain embodiments of the present disclosure, the antibodies or antigen-binding fragment thereof can bind to a human cancer antigen but not to a cancer antigen from other species. Alternatively, the antibodies or antigen-binding fragment thereof, in certain embodiments, bind to human cancer antigen and to cancer antigen from one or more non-human species. For example, the antibodies or antigen-binding fragment thereof can bind to human cancer antigen and can bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee cancer antigen.

The affinity, represented by the equilibrium constant for the dissociation ($K_D$) of an antigen with an antigen-binding protein, is a measure for the binding strength between an antigenic determinant and an antigen-binding site on the antigen-binding protein: the lesser the value of the $K_D$, the stronger the binding strength between an antigenic determinant and the antigen-binding molecule. Alternatively, the affinity can also be expressed as the affinity constant ($K_A$), which is $1/K_D$). As will be clear to the skilled person, affinity can be determined in a manner known per se, depending on the specific antigen of interest. Accordingly, an antibody or antigen-binding fragment thereof as defined herein is said to be "specific for" a first target or antigen compared to a second target or antigen when it binds to the first antigen with an affinity (as described above, and suitably expressed, for example as a $K_D$ value) that is at least 50 times, such as at least 100 times, and preferably at least 1000 times, and up to 10,000 times or more better than the affinity with which said amino acid sequence or polypeptide binds to another target or polypeptide. Preferably, when an antibody or antigen-binding fragment thereof is "specific for" a target or antigen, compared to another target or antigen, it can bind the target or antigen, but does not bind the other target or antigen. However, as understood by one of ordinary skill in the art, in some embodiments, where a binding site on a target is shared or partially shared by multiple, different ligands, an antibody or antigen-binding fragment thereof can specifically bind to a target, such as cancer associated antigen, and have the functional effect of, for example, inhibiting/preventing tumor progression.

In some embodiments, an antibody provided herein has a dissociation constant ($K_D$) of about 1 µM, 100 nM, 10 nM, 5 nM, 2 nM, 1 nM, 0.5 nM, 0.1 nM, 0.05 nM, 0.01 nM, or 0.001 nM or less (e.g., $10^{-8}$ M or less, e.g., from $10^{-8}$ M to $10^{-13}$ M, e.g., from $10^{-9}$ M to $10^{-13}$ M). Another aspect of the invention provides for an antibody or antigen-binding fragment thereof with an increased affinity for its target, for example, an affinity matured antibody. An affinity matured antibody is an antibody with one or more alterations in one or more hypervariable regions (HVRs), compared to a parent antibody which does not possess such alterations, such alterations resulting in an improvement in the affinity of the antibody for antigen. These antibodies can bind to antigen with a $K_D$ of about $5 \times 10^{-9}$ M, $2 \times 10^{-9}$ M, $1 \times 10^{-9}$ M, $5 \times 10^{-10}$ M, $2 \times 10^{-10}$ M, $1 \times 10^{10}$ M, $5 \times 10^{-11}$ M, $1 \times 10^{-11}$ M, $5 \times 10^{-12}$ M, $1 \times 10^{-12}$ M, or less. In some embodiments, the present disclosure provides an antibody or antigen-binding fragment thereof which has an increased affinity of at least 1.5 fold, 2 fold, 2.5 fold, 3 fold, 4 fold, 5 fold, 10 fold, 20 fold or greater as compared to a WT IgA antibody or a WT IgG antibody, containing the heavy chain sequence and light chain sequence, or both. In other embodiments, the antibody or a functional fragment thereof provided herein competes for binding to the same epitope as a corresponding antibody from which the variable domains are derived. In some embodiments, the antibody or antigen-binding fragment thereof that binds to the same epitope, and/or competes for binding to the same epitope as an antibody exhibits effector function activities, such as, for example, Fc-mediated cellular cytotoxicity, including ADCC activity.

$K_D$ can be measured by any suitable assay. For example, $K_D$ can be measured by a radiolabeled antigen-binding assay (RIA) (See, e.g., Chen et al., J. Mol. Biol. 293:865-881 (1999); Presta et al., Cancer Res. 57:4593-4599 (1997)). For example, $K_D$ can be measured using a surface plasmon resonance assay (e.g., using a BIACORE®0-2000 or a BIACORE®0-3000). For example, $K_D$ can be measured using a competitive ELISA.

Avidity is the measure of the strength of binding between an antigen-binding molecule and the pertinent antigen. Avidity is related to both the affinity between an antigenic determinant and its antigen-binding site on the antigen-binding molecule, and the number of pertinent binding sites present on the antigen-binding molecule. Typically, antigen-binding proteins will bind to their cognate or specific antigen with a dissociation constant ($K_D$ of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than $10^4$ M$^{-1}$) is generally considered to indicate non-specific binding. The $K_D$ for biological interactions which are considered meaningful (e.g., specific) are typically in the range of $10^{-10}$ M (0.1 nM) to $10^{-5}$ M (10000 nM). The stronger an interaction is, the lower is its $K_D$. Preferably, a binding site on an anti-LAP antibody or antigen-binding fragment thereof described herein will bind with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

The term "Ikon", as used herein, is intended to refer to the rate constant for association of an antibody or antigen-binding fragment thereof to an antigen.

The term "Koff", as used herein, is intended to refer to the rate constant for dissociation of an antibody or antigen-binding fragment thereof from the antibody/antigen complex.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from immunoglobulin sequences, disclosed herein. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human immunoglobulin VH and VL sequences, may not naturally exist within the human antibody germline repertoire in vivo.

In the context of an antibody or antigen-binding fragment thereof, the term "specificity" or "specific for" refers to the number of different types of antigens or antigenic determinants to which a particular antibody or antigen-binding fragment thereof can bind. The specificity of an antibody or antigen-binding fragment or portion thereof can be determined based on affinity and/or avidity. The affinity, represented by the equilibrium constant for the dissociation ($K_D$) of an antigen with an antigen-binding protein, is a measure for the binding strength between an antigenic determinant and an antigen-binding site on the antigen-binding protein: the lesser the value of the $K_D$, the stronger the binding strength between an antigenic determinant and the antigen-binding molecule. Alternatively, the affinity can also be expressed as the affinity constant ($K_A$), which is $1/K_D$). As will be clear to the skilled person, affinity can be determined in a manner known per se, depending on the specific antigen of interest. Accordingly, an antibody or antigen-binding fragment thereof as defined herein is said to be "specific for" a first target or antigen compared to a second target or antigen when it binds to the first antigen with an affinity (as described above, and suitably expressed, for example as a $K_D$ value) that is at least 50 times, such as at least 100 times, and preferably at least 1000 times, and up to 10,000 times or more better than the affinity with which said amino acid sequence or polypeptide binds to another target or polypeptide. Preferably, when an antibody or antigen-binding fragment thereof is "specific for" a target or antigen, compared to another target or antigen, it can bind the target or antigen, but does not bind the other target or antigen.

However, as understood by one of ordinary skill in the art, in some embodiments, where a binding site on a target is shared or partially shared by multiple, different ligands, an antibody or antigen binding fragment thereof can specifically bind to a target antigen, and have the functional effect of, for example, inhibiting/preventing tumor progression.

Avidity is the measure of the strength of binding between an antigen-binding molecule and the pertinent antigen. Avidity is related to both the affinity between an antigenic determinant and its antigen binding site on the antigen-binding molecule, and the number of pertinent binding sites present on the antigen-binding molecule. Typically, antigen-binding proteins will bind to their cognate or specific antigen with a dissociation constant ($K_D$ of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than $10^4$ $M^{-1}$) is generally considered to indicate non-specific binding. The $K_D$ for biological interactions which are considered meaningful (e.g., specific) are typically in the range of $10^{-10}$ M (0.1 nM) to $10^{-5}$ M (10000 nM). The stronger an interaction is, the lower is its $K_D$. Preferably, a binding site on an anti-LAP antibody or antigen-binding fragment thereof described herein will bind with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art as well as other techniques as mentioned herein.

The term "fusion protein" as used herein refers to a polypeptide that comprises an amino acid sequence of an antibody or fragment thereof and an amino acid sequence of a heterologous polypeptide (i.e., an unrelated polypeptide).

In some embodiments, the antibody or antigen binding fragment thereof of the present disclosure is is a single domain antibody. The expression "single domain antibody" (sdAbs) or "single variable domain (SVD) antibody" generally refers to a single variable region (VH or ') wherein the antibody-antigen binding can be imparted. In other words, single variable domain does not need to recognize the target antigen by interacting with another variable region. A single domain antibody monomers single arm antigen binding by each antibody variable region (VH*VJ composition. Examples of single domain antibodies include those derived from camelids (camels and llamas) and cartilaginous fish (e.g. nurse sharks) antibodies and those antibodies (Ward et al from human and mouse antibodies by recombinant methods, Nature (1989) 341: 544-546; Dooley and Flajnik, Dev Comp Immunol (2006) 30: 43-56; Muyldermans et, Trend-Biochem Sci (2001) 26: 230-235; Holt et, Trends Biotechnol (2003): 21: 484-490; WO 2005/035572; TO 03/035694; Davies and Riechmann, Febs Lett (1994) 339: 285-290; WO00/29 004; WO 02/051870) and a single variable region of an antibody can be other than a single domain antibody variable regions or variable domains are present in an antigen binding arm (e.g., homo- or hetero-multimer together).

As used herein the term 'modification" refers to an amino acid substitution or an amino acid deletion of one or more amino acid residues in a heavy chain constant region of an antibody, compared to a WT heavy chain constant region of a WT antibody. In some embodiments, the modification is in an amino acid residue in the IgA CH1 region of the heavy chain constant region. In some embodiments, the modification is in an amino acid residue in the IgA CH2 region of the heavy chain constant region. In some embodiments, the modification is in an amino acid residue in the IgA CH3 region of the heavy chain constant region. In some embodiments, the modification is selected from Table 2. In some embodiments, the one or more modifications disclosed herein result in an improved property of the antibody comprising the one or more modifications compared to a corresponding WT antibody.

The term "improved property" means a characteristic associated with an antibody comprising the one or more modifications disclosed herein, that is improved compared to the parent WT antibody not comprising the one or more modifications. Such an improved property includes, but is not limited to, increased thermostability, increased circulating half-life, increased ADCC, decreased aggregation, decreased aggregation with serum proteins, increased tumor targeting, increased stability, decreased glycosylation, increased binding a FcαR expressed on an immune cell. In some embodiments, the improved property is an increase in one or more effector functions of the antibody or the functional fragment thereof, as compared to a corresponding WT IgA. Effector functions are biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis.

In some embodiments, the antibodies or a functional fragment thereof disclosed herein (e.g., comprising the one or modifications disclosed herein in the IgA heavy chain constant region), have at least 2%, 3%, 4%, 5%, 7%, 8%, 10%, 20%, 30%, 40%, 50%, 60%, 70%, 80%, 90%, or at least 100% of one or more improved property, compared to a corresponding WT IgA antibody or a corresponding WT IgG antibody.

As used herein the term "corresponding" unmodified antibody means a wild type antibody of the same sequence as the antibody comprising one or more select modifications disclosed herein, but without the one or more selected modifications described herein, in particular in the heavy chain constant region. In some embodiments, the corresponding antibody can be a WT IgA antibody comprising a WT IgA heavy chain constant region. In some embodiments, the corresponding antibody can be a WT IgG antibody comprising a WT IgG heavy chain constant region. In some embodiments, a corresponding WT IgA antibody is a WT IgA1 antibody. In some embodiments, the corresponding WT IgA antibody is WT IgA2 antibody. In some embodiments, a corresponding WT IgA antibody comprises a wild type IgA heavy chain constant region comprising an amino acid sequence set forth in SEQ ID NO: 1. In some embodiments, a corresponding WT IgA2 antibody comprises a wild type IgA2 heavy chain constant region comprising an amino acid sequence set forth in SEQ ID NO: 1. In some embodiments, a corresponding WT IgA antibody comprises a wild type IgA heavy chain constant region comprising an amino acid sequence set forth in SEQ ID NO: 2 In some embodiments, a corresponding WT IgA antibody comprises a wild type IgA heavy chain constant region comprising an amino acid sequence set forth in SEQ ID NO: 2. In some embodiments, the WT IgA heavy chain constant region comprises an amino acid sequence set forth in SEQ ID NO: 1. In some embodiments, the WT IgA2 heavy chain constant region comprises an amino acid sequence set forth in SEQ ID NO: 1. In some embodiments, the amino acid modifications disclosed herein are relative to amino acid residues at select positions in the WT IgA heavy chain constant region (e.g., WT IgA2 heavy chain constant region) comprising an amino acid sequence set forth in SEQ ID NO: 1, numbering according to IMGT® scheme.

In some embodiments, the WT IgA heavy chain constant region comprises an amino acid sequence set forth in SEQ ID NO: 2. In some embodiments, the WT IgA2 heavy chain constant region comprises an amino acid sequence set forth in SEQ ID NO: 2. In some embodiments, the amino acid modifications disclosed herein are relative to amino acid residues at select positions in the WT IgA heavy chain constant region (e.g., WT IgA2 heavy chain constant region) comprising an amino acid sequence set forth in SEQ ID NO: 2, numbering according to IMGT® scheme.

In some embodiments, the WT IgA heavy chain constant region comprises an amino acid sequence set forth in SEQ ID NO: 3. In some embodiments, the WT IgA2 heavy chain constant region comprises an amino acid sequence set forth in SEQ ID NO: 3. In some embodiments, the amino acid modifications disclosed herein are relative to amino acid residues at select positions in the WT IgA heavy chain constant region (e.g., WT IgA2 heavy chain constant region) comprising an amino acid sequence set forth in SEQ ID NO: 3, numbering according to IMGT® scheme.

The term "Fab" as used herein is intended to refer to a region of an antibody composed of one constant and one variable domain of each of the heavy and the light chains (monovalent antigen-binding fragment), but wherein the heavy chain is truncated such that it lacks the CH2 and CH3 domain (ie VH, CH1, VL, and CL), and may also lack some or all of the hinge region. It can be produced by digestion of a whole antibody with the enzyme papain. Fab may refer to this region in isolation, or this region in the context of a full length antibody, immunoglobulin construct or Fab fusion protein.

The term Fab' as used herein can be obtained by treating a whole antibody with pepsin, followed by reduction, to yield a molecule consisting of an intact light chain and a portion of a heavy chain comprising a VH and a single constant domain. Two Fab' fragments are obtained per antibody treated in this manner.

By "scFv" it is meant an antibody fragment comprising the VFI and VL domains of an antibody, wherein these domains are present in a single polypeptide chain. See, for example, U.S. Pat. Nos. 4,946,778, 5,260,203, 5,455,030, and 5,856,456. Generally, the Fv polypeptide further comprises a polypeptide linker between the VH and VL domains that enables the scFv to form the desired structure for antigen-binding. For a review of scFv see Pluckthun (1994) The Pharmacology of Monoclonal Antibodies vol 113 ed. Rosenburg and Moore (Springer-Verlag, New York) pp 269-315. The VFI and VL domain complex of Fv fragments may also be stabilized by a disulfide bond (U.S. Pat. No. 5,747,654).

The term "in vivo half-life" or "circulating half-life" as used herein refers to the circulation of an antibody or a functional fragment thereof in a given animal and is represented by a time required for half the quantity administered in the animal to be cleared from the circulation.

The term "increased circulating half life" as used herein means that the antibody comprising one or more modifications relative to a WT IgA antibody as provided according to the invention has a greater persistence in the serum or plasma and/or takes a greater period of time to reduce to half the maximal measured serum or plasma concentration relative to the same antibody, that does not contain the same modifications, i.e., a WT antibody e.g., WT IgA antibody.

The term "increased thermostability" means a higher retention of a biological activity e.g., ADCC, binding to an antigen, binding to a FcαR, of an antibody or a functional fragment disclosed herein after a period of incubation at a temperature relative to a corresponding WT IgA antibody. The increased thermostability of the can be assessed, for example, under conditions of one or more (e.g., several) temperatures. For example, the one or more (e.g., several) temperatures can be any temperature or temperatures in the range of 45° C. to 95° C., e.g., 45, 50, 55, 60, 65, 70, 75, 80, 85, or 95° C. (or in between, e.g., 62° C., 68° C., 72° C., etc.) at one or more (e.g., several) pHs in the range of 3 to 9, e.g., 3.0, 3.5, 4.0, 4.5, 5.0, 5.5, 6.0, 6.5, 7.0, 7.5, 8.0, 8.5, or 9.0 (or in between) for a suitable period (time) of incubation, e.g., 1 minute, 5 minutes, 10 minutes, 15 minutes, 20 minutes, 25 minutes, 30 minutes, 45 minutes, or 60 minutes (or in between, e.g., 23 minutes, 37 minutes, etc.), such that the variant retains residual activity. However, longer periods of incubation can also be used. The term "increased thermostability" can be used interchangeably with "improved thermostability".

As used herein, the term "naturally occurring" as it relates to a glycosylation site or an amino acid residue in a IgA heavy chain constant region, refers to the fact that the glycosylation site or the amino acid residue can be found in nature in the IgA heavy chain constant region, for example, can be isolated from a source in nature and has not been intentionally modified in the laboratory by a human (including a virus). A polypeptide or polynucleotide sequence present in an organism is a sequence naturally occurring.

The terms "disease", "disorder", or "condition" are used interchangeably herein, refer to any alternation in state of the body or of some of the organs, interrupting or disturbing the performance of the functions and/or causing symptoms such as discomfort, dysfunction, distress, or even death to the person afflicted or those in contact with a person. A disease or disorder can also be related to a distemper, ailing, ailment, malady, disorder, sickness, illness, complaint, or affectation.

The term "in need thereof" when used in the context of a therapeutic or prophylactic treatment, means having a disease, being diagnosed with a disease, or being in need of preventing a disease, e.g., for one at risk of developing the disease. Thus, a subject in need thereof can be a subject in need of treating or preventing a disease.

As used herein, the term "administering," refers to the placement of a compound (e.g., an antibody or antigen binding fragment thereof as disclosed herein) into a subject by a method or route that results in at least partial delivery of the agent at a desired site. Pharmaceutical compositions comprising an antibody or antigen binding fragment thereof, disclosed herein can be administered by any appropriate route which results in an effective treatment in the subject, including but not limited to intravenous, intraarterial, injection or infusion directly into a tissue parenchyma, etc. Where necessary or desired, administration can include, for example, intracerebroventricular ("icv") administration, intranasal administration, intracranial administration, intracelial administration, intracerebellar administration, or intrathecal administration.

The term "cancer" refers to a disease characterized by the rapid and uncontrolled growth of aberrant cells. Cancer cells can spread locally or through the bloodstream and lymphatic system to other parts of the body.

The term "anti-tumor effect" refers to a biological effect which can be manifested by various means, including but not limited to, e.g., a decrease in tumor volume, a decrease in the number of tumor cells, a decrease in the number of metastases, an increase in life expectancy, decrease in tumor cell proliferation, decrease in tumor cell survival, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

As used herein, a "subject", "patient", "individual" and like terms are used interchangeably and refers to a vertebrate, a mammal, a primate, or a human. Mammals include, without limitation, humans, primates, rodents, wild or domesticated animals, including feral animals, farm animals, sport animals, and pets. Primates include, for example, chimpanzees, cynomolgus monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, and canine species, e.g., dog, fox, wolf, avian species, e.g., chicken, emu, ostrich, and fish, e.g., trout, catfish and salmon. The terms, "individual," "patient" and "subject" are used interchangeably herein. A subject can be male or female.

In some embodiments, the subject is a mammal. The mammal can be a human, non-human primate, mouse, rat, dog, cat, horse, or cow, but is not limited to these examples. Mammals other than humans can be advantageously used as subjects that represent animal models of conditions or disorders associated with uncontrolled cell growth (e.g., a cancer). Non-limiting examples include murine tumor models. In addition, the compositions and methods described herein can be used to treat domesticated animals and/or pets. A subject can be one who has been previously diagnosed with or identified as suffering from a cancer. A subject can be one who is diagnosed and currently being treated for, or seeking treatment, monitoring, adjustment or modification of an existing therapeutic treatment, or is at a risk of developing a given disorder (e.g., cancer).

A "cytotoxic agent" refers to an agent that has a cytotoxic and/or cytostatic effect on a cell. A "cytotoxic effect" refers to the depletion, elimination and/or the killing of a target cell(s). A "cytostatic effect" refers to the inhibition of cell proliferation.

As used herein, the terms "protein", "peptide" and "polypeptide" are used interchangeably to designate a series of amino acid residues connected to each other by peptide bonds between the alpha-amino and carboxy groups of adjacent residues. The terms "protein", "peptide" and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein", "peptide" and "polypeptide" are used interchangeably herein when referring to a gene product and fragments thereof. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric. A polypeptide can have the amino acid sequence of naturally occurring polypeptide from any mammal. Such native sequence polypeptide can be isolated from nature or can be produced by recombinant or synthetic means. In some embodiments, the polypeptide is a "variant". "Variant" means a biologically active polypeptide having at least about 80% amino acid sequence identity with the native sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, or deleted, at the N- or C-terminus of the polypeptide. In some embodiments, a variant will have at least about 80% amino acid sequence identity. In some embodiments, a variant will have at least about 90% amino acid sequence identity. In some embodiments, a variant will have at least about 95% amino acid sequence identity with the native sequence polypeptide. A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and glycosylation The terms "increased", "increase", or "enhance" are all used herein to generally mean an increase by a statically significant amount; for the avoidance of doubt, the terms "increased", "increase", or "enhance", mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "fusion protein" as used herein refers to a polypeptide that comprises an amino acid sequence of an antibody or fragment thereof and an amino acid sequence of a heterologous polypeptide (i.e., an unrelated polypeptide).

The terms, "decrease", "reduce", "reduction", "lower" or "lowering," or "inhibit" are all used herein generally to mean a decrease by a statistically significant amount. For example, "decrease", "reduce", "reduction", or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., tumor size after treatment as compared to a reference level prior to the treatment), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease. Reduce or inhibit can refer to, for example, the symptoms of the disorder being treated, the presence or size of metastases or micrometastases, the size of the primary tumor, the presence or the size of the dormant tumor.

The terms "synthetic polynucleotide," "synthetic gene" or "synthetic polypeptide," as used herein, mean that the corresponding polynucleotide sequence or portion thereof, or amino acid sequence or portion thereof, is derived, from a sequence that has been designed, or synthesized de novo, or modified, compared to an equivalent naturally-occurring sequence. Synthetic polynucleotides (antibodies or antigen-binding fragments) or synthetic genes can be prepared by methods known in the art, including but not limited to, the chemical synthesis of nucleic acid or amino acid sequences. Synthetic genes are typically different from naturally-occurring genes, either at the amino acid, or polynucleotide level, (or both) and are typically located within the context of synthetic expression control sequences. Synthetic gene polynucleotide sequences, may not necessarily encode proteins with different amino acids, compared to the natural gene; for example, they can also encompass synthetic polynucleotide sequences that incorporate different codons but which encode the same amino acid (i.e., the nucleotide changes represent silent mutations at the amino acid level).

IgA Antibodies

IgA has two subclasses (IgA1 and IgA2) and can be produced as a monomeric as well as a dimeric form and secretory form. In some embodiments, the IgA antibody can be monomeric. In some embodiments, the IgA antibody can comprise one or more IgA1 amino acid sequences. In some embodiments, the IgA antibody can comprise one or more IgA2 amino acid sequences. In some embodiments, the IgA antibody can comprise one or more IgA1 amino acid sequences and one or more IgA2 amino acid sequences.

In some embodiments, the IgA antibody is an IgA is an IgA2 antibody of allotype: IgA2m(1), IgA2(m)2, or IgA2n. In some embodiments, the IgA2m(1) antibody is a Caucasian IgA2m(1) antibody. In some embodiments, the IgA2m(2) antibody is an African IgA2m(2) antibody or an Asian IgA2m(2) antibody.

In some embodiments, the IgA antibody comprises a heavy chain constant region comprising at least 60%, 70%, 75%, 80%, 85%, 90%, 95%, or 99% IgA amino acids. In some embodiments, the IgA antibody comprises a light chain constant region comprising at least 50, 60%, 70%, 75%, 80%, 85%, 90%, 95%, or 99% IgA amino acids.

In some embodiments, the IgA antibody comprises a heavy chain constant region comprising one or more of an IgA CH3 region, an IgA CH2, or an IgA CH1 region, or any combination thereof. In some embodiments, the IgA antibody comprises a light chain region comprising an IgA CH1 region. In some embodiments, the IgA antibody comprises a light chain region comprising a kappa light chain constant region. In some embodiments, the IgA antibody comprises a heavy chain constant region comprising one or more amino acid of an IgG CH3 region, an IgG CH2, or an IgG CH1 region, or any combination thereof. In some embodiments, the IgA antibody comprises a heavy chain constant region comprising an IgA CH3 region, an IgA CH2, and an IgA CH1 region, or any combination thereof. In some embodiments, the IgA antibody comprises a heavy chain constant region comprising an IgA CH3 region, an IgA CH2, and an IgG CH1 region, or any combination thereof. In some embodiments, the IgA2 antibody comprises a heavy chain constant region comprising one or more of an IgA2 CH3 region, an IgA2 CH2, or an IgA2 CH1 region, or any combination thereof.

In some embodiments, the IgA antibody comprises an IgG light chain variable region. In some embodiments, the IgA antibody comprises an IgG heavy chain variable region. In some embodiments, the IgA antibody comprises an IgG light chain variable region and an IgG heavy chain variable region.

In some embodiments, the IgA antibody can be a humanized antibody. In some embodiments, the IgA antibody can be a chimeric antibody. In some embodiments, the IgA antibody can be a human antibody.

In some embodiments, the IgA antibody can be a monospecific antibody. In some embodiments, the IgA antibody can be a bi-specific antibody. In some embodiments, the IgA antibody can be a tri-specific antibody. In some embodiments, the IgA antibody can be a multi-specific antibody.

In some embodiments, the IgA antibody can be a bispecific antibody. In some embodiments, the IgA antibody co-engages two antigens at the cell surface. In some examples, the binding of the IgA antibody to two different antigens is sequential. For example, the binding of the IgA antibody to the first antigen occurs first and thereby restricts the space explored by the second antibody arm. Consequentially, there can be a significant increase in local concentration of the second antigen, which can facilitate the binding of the second antibody arm.

In some embodiments, the IgA antibody can comprise at least a portion of the Fc domain. In some embodiments, the IgA antibody comprises a heavy chain constant region comprising a CH3, CH2, and CH1 domain. In some embodiments, the IgA antibody comprises a light chain constant region comprising a CH1.

In some embodiments, the IgA antibody induces complement-dependent cytotoxicity (CDC). In some embodiments, the IgA antibody induces polymorphonuclear neutrophil (PMN)-mediated tumor cell lysis. In some embodiments, the IgA antibody induces programmed cell death (PCD) via a caspase-independent pathway. In some embodiments, the IgA antibody induces antibody-dependent cell-mediated cytotoxicity (ADCC). In some embodiments, the IgA antibody induces antibody-dependent cell-mediated cytotoxicity (ADCC) mediated by neutrophils.

In some embodiments, the IgA antibody can have a superior ability to recruit neutrophils for antibody-dependent cell-mediated cytotoxicity (ADCC) compared to a corresponding IgG antibody. In some embodiments, the IgA antibody can require lower effector:target (E:T) ratios. In some embodiments, the IgA antibody can require lower tumor-opsonizing antibody concentrations compared to other types of antibodies (e.g., IgG). In some embodiments, the IgA antibody can trigger neutrophil-mediated phagocytosis or trogocytosis of tumor cells following IgA antibody-neutrophil engagement. In some embodiments, the IgA antibody can trigger trogoptosis of tumor cells following IgA antibody-neutrophil engagement. This mechanism of killing tumor cells is mediated mainly by interacting with the Fc receptor for IgA (FcαRI; CD89), which is the best characterized IgA receptor. FcαRI is expressed on monocytes, macrophages, granulocytes, subsets of dendritic cells, and Kupffer cells and binds both monomeric and dimeric IgA isoforms with median affinity. Binding of IgA to FcαRI mediates effector functions such as phagocytosis, oxidative burst, cytokine release, antigen presentation, and ADCC. In humans, two IgA isotypes, IgA1 and IgA2, and three allotypes, IgA2m(1), IgA2m(2) and IgA2n, have been distinguished. In some embodiments, IgA antibodies trigger polymorphonuclear cell (PMN) mediated ADCC more efficiently than IgG antibodies.

In some embodiments, the IgA does not bind a B cell, a T cell, a platelet, and/or an erythrocyte. For example, in some embodiments, the IgA antibody can have low immunogenicity.

In some embodiments, the IgA antibody is a therapeutic antibody. In some embodiments, the IgA antibody can be a recombinant antibody. In some embodiments, the IgA antibody is made in a cell line. In some embodiments, the cell line is CHO. In some embodiments, the cell line is SP20. In some embodiments, the cell line is a HEK 239 cell line. In some embodiments, the HEK 293 cell line is HEK 293 F.

In some embodiments, the antibody or a functional fragment thereof provided herein comprises an IgA heavy chain constant region comprises having at least 90%, 91%, 92%, 93%, 94%, 95%, 96%, 97%, 98%, 99%, or 100% sequence identity to the amino acid sequence of any one of SEQ ID NO:16-21. In some embodiments, the antibody or a functional fragment thereof provided herein comprises a variable heavy chain domain from an IgG antibody. In some embodiments, the antibody or a functional fragment thereof provided herein comprises a variable light chain domain from an IgG antibody. The variable domains can be derived from, for example, Dinutuximab, Obinutuzumab, Unituxin®, TA99, 2.3D11, C47A8-CQ, UMAB10, and Trastuzumab and Rituxan® (Rituximab), other antibodies having therapeutic activity encompassed within the scope of the invention include, but are not limited to, Avastin®, Herceptin®, 3F8, 8H9, Abagovomab, Abciximab, Actoxumab, Adalimumab, Adecatumumab, Aducanumab, Afelimomab, Afutuzumab, Alacizumab pegol, ALD518, Alemtuzumab, Alirocumab, Altumomab pentetate, Amatuximab, Anatumomab mafenatox, Anifrolumab, Anrukinzumab, Apolizumab, Arcitumomab, Aselizumab, Atinumab, Atlizumab, Atorolimumab, Bapineuzumab, Basiliximab, Bavituximab, Bectumomab, Belimumab, Benralizumab, Bertilimumab, Besilesomab, Bevacizumab, Bezlotoxumab, Biciromab, Bimagrumab, Bivatuzumab mertansine, Blinatumomab, Blosozumab, Brentuximab vedotin, Briakinumab, Brodalumab, Canakinumab, Cantuzumab mertansine, Cantuzumab ravtansine, Caplacizumab, Capromab pendetide, Carlumab, Catumaxomab, cBR96-doxorubicin immunoconjugate, CC49, Cedelizumab, Certolizumab pegol, Cetuximab, Ch.14.18, Citatuzumab bogatox, Cixutumumab, Clazakizumab, Clenoliximab, Clivatuzumab tetraxetan, Conatumumab, Concizumab, CR6261, Crenezumab, Dacetuzumab, Daclizumab, Dalotuzumab, Daratumumab, Demcizumab, Denosumab, Detumomab, Dorlimomab aritox, Drozitumab, Duligotumab, Dupilumab, Dusigitumab, Ecromeximab, Eculizumab, Edobacomab, Edrecolomab, Efalizumab, Efungumab, Eldelumab, Elotuzumab, Elsilimomab, Enavatuzumab, Enlimomab pegol, Enokizumab, Enoticumab, Ensituximab, Epitumomab cituxetan, Epratuzumab, Erlizumab, Ertumaxomab, Etaracizumab, Etrolizumab, Evolocumab, Exbivirumab, Fanolesomab, Faralimomab, Farletuzumab, Fasinumab, FBTA05, Felvizumab, Fezakinumab, Ficlatuzumab, Figitumumab, Flanvotumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Igovomab, IMAB362, Imciromab, Imgatuzumab, Inclacumab, Indatuximab ravtansine, Infliximab, Inolimomab, Inotuzumab ozogamicin, Intetumumab, Ipilimumab, Iratumumab, Itolizumab, Ixekizumab, Keliximab, Labetuzumab, Lambrolizumab, Lampalizumab, Lebrikizumab, Lemalesomab, Lerdelimumab, Lexatumumab, Libivirumab, Ligelizumab, Lintuzumab, Lirilumab, Lodelcizumab, Lorvotuzumab mertansine, Lucatumumab, Lumiliximab, Mapatumumab, Margetuximab, Maslimomab, Matuzumab, Mavrilimumab, Mepolizumab, Metelimumab, Milatuzumab, Minretumomab, Mitumomab, Mogamulizumab, Morolimumab, Motavizumab, Moxetumomab pasudotox, Muromonab-CD3, Nacolomab tafenatox, Namilumab, Naptumomab estafenatox, Namatumab, Natalizumab, Nebacumab, Necitumumab, Nerelimomab, Nesvacumab, Nimotuzumab, Nivolumab, Nofetumomab merpentan, Ocaratuzumab, Ocrelizumab, Odulimomab, Ofatumumab, Olaratumab, Olokizumab, Omalizumab, Onartuzumab, Ontuxizumab, Oportuzumab monatox, Oregovomab, Orticumab, Otelixizumab, Otlertuzumab, Oxelumab, Ozanezumab, Ozoralizumab, Pagibaximab, Palivizumab, Panitumumab, Pankomab, Panobacumab, Parsatuzumab, Pascolizumab, Pateclizumab, Patritumab, Pemtumomab, Perakizumab, Pertuzumab, Pexelizumab, Pidilizumab, Pinatuzumab vedotin, Pintumomab, Placulumab, Polatuzumab vedotin, Ponezumab, Priliximab, Pritoxaximab, Pritumumab, PRO 140, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Seribantumab, Setoxaximab, Sevirumab, SGN-CD19A, SGN-CD33A, Sibrotuzumab, Sifalimumab, Siltuximab, Simtuzumab, Siplizumab, Sirukumab, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tefibazumab, Telimomab aritox, Tenatumomab, Teneliximab, Teplizumab, Teprotumumab, TGN1412, Ticilimumab, Tigatuzumab, Tildrakizumab, TNX-650, Tocilizumab, Toralizumab, Tositumomab, Tovetumab, Tralokinumab, Trastuzumab, TRBS07, Tregalizumab, Tremelimumab, Tucotuzumab celmoleukin, Tuvirumab, Ublituximab, Urelumab, Urtoxazumab, Ustekinumab, Vantictumab, Vapaliximab, Vatelizumab, Vedolizumab, Veltuzumab, Vepalimomab, Vesencumab, Visilizumab, Volociximab, Vorsetuzumab mafodotin, Votumumab, Zalutumumab, Zanolimumab, Zatuximab, Ziralimumab, hu14.18K322A, Zolimomab aritox, rituximab (Rituxan®, CD20), trastuzumab (Herceptin®), alemtuzumab (Campath®, CD52), ibritumomab tiuxetan (Zevalin®, CD20) tositumomab-I-131 (Bexxar®: CD20), cetuximab (Erbitux®), bevacizumab (VEGF), panitumumab (Vectibix®, EGFR), ofatumumab (Arzerra®, CD20), ipilimumab (Ypervoy®, CTLA-4), brentiuximab vedotin (Adectris®, CD30), pertuzumab (Perjecta®, HER2), adotrastuzumab ematansine (Kadcyla®, HER2), obinutuzumab (Gazyva®, CD20), nivolumab and pembrolizumab (anti-PD-1s).

In one aspect, an antibody or antigen-binding fragment thereof comprises a heavy chain variable region (VH) sequence having at least 90%, 91%, 92%, 93%, 94%, 95%, %%, 97%, 98%, 99%, or 100% sequence identity to the amino acid sequence of any one of SEQ ID NOs: 4, 7, 81-86. In some embodiments, a VH sequence having at least 90%, 91%, 92%, 93%, 94%, 95%, %%, 97%, 98%, or 99% identity contains substitutions (e.g., conservative substitutions), insertions, or deletions relative to the reference sequence, but an antibody comprising that sequence retains the ability to bind to same antigen as of the WT antibody. In some embodiments, a total of 1 to 10 amino acids have been substituted, inserted and/or deleted in the amino acid sequence of any one of SEQ ID NOs: 4, 7, 81-86. In some embodiments, substitutions, insertions, or deletions occur in regions outside the CDRs (e.g., in the FRs). Optionally, the antibody comprises the VH sequence of the amino acid sequence of SEQ ID NOs: 4, 7, 81-86, including one or more post-translational modifications of that sequence. In a particular embodiment, the VH comprises one, two or three CDRs selected from: (a) HC-CDR1 comprising the amino acid sequence of any one of SEQ ID NOs: 33-40, (b) HC-CDR2 comprising the amino acid sequence of any one of SEQ ID NO: 41-48, and (c) HC-CDR3 comprising the amino acid sequence of any one of SEQ ID NO: 49-56.

In one aspect, an antibody or antigen-binding fragment thereof, is provided, wherein the antibody or antigen-binding fragment thereof comprises a light chain variable region (VL) having at least 90%, 91%, 92%, 93%, 94%, 95%, 96%, 97%, 98%, 99%, or 100% sequence identity to the amino acid sequence of any one of SEQ ID NOs: 5, 8, 95-100. In some embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to same antigen as the WT antibody. In some embodiments, a total of 1 to 10 amino acids have been substituted, inserted and/or deleted in any one of the amino acid sequences of any one of SEQ ID NOs: 5, 8, 95-100. In some embodiments, the substitutions, insertions, or deletions occur in regions outside the CDRs (e.g., in the FRs). Optionally, the antibody or antigen-binding fragment thereof comprises the VL sequence of any one of SEQ ID NO: 5, 8, 95-100, including post-translational modifications of that sequence. In a particular embodiment, the VL comprises one, two or three CDRs selected from (a) LC-CDR1 comprising the amino acid sequence of any one of SEQ ID NOS: 57-64; (b) LC-CDR2 comprising the amino acid sequence of any one of SEQ ID NOS: 65-72; and (c) LC-CDR3 comprising the amino acid sequence of any one of SEQ ID NOS: 73-80.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody or antigen-binding fragment thereof comprises a VH and a VL, wherein the VH comprises the amino acid sequence of any one of SEQ ID NOS: 4, 7, 81-86, and wherein the VL comprises the amino acid sequence in any one of SEQ ID NOS: 5, 8, 95-100, and optionally including post-translational modifications of those sequences.

In one aspect, an antibody or antigen-binding fragment thereof is provided, wherein the antibody or antigen-binding fragment thereof comprises a VH selected from any VH in Table 9. In one aspect, an antibody or antigen-binding fragment thereof is provided, wherein the antibody or antigen-binding fragment thereof comprises a VL selected from any VL in Table 9. In one aspect, an antibody or antigen-binding fragment thereof is provided, wherein the antibody or antigen-binding fragment thereof comprises a VH selected from any VH in Table 9 and a VL selected from any VL in Table 9. In one aspect, an antibody or antigen-binding fragment thereof is provided, wherein the antibody or antigen-binding fragment thereof comprises a VH selected from any VH in Table 9 and a VL selected from any VL in Table 9, wherein the selected VH and VL are paired according to Table 9. In one aspect, an antibody or antigen-binding fragment thereof is provided, wherein the antibody or antigen-binding fragment thereof comprises a HC-CDR3 selected from any HC-CDR3 in Table 5 and a LC-CDR3 selected from any LC-CDR3 in Table 6, wherein the selected HC-CDR3 and LC-CDR3 are paired according to Table 9. In one aspect, an antibody or antigen-binding fragment thereof is provided, wherein the antibody or antigen-binding fragment thereof comprises a HC-CDR2 selected from any CDR-H2 in Table 5 and a LC-CDR2 selected from any CDR-L2 in Table 6, wherein the selected HC-CDR2 and LC-CDR2 are paired according to Table 9. In one aspect, an antibody or antigen-binding fragment thereof is provided, wherein the antibody or antigen-binding fragment thereof comprises a HC-CDR1 selected from any HC-CDR1 in Table 5 and a LC-CDR1 selected from any LC-CDR1 in Table 6, wherein the selected HC-CDR1 and LC-CDR1 are paired according to Table 9. In one aspect, an antibody or antigen-binding fragment thereof is provided, wherein the antibody or antigen-binding fragment thereof comprises a HC-CDR1, a HC-CDR2, and a HC-CDR3 selected from any HC-CDR1, a HC-CDR2, and a HC-CDR3 in Table 5 and a LC-CDR1, a LC-CDR2, and a LC-CDR3 selected from any LC-CDR1, a LC-CDR2, and a LC-CDR3 in Table 6, wherein the selected HC-CDR1, a HC-CDR2, a HC-CDR3, LC-CDR1, a LC-CDR2, and a LC-CDR3 are paired according to Table 9. In some embodiments, the antibody or an antigen binding fragment thereof comprises any one of a HC-CDR1, a HC-CDR2, and a HC-CDR3 selected from any HC-CDR1, a HC-CDR2, and a HC-CDR3 in Table 5 and any IgA heavy chain constant region selected from SEQ ID NOs: 16-21. In some embodiments, the antibody or an antigen binding fragment thereof comprises any one of a LC-CDR1, a LC-CDR2, and a LC-CDR3 selected from any LC-CDR1, a LC-CDR2, and a LC-CDR3 in Table 6 and any IgA heavy chain constant region selected from SEQ ID NOs: 16-21.

In some embodiments, the antibody or an antigen binding fragment thereof comprises any one of a HC-CDR1, a HC-CDR2, and a HC-CDR3 selected from any HC-CDR1, a HC-CDR2, and a HC-CDR3 in Table 5 and any one of a LC-CDR1, a LC-CDR2, and a LC-CDR3 selected from any LC-CDR1, a LC-CDR2, and a LC-CDR3 in Table 6 and any IgA heavy chain constant region selected from SEQ ID NOs: 16-21, wherein the selected HC-CDR1, HC-CDR2, HC-CDR3, selected LC-CDR1, LC-CDR2, LC-CDR3 and selected IgA heavy chain constant region are paired according to Table 9.

IgA Antibody Modifications

Described herein are IgA antibodies comprising one or more amino acid substitution and/or one or more amino acid deletions.

In some embodiments, the amino acid numbering of an IgA antibody described herein is indicated according to IMGT® unique numbering for C-DOMAIN and C-LIKE-DOMAIN (as disclosed in "IMGT® unique numbering for immunoglobulin and T cell receptor constant domains and Ig superfamily C-like domains." Dev Comp Immunol. 2005; 29(3):185-203, the entire contents of which are incorporated by reference herein). In some embodiments, the amino acid modifications disclosed herein are relative to amino acid residues at select positions in the WT IgA heavy chain constant region (e.g., WT IgA2 heavy chain constant region) comprising an amino acid sequence set forth in SEQ ID NO: 1, numbering according to IMGT® scheme. It is noted that U.S. 62/824,864 which is incorporated in its entirety herein also includes antibodies and antibody constructs comprising modified IgA heavy chain constant regions numbered according to the IMGT® numbering scheme. Some amino acids were inadvertently mislabeled therein and specific amino acid positions as described in U.S. 62/824,864 correspond to the following specific amino acid positions as provided herein. Positions C92, N120, I121, and T122 as referred to in U.S. 62/824,864 correspond to amino acid residues C86, N114, I115, and T116 in antibodies described herein which are correctly labeled as per the IMGT® numbering scheme (IMGT® numbering depicted in table 11, for reference to position numbering only). The reference wild type heavy chain constant region sequence for these antibodies as disclosed in U.S. 62/824,864 and the current application is the same, namely SEQ ID NO:1 as shown in FIG. 1. As such the inadvertent mislabeling in U.S. 62/824,864 of residues C86, N114, I115, and T116 in the IMGT® naming scheme as C92, N120, I121, and T122 would be evident to the skilled artisan.

In some embodiments, the IgA antibody disclosed herein comprises a deletion of at least four glycosylation sites within the constant region. In some embodiments, the IgA antibody disclosed herein comprises a deletion of at least three N-linked glycosylation sites in the constant region of the antibody. In some embodiments, the IgA antibody comprises a deletion of at least three N-linked glycosylation sites in the constant region of the antibody and at least one O-linked glycosylation site in the constant region of the antibody. In some embodiments, the IgA antibodies, or a functional fragment disclosed herein comprises one or more modifications disclosed herein (e.g., Table 2) in an IgA heavy chain constant region. In some embodiments, the IgA antibodies, or a functional fragment disclosed herein comprises one or more modifications disclosed herein (e.g., Table 2) in an IgA1 heavy chain constant region. In some embodiments, the IgA antibodies disclosed herein, or a functional fragment disclosed herein comprises one or more modifications disclosed herein (e.g., Table 2) in an IgA2 heavy chain constant region. In some embodiments, the one or more modifications are in an amino acid residue within a CH1 region, CH2 region and/or CH3 region of a IgA1 heavy chain constant region. In some embodiments, In some embodiments, the IgA antibodies comprise a deleted tail piece. In some embodiments, the one or more modifications are in an amino acid residue within a CH1 region, a CH2 region and/or a CH3 region of an IgA2 heavy chain constant region. In some embodiments, an IgA CH1 region comprises an amino acid sequence that at least about 80%, 85%, 90%, 95%, 99% or 100% identical to an amino acid sequence set forth in SEQ ID NO: 109. In some embodiments, a IgA CH2 region comprises an amino acid sequence that at least about 80%, 85%, 90%, 95%, 99% or 100% identical to an amino acid sequence set forth in SEQ ID NO: 110. In some embodiments, a IgA CH2 region comprises an amino acid sequence that at least about 80%, 85%, 90%, 95%, 99% or 100% identical to an amino acid sequence set forth in SEQ ID NO: 111.

In some embodiments, a IgA antibody, or a functional fragment thereof as disclosed herein comprises a deletion of the 3-20, 3-19, 3-18, 3-17, 3-16, 3-15, 3-14, 3-13, 3-12, 3-11, 3-10, 3-9, 3-8, 3-7, 3-6, 3-5, 3-4 C-terminal amino acids. In some embodiments, the IgA2 antibody comprises a deletion of the 3-20, 3-19, 3-18, 3-17, 3-16, 3-15, 3-14, 3-13, 3-12, 3-11, 3-10, 3-9, 3-8, 3-7, 3-6, 3-5, 3-4 C-terminal amino acids. In some embodiments, the C-terminal amino acids are from amino acids 131-148 of the IgA2 antibody, numbering according to IMGT® scheme.

In some embodiments, the IgA2 antibody comprises a deletion of amino acids 131-148, numbering according to IMGT® scheme. In some embodiments, the IgA2 antibody comprises a deletion of amino acids 147-148, numbering according to IMGT® scheme. In some embodiments, the IgA2 antibody comprises a deletion of amino acids 146-148, numbering according to IMGT® scheme. In some embodiments, the IgA2 antibody comprises a deletion of amino acids 145-148, numbering according to IMGT® scheme. In some embodiments, the IgA2 antibody comprises a deletion of amino acids 144-148, numbering according to IMGT® scheme. In some embodiments, the IgA2 antibody comprises a deletion of amino acids 143-148, numbering according to IMGT® scheme. In some embodiments, the IgA2 antibody comprises a deletion of amino acids 142-148, numbering according to IMGT® scheme. In some embodiments, the IgA2 antibody comprises a deletion of amino acids 141-148, numbering according to IMGT® scheme. In some embodiments, the IgA2 antibody comprises a deletion of amino acids 140-148, numbering according to IMGT® scheme. In some embodiments, the IgA2 antibody comprises a deletion of amino acids 139-148, numbering according to IMGT® scheme. In some embodiments, the IgA2 antibody comprises a deletion of amino acids 138-148, numbering according to IMGT® scheme. In some embodiments, the IgA2 antibody comprises a deletion of amino acids 137-148, numbering according to IMGT® scheme. In some embodiments, the IgA2 antibody comprises a deletion of amino acids 136-148, numbering according to IMGT® scheme. In some embodiments, the IgA2 antibody comprises a deletion of amino acids 135-148, numbering according to IMGT® scheme. In some embodiments, the IgA2 antibody comprises a deletion of amino acids 134-148, numbering according to IMGT® scheme. In some embodiments, the IgA2 antibody comprises a deletion of amino acids 133-148, numbering according to IMGT® scheme. In some embodiments, the IgA2 antibody comprises a deletion of amino acids 132-148, numbering according to IMGT® scheme. In some embodiments, the IgA2 antibody comprises a deletion of amino acids 131-148, numbering according to IMGT® scheme. In some embodiments, the IgA2 antibody comprises a deletion of amino acids P131-Y148, numbering according to IMGT® scheme.

In some embodiments, the IgA antibody comprises a mutation of the C-terminal asparagine (N) amino acid. In some embodiments, the mutation is a non-conservative amino acid substitution. In some embodiments, the mutation deletes the glycosylation site of the C-terminal asparagine (N) amino acid of the IgA. In some embodiments, the IgA2 antibody comprises a mutation of N135, numbering according to IMGT® scheme. In some embodiments, the IgA2 antibody comprises a non-conservative mutation of N135, numbering according to IMGT® scheme. In some embodiments, the IgA2 antibody comprises a N135Q mutation, numbering according to IMGT® scheme.

In some embodiments, the IgA antibody or a functional fragment thereof disclosed herein comprises a modification in at least two naturally occurring glycosylation sites in the IgA heavy chain constant region. In some embodiments, the IgA antibody or a functional fragment thereof disclosed herein comprises a modification in at least three naturally occurring glycosylation sites in the IgA heavy chain constant region. In some embodiments, the IgA antibody or a functional fragment thereof disclosed herein comprises a modification in at least four naturally occurring glycosylation site. In some embodiments, the glycosylation site comprises a N-linked glycosylation site. In some embodiments, the glycosylation site comprises a naturally occurring asparagine residue. In some embodiments, the glycosylation site is in a CH2 region, in a CH3 region, and/or a CH1 region. In some embodiments, the IgA heavy chain constant region comprises a modification at N45.2G, N15.2, L15.3, T16, N114, I115, T116, N135, or a combination thereof, numbering according to IMGT® scheme. In some embodiments, the IgA heavy chain constant region comprises an amino acid substitution that is N45.2G, N45.2A, N15.2G, N15.2Q, N15.2T, L15.3I, T16S, N114T, I115L, T116S, N135Q, or a combination thereof, numbering according to IMGT® scheme. In some embodiments, provided herein is an aglycosylated antibody or a functional fragment thereof. In some embodiments, the aglycosylated antibody comprises a modification at all four naturally occurring glycosylation site in IgA2 heavy chain constant region. In some embodiments, an aglycosylated antibody provided herein comprises a modification at residues; N45.2, N15.2, L15.3, T16, N114, I115, T116, and N135, numbering according to IMGT® scheme. In some embodiments, an aglycosylated antibody provided herein comprises a modification at residues; N45.2, N15.2, N114, I115, T116, and N135, numbering according to IMGT® scheme.

In some embodiments, an aglycosylated antibody provided herein comprises a modification at residues; N45.2, N15.2, L15.3, T16, N114, I115, T116, and a deletion of the C-terminal tailpiece residues P131-Y148, numbering according to IMGT® scheme. In some embodiments, an aglycosylated antibody provided herein comprises a modification at residues; N45.2, N15.2, N114, I115, T116, and P131-Y148, numbering according to IMGT® scheme.

In some embodiments, provided herein is an antibody or a functional fragment thereof that comprises a modification at residue N45.2, N15.2, L15.3, T16, N114, I115, T116, and N135, numbering according to IMGT® scheme. In some embodiments, provided herein is an antibody or a functional fragment thereof that comprises a modification at residue N45.2, N15.2, N114, I115, T116, and N135, numbering according to IMGT® scheme. In some embodiments, the IgA heavy chain constant region comprises an amino acid substitution that is N45.2G, N45.2A, N15.2G, N114T, I115L, T116S, and N135Q, numbering according to IMGT® scheme. In some embodiments, the IgA heavy chain constant region comprises an amino acid substitution that is N45.2G, N45.2A, N15.2Q, L15.3I, T16S, N114T, I115L, T116S, and N135Q. In some embodiments, the IgA heavy chain constant region comprises an amino acid substitution that is N45.2G, N45.2A, N15.2G, N15.2T, N114T, I115L, T116S, and N135Q, numbering according to IMGT® scheme In some embodiments, an antibody comprises a combination of acid substitution that is N45.2G, N45.2A, N15.2G, N114T, I115L, T116S, and N135Q in the IgA heavy chain constant region is an aglycosylated antibody, numbering according to IMGT® scheme. In some embodiments, the aglycosylated antibody a combination of acid substitution that is N45.2G, N45.2A, N15.2G, T16S, N114T, I115L, T116S, and deletion of the C-terminal tailpiece.

In some embodiments, an antibody comprises a combination of acid substitution that is N45.2G, N45.2A, N15.2Q, N114T, I115L, T116S, and N135Q in the IgA heavy chain constant region is an aglycosylated antibody, numbering according to IMGT® scheme. In some embodiments, the aglycosylated antibody a combination of acid substitution that is N45.2G, N45.2A, N15.2Q, T16S, N114T, I115L, T116S, and deletion of the C-terminal tailpiece. In some embodiments, an antibody comprises a combination of acid substitution that is N45.2G, N45.2A, N15.2T, N114T, I115L, T116S, and N135Q in the IgA heavy chain constant region is an aglycosylated antibody, numbering according to IMGT® scheme. In some embodiments, the aglycosylated antibody a combination of acid substitution that is N45.2G, N45.2A, N15.2T, T16S, N114T, I115L, T116S, and deletion of the C-terminal tailpiece. In some embodiments, an antibody comprises a combination of acid substitution that is N45.2G, N45.2A, N15.2T, L15.3I, T16S N114T, I115L, T116S, and N135Q in the IgA heavy chain constant region is an aglycosylated antibody, numbering according to IMGT® scheme. In some embodiments, the aglycosylated antibody a combination of acid substitution that is N45.2G, N45.2A, N15.2T, L15.3I, T16S, T16S, N114T, I115L, T116S, and deletion of the C-terminal tailpiece.

In some embodiments, the aglycosylated antibody exhibits increased circulating half-life relative to a corresponding antibody comprising at least one glycosylation site (e.g., WT residues N45.2, N114, N15.2. and N135, numbering according to IMGT® scheme) or a corresponding WT IgA antibody. In some embodiments, the aglycosylated antibody exhibits decreased aggregation relative to a corresponding antibody comprising at least one glycosylation site (e.g., WT residues N45.2, N114, N15.2. and N135, numbering according to IMGT® scheme) or a WT IgA antibody. In some embodiments, the aglycosylated antibody exhibits decreased aggregation with serum proteins relative to a corresponding antibody comprising at least one glycosylation site (e.g., WT residues N45.2, N114, N15.2. and N135, numbering according to IMGT® scheme) or a corresponding WT IgA antibody. In some embodiments, the aglycosylated antibody exhibits decreased aggregation relative to a corresponding antibody comprising at least one glycosylation site (e.g., WT residues N45.2, N114, N15.2. and N135, numbering according to IMGT® scheme) or a corresponding WT IgA antibody. In some embodiments, the aglycosylated antibody exhibits increased thermostability relative to a corresponding antibody comprising at least one glycosylation site (e.g., WT residues N45.2, N114, N15.2. and N135, numbering according to IMGT® scheme) or a corresponding WT IgA antibody. In some embodiments, the aglycosylated antibody exhibits binding to Fc receptor with increased binding affinity relative to a corresponding WT IgA. In some embodiments, the aglycosylated antibody induces ADCC of a target cell. In some embodiments, the aglycosylated antibody specifically binds a target antigen. In some embodiments, the aglycosylated antibody specifically binds a target cell.

In some embodiments, an antibody comprises a mutation of N45.2, numbering according to IMGT® scheme. In some embodiments, the IgA2 antibody comprises a non-conservative mutation of N45.2, numbering according to IMGT® scheme. In some embodiments, the IgA2 antibody comprises a N45.2G, numbering according to IMGT® scheme. In some embodiments, the IgA2 antibody has an increased circulating half-life compared to an IgA2 antibody that does not have a mutation in the N45.2 amino acid.

In some embodiments, an antibody comprises a mutation of P124, numbering according to IMGT® scheme. In some embodiments, the IgA2 antibody comprises a non-conservative mutation of P124, numbering according to IMGT® scheme. In some embodiments, the IgA2 antibody comprises a P124R, numbering according to IMGT® scheme. In some embodiments, the IgA2 antibody has an increased circulating half-life compared to an IgA2 antibody that does not have a mutation in the P124 amino acid. In some embodiments, the IgA2 antibody has an increased stability compared to an IgA2 antibody that does not have a mutation in the P124 amino acid.

In some embodiments, an antibody as described herein comprises a mutation of C86 (inadvertently referred to as C92 in U.S. 62/824,864 which is incorporated in its entirety herein, as described above), numbering according to IMGT® scheme. In some embodiments, the antibody comprises a non-conservative mutation of C86, numbering according to IMGT® scheme. In some embodiments, the antibody comprises a C86S, numbering according to IMGT® scheme. In some embodiments, the antibody has a decreased aggregation compared to an antibody that does not have a mutation in the C86 amino acid. In some embodiments, the antibody has a decreased aggregation with serum proteins compared to an antibody that does not have a mutation in the C86 amino acid. In some embodiments, the antibody has a decreased aggregation in vitro or in vivo compared to an antibody that does not have a mutation in the C86 amino acid.

In some embodiments, the IgA2 antibody comprises a mutation of C86 according to IMGT® scheme. In some embodiments, the IgA2 antibody comprises a non-conservative mutation of C86, numbering according to IMGT® scheme. In some embodiments, the IgA2 antibody comprises a C86S, numbering according to IMGT® scheme. In some embodiments, the IgA2 antibody has a decreased aggregation compared to an IgA2 antibody that does not have a mutation in the C86 amino acid. In some embodiments, the IgA2 antibody has a decreased aggregation with serum proteins compared to an IgA2 antibody that does not have a mutation in the C86 amino acid. In some embodiments, the IgA2 antibody has a decreased aggregation in vitro or in vivo compared to an IgA2 antibody that does not have a mutation in the C86 amino acid.

In some embodiments, the antibody comprises a mutation of N114 (inadvertently referred to as N120 in U.S. 62/824,864 which is incorporated in its entirety herein, as described above), numbering according to IMGT® scheme. In some embodiments, the antibody comprises a non-conservative mutation of N114, numbering according to IMGT® scheme. In some embodiments, the antibody comprises a N114T, numbering according to IMGT® scheme. In some embodiments, the antibody has an increased circulating half-life compared to an IgA2 antibody that does not have a mutation in the N114 amino acid.

In some embodiments, the antibody comprises a mutation of I115 (inadvertently referred to as I121 in U.S. 62/824,864 which is incorporated in its entirety herein, as described above), numbering according to IMGT® scheme. In some embodiments, the antibody comprises a non-conservative mutation of I115, numbering according to IMGT® scheme. In some embodiments, the antibody comprises an I115L, numbering according to IMGT® scheme. In some embodiments, the antibody has an increased circulating half-life compared to an IgA2 antibody that does not have a mutation in the I115 amino acid.

In some embodiments, the antibody comprises a mutation of T116 (inadvertently referred to as T122 in U.S. 62/824,864 which is incorporated in its entirety herein, as described above), numbering according to IMGT® scheme. In some embodiments, the antibody comprises a non-conservative mutation of T116, numbering according to IMGT® scheme. In some embodiments, the antibody comprises a T116S, numbering according to IMGT® scheme. In some embodiments, the IgA2 antibody has an increased circulating half-life compared to an IgA2 antibody that does not have a mutation in the T116 amino acid.

In some embodiments, the IgA2 antibody comprises a mutation of N114, numbering according to IMGT® scheme. In some embodiments, the IgA2 antibody comprises a non-conservative mutation of N114, numbering according to IMGT® scheme. In some embodiments, the IgA2 antibody comprises a N14T, numbering according to IMGT® scheme. In some embodiments, the IgA2 antibody has an increased circulating half-life compared to an IgA2 antibody that does not have a mutation in the N114 amino acid.

In some embodiments, the IgA2 antibody comprises a mutation of I115, according to IMGT® scheme. In some embodiments, the IgA2 antibody comprises a non-conservative mutation of I115, numbering according to IMGT® scheme. In some embodiments, the IgA2 antibody comprises an I115L, numbering according to IMGT® scheme. In some embodiments, the IgA2 antibody has an increased circulating half-life compared to an IgA2 antibody that does not have a mutation in the I115 amino acid.

In some embodiments, the IgA2 antibody comprises a mutation of T116, numbering according to IMGT® scheme. In some embodiments, the IgA2 antibody comprises a non-conservative mutation of T116, numbering according to IMGT® scheme. In some embodiments, the IgA2 antibody comprises a T116S, numbering according to IMGT® scheme. In some embodiments, the IgA2 antibody has an increased circulating half-life compared to an IgA2 antibody that does not have a mutation in the T116 amino acid.

In some embodiments, the IgA2 antibody comprises a mutation of N15.2, according to IMGT® scheme. In some embodiments, the IgA2 antibody comprises a non-conservative mutation of N15.2, numbering according to IMGT® scheme. In some embodiments, the IgA2 antibody comprises an N15.2G, N15.2Q, or N15.2T, numbering according to IMGT® scheme. In some embodiments, the IgA2 antibody has an increased circulating half-life compared to an IgA2 antibody that does not have a mutation in the N15.2 amino acid.

In some embodiments, the IgA2 antibody comprises a mutation of L15.3, according to IMGT® scheme. In some embodiments, the IgA2 antibody comprises a non-conservative mutation of L15.3, numbering according to IMGT® scheme. In some embodiments, the IgA2 antibody comprises an L15.3I, numbering according to IMGT® scheme. In some embodiments, the IgA2 antibody has an increased circulating half-life compared to an IgA2 antibody that does not have a mutation in the L15.3 amino acid.

In some embodiments, the IgA2 antibody comprises a mutation of T16, according to IMGT® scheme. In some embodiments, the IgA2 antibody comprises a non-conservative mutation of T16, numbering according to IMGT® scheme. In some embodiments, the IgA2 antibody comprises an T16S, numbering according to IMGT® scheme. In some embodiments, the IgA2 antibody has an increased circulating half-life compared to an IgA2 antibody that does not have a mutation in the T16S amino acid.

In some embodiments, the IgA2 antibody comprises a mutation of C147, numbering according to IMGT® scheme. In some embodiments, the IgA2 antibody comprises a non-conservative mutation of C147, numbering according to IMGT® scheme. In some embodiments, the IgA2 antibody comprises a deletion of amino acid C147, numbering according to IMGT® scheme. In some embodiments, the IgA2 antibody has a decreased aggregation compared to an IgA2 antibody that does not have a mutation in the C147 amino acid.

In some embodiments, the IgA2 antibody comprises a mutation of Y148, numbering according to IMGT® scheme. In some embodiments, the IgA2 antibody comprises a non-conservative mutation of Y148, numbering according to IMGT® scheme. In some embodiments, the IgA2 antibody comprises a deletion of amino acid Y148, numbering according to IMGT® scheme.

In some embodiments, the IgA antibody comprises one or more albumin binding domains. In some embodiments, the one or more albumin binding domains are fused to a light chain or heavy chain of a IgA constant region. In some embodiments, the one or more albumin binding domains are fused to a heavy chain of a IgA constant region. In some embodiments, the one or more albumin binding domains are fused to a C-terminal region of a CH3 region of a heavy chain of a IgA constant region. In some embodiments, the IgA2 antibody has an increased circulating half-life compared to an IgA2 antibody that does not comprise one or more albumin binding domains. In some embodiments, the IgA2 antibody comprises one or more albumin binding domain and has circulating half-life within that of 1%, 5%, or 10% of a corresponding IgG antibody. In some embodiments, the IgA2 antibody comprises one or more albumin binding domain and has circulating half-life greater than that of a corresponding IgG antibody.

In some embodiments, the IgA antibody comprises one or more mutations described in Lohse S. et al. Cancer Res. 2015; 76(2):403-17; Meyer S. et al. mAbs. 2016; 8(1):87-98; or Leusen J. et al. Molecular Immunology. 2015; 68: 35-39.

In some embodiments, the one or more mutation or deletion results in increased or decreased circulating half-life of the IgA antibody. In some embodiments, the one or more mutation or deletion results in increased circulating half-life of the IgA antibody. For example, the one or more mutations can increase the serum half-life of the IgA antibody to up to 21 days or more in humans. Furthermore, the one or more mutations can increase the serum half-life of the IgA antibody to up to 9 days or more in mice. In some embodiments, the one or more mutations can increase the serum half-life of the IgA antibody to a level comparable to that of an immunoglobulin G (IgG) molecule. In some embodiments, the one or more mutation or deletion results in decreased circulating half-life of the IgA antibody.

In some embodiments, the one or more mutations can increase the serum half-life of the IgA antibody for at least about 7 days to about 30 days or more. In some embodiments, the one or more mutations can increase the serum half-life of the IgA antibody for at least about 7 days. In some embodiments, the one or more mutations can increase the serum half-life of the IgA antibody for at most about 30 days. In some embodiments, the one or more mutations can increase the serum half-life of the IgA antibody for about 7 days to about 8 days, about 7 days to about 9 days, about 7 days to about 10 days, about 7 days to about 15 days, about 7 days to about 20 days, about 7 days to about 25 days, about 7 days to about 30 days, about 8 days to about 9 days, about 8 days to about 10 days, about 8 days to about 15 days, about 8 days to about 20 days, about 8 days to about 25 days, about 8 days to about 30 days, about 9 days to about 10 days, about 9 days to about 15 days, about 9 days to about 20 days, about 9 days to about 25 days, about 9 days to about 30 days, about 10 days to about 15 days, about 10 days to about 20 days, about 10 days to about 25 days, about 10 days to about 30 days, about 15 days to about 20 days, about 15 days to about 25 days, about 15 days to about 30 days, about 20 days to about 25 days, about 20 days to about 30 days, or about 25 days to about 30 days. In some embodiments, the one or more mutations can increase the serum half-life of the IgA antibody for about 7 days, about 8 days, about 9 days, about 10 days, about 15 days, about 20 days, about 25 days, or about 30 days. Accordingly, in some embodiments, the antibodies or a functional fragment thereof disclosed herein exhibit a greater circulating half-life compared to a corresponding WT IgA antibody. In some embodiments, the antibodies exhibit a circulating half-life that is greater by at least about 2%, 5%, 10%, 12%, 15%, 20%, at 25%, 50%, 65%, 70%, 75%, 85%, 90%, 95%, 99%, 100%, 150%, and 200%, relative to a corresponding WT IgA antibody.

In some embodiments, the IgA antibody exhibits increased stability. In some embodiments, the one or more mutation and/or one or more deletion results in increased stability of the IgA antibody compared to a corresponding IgA antibody which does not comprise the one or mutation and/or one or more deletion.

In some embodiments, the IgA antibody exhibits decreased aggregation. Antibody aggregation is a more common manifestation of physical instability. Protein aggregates generally have reduced activity and more importantly, greater immunogenicity potential because of the multiplicity of epitopes and/or conformational changes. Immunoglobulin aggregates are known to cause serious renal failure and anaphylactoid reactions such as headache, fever, and chills. It is therefore advantageous to decrease aggregation in antibody therapeutics. Additionally, the aggregate level in commercial intravenous immunoglobulin products is limited to less than 5% based on the World Health Organization (WHO) standards. In some embodiments, the one or more mutations results in decreased aggregation. In some embodiments, the one or more mutation and/or one or more deletion results in decreased aggregation of the IgA antibody compared to a corresponding IgA antibody which does not comprise the one or mutation and/or one or more deletion. In some embodiments, the antibodies or a functional fragment thereof disclosed herein exhibit a decreased aggregation compared to a corresponding WT IgA antibody. In some embodiments, the antibodies exhibit aggregation that is decreased by at least about 2%, at least 5%, at least 10%, at least 12%, at least 15%, at least 20%, at least 25%, at least 50%, at least 65%, at least 70%, at least 75%, at least 85%, at least 90%, at least 95%, at least 99%, at least 100%, at least 150%, and at least 200%, relative to a corresponding WT IgA antibody. In some embodiments, the antibodies or a functional fragment thereof disclosed herein exhibit a decreased aggregation with serum protein compared to a corresponding WT IgA antibody. In some embodiments, the antibodies exhibit aggregation that is decreased by at least 2%, at least 5%, at least 10%, at least 12%, at least 15%, at least 20%, at least 25%, at least 50%, at least 65%, at least 70%, at least 75%, at least 85%, at least 90%, at least 95%, at least 99%, at least 100%, at least 150%, and at least 200%, relative to a corresponding WT IgA antibody.

In some embodiments, the IgA antibodies provided herein have an aggregate level ranging from at least about 0.1% to about 5% at most. In some embodiments, the IgA antibodies provided herein have an aggregate level ranging from at least about 0.1%. In some embodiments, the IgA antibodies provided herein have an aggregate level ranging from at most about 5%. In some embodiments, the IgA antibody's provided herein have an aggregate level ranging from about 0.1% to about 0.5%, about 0.1% to about 1%, about 0.1% to about 2%, about 0.1% to about 3%, about 0.1% to about 4%, about 0.1% to about 5%, about 0.5% to about 1%, about 0.5% to about 2%, about 0.5% to about 3%, about 0.5% to about 4%, about 0.5% to about 5%, about 1% to about 2%, about 1% to about 3%, about 1% to about 4%, about 1% to about 5%, about 2% to about 3%, about 2% to about 4%, about 2% to about 5%, about 3% to about 4%, about 3% to about 5%, or about 4% to about 5%. In some embodiments, the IgA antibodies provided herein have an aggregate level ranging from about 0.1%, about 0.5%, about 1%, about 2%, about 3%, about 4%, or about 5%.

Therapeutic antibodies disclosed herein may comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

Methods of substituting or deleting amino acids are known in the art. For example, amino acid substitutions or deletions can be made by site-directed mutagenesis (for example, Zoller and Smith Nucl. Acids Res. 10:6487 (1982)). Mutagenesis can be performed by synthesizing an oligonucleotide having one or more modifications within the sequence of the constant domain of an antibody to be modified. The antibodies of the present disclosure (e.g., comprising one or more modifications in the IgA heavy chain constant region) can be prepared using any mutagenesis procedure known in the art, such as site-directed mutagenesis, synthetic gene construction, semi-synthetic gene construction, random mutagenesis, shuffling, etc. Site-specific mutagenesis allows the production of mutants through the use of specific oligonucleotide sequences which encode the DNA sequence of the desired mutation, as well as a sufficient number of adjacent oligonucleotides to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered. A number of such primers introducing a variety of different mutations at one or more positions may be used to generate a library of mutants.

The technique of site-specific mutagenesis is well known in the art, (see, e.g., Kunkel et al., Methods Enzymol, 154:367-82, 1987). In general, site-directed mutagenesis is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as T7 DNA polymerase, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as E. coli cells, and clones are selected which include recombinant vectors bearing the mutated sequence arrangement. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage. Site directed mutagenesis has also been used to identify amino acid residues that influence plasma clearance of murine lgG1 hinge-Fc fragments as described in Kim Jin-Kyoo et al., (1994) Eur. J. Immunol. 24:542-548).

Alternatively, the use of PCR with commercially available thermostable enzymes such as Taq DNA polymerase may be used to incorporate a mutagenic oligonucleotide primer into an amplified DNA fragment that can then be cloned into an appropriate cloning or expression vector. See, e.g., Tomic et al., Nucleic Acids Res., 18(6):1656, 1987, and Upender et al., Biotechniques, 18(1):29-30, 32, 1995, for PCR-mediated mutagenesis procedures. PCR employing a thermostable ligase in addition to a thermostable polymerase may also be used to incorporate a phosphorylated mutagenic oligonucleotide into an amplified DNA fragment that may than be cloned into an appropriate cloning or expression vector (see e.g., Michael, Biotechniques, 16(3):410-2, 1994).

Other methods known to those of skill in art of producing sequence variants of the Fc region of an antibody or an FcR binding domain thereof can be used. For example, recombinant vectors encoding the amino acid sequence of the constant domain of an antibody or a fragment thereof may be treated with mutagenic agents, such as hydroxylamine, to obtain sequence variants. Mutants that result in desirable properties, example, increased ADCC, decreased aggregation, increased affinity for FcR and/or increased in vivo half-life can be screened using routine assays such as those described later.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, Nature 432: 1050-1054) and similar technologies wherein oligonucleotides are synthesized and assembled upon photo-programmable microfluidic chips. Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204) and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/ or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Other Covalent Modifications

Covalent modifications of the antibody are also included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues.

Cysteinyl residues most commonly are reacted with a haloacetate (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-(5 imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0. Lysinyl and amino-terminal residues are reacted with succinic or other carboxylic acid anhydrides. Derivatization with these agents has the effect of reversing the charge of the lysinyl residues. Other suitable reagents for derivatizing alpha amino-containing residues include imidoesters such as methyl picolinimidate, pyridoxal phosphate, pyridoxal, chloroborohydride, trinitrobenzenesulfonic acid, methylisourea, 2,4-pentanedione, and transaminase-catalyzed reaction with glyoxylate.

Arginyl residues are modified by reaction with one or several conventional reagents, among them phenylgly-oxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form 0-acetyl tyrosyl species and 3-nitro derivatives, respectively. Tyrosyl residues are iodinated using 125I or 131I to prepare labeled proteins for use in radioimmunoassay. Carboxyl side groups (aspartyl or glutamyl) are selectively modified by reaction with carbodiimides (R—N. dbd.C.dbd.N—R'), where R and R' are different alkyl groups, such as 1-cyclohexyl-3-(2-morpholinyl-4-ethyl) carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention. Other modifications include hydroxylation of proline and lysine, phosphorylation of hydroxyl groups of seryl or threonyl residues, methylation of the alpha amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO87I 05330 published 11 Sep. 1987, and in Aplin and Wriston, CRC Crit. Rev. Biochem., pp. 259-306 (1981).

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Hakimuddin, et al. Arch. Biochem. Biophys. 259: 52 (1987) and by Edge et al. Anal. Biochem., 118: 131 (1981). Enzymatic cleavage of carbohydrate moieties on antibodies can be achieved by the use of a variety of endo- and exoglycosidases as described by Thotakura et al. Meth. Enzymol. 138: 350 (1987).

Another type of covalent modification of the antibody comprises linking the antibody to one of a variety of nonproteinaceous polymers, e.g., polyethylene glycol, polypropylene glycol, polyoxyethylated polyols, polyoxyethylated sorbitol, polyoxyethylated glucose, polyoxyethylated glycerol, polyoxyalkylenes, or polysaccharide polymers such as dextran. Such methods are known in the art, see, e.g. U.S. Pat. Nos. 4,640,835; 4,496,689; 4,301,144; 4,670,417; 4,791,192, 4,179,337, 4,766,106, 4,179,337, 4,495,285, 4,609,546 or EP 315 456.

IgA Antibody Targets

The IgA antibodies described herein can be used to target an antigen expressed on the surface of a cell. In some embodiments, the IgA antibody comprises an antigen binding region that specifically binds to an antigen expressed on the surface of a target cell (e.g., cancer cell). In some embodiments, the antigen is a human antigen. In some embodiments, the target cell is a human cell. In some embodiments, the IgA antibody comprises an antigen binding domain that specifically binds to an antigen of one of the following proteins: CD20, GD2, CD47, CD38, EGFR, HER2, PD-L1, CD25, CD33, BCMA, CD44, CD21, CD64, α-Folate receptor, CAIX, CD30, ROR1, CEA, EGP-2, EGP-40, HER3, Folate-binding Protein, GD3, IL-13R-a2, KDR, EDB-F, mesothelin, EGFR, MUC-1, MAGE-A1, MUC16, h5T4, PSMA, TAG-72, EGFRvIII, CD123, VEGF-R2, BCMA, CD19, CD22, CD30, CD33, CD123, CD38, CD44, CD70, CD274, CD45, CD123, CD138, CD171, ROR1, EGFR, EphA2, FBP, FAP, CEA, EGP2, EGP40, TAG72, PSMA, PSA, PAP, hsp70-2, M-CSF, LAGE-1a, p53, NKG2D ligand, B7-H6, IL-13 R α 2, IL-11 R α, MUC1, MUC16, CA9, GD3, HMW-MAA, CD171, Lewis Y, G250/ CAIX, HLA-AI MAGE A1, HLA-A2 NY-ESO-1, PSC1, PCTA-1, MAGE, ELF2M, IGF-I, IGF-II, IGF-I receptor, hTERT, WT1, MUC1, LMP2, HPV16, HPV18, RGL4, MelanA, MART, ML-IAP, AFP, BCR, ABL, CYP1B1, PLAC1, BORIS, NY—BR-1, RGS5, SART3, EphA2, Glypican-3, 5T4, 8H9, av06 integrin, B7-H3, B7-H6, CAIX, CA9, CSPG4, EGP2, EGP40, EPCAM, ERBB3, ERBB4, ErbB3/4, FAP, FAR, FBP, KDR, MCSP, Mucl, Mucl6, NCAM, PRAME, ROR1, CD44v7/8, 8H9, NCAM, VEGF-R, TAG72, RAGE-1, MN-CA IX, RU1, RU2 (AS), fetal AchR, TEM1, TEM8, PAX5, OY-TES1, LCK, HMWMAA, AKAP-4, SSX2, XAGE 1, tie 2, PDGFR-β, kallikrein 4, PBF, PRAME, HSDL1, CA125, TADG-12, MUC16, mannan-MIC-1, HERV-K-MEL, KK-LC-1, KM-HN-1, LAGE-1, MAGE-A4, SP17, SSX4, TAG1, TAG2, ENAH, mammaglobin-A, NY—BR-1, BAGE-1, HERV-K-MEL, KK-LC-1, KM-KN-1, LAGE1, MAGE1A, MAGEA2, mucink, TRAG3, c-myc, cyclin B1, p62, DKK1, RU2AS, k-ras, ME1, NFYC, STEAP1, FGF5, RU2AS, hsp70-2, ARTC1, B-RAF, beta-catenin, CDC27, CDK4, CDK12, CDKN2A, CLPP, CSNK1A1, FN1, GAS7, GPNMB, HAUS3, LDLR-fucosyltransferase, MART2, MATN, MUM1, MUM2, MUM3, neo-PAP, myosin, PPPIR3B, PRDX5, PTPRK, RBAF600, SIRT2, SNRPD1, trioephosphate isomerase, OA1, RAB38, TRP1, TRP2, melan-A, BAGE1, GAGE1, GAGE2, GAGE8, GAGE3, GAGE4, GAGE5, GAGE6, GAGE7, GNTVF, LY6K, TRAG3, CASP8, SAGE, DEK-CAN, EFTUD2, FLT3-ITD, cyclin A1, FNDC3B, MAGEAG, G250, hepsin, intestinal carboxyl esterase, PBF, CASP5, COA1, OGT, OS9, CALCA, MDM2, alpha actinin4, elongation factor 2, fos-related antigen 1, legumain, sperm protein 17, carbonic anhydrase IX, folate receptor-α, neutrophil elastase, ephrinB2, glioma-associated antigen, β-human chorionic gonadotropin, alphafetoprotein thyroglobulin, telomerase reverse transcriptase, intestinal carboxy esterase, prostein, or survivin. Ganglioside G2

In some embodiments, the IgA antibody or a functional fragment thereof disclosed herein (i.e., antibodies comprising one or more modifications disclosed herein in the IgA heavy chain constant region) specifically binds GD2. In some embodiments, the IgA antibody binds O-acetylated GD2. In some embodiments, the IgA antibody binds GD2 and does not bind O-acetylated GD2. In some embodiments, the IgA antibody binds O-acetylated GD2 and does not bind GD2. In some embodiments, the antibody binds GD2 and binds 0-acetylated GD2. In some embodiments, an antibody or a functional fragment disclosed herein specifically binds a human GD2 polypeptide. The polypeptide and coding nucleic acid sequences of GD2 of human origin and those of a number of animals are publicly available, e.g., from the NCBI website.

In some embodiments, the IgA antibody comprises at least CDR3 of the heavy chain of antibody ch14.18. In some embodiments, the IgA antibody comprises one, two, or three of CDR1, CDR2, or CDR3 of the heavy chain of antibody ch14.18. In some embodiments, the IgA antibody comprises one, two, or three of CDR1, CDR2, or CDR3 of the light chain of antibody ch14.18. In some embodiments, the IgA antibody comprises one, two, or three of CDR1, CDR2, or CDR3 of the heavy chain of antibody ch14.18, and one, two, or three of CDR1, CDR2, or CDR3 of the light chain of antibody ch14.18. In some embodiments, the IgA antibody comprises CDR1, CDR2, or CDR3 of the heavy chain of antibody ch14.18, and CDR1, CDR2, or CDR3 of the light chain of antibody ch14.18. In some embodiments, the IgA antibody comprises at least CDR3 of the heavy chain of antibody ch14.18 and an IgA hinge. In some embodiments, the IgA antibody comprises at least CDR3 of the heavy chain of antibody ch14.18 an IgA hinge, a CH1 IgA region. In some embodiments, the IgA antibody comprises at least CDR3 of the heavy chain of antibody ch14.18 an IgA hinge, a CH1 IgA region, and a CH2 IgA region. In some embodiments, the IgA antibody comprises at least CDR3 of the heavy chain of antibody ch14.18 an IgA hinge, a CH1 IgA region, a CH2 IgA region, and a CH3 IgA region. In some embodiments, the IgA antibody comprises a heavy chain variable region comprising the amino acid sequence: EVQLLQSGPELEKPGASVMISCKASGSSFTGY-NMNWVRQNIGKSLEWIGAIDPYYGGTSYN-QKFKGRATLTVD KSSSTAYMHLKSLTSED-SAVYYCVSGMEYWGQGTSVTVSS [SEQ ID NO: 4]. In some embodiments, the IgA antibody comprises a light chain variable region comprising the amino acid sequence: EIVMTQSPATLSVSPGERATLSCRSSQSLVHRNGN-TYLHWYLQKPGQSPK LLIHKVSNRFSGVPDRFSGSGSGTDFTLKISRVEAE-DLGVYFCSQSTHVPPLTFGAGTKLELK [SEQ ID NO: 5]. In some embodiments, the IgA antibody comprises a heavy chain variable region comprising the amino acid sequence: EVQLLQSGPELEKPGASVMISCK-ASGSSFTGYNMNWVRQNIGKSLEWIGAIDPYYGGT-SYNQKFKGRATLTVD KSSSTAYMHLKSLTSED-SAVYYCVSGMEYWGQGTSVTVSS [SEQ ID NO: 4], and a light chain variable region comprising the amino acid sequence: EIVMTQSPATLSVSPGER-ATLSCRSSQSLVHRNGNTYLHWYLQKPGQSPKL-LIHKVSNRFSGVPDRFSGSGSG TDFTLKISRVEAE-DLGVYFCSQSTHVPPLTFGAGTKLELK [SEQ ID NO: 5].

In some embodiments, the IgA antibody comprises a variable heavy chain comprising one or more of: CDR1 comprising the amino acid sequence: EFTFTDYY [SEQ ID NO: 10]; CDR2 comprising the amino acid sequence: IRN-RANGYTT [SEQ ID NO: 11]; CDR3 comprising the amino acid sequence: ARVSNWAFDY [SEQ ID NO: 12]. In some embodiments, the IgA antibody comprises a variable light chain comprising one or more of: CDR1 comprising the amino acid sequence: QSLLKNNGNTFL [SEQ ID NO: 13]; CDR2 comprising the amino acid sequence: KVS [SEQ ID NO: 14]; CDR3 comprising the amino acid sequence: SQSTHIPYT [SEQ ID NO: 15].

In some embodiments, the IgA antibody comprises a variable heavy chain comprising one or more of: CDR1 comprising the amino acid sequence: EFTFTDYY [SEQ ID NO: 10]; CDR2 comprising the amino acid sequence: IRN-RANGYTT [SEQ ID NO: 11]; CDR3 comprising the amino acid sequence: ARVSNWAFDY [SEQ ID NO: 12]; and a variable light chain comprising one or more of: CDR1 comprising the amino acid sequence: QSLLKNNGNTFL [SEQ ID NO: 13]; CDR2 comprising the amino acid sequence: KVS [SEQ ID NO: 14]; CDR3 comprising the amino acid sequence: SQSTHIPYT [SEQ ID NO: 15].

In some embodiments, the anti-GD2 IgA antibody comprises one or more of (e.g., two, three, four, five, or six) HC-CDR1, HC-CDR2, HC-CDR3, LC-CDR1, LC-CDR2, LC-CDR3 of 3F8 antibody. In some embodiments, the anti-GD2 antibody comprises a variable heavy and/or variable light chain of 3F8 antibody.

In one aspect, the present disclosure provides an antibody or antigen-binding fragment thereof comprises one or more variable regions selected from the group consisting of (a) VH comprising the amino acid sequence of SEQ ID NO: 4, (b) VL comprising the amino acid sequence of SEQ ID NO: 5, and (c) a combination thereof.

In one aspect, the present disclosure provides an antibody or antigen-binding fragment thereof comprising at least one, two, three, four, five, or six CDRs selected from (a) HC-CDR1 comprising the amino acid sequence of SEQ ID NO: 34; (b) HC-CDR2 comprising the amino acid sequence of SEQ ID NO: 42; (c) HC-CDR3 comprising the amino acid sequence of SEQ ID NO: 50; (d) LC-CDR1 comprising the amino acid sequence of SEQ ID NO: 58; (e) LC-CDR2 comprising the amino acid sequence of SEQ ID NO: 66; and (f) LC-CDR3 comprising the amino acid sequence of SEQ ID NO: 74.

In one aspect, the present disclosure provides an antibody or antigen-binding fragment thereof comprising at least one, at least two, or all three VH CDR sequences selected from (a) HC-CDR1 comprising the amino acid sequence of SEQ ID NO: 34; (b) HC-CDR2 comprising the amino acid sequence of SEQ ID NO: 42; and (c) HC-CDR3 comprising the amino acid sequence of SEQ ID NO: 50; and (d) a VL comprising the amino acid sequence of SEQ ID NO: 5.

In one aspect, the present disclosure provides an antibody or antigen-binding fragment thereof comprising at least one, at least two, or all three VL CDR sequences selected from (a) LC-CDR1 comprising the amino acid sequence of SEQ ID NO: 58; (b) LC-CDR2 comprising the amino acid sequence of SEQ ID NO: 66; and (c) LC-CDR3 comprising the amino acid sequence of SEQ ID NO: 74; and a VH comprising the amino acid sequence of SEQ ID NO: 4.

In one aspect, the present disclosure provides an antibody or antigen-binding fragment thereof comprising the CDRs: HC-CDR3 comprising the amino acid sequence of SEQ ID NO: 50; and LC-CDR3 comprising the amino acid sequence of SEQ ID NO: 74.

In one aspect, the disclosure herein provides an antibody or antigen-binding fragment thereof comprising at least one, at least two, or all three VL CDR sequences selected from (a) LC-CDR1 comprising the amino acid sequence of SEQ ID NO: 58; (b) LC-CDR2 comprising the amino acid sequence of SEQ ID NO: 66 and (c) LC-CDR3 comprising the amino acid sequence of SEQ ID NO: 74. In one aspect, the disclosure provides an antibody or antigen-binding fragment thereof comprising at least one, at least two, or all three VH CDR sequences selected from (a) HC-CDR1 comprising the amino acid sequence of SEQ ID NO: 34; (b) HC-CDR2 comprising the amino acid sequence of SEQ ID NO: 42 and (c) HC-CDR3 comprising the amino acid sequence of SEQ ID NO: 50.

In one aspect, the disclosure provides an antibody or antigen-binding fragment thereof comprising the CDRs: (a) HC-CDR1 comprising the amino acid sequence of SEQ ID NO: 34; (b) HC-CDR2 comprising the amino acid sequence of SEQ ID NO: 42; (c) HC-CDR3 comprising the amino acid sequence of SEQ ID NO: 50; (d) LC-CDR1 comprising the amino acid sequence of SEQ ID NO: 58; (e) LC-CDR2 comprising the amino acid sequence of SEQ ID NO: 66; and (f) LC-CDR3 comprising the amino acid sequence of SEQ ID NO: 74.

In one aspect, an antibody or antigen-binding fragment thereof comprises a VH sequence having at least 90%, 91%, 92%, 93%, 94%, 95%, 96%, 97%, 98%, 99%, or 100% sequence identity to the amino acid sequence of SEQ ID NO: 4. In some embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in the amino acid sequence of SEQ ID NO: 4. In some embodiments, substitutions, insertions, or deletions occur in regions outside the CDRs (e.g., in the FRs). Optionally, the antibody or antigen-binding fragment thereof comprises the VH sequence of the amino acid sequence of SEQ ID NO: 4, including post-translational modifications of that sequence. In a particular embodiment, the VH comprises one, two or three CDRs selected from: (a) HC-CDR1 comprising the amino acid sequence of SEQ ID NO: 34, (b) HC-CDR2 comprising the amino acid sequence of SEQ ID NO: 42, and (c) HC-CDR3 comprising the amino acid sequence of SEQ ID NO: 50.

In one aspect, an antibody or antigen-binding fragment thereof is provided, wherein the antibody or antigen-binding fragment thereof comprises a light chain variable domain (VL) having at least 90%, 91%, 92%, 93%, 94%, 95%, 96%, 97%, 98%, 99%, or 100% sequence identity to the amino acid sequence of SEQ ID NO: 5. In some embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in any one of the amino acid sequence of SEQ ID NO: 5. In some embodiments, the substitutions, insertions, or deletions occur in regions outside the CDRs (e.g., in the FRs). Optionally, the antibody or antigen-binding fragment thereof comprises the VL sequence of SEQ ID NO: 5, including post-translational modifications of that sequence. In a particular embodiment, the VL comprises one, two or three CDRs selected from (a) LC-CDR1 comprising the amino acid sequence of SEQ ID NO: 58; (b) LC-CDR2 comprising the amino acid sequence of SEQ ID NO: 66; and (c) LC-CDR3 comprising the amino acid sequence of SEQ ID NO: 74.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody comprises a VH comprising the amino acid sequence of SEQ ID NO: 4, and a VL sequence in SEQ ID NO: 5, including post-translational modifications of those sequences. In some embodiments, the antibody or antigen binding fragment thereof comprises a IgA heavy chain constant region having at least 90%, 91%, 92%, 93%, 94%, 95%, 96%, 97%, 98%, 99%, or 100% sequence identity to the amino acid sequence of any one of SEQ ID NOs: 16-21. In some embodiments, the antibody or antigen binding fragment thereof comprises a kappa light chain constant region of SEQ ID NO: 31.

CD20

In some embodiments, the IgA antibody specifically binds CD20. In some embodiments, the IgA antibody comprises an antigen binding domain that comprises a Type II or a Type I/II CD20 binding region. In some embodiments, an antibody or a functional fragment disclosed herein specifically binds a human CD20 polypeptide. The polypeptide and coding nucleic acid sequences of CD20 of human origin and those of a number of animals are publicly available, e.g., from the NCBI website. In some embodiments, the IgA antibody comprises an antigen binding domain which specifically binds to a CD20 epitope, wherein said CD20 epitope is within the following amino acid sequence: YNCEPANPSEKNSPSTQYCYS [SEQ ID NO: 6].

In some embodiments, the variable region of the CD20 antibody is described in PCTNL2017050581, which is incorporated by reference herein in it is entirety. In some embodiments, the heavy chain variable region comprises one, two, or three of CDR1, CDR2, OR CDR3 within the following amino acid sequence: QAYLQQSGAELVRP-GASVKMSCKASGYTFT SYNLHWVKQTPRQGLEWI-GAIYPGNGDTSYN-QKFKGKATLTVDKSSSTAYMQLSRLTSED SAVYFCARSNSYGSTYWYFDVWGTGTTVTVSS [SEQ ID NO: 7]. In some embodiments, the light chain variable region comprises one, two, or three of CDR1, CDR2, OR CDR3 within the following amino acid sequence: QIVLSQSPAVLFASPGEKVTMT-CRARSSVSYMDWYQQKPRSSPKPWIYATSN-LASGVPARFSGSG SGTSYSLTISRVEAE-DAATYYCQQWTSNPPTFGSGTKLEIKRADAAPTVSI-FPPSS [SEQ ID NO: 8].

In some embodiments, the heavy chain variable region comprises the following amino acid sequence: QAYLQQS-GAELVRPGASVKMSCKASGYTFTSYNLHWVKQT-PRQGLEWIGAIYPGNGDTSYNQKFKGKATLTVD KSSSTAYMQLSRLTSED SAVYFCARSNSYG-STYWYFDVWGTGTTVTVSS [SEQ ID NO: 7]. In some embodiments, the light chain variable region comprises the following amino acid sequence: QIVLSQSPAVL-FASPGEKVTMTCRARSSVSYMDWYQQKPRSSPKP-WIYATSNLASGVPARFSGSG SGTSYSLTISRVEAE-DAATYYCQQWTSNPPTFGSGTKLEIKRADAAPTVSI-FPPSS [SEQ ID NO: 8].

In some embodiments, the IgA antibody comprises at least CDR3 of the heavy chain of antibody Obinutuzumab. In some embodiments, the IgA antibody comprises one, two, or three of CDR1, CDR2, or CDR3 of the heavy chain of antibody Obinutuzumab. In some embodiments, the IgA antibody comprises one, two, or three of CDR1, CDR2, or CDR3 of the light chain of antibody Obinutuzumab. In some embodiments, the IgA antibody comprises one, two, or three of CDR1, CDR2, or CDR3 of the heavy chain of antibody Obinutuzumab, and one, two, or three of CDR1, CDR2, or CDR3 of the light chain of antibody Obinutuzumab. In some embodiments, the IgA antibody comprises CDR1, CDR2, or CDR3 of the heavy chain of antibody Obinutuzumab, and CDR1, CDR2, or CDR3 of the light chain of antibody Obinutuzumab. In some embodiments, the IgA antibody comprises at least CDR3 of the heavy chain of antibody Obinutuzumab and an IgA hinge. In some embodiments, the IgA antibody comprises at least CDR3 of the heavy chain of antibody Obinutuzumab an IgA hinge, a CH1 IgA region. In some embodiments, the IgA antibody comprises at least CDR3 of the heavy chain of antibody Obinutuzumab an IgA hinge, a CH1 IgA region, and a CH2 IgA region. In some embodiments, the IgA antibody comprises at least CDR3 of the heavy chain of antibody Obinutuzumab an IgA hinge, a CH1 IgA region, a CH2 IgA region, and a CH3 IgA region.

In some embodiments, the IgA antibody specifically binds the CD20 epitope EPANPSEK.

In some embodiments, the IgA antibody specifically binds CD20 and has increased programmed cell death (PCD) function compared to rituximab with a constant region of the same isotype. In some embodiments, the IgA antibody specifically binds CD20 and has increased antibody dependent cell mediated cytotoxicity (ADCC) functionality compared to rituximab with a constant region of the same isotype. In some embodiments, the IgA antibody specifically binds CD20 and has increased complement dependent cytotoxicity (CDC) functionality compared to rituximab with a constant region of the same isotype.

In some embodiments, the IgA antibody has a shorter circulating half-life compared to a corresponding IgG antibody. In some embodiments, administration of the anti-CD20 IgA antibody is associated with fewer side effects from B cell depletion compared to a corresponding IgG antibody. In some embodiments, administration of the anti-CD20 antibody is associated with faster B-cell replenishment compared to a corresponding IgG antibody.

In one aspect, the present disclosure provides an antibody or antigen-binding fragment thereof comprises one or more variable regions selected from the group consisting of (a) VH comprising the amino acid sequence of SEQ ID NO: 81, (b) VL comprising the amino acid sequence of SEQ ID NO: 95, and (c) a combination thereof.

In one aspect, the present disclosure provides an antibody or antigen-binding fragment thereof comprising at least one, two, three, four, five, or six CDRs selected from (a) HC-CDR1 comprising the amino acid sequence of SEQ ID NO: 33; (b) HC-CDR2 comprising the amino acid sequence of SEQ ID NO: 41; (c) HC-CDR3 comprising the amino acid sequence of SEQ ID NO: 49; (d) LC-CDR1 comprising the amino acid sequence of SEQ ID NO: 57; (e) LC-CDR2 comprising the amino acid sequence of SEQ ID NO: 65; and (f) LC-CDR3 comprising the amino acid sequence of SEQ ID NO: 73.

In one aspect, the present disclosure provides an antibody or antigen-binding fragment thereof comprising at least one, at least two, or all three VH CDR sequences selected from (a) HC-CDR1 comprising the amino acid sequence of SEQ ID NO: 33; (b) HC-CDR2 comprising the amino acid sequence of SEQ ID NO: 41; and (c) HC-CDR3 comprising the amino acid sequence of SEQ ID NO: 49; and (d) a VL comprising the amino acid sequence of SEQ ID NO: 95.

In one aspect, the present disclosure provides an antibody or antigen-binding fragment thereof comprising at least one, at least two, or all three VL CDR sequences selected from (a) LC-CDR1 comprising the amino acid sequence of SEQ ID NO: 57; (b) LC-CDR2 comprising the amino acid sequence of SEQ ID NO: 65; and (c) LC-CDR3 comprising the amino acid sequence of SEQ ID NO: 73; and a VH comprising the amino acid sequence of SEQ ID NO: 81.

In one aspect, the present disclosure provides an antibody or antigen-binding fragment thereof comprising the CDRs: HC-CDR3 comprising the amino acid sequence of SEQ ID NO: 49; and LC-CDR3 comprising the amino acid sequence of SEQ ID NO: 73.

In one aspect, the disclosure herein provides an antibody or antigen-binding fragment thereof comprising at least one, at least two, or all three VL CDR sequences selected from (a) LC-CDR1 comprising the amino acid sequence of SEQ ID NO: 57; (b) LC-CDR2 comprising the amino acid sequence of SEQ ID NO: 65 and (c) LC-CDR3 comprising the amino acid sequence of SEQ ID NO: 73. In one aspect, the disclosure provides an antibody or antigen-binding fragment thereof comprising at least one, at least two, or all three VH CDR sequences selected from (a) HC-CDR1 comprising the amino acid sequence of SEQ ID NO: 33; (b) HC-CDR2 comprising the amino acid sequence of SEQ ID NO: 41 and (c) HC-CDR3 comprising the amino acid sequence of SEQ ID NO: 49.

In one aspect, the disclosure provides an antibody or antigen-binding fragment thereof comprising the CDRs: (a)

HC-CDR1 comprising the amino acid sequence of SEQ ID NO: 33; (b) HC-CDR2 comprising the amino acid sequence of SEQ ID NO: 41; (c) HC-CDR3 comprising the amino acid sequence of SEQ ID NO: 49; (d) LC-CDR1 comprising the amino acid sequence of SEQ ID NO: 57; (e) LC-CDR2 comprising the amino acid sequence of SEQ ID NO: 65; and (f) LC-CDR3 comprising the amino acid sequence of SEQ ID NO: 73.

In one aspect, an antibody or antigen-binding fragment thereof comprises a VH sequence having at least 90%, 91%, 92%, 93%, 94%, 95%, 96%, 97%, 98%, 99%, or 100% sequence identity to the amino acid sequence of SEQ ID NO: 81. In some embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in the amino acid sequence of SEQ ID NO: 81. In some embodiments, substitutions, insertions, or deletions occur in regions outside the CDRs (e.g., in the FRs). Optionally, the antibody or antigen-binding fragment thereof comprises the VH sequence of the amino acid sequence of SEQ ID NO: 81, including post-translational modifications of that sequence. In a particular embodiment, the VH comprises one, two or three CDRs selected from: (a) HC-CDR1 comprising the amino acid sequence of SEQ ID NO: 33, (b) HC-CDR2 comprising the amino acid sequence of SEQ ID NO: 41, and (c) HC-CDR3 comprising the amino acid sequence of SEQ ID NO: 49.

In one aspect, an antibody or antigen-binding fragment thereof is provided, wherein the antibody or antigen-binding fragment thereof comprises a light chain variable domain (VL) having at least 90%, 91% 92%, 93%, 94%, 95%, 96%, 97%, 98%, 99%, or 100% sequence identity to the amino acid sequence of SEQ ID NO: 95. In some embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in any one of the amino acid sequence of SEQ ID NO: 95. In some embodiments, the substitutions, insertions, or deletions occur in regions outside the CDRs (e.g., in the FRs). Optionally, the antibody or antigen-binding fragment thereof comprises the VL sequence of SEQ ID NO: 95, including post-translational modifications of that sequence. In a particular embodiment, the VL comprises one, two or three CDRs selected from (a) LC-CDR1 comprising the amino acid sequence of SEQ ID NO: 57; (b) LC-CDR2 comprising the amino acid sequence of SEQ ID NO: 5; and (c) LC-CDR3 comprising the amino acid sequence of SEQ ID NO: 73.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody comprises a VH comprising the amino acid sequence of SEQ ID NO: 81, and a VL sequence in SEQ ID NO: 95, including post-translational modifications of those sequences. In some embodiments, the antibody or antigen binding fragment thereof comprises a IgA heavy chain constant region having at least 90%, 91%, 92%, 93%, 94%, 95%, 96%, 97%, 98%, 99%, or 100% sequence identity to the amino acid sequence of any one of SEQ ID NOs: 16-21. In some embodiments, the antibody or antigen binding fragment thereof comprises a kappa light chain constant region of SEQ ID NO: 31.

In some embodiments, provided herein is an antibody or a functional fragment thereof that specifically binds CD47. In some embodiments, the IgA antibody comprises at least CDR3 of the heavy chain of antibody UMAB10. In some embodiments, the IgA antibody comprises one, two, or three of CDR1, CDR2, or CDR3 of the heavy chain of antibody UMAB10. In some embodiments, the IgA antibody comprises one, two, or three of CDR1, CDR2, or CDR3 of the light chain of antibody UMAB10. In some embodiments, the IgA antibody comprises one, two, or three of CDR1, CDR2, or CDR3 of the heavy chain of antibody UMAB10, and one, two, or three of CDR1, CDR2, or CDR3 of the light chain of antibody UMAB10. In some embodiments, the IgA antibody comprises CDR1, CDR2, or CDR3 of the heavy chain of antibody UMAB10, and CDR1, CDR2, or CDR3 of the light chain of antibody UMAB10. In some embodiments, the IgA antibody comprises at least CDR3 of the heavy chain of antibody UMAB10 and an IgA hinge. In some embodiments, the IgA antibody comprises at least CDR3 of the heavy chain of antibody UMAB10 an IgA hinge, a CH1 IgA region. In some embodiments, the IgA antibody comprises at least CDR3 of the heavy chain of antibody UMAB10 an IgA hinge, a CH1 IgA region, and a CH2 IgA region. In some embodiments, the IgA antibody comprises at least CDR3 of the heavy chain of antibody UMAB10 an IgA hinge, a CH1 IgA region, a CH2 IgA region, and a CH3 IgA region.

In one aspect, the present disclosure provides an antibody or antigen-binding fragment thereof comprises one or more variable regions selected from the group consisting of (a) VH comprising the amino acid sequence of SEQ ID NO: 86, (b) VL comprising the amino acid sequence of SEQ ID NO: 100, and (c) a combination thereof.

In one aspect, the present disclosure provides an antibody or antigen-binding fragment thereof comprising at least one, two, three, four, five, or six CDRs selected from (a) HC-CDR1 comprising the amino acid sequence of SEQ ID NO: 40; (b) HC-CDR2 comprising the amino acid sequence of SEQ ID NO: 48; (c) HC-CDR3 comprising the amino acid sequence of SEQ ID NO: 56; (d) LC-CDR1 comprising the amino acid sequence of SEQ ID NO: 64; (e) LC-CDR2 comprising the amino acid sequence of SEQ ID NO:72; and (f) LC-CDR3 comprising the amino acid sequence of SEQ ID NO: 80.

In one aspect, the present disclosure provides an antibody or antigen-binding fragment thereof comprising at least one, at least two, or all three VH CDR sequences selected from (a) HC-CDR1 comprising the amino acid sequence of SEQ ID NO: 40; (b) HC-CDR2 comprising the amino acid sequence of SEQ ID NO: 48; and (c) HC-CDR3 comprising the amino acid sequence of SEQ ID NO: 56; and (d) a VL comprising the amino acid sequence of SEQ ID NO: 8.

In one aspect, the present disclosure provides an antibody or antigen-binding fragment thereof comprising at least one, at least two, or all three VL CDR sequences selected from (a) LC-CDR1 comprising the amino acid sequence of SEQ ID NO: 64; (b) LC-CDR2 comprising the amino acid sequence of SEQ ID NO: 72; and (c) LC-CDR3 comprising the amino acid sequence of SEQ ID NO: 80; and a VH comprising the amino acid sequence of SEQ ID NO: 7.

In one aspect, the present disclosure provides an antibody or antigen-binding fragment thereof comprising the CDRs:

HC-CDR3 comprising the amino acid sequence of SEQ ID NO: 56; and LC-CDR3 comprising the amino acid sequence of SEQ ID NO: 80.

In one aspect, the disclosure herein provides an antibody or antigen-binding fragment thereof comprising at least one, at least two, or all three VL CDR sequences selected from (a) LC-CDR1 comprising the amino acid sequence of SEQ ID NO: 64; (b) LC-CDR2 comprising the amino acid sequence of SEQ ID NO: 72 and (c) LC-CDR3 comprising the amino acid sequence of SEQ ID NO: 80. In one aspect, the disclosure provides an antibody or antigen-binding fragment thereof comprising at least one, at least two, or all three VH CDR sequences selected from (a) HC-CDR1 comprising the amino acid sequence of SEQ ID NO: 40; (b) HC-CDR2 comprising the amino acid sequence of SEQ ID NO: 48 and (c) HC-CDR3 comprising the amino acid sequence of SEQ ID NO: 56.

In one aspect, the disclosure provides an antibody or antigen-binding fragment thereof comprising the CDRs: (a) HC-CDR1 comprising the amino acid sequence of SEQ ID NO: 40; (b) HC-CDR2 comprising the amino acid sequence of SEQ ID NO: 48; (c) HC-CDR3 comprising the amino acid sequence of SEQ ID NO: 56; (d) LC-CDR1 comprising the amino acid sequence of SEQ ID NO: 64; (e) LC-CDR2 comprising the amino acid sequence of SEQ ID NO: 72; and (f) LC-CDR3 comprising the amino acid sequence of SEQ ID NO: 80.

In one aspect, an antibody or antigen-binding fragment thereof comprises a VH sequence having at least 90%, 91%, 92%, 93%, 94%, 95%, 96%, 97%, 98%, 99%, or 100% sequence identity to the amino acid sequence of SEQ ID NO: 7. In some embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in the amino acid sequence of SEQ ID NO: 7. In some embodiments, substitutions, insertions, or deletions occur in regions outside the CDRs (e.g., in the FRs). Optionally, the antibody or antigen-binding fragment thereof comprises the VH sequence of the amino acid sequence of SEQ ID NO: 7, including post-translational modifications of that sequence. In a particular embodiment, the VH comprises one, two or three CDRs selected from: (a) HC-CDR1 comprising the amino acid sequence of SEQ ID NO: 40, (b) HC-CDR2 comprising the amino acid sequence of SEQ ID NO: 48, and (c) HC-CDR3 comprising the amino acid sequence of SEQ ID NO: 56.

In one aspect, an antibody or antigen-binding fragment thereof is provided, wherein the antibody or antigen-binding fragment thereof comprises a light chain variable domain (VL) having at least 90%, 91%, 92%, 93%, 94%, 95%, 96%, 97%, 98%, 99%, or 100% sequence identity to the amino acid sequence of SEQ ID NO: 8. In some embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in any one of the amino acid sequence of SEQ ID NO: 8. In some embodiments, the substitutions, insertions, or deletions occur in regions outside the CDRs (e.g., in the FRs). Optionally, the antibody or antigen-binding fragment thereof comprises the VL sequence of SEQ ID NO: 8, including post-translational modifications of that sequence. In a particular embodiment, the VL comprises one, two or three CDRs selected from (a) LC-CDR1 comprising the amino acid sequence of SEQ ID NO: 64; (b) LC-CDR2 comprising the amino acid sequence of SEQ ID NO: 72; and (c) LC-CDR3 comprising the amino acid sequence of SEQ ID NO: 80.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody comprises a VH comprising the amino acid sequence of SEQ ID NO: 7, and a VL sequence in SEQ ID NO: 8, including post-translational modifications of those sequences. In some embodiments, the antibody or antigen binding fragment thereof comprises an IgA heavy chain constant region having at least 90%, 91%, 92%, 93%, 94%, 95%, 96%, 97%, 98%, 99%, or 100% sequence identity to the amino acid sequence of any one of SEQ ID NOs: 16-21. In some embodiments, the antibody or antigen binding fragment thereof comprises a kappa light chain constant region of SEQ ID NO: 31.

Her2

In some embodiments, provided herein is an antibody or a functional fragment thereof that specifically binds Her2. In some embodiments, the IgA antibody comprises at least CDR3 of the heavy chain of antibody Trastuzumab. In some embodiments, the IgA antibody comprises one, two, or three of CDR1, CDR2, or CDR3 of the heavy chain of antibody Trastuzumab. In some embodiments, the IgA antibody comprises one, two, or three of CDR1, CDR2, or CDR3 of the light chain of antibody Trastuzumab. In some embodiments, the IgA antibody comprises one, two, or three of CDR1, CDR2, or CDR3 of the heavy chain of antibody Trastuzumab, and one, two, or three of CDR1, CDR2, or CDR3 of the light chain of antibody Trastuzumab. In some embodiments, the IgA antibody comprises CDR1, CDR2, or CDR3 of the heavy chain of antibody Trastuzumab, and CDR1, CDR2, or CDR3 of the light chain of antibody Trastuzumab. In some embodiments, the IgA antibody comprises at least CDR3 of the heavy chain of antibody Trastuzumab and an IgA hinge. In some embodiments, the IgA antibody comprises at least CDR3 of the heavy chain of antibody Trastuzumab an IgA hinge, a CH1 IgA region. In some embodiments, the IgA antibody comprises at least CDR3 of the heavy chain of antibody Trastuzumab an IgA hinge, a CH1 IgA region, and a CH2 IgA region. In some embodiments, the IgA antibody comprises at least CDR3 of the heavy chain of antibody Trastuzumab, an IgA hinge, a CH1 IgA region, a CH2 IgA region, and a CH3 IgA region.

In one aspect, the present disclosure provides an antibody or antigen-binding fragment thereof comprises one or more variable regions selected from the group consisting of (a) VH comprising the amino acid sequence of SEQ ID NO: 82, (b) VL comprising the amino acid sequence of SEQ ID NO: 96, and (c) a combination thereof.

In one aspect, the present disclosure provides an antibody or antigen-binding fragment thereof comprising at least one, two, three, four, five, or six CDRs selected from (a) HC-CDR1 comprising the amino acid sequence of SEQ ID NO: 35; (b) HC-CDR2 comprising the amino acid sequence of SEQ ID NO: 43; (c) HC-CDR3 comprising the amino acid sequence of SEQ ID NO: 51; (d) LC-CDR1 comprising the amino acid sequence of SEQ ID NO: 59; (e) LC-CDR2 comprising the amino acid sequence of SEQ ID NO: 67; and (f) LC-CDR3 comprising the amino acid sequence of SEQ ID NO: 75.

In one aspect, the present disclosure provides an antibody or antigen-binding fragment thereof comprising at least one, at least two, or all three VH CDR sequences selected from (a) HC-CDR1 comprising the amino acid sequence of SEQ ID NO: 35; (b) HC-CDR2 comprising the amino acid sequence of SEQ ID NO: 43; and (c) HC-CDR3 comprising the amino acid sequence of SEQ ID NO: 51; and (d) a VL comprising the amino acid sequence of SEQ ID NO: 96.

In one aspect, the present disclosure provides an antibody or antigen-binding fragment thereof comprising at least one, at least two, or all three VL CDR sequences selected from (a) LC-CDR1 comprising the amino acid sequence of SEQ ID NO: 59; (b) LC-CDR2 comprising the amino acid sequence of SEQ ID NO: 67; and (c) LC-CDR3 comprising the amino acid sequence of SEQ ID NO: 75; and a VH comprising the amino acid sequence of SEQ ID NO: 82.

In one aspect, the present disclosure provides an antibody or antigen-binding fragment thereof comprising the CDRs: HC-CDR3 comprising the amino acid sequence of SEQ ID NO: 51; and LC-CDR3 comprising the amino acid sequence of SEQ ID NO: 75.

In one aspect, the disclosure herein provides an antibody or antigen-binding fragment thereof comprising at least one, at least two, or all three VL CDR sequences selected from (a) LC-CDR1 comprising the amino acid sequence of SEQ ID NO: 59; (b) LC-CDR2 comprising the amino acid sequence of SEQ ID NO: 67 and (c) LC-CDR3 comprising the amino acid sequence of SEQ ID NO: 75. In one aspect, the disclosure provides an antibody or antigen-binding fragment thereof comprising at least one, at least two, or all three VH CDR sequences selected from (a) HC-CDR1 comprising the amino acid sequence of SEQ ID NO: 35; (b) HC-CDR2 comprising the amino acid sequence of SEQ ID NO: 43 and (c) HC-CDR3 comprising the amino acid sequence of SEQ ID NO: 51.

In one aspect, the disclosure provides an antibody or antigen-binding fragment thereof comprising the CDRs: (a) HC-CDR1 comprising the amino acid sequence of SEQ ID NO: 35; (b) HC-CDR2 comprising the amino acid sequence of SEQ ID NO: 43; (c) HC-CDR3 comprising the amino acid sequence of SEQ ID NO: 51; (d) LC-CDR1 comprising the amino acid sequence of SEQ ID NO: 59; (e) LC-CDR2 comprising the amino acid sequence of SEQ ID NO: 67; and (f) LC-CDR3 comprising the amino acid sequence of SEQ ID NO: 75.

In one aspect, an antibody or antigen-binding fragment thereof comprises a VH sequence having at least 90%, 91%, 92%, 93%, 94%, 95%, 96%, 97%, 98%, 99%, or 100% sequence identity to the amino acid sequence of SEQ ID NO: 82. In some embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in the amino acid sequence of SEQ ID NO: 82. In some embodiments, substitutions, insertions, or deletions occur in regions outside the CDRs (e.g., in the FRs). Optionally, the antibody or antigen-binding fragment thereof comprises the VH sequence of the amino acid sequence of SEQ ID NO: 82, including post-translational modifications of that sequence. In a particular embodiment, the VH comprises one, two or three CDRs selected from: (a) HC-CDR1 comprising the amino acid sequence of SEQ ID NO: 35, (b) HC-CDR2 comprising the amino acid sequence of SEQ ID NO: 43, and (c) HC-CDR3 comprising the amino acid sequence of SEQ ID NO: 51.

In one aspect, an antibody or antigen-binding fragment thereof is provided, wherein the antibody or antigen-binding fragment thereof comprises a light chain variable domain (VL) having at least 90%, 91% 92% 93% 94% 95% 96% 97% 98% 99%, or 100% sequence identity to the amino acid sequence of SEQ ID NO: 96. In some embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in any one of the amino acid sequence of SEQ ID NO: 96. In some embodiments, the substitutions, insertions, or deletions occur in regions outside the CDRs (e.g., in the FRs). Optionally, the antibody or antigen-binding fragment thereof comprises the VL sequence of SEQ ID NO: 96, including post-translational modifications of that sequence. In a particular embodiment, the VL comprises one, two, or three CDRs selected from (a) LC-CDR1 comprising the amino acid sequence of SEQ ID NO: 59; (b) LC-CDR2 comprising the amino acid sequence of SEQ ID NO: 67; and (c) LC-CDR3 comprising the amino acid sequence of SEQ ID NO: 75.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody comprises a VH comprising the amino acid sequence of SEQ ID NO: 82, and a VL sequence in SEQ ID NO: 96, including post-translational modifications of those sequences. In some embodiments, the antibody or antigen binding fragment thereof comprises an IgA heavy chain constant region having at least 90%, 91%, 92%, 93%, 94%, 95%, 96%, 97%, 98%, 99%, or 100% sequence identity to the amino acid sequence of any one of SEQ ID NOs: 16-21. In some embodiments, the antibody or antigen binding fragment thereof comprises a kappa light chain constant region of SEQ ID NO: 31.

gp75

In some embodiments, provided herein is an antibody or a functional fragment thereof that specifically binds gp75 or tyrosine related protein 1. In some embodiments, an antibody or a functional fragment disclosed herein specifically binds a human gp75 polypeptide. The polypeptide and coding nucleic acid sequences of gp75 of human origin and those of a number of animals are publicly available, e.g., from the NCBI website. In some embodiments, the IgA antibody comprises at least CDR3 of the heavy chain of antibody TA99. In some embodiments, the IgA antibody comprises one, two, or three of CDR1, CDR2, or CDR3 of the heavy chain of antibody TA99. In some embodiments, the IgA antibody comprises one, two, or three of CDR1, CDR2, or CDR3 of the light chain of antibody TA99. In some embodiments, the IgA antibody comprises one, two, or three of CDR1, CDR2, or CDR3 of the heavy chain of antibody TA99, and one, two, or three of CDR1, CDR2, or CDR3 of the light chain of antibody TA99. In some embodiments, the IgA antibody comprises CDR1, CDR2, or CDR3 of the heavy chain of antibody TA99, and CDR1, CDR2, or CDR3 of the light chain of antibody TA99. In some embodiments, the IgA antibody comprises at least CDR3 of the heavy chain of antibody TA99 and an IgA hinge. In some embodiments, the IgA antibody comprises at least CDR3 of the heavy chain of antibody TA99 an IgA hinge, a CH1 IgA region. In some embodiments, the IgA antibody comprises at least CDR3 of the heavy chain of antibody TA99 an IgA hinge, a CH1 IgA region, and a CH2 IgA region. In some embodiments, the IgA antibody comprises at least CDR3 of the heavy chain of antibody TA99 an IgA hinge, a CH1 IgA region, a CH2 IgA region, and a CH3 IgA region.

In one aspect, the present disclosure provides an antibody or antigen-binding fragment thereof comprises one or more variable regions selected from the group consisting of (a) VH comprising the amino acid sequence of SEQ ID NO: 83, (b) VL comprising the amino acid sequence of SEQ ID NO: 97, and (c) a combination thereof.

In one aspect, the present disclosure provides an antibody or antigen-binding fragment thereof comprising at least one, two, three, four, five, or six CDRs selected from (a) HC-CDR1 comprising the amino acid sequence of SEQ ID NO: 36; (b) HC-CDR2 comprising the amino acid sequence of SEQ ID NO: 44; (c) HC-CDR3 comprising the amino acid sequence of SEQ ID NO: 52; (d) LC-CDR1 comprising the amino acid sequence of SEQ ID NO: 60; (e) LC-CDR2 comprising the amino acid sequence of SEQ ID NO: 68; and (f) LC-CDR3 comprising the amino acid sequence of SEQ ID NO: 76.

In one aspect, the present disclosure provides an antibody or antigen-binding fragment thereof comprising at least one, at least two, or all three VH CDR sequences selected from (a) HC-CDR1 comprising the amino acid sequence of SEQ ID NO: 36; (b) HC-CDR2 comprising the amino acid sequence of SEQ ID NO: 44; and (c) HC-CDR3 comprising the amino acid sequence of SEQ ID NO: 52; and (d) a VL comprising the amino acid sequence of SEQ ID NO: 97.

In one aspect, the present disclosure provides an antibody or antigen-binding fragment thereof comprising at least one, at least two, or all three VL CDR sequences selected from (a) LC-CDR1 comprising the amino acid sequence of SEQ ID NO: 60; (b) LC-CDR2 comprising the amino acid sequence of SEQ ID NO: 68; and (c) LC-CDR3 comprising the amino acid sequence of SEQ ID NO: 76; and a VH comprising the amino acid sequence of SEQ ID NO: 83.

In one aspect, the present disclosure provides an antibody or antigen-binding fragment thereof comprising the CDRs: HC-CDR3 comprising the amino acid sequence of SEQ ID NO: 52; and LC-CDR3 comprising the amino acid sequence of SEQ ID NO: 76.

In one aspect, the disclosure herein provides an antibody or antigen-binding fragment thereof comprising at least one, at least two, or all three VL CDR sequences selected from (a) LC-CDR1 comprising the amino acid sequence of SEQ ID NO: 60; (b) LC-CDR2 comprising the amino acid sequence of SEQ ID NO: 68 and (c) LC-CDR3 comprising the amino acid sequence of SEQ ID NO: 76. In one aspect, the disclosure provides an antibody or antigen-binding fragment thereof comprising at least one, at least two, or all three VH CDR sequences selected from (a) HC-CDR1 comprising the amino acid sequence of SEQ ID NO: 36; (b) HC-CDR2 comprising the amino acid sequence of SEQ ID NO: 44 and (c) HC-CDR3 comprising the amino acid sequence of SEQ ID NO: 52.

In one aspect, the disclosure provides an antibody or antigen-binding fragment thereof comprising the CDRs: (a) HC-CDR1 comprising the amino acid sequence of SEQ ID NO: 36; (b) HC-CDR2 comprising the amino acid sequence of SEQ ID NO: 44; (c) HC-CDR3 comprising the amino acid sequence of SEQ ID NO: 52; (d) LC-CDR1 comprising the amino acid sequence of SEQ ID NO: 60; (e) LC-CDR2 comprising the amino acid sequence of SEQ ID NO: 68; and (f) LC-CDR3 comprising the amino acid sequence of SEQ ID NO: 76.

In one aspect, an antibody or antigen-binding fragment thereof comprises a VH sequence having at least 90%, 91%, 92%, 93%, 94%, 95%, 96%, 97%, 98%, 99%, or 100% sequence identity to the amino acid sequence of SEQ ID NO: 83. In some embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in the amino acid sequence of SEQ ID NO: 83. In some embodiments, substitutions, insertions, or deletions occur in regions outside the CDRs (e.g., in the FRs). Optionally, the antibody or antigen-binding fragment thereof comprises the VH sequence of the amino acid sequence of SEQ ID NO: 83, including post-translational modifications of that sequence. In a particular embodiment, the VH comprises one, two or three CDRs selected from: (a) HC-CDR1 comprising the amino acid sequence of SEQ ID NO: 36, (b) HC-CDR2 comprising the amino acid sequence of SEQ ID NO: 44, and (c) HC-CDR3 comprising the amino acid sequence of SEQ ID NO: 52.

In one aspect, an antibody or antigen-binding fragment thereof is provided, wherein the antibody or antigen-binding fragment thereof comprises a light chain variable domain (VL) having at least 90%, 91% 92%, 93%, 94%, 95%, 96%, 97%, 98%, 99%, or 100% sequence identity to the amino acid sequence of SEQ ID NO: 97. In some embodiments, a VL sequence having at least 90%, 91, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in any one of the amino acid sequence of SEQ ID NO: 97. In some embodiments, the substitutions, insertions, or deletions occur in regions outside the CDRs (e.g., in the FRs). Optionally, the antibody or antigen-binding fragment thereof comprises the VL sequence of SEQ ID NO: 97, including post-translational modifications of that sequence. In a particular embodiment, the VL comprises one, two or three CDRs selected from (a) LC-CDR1 comprising the amino acid sequence of SEQ ID NO: 60; (b) LC-CDR2 comprising the amino acid sequence of SEQ ID NO: 68; and (c) LC-CDR3 comprising the amino acid sequence of SEQ ID NO: 76.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody comprises a VH comprising the amino acid sequence of SEQ ID NO: 83, and a VL sequence in SEQ ID NO: 97, including post-translational modifications of those sequences. In some embodiments, the antibody or antigen binding fragment thereof comprises an IgA heavy chain constant region having at least 90%, 91, 92%, 93%, 94%, 95%, 96%, 97%, 98%, 99%, or 100% sequence identity to the amino acid sequence of any one of SEQ ID NOs: 16-21. In some embodiments, the antibody or antigen binding fragment thereof comprises a kappa light chain constant region of SEQ ID NO: 31.

CTLA4

In some embodiments, provided herein is an antibody or a functional fragment thereof that specifically binds cytotoxic T-lymphocyte-associated protein 4 (CTLA4). In some embodiments, an antibody or a functional fragment disclosed herein specifically binds a human CTLA4 polypeptide. In some embodiments, an antibody or a functional fragment disclosed herein specifically binds a mouse CTLA4 polypeptide. The polypeptide and coding nucleic acid sequences of CTLA4 of human origin and those of a number of animals are publicly available, e.g., from the NCBI website.

In one aspect, the present disclosure provides an antibody or antigen-binding fragment thereof comprises one or more variable regions selected from the group consisting of (a) VH comprising the amino acid sequence of SEQ ID NO: 84, (b) VL comprising the amino acid sequence of SEQ ID NO: 98, and (c) a combination thereof.

In one aspect, the present disclosure provides an antibody or antigen-binding fragment thereof comprising at least one, two, three, four, five, or six CDRs selected from (a) HC-CDR1 comprising the amino acid sequence of SEQ ID NO: 37; (b) HC-CDR2 comprising the amino acid sequence of SEQ ID NO: 45; (c) HC-CDR3 comprising the amino acid sequence of SEQ ID NO: 53; (d) LC-CDR1 comprising the amino acid sequence of SEQ ID NO: 61; (e) LC-CDR2 comprising the amino acid sequence of SEQ ID NO: 69; and (f) LC-CDR3 comprising the amino acid sequence of SEQ ID NO: 77.

In one aspect, the present disclosure provides an antibody or antigen-binding fragment thereof comprising at least one, at least two, or all three VH CDR sequences selected from (a) HC-CDR1 comprising the amino acid sequence of SEQ ID NO: 37; (b) HC-CDR2 comprising the amino acid sequence of SEQ ID NO: 45; and (c) HC-CDR3 comprising the amino acid sequence of SEQ ID NO: 53; and (d) a VL comprising the amino acid sequence of SEQ ID NO: 98.

In one aspect, the present disclosure provides an antibody or antigen-binding fragment thereof comprising at least one, at least two, or all three VL CDR sequences selected from (a) LC-CDR1 comprising the amino acid sequence of SEQ ID NO: 61; (b) LC-CDR2 comprising the amino acid sequence of SEQ ID NO: 69; and (c) LC-CDR3 comprising the amino acid sequence of SEQ ID NO: 77; and a VH comprising the amino acid sequence of SEQ ID NO: 84.

In one aspect, the present disclosure provides an antibody or antigen-binding fragment thereof comprising the CDRs: HC-CDR3 comprising the amino acid sequence of SEQ ID NO: 53; and LC-CDR3 comprising the amino acid sequence of SEQ ID NO: 77.

In one aspect, the disclosure herein provides an antibody or antigen-binding fragment thereof comprising at least one, at least two, or all three VL CDR sequences selected from (a) LC-CDR1 comprising the amino acid sequence of SEQ ID NO: 61; (b) LC-CDR2 comprising the amino acid sequence of SEQ ID NO: 69 and (c) LC-CDR3 comprising the amino acid sequence of SEQ ID NO: 77. In one aspect, the disclosure provides an antibody or antigen-binding fragment thereof comprising at least one, at least two, or all three VH CDR sequences selected from (a) HC-CDR1 comprising the amino acid sequence of SEQ ID NO: 37; (b) HC-CDR2 comprising the amino acid sequence of SEQ ID NO: 45 and (c) HC-CDR3 comprising the amino acid sequence of SEQ ID NO: 53.

In one aspect, the disclosure provides an antibody or antigen-binding fragment thereof comprising the CDRs: (a) HC-CDR1 comprising the amino acid sequence of SEQ ID NO: 37; (b) HC-CDR2 comprising the amino acid sequence of SEQ ID NO: 45; (c) HC-CDR3 comprising the amino acid sequence of SEQ ID NO: 53; (d) LC-CDR1 comprising the amino acid sequence of SEQ ID NO: 61; (e) LC-CDR2 comprising the amino acid sequence of SEQ ID NO: 69; and (f) LC-CDR3 comprising the amino acid sequence of SEQ ID NO: 77.

In one aspect, an antibody or antigen-binding fragment thereof comprises a VH sequence having at least 90%, 91%, 92%, 93%, 94%, 95%, 96%, 97%, 98%, 99%, or 100% sequence identity to the amino acid sequence of SEQ ID NO: 84. In some embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in the amino acid sequence of SEQ ID NO: 84. In some embodiments, substitutions, insertions, or deletions occur in regions outside the CDRs (e.g., in the FRs). Optionally, the antibody or antigen-binding fragment thereof comprises the VH sequence of the amino acid sequence of SEQ ID NO: 84, including post-translational modifications of that sequence. In a particular embodiment, the VH comprises one, two or three CDRs selected from: (a) HC-CDR1 comprising the amino acid sequence of SEQ ID NO: 37, (b) HC-CDR2 comprising the amino acid sequence of SEQ ID NO: 45, and (c) HC-CDR3 comprising the amino acid sequence of SEQ ID NO: 53.

In one aspect, an antibody or antigen-binding fragment thereof is provided, wherein the antibody or antigen-binding fragment thereof comprises a light chain variable domain (VL) having at least 90%, 91%, 92%, 93%, 94%, 95%, 96%, 97%, 98%, 99%, or 100% sequence identity to the amino acid sequence of SEQ ID NO: 98. In some embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in any one of the amino acid sequence of SEQ ID NO: 98. In some embodiments, the substitutions, insertions, or deletions occur in regions outside the CDRs (e.g., in the FRs). Optionally, the antibody or antigen-binding fragment thereof comprises the VL sequence of SEQ ID NO: 98, including post-translational modifications of that sequence. In a particular embodiment, the VL comprises one, two or three CDRs selected from (a) LC-CDR1 comprising the amino acid sequence of SEQ ID NO: 61; (b) LC-CDR2 comprising the amino acid sequence of SEQ ID NO: 69; and (c) LC-CDR3 comprising the amino acid sequence of SEQ ID NO: 77.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody comprises a VH comprising the amino acid sequence of SEQ ID NO: 84, and a VL sequence in SEQ ID NO: 98, including post-translational modifications of those sequences. In some embodiments, the antibody or antigen binding fragment thereof comprises an IgA heavy chain constant region having at least 90%, 91%, 92%, 93%, 94%, 95%, 96%, 97%, 98%, 99%, or 100% sequence identity to the amino acid sequence of any one of SEQ ID NOs: 16-21. In some embodiments, the antibody or antigen binding fragment thereof comprises a kappa light chain constant region of SEQ ID NO: 31.

CD47

In some embodiments, the IgA antibody specifically binds CD47. In some embodiments, an antibody or a functional fragment disclosed herein specifically binds a human CD47 polypeptide. The polypeptide and coding nucleic acid sequences of CD47 of human origin and those of a number of animals are publicly available, e.g., from the NCBI website. In some embodiments, the IgA antibody reduces SIRPα binding to CD47 expressed on the surface of a cancer cell. In some embodiments, the IgA antibody binds to CD47 with a binding affinity ($K_d$) ranging from about 0.5 μM to about 999 μM as compared to a corresponding wild type antibody. In some embodiments, the IgA antibody binds to CD47 with a binding affinity ($K_d$) ranging from about 1 mM to about 1000 mM as compared to a corresponding wild type antibody. In some embodiments, the IgA antibody inhibits a human CD47 interaction with a signal regulatory protein a (SIRPα). In some embodiments, the inhibition of interaction between said human CD47 and said SIRPα increases a potential of said IgA antibody. In some embodiments, the inhibition of the interaction between said human CD47 and said SIRPα increases phagocytosis and clearance of cancer cells at a tumor site. In some embodiments, the cancer cells are IgA-opsonized cancer cells. In some embodiments, the IgA antibody comprises an antigen binding domain that binds CD47 and an antigen binding domain that specifically binds a tumor associated antigen (e.g., one described herein).

In some embodiments, the IgA antibody binds CD47. In some embodiments, the IgA antibody reduces CD47 binding of a cancer cell. For example, the IgA antibody can inhibit a human CD47 interaction with a signal regulatory protein a (SIRPα). Furthermore, the inhibition of interaction between the human CD47 and the SIRPα can increase a potential of the IgA antibody. The inhibition of interaction between the human CD47 and SIRPα can increase phagocytosis and clearance of cancer cells at a tumor site. For example, the cancer cells can be IgA-opsonized cancer cells. In some embodiments, the IgA antibodies described herein have a low affinity binding to CD47 that prevents the binding of the IgA antibody to CD47 on a cell other than a cancer cell. In some embodiments, the low affinity CD47 arm of the IgA antibody described herein binds to a tumor cell expressing CD47. In some examples, the low affinity CD47 arm of the IgA antibody described herein does not bind to a cell expressing CD47 that is not a tumor cell. In some embodiments, the IgA antibody binds to CD47 with a binding affinity ($K_d$) of at least about 0.01 micromolar (μM) to about 999 μM or more. In some embodiments, the IgA antibody binds to CD47 with a binding affinity ($K_d$) of at least about 0.01 μM. In some embodiments, the IgA antibody binds to CD47 with a binding affinity ($K_d$) of at most about 999 μM. In some embodiments, the IgA antibody binds to CD47 with a binding affinity ($K_d$) of about 0.01 μM to about 0.1 μM, about 0.01 μM to about 0.5 μM, about 0.01 μM to about 1 μM, about 0.01 μM to about 5 μM, about 0.01 μM to about 10 μM, about 0.01 μM to about 50 M, about 0.01 μM to about 100 M, about 0.01 μM to about 200 μM, about 0.01 μM to about 300 M, about 0.01 μM to about 500 μM, about 0.01 μM to about 999 μM, about 0.1 μM to about 0.5 μM, about 0.1 μM to about 1 μM, about 0.1 μM to about 5 μM, about 0.1 μM to about 10 μM, about 0.1 μM to about 50 μM, about 0.1 μM to about 100 M, about 0.1 μM to about 200 μM, about 0.1 μM to about 300 M, about 0.1 μM to about 500 μM, about 0.1 μM to about 999 μM, about 0.5 μM to about 1 μM, about 0.5 μM to about 5 μM, about 0.5 μM to about 10 M, about 0.5 μM to about 50 M, about 0.5 μM to about 100 μM, about 0.5 μM to about 200 μM, about 0.5 μM to about 300 μM, about 0.5 μM to about 500 μM, about 0.5 μM to about 999 μM, about 1 μM to about 5 M, about 1 μM to about 10 μM, about 1 μM to about 50 M, about 1 μM to about 100 M, about 1 μM to about 200 M, about 1 μM to about 300 μM, about 1 μM to about 500 μM, about 1 μM to about 999 μM, about 5 μM to about 10 μM, about 5 μM to about 50 μM, about 5 μM to about 100 μM, about 5 μM to about 200 M, about 5 μM to about 300 μM about 5 μM to about 500 μM about 5 μM to about 999 about 10 μM to about 50 M, about 10 μM to about 100 M about 10 μM to about 200 μM about 10 μM to about 300 M, about 10 μM to about 500 M about 10 μM to about 999 μM, about 50 μM to about 100 M, about 50 M to about 200 μM about 50 μM to about 300 μM about 50 μM to about 500 μM, about 50 μM to about 999 M, about 100 μM to about 200 μM, about 100 μM to about 300 M, about 100 μM to about 500 M, about 100 μM to about 999 μM, about 200 μM to about 300 μM, about 200 μM to about 500 μM, about 200 μM to about 999 μM, about 300 μM to about 500 μM, about 300 μM to about 999 μM, or about 500 μM to about 999 μM. In some embodiments, the IgA antibody binds to CD47 with a binding affinity ($K_d$) of about 0.01 μM, about 0.1 μM, about 0.5 μM, about 1 μM, about 5 μM, about 10 μM, about 50 μM, about 100 μM, about 200 μM, about 300 μM, about 500 μM, or about 999 μM.

In some embodiments, the IgA antibody binds to CD47 with a binding affinity ($K_d$) of about 1 mM to about 1,000 millimolar (mM). In some embodiments, the IgA antibody binds to CD47 with a binding affinity ($K_d$) of at least about 1 mM. In some embodiments, the IgA antibody binds to CD47 with a binding affinity ($K_d$) of at most about 1,000 mM. In some embodiments, the IgA antibody binds to CD47 with a binding affinity ($K_d$) of about 1 mM to about 5 mM, about 1 mM to about 10 mM, about 1 mM to about 50 mM, about 1 mM to about 100 mM, about 1 mM to about 200 mM, about 1 mM to about 300 mM, about 1 mM to about 400 mM, about 1 mM to about 500 mM, about 1 mM to about 600 mM, about 1 mM to about 800 mM, about 1 mM to about 1,000 mM, about 5 mM to about 10 mM, about 5 mM to about 50 mM, about 5 mM to about 100 mM, about 5 mM to about 200 mM, about 5 mM to about 300 mM, about 5 mM to about 400 mM, about 5 mM to about 500 mM, about 5 mM to about 600 mM, about 5 mM to about 800 mM, about 5 mM to about 1,000 mM, about 10 mM to about 50 mM, about 10 mM to about 100 mM, about 10 mM to about 200 mM, about 10 mM to about 300 mM, about 10 mM to about 400 mM, about 10 mM to about 500 mM, about 10 mM to about 600 mM, about 10 mM to about 800 mM, about 10 mM to about 1,000 mM, about 50 mM to about 100 mM, about 50 mM to about 200 mM, about 50 mM to about 300 mM, about 50 mM to about 400 mM, about 50 mM to about 500 mM, about 50 mM to about 600 mM, about 50 mM to about 800 mM, about 50 mM to about 1,000 mM, about 100 mM to about 200 mM, about 100 mM to about 300 mM, about 100 mM to about 400 mM, about 100 mM to about 500 mM, about 100 mM to about 600 mM, about 100 mM to about 800 mM, about 100 mM to about 1,000 mM, about 200 mM to about 300 mM, about 200 mM to about 400 mM, about 200 mM to about 500 mM, about 200 mM to about 600 mM, about 200 mM to about 800 mM, about 200 mM to about 1,000 mM, about 300 mM to about 400 mM, about 300 mM to about 500 mM, about 300 mM to about 600 mM, about 300 mM to about 800 mM, about 300 mM to about 1,000 mM, about 400 mM to about 500 mM, about 400 mM to about 600 mM, about 400 mM to about 800 mM, about 400 mM to about 1,000 mM, about 500 mM to about 600 mM, about 500 mM to about 800 mM, about 500 mM to about 1,000 mM, about 600 mM to about 800 mM, about 600 mM to about 1,000 mM, or about 800 mM to about 1,000 mM. In some embodiments, the IgA antibody binds to CD47 with a binding affinity ($K_d$) of about 1 mM, about 5 mM, about 10 mM, about 50 mM, about 100 mM, about 200 mM, about 300 mM, about 400 mM, about 500 mM, about 600 mM, about 800 mM, or about 1,000 mM.

In some embodiments, provided herein is an antibody or a functional fragment thereof that specifically binds CD47. In some embodiments, the IgA antibody comprises at least CDR3 of the heavy chain of antibody 2.3D11 or of antibody C47A8-CQ. In some embodiments, the IgA antibody comprises one, two, or three of CDR1, CDR2, or CDR3 of the heavy chain of antibody 2.3D11 or of antibody C47A8-CQ. In some embodiments, the IgA antibody comprises one, two, or three of CDR1, CDR2, or CDR3 of the light chain of antibody 2.3D11 or of antibody C47A8-CQ. In some embodiments, the IgA antibody comprises one, two, or three of CDR1, CDR2, or CDR3 of the heavy chain of antibody 2.3D11 or of antibody C47A8-CQ, and one, two, or three of CDR1, CDR2, or CDR3 of the light chain of antibody 2.3D11 or of antibody C47A8-CQ. In some embodiments, the IgA antibody comprises CDR1, CDR2, or CDR3 of the heavy chain of antibody 2.3D11 or of antibody C47A8-CQ, and CDR1, CDR2, or CDR3 of the light chain of antibody 2.3D11 or of antibody C47A8-CQ. In some embodiments, the IgA antibody comprises at least CDR3 of the heavy chain of antibody 2.3D11 or of antibody C47A8-CQ and an IgA hinge. In some embodiments, the IgA antibody comprises at least CDR3 of the heavy chain of antibody 2.3D11 or of antibody C47A8-CQ an IgA hinge, a CH1 IgA region. In some embodiments, the IgA antibody comprises at least CDR3 of the heavy chain of antibody 2.3D11 or of antibody C47A8-CQ an IgA hinge, a CH1 IgA region, and a CH2 IgA region. In some embodiments, the IgA antibody comprises at least CDR3 of the heavy chain of antibody 2.3D11 or of antibody C47A8-CQ an IgA hinge, a CH1 IgA region, a CH2 IgA region, and a CH3 IgA region.

In one aspect, the present disclosure provides an antibody or antigen-binding fragment thereof comprises one or more variable regions selected from the group consisting of (a) VH comprising the amino acid sequence of SEQ ID NO: 85, (b) VL comprising the amino acid sequence of SEQ ID NO: 99, and (c) a combination thereof.

In one aspect, the present disclosure provides an antibody or antigen-binding fragment thereof comprising at least one, two, three, four, five, or six CDRs selected from (a) HC-CDR1 comprising the amino acid sequence of SEQ ID NO: 38; (b) HC-CDR2 comprising the amino acid sequence of SEQ ID NO: 46; (c) HC-CDR3 comprising the amino acid sequence of SEQ ID NO: 54; (d) LC-CDR1 comprising the amino acid sequence of SEQ ID NO: 62; (e) LC-CDR2 comprising the amino acid sequence of SEQ ID NO:70; and (f) LC-CDR3 comprising the amino acid sequence of SEQ ID NO: 78.

In one aspect, the present disclosure provides an antibody or antigen-binding fragment thereof comprising at least one, at least two, or all three VH CDR sequences selected from (a) HC-CDR1 comprising the amino acid sequence of SEQ ID NO: 38; (b) HC-CDR2 comprising the amino acid sequence of SEQ ID NO: 46; and (c) HC-CDR3 comprising the amino acid sequence of SEQ ID NO: 54; and (d) a VL comprising the amino acid sequence of SEQ ID NO: 99.

In one aspect, the present disclosure provides an antibody or antigen-binding fragment thereof comprising at least one, at least two, or all three VL CDR sequences selected from (a) LC-CDR1 comprising the amino acid sequence of SEQ ID NO: 62; (b) LC-CDR2 comprising the amino acid sequence of SEQ ID NO: 70; and (c) LC-CDR3 comprising the amino acid sequence of SEQ ID NO: 78; and a VH comprising the amino acid sequence of SEQ ID NO: 85.

In one aspect, the present disclosure provides an antibody or antigen-binding fragment thereof comprising the CDRs: HC-CDR3 comprising the amino acid sequence of SEQ ID NO: 54; and LC-CDR3 comprising the amino acid sequence of SEQ ID NO: 78.

In one aspect, the disclosure herein provides an antibody or antigen-binding fragment thereof comprising at least one, at least two, or all three VL CDR sequences selected from (a) LC-CDR1 comprising the amino acid sequence of SEQ ID NO: 62; (b) LC-CDR2 comprising the amino acid sequence of SEQ ID NO: 70 and (c) LC-CDR3 comprising the amino acid sequence of SEQ ID NO: 78. In one aspect, the disclosure provides an antibody or antigen-binding fragment thereof comprising at least one, at least two, or all three VH CDR sequences selected from (a) HC-CDR1 comprising the amino acid sequence of SEQ ID NO: 38; (b) HC-CDR2 comprising the amino acid sequence of SEQ ID NO: 46 and (c) HC-CDR3 comprising the amino acid sequence of SEQ ID NO: 54.

In one aspect, the disclosure provides an antibody or antigen-binding fragment thereof comprising the CDRs: (a) HC-CDR1 comprising the amino acid sequence of SEQ ID NO: 38; (b) HC-CDR2 comprising the amino acid sequence of SEQ ID NO: 46; (c) HC-CDR3 comprising the amino acid sequence of SEQ ID NO: 54; (d) LC-CDR1 comprising the amino acid sequence of SEQ ID NO: 62; (e) LC-CDR2 comprising the amino acid sequence of SEQ ID NO: 70; and (f) LC-CDR3 comprising the amino acid sequence of SEQ ID NO: 78.

In one aspect, an antibody or antigen-binding fragment thereof comprises a VH sequence having at least 90%, 91%, 92%, 93%, 94%, 95%, 96%, 97%, 98%, 99%, or 100% sequence identity to the amino acid sequence of SEQ ID NO: 85. In some embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in the amino acid sequence of SEQ ID NO: 85. In some embodiments, substitutions, insertions, or deletions occur in regions outside the CDRs (e.g., in the FRs). Optionally, the antibody or antigen-binding fragment thereof comprises the VH sequence of the amino acid sequence of SEQ ID NO: 85, including post-translational modifications of that sequence. In a particular embodiment, the VH comprises one, two or three CDRs selected from: (a) HC-CDR1 comprising the amino acid sequence of SEQ ID NO: 38, (b) HC-CDR2 comprising the amino acid sequence of SEQ ID NO: 46, and (c) HC-CDR3 comprising the amino acid sequence of SEQ ID NO: 54.

In one aspect, an antibody or antigen-binding fragment thereof is provided, wherein the antibody or antigen-binding fragment thereof comprises a light chain variable domain (VL) having at least 90%, 91%, 92%, 93%, 94%, 95%, 96%, 97%, 98%, 99%, or 100% sequence identity to the amino acid sequence of SEQ ID NO: 99. In some embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in any one of the amino acid sequence of SEQ ID NO: 99. In some embodiments, the substitutions, insertions, or deletions occur in regions outside the CDRs (e.g., in the FRs). Optionally, the antibody or antigen-binding fragment thereof comprises the VL sequence of SEQ ID NO: 99, including post-translational modifications of that sequence. In a particular embodiment, the VL comprises one, two or three CDRs selected from (a) LC-CDR1 comprising the amino acid sequence of SEQ ID NO: 62; (b) LC-CDR2 comprising the amino acid sequence of SEQ ID NO: 70; and (c) LC-CDR3 comprising the amino acid sequence of SEQ ID NO: 78.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody comprises a VH comprising the amino acid sequence of SEQ ID NO: 85, and a VL sequence in SEQ ID NO: 99, including post-translational modifications of those sequences. In some embodiments, the antibody or antigen binding fragment thereof comprises an IgA heavy chain constant region having at least 90%, 91%, 92%, 93%, 94%, 95%, 96%, 97%, 98%, 99%, or 100% sequence identity to the amino acid sequence of any one of SEQ ID NOs: 16-21. In some embodiments, the antibody or antigen binding fragment thereof comprises a kappa light chain constant region of SEQ ID NO: 31.

In one aspect, the present disclosure provides an antibody or antigen-binding fragment thereof comprises one or more variable regions selected from the group consisting of (a) VH comprising the amino acid sequence of SEQ ID NO: 86, (b) VL comprising the amino acid sequence of SEQ ID NO: 100, and (c) a combination thereof.

In one aspect, the present disclosure provides an antibody or antigen-binding fragment thereof comprising at least one, two, three, four, five, or six CDRs selected from (a) HC-CDR1 comprising the amino acid sequence of SEQ ID NO: 39; (b) HC-CDR2 comprising the amino acid sequence of SEQ ID NO: 47; (c) HC-CDR3 comprising the amino acid sequence of SEQ ID NO: 54; (d) LC-CDR1 comprising the amino acid sequence of SEQ ID NO: 63; (e) LC-CDR2 comprising the amino acid sequence of SEQ ID NO:71; and (f) LC-CDR3 comprising the amino acid sequence of SEQ ID NO: 79.

In one aspect, the present disclosure provides an antibody or antigen-binding fragment thereof comprising at least one, at least two, or all three VH CDR sequences selected from (a) HC-CDR1 comprising the amino acid sequence of SEQ ID NO: 39; (b) HC-CDR2 comprising the amino acid sequence of SEQ ID NO: 47; and (c) HC-CDR3 comprising the amino acid sequence of SEQ ID NO: 55; and (d) a VL comprising the amino acid sequence of SEQ ID NO: 100.

In one aspect, the present disclosure provides an antibody or antigen-binding fragment thereof comprising at least one, at least two, or all three VL CDR sequences selected from (a) LC-CDR1 comprising the amino acid sequence of SEQ ID NO: 63; (b) LC-CDR2 comprising the amino acid sequence of SEQ ID NO: 71; and (c) LC-CDR3 comprising the amino acid sequence of SEQ ID NO: 79; and a VH comprising the amino acid sequence of SEQ ID NO: 86.

In one aspect, the present disclosure provides an antibody or antigen-binding fragment thereof comprising the CDRs: HC-CDR3 comprising the amino acid sequence of SEQ ID NO: 55; and LC-CDR3 comprising the amino acid sequence of SEQ ID NO: 79.

In one aspect, the disclosure herein provides an antibody or antigen-binding fragment thereof comprising at least one, at least two, or all three VL CDR sequences selected from (a) LC-CDR1 comprising the amino acid sequence of SEQ ID NO: 63; (b) LC-CDR2 comprising the amino acid sequence of SEQ ID NO: 71 and (c) LC-CDR3 comprising the amino acid sequence of SEQ ID NO: 79. In one aspect, the disclosure provides an antibody or antigen-binding fragment thereof comprising at least one, at least two, or all three VH CDR sequences selected from (a) HC-CDR1 comprising the amino acid sequence of SEQ ID NO: 39; (b) HC-CDR2 comprising the amino acid sequence of SEQ ID NO: 47 and (c) HC-CDR3 comprising the amino acid sequence of SEQ ID NO: 55.

In one aspect, the disclosure provides an antibody or antigen-binding fragment thereof comprising the CDRs: (a) HC-CDR1 comprising the amino acid sequence of SEQ ID NO: 39; (b) HC-CDR2 comprising the amino acid sequence of SEQ ID NO: 47; (c) HC-CDR3 comprising the amino acid sequence of SEQ ID NO: 55; (d) LC-CDR1 comprising the amino acid sequence of SEQ ID NO: 63; (e) LC-CDR2 comprising the amino acid sequence of SEQ ID NO: 71; and (f) LC-CDR3 comprising the amino acid sequence of SEQ ID NO: 79.

In one aspect, an antibody or antigen-binding fragment thereof comprises a VH sequence having at least 90%, 91%, 92%, 93%, 94%, 95%, 96%, 97%, 98%, 99%, or 100% sequence identity to the amino acid sequence of SEQ ID NO: 86. In some embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in the amino acid sequence of SEQ ID NO: 86. In some embodiments, substitutions, insertions, or deletions occur in regions outside the CDRs (e.g., in the FRs). Optionally, the antibody or antigen-binding fragment thereof comprises the VH sequence of the amino acid sequence of SEQ ID NO: 86, including post-translational modifications of that sequence. In a particular embodiment, the VH comprises one, two or three CDRs selected from: (a) HC-CDR1 comprising the amino acid sequence of SEQ ID NO: 39, (b) HC-CDR2 comprising the amino acid sequence of SEQ ID NO: 47, and (c) HC-CDR3 comprising the amino acid sequence of SEQ ID NO: 55.

In one aspect, an antibody or antigen-binding fragment thereof is provided, wherein the antibody or antigen-binding fragment thereof comprises a light chain variable domain (VL) having at least 90%, 91% 92%, 93%, 94%, 95%, 96%, 97%, 98%, 99%, or 100% sequence identity to the amino acid sequence of SEQ ID NO: 100. In some embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody or antigen-binding fragment thereof comprising that sequence retains the ability to bind to antigen. In some embodiments, a total of 1 to 10 amino acids have been substituted, inserted and/or deleted in any one of the amino acid sequence of SEQ ID NO: 100. In some embodiments, the substitutions, insertions, or deletions occur in regions outside the CDRs (e.g., in the FRs). Optionally, the antibody or antigen-binding fragment thereof comprises the VL sequence of SEQ ID NO: 100, including post-translational modifications of that sequence. In a particular embodiment, the VL comprises one, two or three CDRs selected from (a) LC-CDR1 comprising the amino acid sequence of SEQ ID NO: 63; (b) LC-CDR2 comprising the amino acid sequence of SEQ ID NO: 71; and (c) LC-CDR3 comprising the amino acid sequence of SEQ ID NO: 79.

In one aspect, an antibody or antigen-binding fragment thereof is provided, wherein the antibody or antigen-binding fragment thereof comprises a VH as in any of the embodiments provided above, and a VL as in any of the embodiments provided above. In some embodiments, the antibody comprises a VH comprising the amino acid sequence of SEQ ID NO: 86, and a VL sequence in SEQ ID NO: 100, including post-translational modifications of those sequences. In some embodiments, the antibody or antigen binding fragment thereof comprises an IgA heavy chain constant region having at least 90%, 91%, 92%, 93%, 94%, 95%, 96%, 97%, 98%, 99%, or 100% sequence identity to the amino acid sequence of any one of SEQ ID NOs: 16-21. In some embodiments, the antibody or antigen binding fragment thereof comprises a kappa light chain constant region of SEQ ID NO: 31.

Improved Property and Function of IgA Antibodies

In some embodiments, the antibodies or a functional fragment thereof disclosed herein exhibit an improved stability relative to a corresponding wild type IgA antibody. The term "increased stability" as used herein includes increased thermostability and/or decreased aggregation. Enhanced or improved stability can be determined, for example, by accelerated stability studies. Exemplary accelerated stability studies include, but are not limited to, studies featuring increased storage temperatures. A decrease in the formation of aggregates observed for a antibody as compared to a corresponding WT IgA antibody indicates an increased stability. Stability of antibodies and functional fragment thereof of the present disclosure can be tested by measuring the change in the melting temperature transition of an antibody as compared to the corresponding wild type IgA antibody. immunoglobulin. In such an embodiment, increased stability or increased thermostability would be evident as an increase in the melting temperature transition in the antibody or a functional fragment thereof relative to a corresponding WT IgA or a functional fragment thereof. In some embodiments, the antibodies of a functional fragment thereof have a higher melting temperature than a corresponding WT IgA antibody. In some embodiments, the melting temperature of the antibodies or a functional fragment thereof of the present disclosure is higher than a corresponding WT IgA antibody by at least about 0.2 fold, 0.3 fold, 0.4 fold, 0.5 fold, 0.6 fold, 0.8 fold, 1.0 fold or higher. In some embodiments, the melting temperature of the antibodies or a functional fragment thereof of the present disclosure is higher than a corresponding WT IgA antibody by at least about 1° C., 2° C., 3° C., 4° C., 5° C., 6° C., 7° C., 8° C., 9° C., 10° C., 12° C., 15° C., or more. In some embodiments, the antibodies, or a functional fragment thereof of the present disclosure have a melting temperature of at least about 60° C., 65° C., 70° C., 75° C., 80° C., 85° C., 90° C. or more. In some embodiments, this increased stability is in the absence of additional disulfide bonds. Specifically, the increased stability is in the absence of additional disulfide bonds in the IgA heavy chain constant region. In one embodiment, the CH3 domain of the antibody disclosed herein does not contain additional disulfide bonds compared to the wild type CH3 domain. In an alternative embodiment, the CH3 domain of the antibody disclosed herein contains at least one disulfide bond compared to the wild type CH3 domain Additional methods for measuring protein aggregation are described in U.S. patent application Ser. No. 10/176,809, and US20030022243A1, the contents of which are incorporated herein by reference in their entities. A variety of analytical techniques for measuring protein stability are available in the art, such as those outlined below: Peptide and Protein Drug Delivery, 247-301, Vincent Lee Ed., Marcel Dekker, Inc., New York, New York, Pubs., 1991; and Jones, A. Adv. Drug Delivery Rev. 10: 29-90, 1993. Stability can be measured at a selected temperature for a selected time. Stability is determined qualitatively and/or quantitatively in a variety of different ways, including determination of aggregate formation (e.g., using size exclusion chromatography or by measuring turbidity and/or visual inspection). it can. The method is as follows: assessment of charge heterogeneity using cation exchange chromatography or capillary zone electrophoresis; analysis of amino-terminal or carboxy-terminal sequences; mass spectrometric analysis; comparing reduced or complete antibodies SDS-PAGE analysis; peptide map (eg, trypsin or LYS-C) analysis; determination of biological activity or antigen-binding function of an antibody. Instability includes one or more of any of the following: aggregation, oxidation (e.g. Met oxidation), isomerization (e.g. Asp isomerization), clipping/hydrolysis/fragmentation (E.g., fragmentation of the hinge region), succinimide formation, unpaired cysteine, N-terminal extension, C-terminal processing, and the like. The term "reduced aggregation" refers to reduction of aggregation of an antibody or a functional fragment thereof of the present disclosure with other antibody molecules and/or with other macromolecule including serum proteins such as albumin, as compared to aggregation exhibited by a corresponding WT IgA antibody.

The increased thermostability of an antibody relative to a corresponding WT IgA antibody or a variant thereof can be determined by differential scanning calorimetry (DSC) using methods standard in the art (see, for example, Sturtevant, 1987, Annual Review of Physical Chemistry 38: 463-488). The increased thermostability of an antibody relative to a corresponding WT IgA antibody or a variant thereof can also be determined using protein thermal unfolding analysis. Alternatively, the increased thermostability of of an antibody relative to a corresponding WT IgA antibody or a variant thereof can be determined using any application assay for the antibody, where the performance of the antibody is compared to the WT. For example, ADCC of a target cell, binding to an antigen, or binding to a FcαR on an immune cell.

Immune Effector Functions of IgA Antibodies

Provided herein are engineered IgA variants or antibody comprising one or more modifications within their heavy chain constant region relative to a corresponding WT IgA antibody comprising a WT heavy chain constant region. In some embodiments, the antibodies or the functional fragments thereof disclosed herein (e.g., antibodies comprising one or more modifications disclosed herein) exhibit improved properties.

In some embodiments, an antibody or a functional fragment thereof, disclosed herein, exhibits at least one increase in effector function as compared to a corresponding WT IgA antibody or a functional fragment thereof. Effector functions are biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis. For example, an antibody or a functional fragment thereof, disclosed herein exhibits at least one increase in effector function as compared to a corresponding WT IgA antibody or a functional fragment thereof or a corresponding WT IgG antibody. Antibody-dependent cellular cytotoxicity (ADCC) is the result of the formation of a complex between the IgA Fab portion of the antibody with an antigen on a cell surface and binding of the Fc portion to the Fc receptors (FcαRs), on immune effector cells. For example, an increase in effector function can be increased binding affinity to an Fc receptor (e.g., FcαRs), increased ADCC; increased cell mediated immunity; increased binding to cytotoxic CD8 T cells; increased binding to NK cells; increased binding to macrophages; increased binding to polymorphonuclear cells; increased binding to monocytes; increased binding to macrophages; increased binding to large granular lymphocytes; increased binding to granulocytes; direct signaling inducing apoptosis; increased dendritic cell maturation; or increased T cell priming, increased opsonization, or increased opsonophagocytosis. In some embodiments, the antibodies or functional fragment thereof induce lysis of cancer cells. Lysis can be induced by any mechanism, such as by mediating an effector function, such as C1q binding and complement dependent cytotoxicity (CDC); Fc receptor binding; antibody-dependent cell-mediated cytotoxicity (ADCC); phagocytosis, or direct induction of cell apoptosis.

ADCC

"ADCC activity" refers to the ability of an antibody to elicit an ADCC reaction. ADCC is a cell-mediated reaction in which antigen-nonspecific cytotoxic cells that express FcRs (e.g., natural killer (NK) cells, neutrophils, and macrophages) recognize antibody bound to the surface of a target cell and subsequently cause lysis of (i.e., "kill") the target cell (e.g., cancer cell). The primary mediator cells can be natural killer (NK) cells, neutrophils. ADCC activity can be assessed directly using an in vitro assay, e.g., a 51Cr release assay using peripheral blood mononuclear cells (PBMC) and/or NK effector cells as described in the Examples and Shields et al. (2001) J. Biol. Chem., 276: 6591-6604, or another suitable method known in the art. ADCC activity may be expressed as a concentration of antibody at which the lysis of target cells is half-maximal. Accordingly, in some embodiments, the concentration of an antibody or antigen binding fragment thereof of the disclosure, at which the lysis level is the same as the half-maximal lysis level by the wild-type control, is at least 2-, 3-, 5-, 10-, 20-, 50-, 100-fold lower than the concentration of the wild-type control itself.

Additionally, in some embodiments, the antibody or a functional fragment thereof of the present disclosure can exhibit a higher maximal target cell lysis as compared to a corresponding wild-type IgA. For example, the maximal target cell lysis of an antibody or a functional fragment thereof of the disclosure can be 2%, 3%, 4%, 5%, 10%, 15%, 20%, 25% or more higher than that of a corresponding WT IgA antibody or a corresponding WT IgG antibody. In some embodiments, the antibodies or a functional fragment thereof disclosed herein induces increased ADCC, compared to a corresponding WT IgG antibody comprising an IgG heavy chain constant domain. In some embodiments, the ADCC is increased by at least 2%, at least 5%, at least 10%, at least 12%, at least 15%, at least 20%, at least 25%, at least 50%, at least 65%, at least 70%, at least 75%, at least 85%, at least 90%, at least 95%, at least 99%, at least 100%, at least 150%, and at least 200%, relative to a corresponding WT IgG antibody.

CDC

"Complement dependent cytotoxicity" or "CDC" refer to the ability of a molecule to lyse a target (e.g. cancer cell) in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods 202:163 (1996), may be performed.

Fc Receptor Binding

In some embodiments, the antibodies or a functional fragment thereof bind a Fc receptor. In some embodiments, the Fc receptor is expressed on an immune effector cell. In some embodiments, the antibodies, or a functional fragment thereof the present disclosure bind an Fc receptor on an immune effector cell and induce an effector function such as ADCC, CDC, and/or cytolysis of a target cell (e.g., a cancer cell). In some embodiments, the antibodies or a functional fragment thereof bind an IgA receptor. In one embodiment, the IgA receptor is an Fc-alpha receptor (FcαR), such as an FcαR for human IgA. In some embodiments, the FcαR are expressed on an immune effector cell. FcαRs are present on immune effector cells, for example, monocytes, macrophages, neutrophils, and other myeloid cells. FcαRs can also be found on metamyelocytes, myelocytes, promyelocytes and some myeloblasts from, e.g., bone marrow. Such receptors can also be found on myeloid cell lines, e.g., U937, PLB985, and HL60 cells. It has also been suggested that FcαRs are present on lymphocytes. Expression of FcαRs can be increased by activation of myeloid cells. For example, stimulation of U937 cells and PLB985 cells with Phorbol Myristic Acetate (PMA) increases the cell surface level of FcαR several folds (Maliszewski, et al. (1990) J Exp. Med. 172:1665). Other agents which can increase the surface level of FcαRs include calcitriol, 1-25 dihydroxy vitamin D3, and interferon-γ (IFN-γ). FcαRs are capable of interacting with IgA1 and IgA2, in the form of monomers, dimers, and polymers. Binding of antibodies or a functional fragment thereof of the present disclosure to an immune effector cell bearing these receptors (e.g., neutrophils) induces a variety of effector functions, such as phagocytosis, antibody dependent cellular cytotoxicity (ADCC), inflammatory mediator release, lysozyme production, and superoxide anion production (Maliszewski, et al. (1990) J Exp. Med. 172:1665).

Accordingly, the antibodies or a functional fragment thereof of the present disclosure (e.g., antibodies comprising one or more modifications disclosed herein) are capable of triggering at least one Fc-receptor mediated effector cell function. The term "Fc-receptor mediated effector cell function" is intended to include effector functions, such as those set forth above, which are triggered by binding of immunoglobulin, e.g., IgA, to an Fc receptor on an effector immune cell. An effector immune cell is a cell which is involved in the effector phase of an immune response, as opposed to the cognitive and activation phases of an immune response. Effector immune cells include lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. An effector immune cell can phagocytose a target antigen, target cell, or microorganism. An effector immune cell can also lyse a target cell or a microorganism.

In some embodiments, an effector immune cell is one that can induce ADCC (e. G. That, neutrophils are capable of inducing ADCC)—dependent cells. For example, monocytes, macrophages, which express FcR are to kill target cells specifically, is involved in presenting antigens to other components of the immune system, or binding to antigen-presenting cells. In another embodiment, the effector immune cells can one that induces phagocytosis for the target antigen, target cell, or microorganism. Effector immune cell can be a macrophage inducing macrophage activity against a target antigen or a target cell or soluble.

The term "target cell" as used herein refers to a cell that can be targeted by the antibodies or a functional fragment thereof of the present disclosure. In some embodiments, a target cell is a cell expressing or overexpressing an antigen specifically recognized by the antibodies or a functional fragment thereof of the present disclosure. It refers to any cell. In other embodiments, the target cells include tumor cells. The tumor cells can be, for example, of any type, including breast cancer, ovarian cancer, prostate cancer, testicular cancer, lung cancer, colon cancer, rectal cancer, pancreatic cancer, liver cancer, CNS cancer, renal cancer, head cancer, neck cancer, blood cancer and lymphatic cancer of the tumor cells in cancer. In addition to tumor cells, a target cell can be, for example, IgE-producing lymphocytes for the treatment of autoantibodies targeting or for the production of lymphocytes, allergy or for the treatment of autoimmune diseases. Further, the target may be a microorganism (bacterium or virus) or a soluble antigen (such as rheumatoid factor similar to, or different autoantibodies and toxins). Microorganism includes a pathogen (e.g., virus, bacteria, fungi, protozoa). In some embodiments, a target cell can be a lymphocyte, for example, a CD20 expressing B cell.

In some embodiments, the antibody disclosed herein, exhibit increased binding affinity of to the Fc receptor on an effector immune cell by at least about 2%, at least 5%, at least 10%, at least 12%, at least 15%, at least 20%, at least 25%, at least 50%, at least 65%, at least 70%, at least 75%, at least 85%, at least 90%, at least 95%, or more relative to a corresponding WT IgA.

Binding to Target Antigen

In some embodiments, the antibody and functional fragment thereof of the present disclosure bind a specific target antigen. The term "antigen" refers to any natural or synthetic immunogenic substance immunogenic substance, a fragment or portion of an immunogenic substance, a peptide epitope or a hapten (hapten). Also the term "antigen" is also included in the non-composite material in the form of a non-immunogenic and, when complexed immunogenic. The term "non-complexed" is connected to form a molecular complex of the present invention includes the transfer of material. The term is connected to "composite" includes a substance that forms a molecular complex of the present invention. In some embodiments a target antigen is expressed or overexpressed on a target cell. In some embodiments, binding of the antibodies or a functional fragment thereof to a target antigen induces Fc mediated cytolysis of the target cell expressing the target antigen (e.g., by ADCC). In some embodiments binding of the antibodies or a functional fragment thereof of a present disclosure to a target antigen induces "neutralizing activity" of the target antigen. The term "neutralizing activity" as used herein refers to the ability of the antibodies or a functional fragment thereof to block binding of a cognate ligand to a target antigen.

Reduced Glycosylation

In some embodiments, the antibodies or the functional fragment thereof of the present disclosure exhibit reduced glycosylation compared to a corresponding WT IgA. The antibodies can be completely aglycosylated or partially. The term "glycosylation" refers to the covalent linking of one or more carbohydrates to a polypeptide. Typically, glycosylation is a posttranslational event which can occur within the intracellular milieu of a cell or extract therefrom. The term glycosylation includes, for example, N-linked glycosylation (where one or more sugars are linked to an asparagine residue) and/or O-linked glycosylation (where one or more sugars are linked to an amino acid residue having a hydroxyl group (e.g., serine or threonine). In preferred embodiments, glycosylation refers to N-linked glycosylation. In some embodiments, reduced glycosylation can be achieved by modifying the asparagine residue in a naturally occurring glycosylation site. In some embodiments, reduced glycosylation is achieved by modifying amino acid residues that are near or within a naturally occurring glycosylation motif or a naturally occurring glycosylation site, for example, an N-linked glycosylation site that contains the amino acid sequence NXT or NXS. In some embodiments, reduced glycosylation is achieved by modifying at least one, at least two, at least three, at least four or more naturally occurring glycosylation site. In some embodiments, the naturally occurring glycosylation site is in a CH2 region. In some embodiments, the naturally occurring glycosylation site is in a CH3 region. In some embodiments, the naturally occurring glycosylation site is in a CH1 region. Consensus motifs, that is, the amino acid sequence recognized by various glycosyl transferases, have been described. For example, the consensus motif for an N-linked glycosylation motif is frequently NXT or NXS, where X can be any amino acid except proline Accordingly, to identify potential glycosylation sites within an antibody or Fc-containing fragment, the sequence of the antibody is examined, for example, by using publicly available databases such as the website provided by the Center for Biological Sequence Analysis (see www.cbs.dtu.dk/services/NetNGlyc/ for predicting N-linked glycosylation sites) and www.cbs.dtu.dk/services/NetOGlyc/ for predicting O-linked glycosylation sites). Methods to measure glycosylation are known in the art, for example, see Roth et al, International Journal of Carbohydrate Chemistry, Volume 2012, Article ID 640923, and WO2003102018A2, the contents of which are incorporated herein by reference in its entirety.

In some embodiments, the antibody disclosed herein, exhibit reduced glycosylation by at least about 2%, at least 5%, at least 10%, at least 12%, at least 15%, at least 20%, at least 25%, at least 50%, at least 65%, at least 70%, at least 75%, at least 85%, at least 90%, at least 95%, or more relative to a corresponding WT IgA. In some embodiments, the antibodies or a functional fragment disclosed herein are partially glycosylated relative to a corresponding WT IgA antibody, for example, less than 100%, 90%, 80%, 70%, 60%, 50%, 40%, 30%, 20%, 10%, 5% or less. In some embodiments, antibodies or a functional fragment thereof disclosed herein are completely glycosylated relative to a corresponding WT IgA antibody.

Biodistribution

In some embodiments, the IgA antibodies or a functional fragment thereof disclosed herein exhibit increased biodistribution relative to a corresponding WT IgA antibody. As used herein, the term "biodistribution" refers to the cellular and/or tissue and/or organ distribution of an IgA antibody or a functional fragment thereof disclosed herein that is administered or delivered to a subject. As used herein, the terms "increased biodistribution" generally refer to the ability of an IgA antibody or a functional fragment thereof disclosed herein that has an increased distribution to a target site, for example, targeted to a tumor or a tumor cell, as compared to the response caused by either vehicle or a corresponding WT IgA antibody. Various methods known to the skilled artisan can be used to assessed and increased biodistribution of cells or tissues, including, but not limited to: nuclear medicine, whole body autoradiography, micro-autoradiography; phosphor imaging, cryo-imaging, nano-secondary ion mass spectroscopy (nanoSIMS), matrix-assisted laser desorption imaging (MALDI-MS), radiography (X-Ray), magnetic resonance imaging (MRI), computed tomography (CT), micro-ultrasound single photon emission CT (SPECT), positron emission tomography (PET) and the like. An increased biodistribution of the antibody to a target site, includes an at least 5%, 10%, 20%, 30%, 40%, 50%, 60%, 70%, 80%, 90%, 100%, 125%, 150%, 175%, 200%, or greater increase compared to a vehicle or a WT IgA antibody. An "increased" or "enhanced" tissue distribution or biodistribution is typically a "statistically significant" increase, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the distribution of a vehicle or a control composition.

Methods of Making an Antibody:

In some embodiments, the antibody or antigen binding fragment thereof is prepared in a host cell. In some embodiments, the antibody or antigen binding fragment thereof is isolated from a host cell. In some embodiments, the antibody or antigen binding fragment thereof is prepared in a cell-free system. An isolated nucleic acid molecule encoding the antibody, portion or polypeptide of the present disclosure can be recombined with vector DNA (e.g., expression vector) in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., Molecular Cloning, Lab. Manual (Cold Spring Harbor Lab. Press, NY, 1982 and 1989), and Ausubel, 1987, 1993, and can be used to construct nucleic acid sequences which encode an antibody molecule or antigen binding region thereof. Accordingly, the disclosure provides for a vector or expression vector comprising the isolated nucleic acids set forth herein. In one embodiment, the nucleic acid coding for the light chain and that coding for the heavy chain are isolated separately by the procedures outlined above. In one embodiment, the isolated nucleic acid encoding the light chain and that coding for the heavy chain may be inserted into separate expression plasmids, or together in the same plasmid, so long as each is under suitable promoter and translation control.

Once the isolated nucleic acid molecule is placed into an expression vector, they are then transfected into host cells such as *E. coli* cells, simian COS cells, human embryonic kidney 293 cells (e.g., 293E cells), Chinese hamster ovary (CHO) cells, or myeloma cells that do not otherwise produce immunoglobulin protein, to obtain the synthesis of the antibody or an antigen-binding fragment thereof in the recombinant host cells. Recombinant production of antibodies is well known in the art. Many vectors are available. The vector components generally include, but are not limited to, one or more of the following: a signal sequence, an origin of replication, one or more selective marker genes, an enhancer element, a promoter, and a transcription termination sequence.

The isolated nucleic acid molecules are operably linked to an expression control sequence in the vector DNA. Expression control sequence refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers. The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

Nucleic acid is operably linked when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous, and/or can contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Cell, cell line, and cell culture are often used interchangeably and all such designations herein include progeny. Transformants and transformed cells include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context. In an alternative embodiment, suitable encoding nucleic acid sequences can be designed according to a universal codon table, based on the known amino acid sequence of an immunoglobulin of interest.

Amino acid sequence variants of the desired antibody may be prepared by introducing appropriate nucleotide changes into the encoding DNA, or by peptide synthesis. Such variants include, for example, deletions from, and/or insertions into and/or substitutions of, residues within the amino acid sequences of the antibodies. Any combination of deletion, insertion, and substitution is made to arrive at the final construct, provided that the final construct possesses the desired characteristics. The amino acid changes also may alter post-translational processes of the monoclonal, human, humanized, or variant antibody, such as changing the number or position of glycosylation sites.

Nucleic acid molecules encoding amino acid sequence variants of the antibody are prepared by various methods. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

The present disclosure also provides isolated nucleic acid molecules encoding for antibodies or antigen binding fragment thereof, described herein, optionally operably linked to regulatory control sequences recognized by a host cell, vectors and host cells comprising the nucleic acids, and recombinant techniques for the production of the antibodies, which may comprise culturing the host cell so that the nucleic acid is expressed and, optionally, recovering the antibody from the host cell culture or culture medium.

For recombinant production of an antibody or antigen binding fragment thereof, the nucleic acid molecule encoding it can be isolated and inserted into a replicable vector for further cloning (amplification of the DNA) or for expression. Accordingly provided herein are isolated antibody or antigen binding fragment thereof. In some embodiments, the antibodies or the present disclosure or antigen binding fragment thereof can be recombinant antibody. The term "recombinant antibody" refers to an antibody that is expressed from a cell or cell line transfected with an expression vector (or possibly more than one expression vector, typically two expression vectors) comprising the coding sequence of the antibody, where said coding sequence is not naturally associated with the cell. In one embodiment, a recombinant antibody has a glycosylation pattern that is different than the glycosylation pattern of an antibody having the same sequence if it were to exist in nature. In one embodiment, a recombinant antibody is expressed in a mammalian host cell which is not a human host cell. Notably, individual mammalian host cells have unique glycosylation patterns.

In some embodiments, the antibodies or antigen binding fragment of the present disclosure is synthetic. The polypeptides of the present disclosure can be purified by isolation/purification methods for proteins generally known in the field of protein chemistry.

In one aspect, provided herein is a host cell comprising the isolated nucleic acid molecules described herein or a vector comprising said isolated nucleic acid molecules described herein. The vector can be a cloning vector or an expression vector. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC® 31,446), although other strains such as *E. coli* B, *E. coli* Xl 776 (ATCC® 31,537), and *E. coli* W3110 (ATCC® 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC® 12,424), *K. bulgaricus* (ATCC® 16,045), *K. wickeramii* (ATCC® 24,178), *K. waltii* (ATCC® 56,500), *K. drosophilarum* (ATCC® 36,906), *K. thermotolerans*, and *K. marxianus; yarrowia* (EP 402,226); *Pichia* pastors (EP 183,070); *Candida; Trichoderma* reesia (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NP\7, and such viruses may be used as the virus herein according to the present invention, particularly for transfection of *Spodoptera frugiperda* cells.

Plant cell cultures of cotton, corn, potato, soybean, *petunia*, tomato, tobacco, *lemna*, and other plant cells can also be utilized as hosts. However, interest has been greatest in vertebrate cells, and propagation of vertebrate cells in culture (tissue culture) has become routine procedure. Examples of useful mammalian host cell lines are Chinese hamster ovary cells, including CHOK1 cells (ATCC® CCL61™), DXB-11, DG-44, and Chinese hamster ovary cells/-DHFR (CHO, Urlaub et al., Proc. Natl. Acad. Sci. USA 77: 4216 (1980)); monkey kidney CV1 line transformed by SV40 (COS-7, ATCC® CRL 1651™); human embryonic kidney line (293 or 293 cells subcloned for growth in suspension culture, [Graham et al., J. Gen Viral. 36: 59 (1977)]; baby hamster kidney cells (BHK, ATCC® CCL 10™); mouse sertoli cells (TM4, Mather, Biol. Reprod. 23: 243-251 (1980)); monkey kidney cells (CVI ATCC® CCL 70™); African green monkey kidney cells (VERO-76, ATCC® CRL-1587™); human cervical carcinoma cells (HELA, ATCC® CCL 2™); canine kidney cells (MDCK, ATCC® CCL 34™); buffalo rat liver cells (BRL 3A, ATCC® CRL 1442™); human lung cells (W138, ATCC® CCL 75™); human liver cells (Hep G2, HB 8065); mouse mammary tumor (MMT 060562, ATCC® CCL51 ™); TRI cells (Mather et al., Annals N.Y Acad. Sci. 383: 44-68 (1982)); MRC 5 cells; FS4 cells; and a human hepatoma line (Hep G2).

Host cells are transformed or transfected with the above-described expression or cloning vectors for antibody production and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful and preferred for the expression of antibodies, described herein.

For transfection of the expression vectors and production of the chimeric, humanized, or composite human antibodies described herein, the recipient cell line can be a myeloma cell. Myeloma cells can synthesize, assemble and secrete immunoglobulins encoded by transfected immunoglobulin nucleic acid sequences and possess the mechanism for glycosylation of the immunoglobulin. For example, in some embodiments, the recipient cell is the recombinant Ig-producing myeloma cell SP2/0 (ATCC® #CRL 8287™). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells. An expression vector carrying a chimeric, humanized, or composite human antibody construct or antibody polypeptide described herein can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment. Johnston et al., 240 Science 1538 (1988), as known to one of ordinary skill in the art.

Yeast provides certain advantages over bacteria for the production of immunoglobulin H and L chains. Yeasts carry out post-translational peptide modifications including glycosylation. A number of recombinant DNA strategies exist that utilize strong promoter sequences and high copy number plasmids which can be used for production of the desired proteins in yeast. Yeast recognizes leader sequences of cloned mammalian gene products and secretes peptides bearing leader sequences (i.e., pre-peptides). Hitzman et al., 11th Intl. Conf. Yeast, Genetics & Molec. Biol. (Montpelier, France, 1982). Yeast gene expression systems can be routinely evaluated for the levels of production, secretion and the stability of antibody polypeptide or antigen binding fragment peptide thereof, and assembled chimeric, humanized, or composite human antibodies, fragments and regions thereof. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. A number of approaches can be taken for evaluating optimal expression plasmids for the expression of cloned immunoglobulin cDNAs in yeast.

Bacterial strains can also be utilized as hosts for the production of the antibody molecules or fragments thereof described herein, E. coli K12 strains such as E. coli W3110 (ATCC® 27325), Bacillus species, enterobacteria such as Salmonella typhimurium or Serratia marcescens, and various Pseudomonas species can be used. Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of chimeric, humanized, or composite humanized antibodies and fragments thereof encoded by the cloned immunoglobulin cDNAs or CDRs in bacteria (see Glover, 1985; Ausubel, 1987, 1993; Sambrook, 1989; Colligan, 1992-1996).

Host mammalian cells can be grown in vitro or in vivo. Mammalian cells provide post-translational modifications to immunoglobulin protein molecules including leader peptide removal, folding and assembly of H and L chains, glycosylation of the antibody molecules, and secretion of functional antibody protein. Mammalian cells which can be useful as hosts for the production of antibody proteins, in addition to the cells of lymphoid origin described above, include cells of fibroblast origin, such as Vero (ATCC® CRL 81™) or CHO-K1 (ATCC® CRL 61™) cells. Exemplary eukaryotic cells that can be used to express polypeptides include, but are not limited to, COS cells, including COS 7 cells; 293 cells, including 293-6E cells; CHO cells, including CHO-S and DG44 cells; PER.C6® cells (Crucell); and NS0 cells. In some embodiments, a particular eukaryotic host cell is selected based on its ability to make desired post-translational modifications to the variable heavy chains and/or variable light chains. For example, in some embodiments, CHO cells produce polypeptides that have a higher level of sialylation than the same polypeptide produced in 293 cells.

In some embodiments, polypeptides of the antibodies or antigen binding fragment thereof, disclosed herein can be produced in vivo in an animal that has been engineered or transfected with one or more nucleic acid molecules encoding the polypeptides, according to any suitable method.

In some embodiments, an antibody or antigen binding fragment thereof is produced in a cell-free system. Nonlimiting exemplary cell-free systems are described, e.g., in Sitaraman et al., Methods Mol. Biol. 498: 229-44 (2009); Spirin, Trends Biotechnol. 22: 538-45 (2004); Endo et al., Biotechnol. Adv. 21: 695-713 (2003).

Many vector systems are available for the expression of H and L chain nucleic acid sequence in mammalian cells (see Glover, 1985). Different approaches can be followed to obtain complete H2L2 antibodies. As discussed above, it is possible to co-express H and L chains in the same cells to achieve intracellular association and linkage of H and L chains into complete tetrameric H2L2 antibodies and/or antigen binding fragment peptides. The co-expression can occur by using either the same or different plasmids in the same host. Genes for both H and L chains and/or CDR3 regions peptides can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. Cell lines producing antigen binding peptide fragments and/or H2L2 molecules via either route could be transfected with plasmids encoding additional copies of peptides, H, L, or H plus L chains in conjunction with additional selectable markers to generate cell lines with enhanced properties, such as higher production of assembled H2L2 antibody molecules or enhanced stability of the transfected cell lines.

Additionally, plants have emerged as a convenient, safe and economical alternative main-stream expression systems for recombinant antibody production, which are based on large scale culture of microbes or animal cells. Antibodies can be expressed in plant cell culture, or plants grown conventionally. The expression in plants may be systemic, limited to sub-cellular plastids, or limited to seeds (endosperms). Several plant-derived antibodies have reached advanced stages of development (see, e.g., Biolex, NC).

In some aspects, provided herein are methods and systems for the production of a humanized antibody, which is prepared by a process which comprises maintaining a host transformed with a first expression vector which encodes the light chain of the humanized antibody and with a second expression vector which encodes the heavy chain of the humanized antibody under such conditions that each chain is expressed and isolating the humanized antibody formed by assembly of the thus-expressed chains. The first and second expression vectors can be the same vector. Also provided herein are DNA sequences encoding the light chain or the heavy chain of the humanized antibody; an expression vector which incorporates a said DNA sequence; and a host transformed with a said expression vector. Generating a humanized antibody from the sequences and information provided herein can be practiced by those of ordinary skill in the art without undue experimentation. In one approach, there are four general steps employed to humanize a monoclonal antibody. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

Purification

The term "isolated" means altered or removed from the natural state. For example, a nucleic acid or a polypeptide (e.g. antibodies or antigen binding fragment thereof disclosed herein) naturally present in a living animal is not "isolated," but the same nucleic acid or polypeptide partially or completely separated from the coexisting materials of its natural state is "isolated." An isolated nucleic acid molecule or polypeptide can exist in substantially purified form, or can exist in a non-native environment such as, for example, a host cell. An isolated polypeptide is one that has been separated and/or recovered from a component of its natural environment. Contaminant components of its natural environment are materials that would interfere with diagnostic or therapeutic uses of the polypeptide, and may include enzymes, hormones, and other proteinaceous or non-proteinaceous components. In some embodiments, the antibodies or antigen binding fragments thereof of the instant disclosure can be purified by a suitable method. In preferred embodiments, the polypeptide is purified: (1) to greater than 95% by weight of polypeptide as determined by the Lowry method, and most preferably more than 99% by weight; (2) to a degree sufficient to obtain at least 15 residues of N-terminal or internal amino acid sequence by use of a spinning cup sequenator; or (3) to homogeneity as shown by SDS-PAGE under reducing or non-reducing conditions and using Coomassie blue or, preferably, silver staining. Isolated antibody includes the polypeptide in situ within recombinant cells since at least one component of the polypeptide's natural environment will not be present. Ordinarily, however, isolated polypeptide will be prepared by at least one purification step. In one aspect, disclosed herein is a purified antibody or antigen-binding fragment as provided herein.

Once expressed, the whole antibodies, their dimers, individual light and heavy chains, or other immunoglobulin forms of the present invention can be recovered and purified by known techniques, e.g., immunoabsorption or immunoaffinity chromatography, chromatographic methods such as HPLC (high performance liquid chromatography), ammonium sulfate precipitation, gel electrophoresis, or any combination of these. See generally, Scopes, PROTEIN PURIF. (Springer-Verlag, NY, 1982). Substantially pure immunoglobulins of at least about 90% to 95% homogeneity are advantageous, as are those with 98% to 99% or more homogeneity, particularly for pharmaceutical uses. When using recombinant techniques, the antibody can be produced intracellularly, in the periplasmic space, or directly secreted into the medium, including from microbial cultures. If the antibody is produced intracellularly, as a first step, the particulate debris, either host cells or lysed fragments, is removed, for example, by centrifugation or ultrafiltration. Better et al. Science 240: 1041-1043 (1988); ICSU Short Reports 10: 105 (1990); and Proc. Natl. Acad. Sci. USA 90: 457-461 (1993) describe a procedure for isolating antibodies which are secreted to the periplasmic space of E. coli. (See also, [Carter et al., Bio/Technology 10: 163-167 (1992)].

The antibody composition isolated from microbial or mammalian cells can be purified using, for example, hydroxylapatite chromatography cation or avian exchange chromatography, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human y1, y2, or y4 heavy chains (Lindmark et al., J. Immunol. Meth. 62: 1-13 (1983)). Protein G is recommended for all mouse isotypes and for human y3 (Guss et al., EMBO J. 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH 3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered. Once purified, partially or to homogeneity as desired, a humanized or composite human antibody can then be used therapeutically or in developing and performing assay procedures, immunofluorescent staining, and the like. See generally, Vols. I & II Immunol. Meth. (Lefkovits & Pernis, eds., Acad. Press, NY, 1979 and 1981).

Functional activities of an antibody or antigen-binding fragment disclosed herein. Such functional activities include biological activity and ability to bind to a cancer cell antigen. Additionally, a polypeptide having functional activity means the polypeptide exhibits activity similar, but not necessarily identical to, an activity of an antibody described herein, including mature forms, as measured in a particular assay, such as, for example, a biological assay, with or without dose dependency. In the case where dose dependency does exist, it need not be identical to that of the antibodies of the disclosure, but rather substantially similar to the dose-dependence in a given activity as compared to the antibodies set forth herein (i.e., the candidate polypeptide will exhibit greater activity, or not more than about 25-fold less, about 10-fold less, or about 3-fold less activity relative to the antibodies described herein).

Nucleic Acid Molecules Encoding Antibodies

Using the information provided herein, for example, nucleic acid and amino acid sequences of the antibodies; a nucleic acid molecule encoding the antibodies or antigen-binding fragment thereof can be easily obtained by a skilled artisan. Such a nucleic acid molecule can be obtained, for example, using conventional methods disclosed in the art. Nucleic acid molecules of the present disclosure may be in the form of RNA, such as mRNA, hnRNA, tRNA or any other form, or in the form of DNA, including but not limited to, cDNA and genomic DNA obtained by cloning or produced synthetically, or any combinations thereof. The DNA may be triplex, duplex or single-stranded, or any combination thereof. Any portion of at least one strand of the DNA or RNA may be the coding strand, also known as the sense strand, or it can be the antisense strand, also known as the antisense strand.

"Polynucleotide," or "nucleic acid molecule," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A nucleic acid molecule can comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including isolated nucleic acid, RNA and DNA.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine. In some embodiments, the nucleic acid molecule comprises an isolated nucleic acid.

The nucleic acids can be present in whole cells, in a cell lysate, or in a partially purified or substantially pure form. A nucleic acid molecule is "isolated" or "rendered substantially pure" when purified away from other cellular components or other contaminants, e.g., other cellular nucleic acids or proteins, by standard techniques, including, but not limited to alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid according to at least some embodiments of the disclosure can be, for example, DNA or RNA and may or may not contain intronic sequences. In a preferred embodiment, the nucleic acid is a cDNA molecule.

Another aspect of the present disclosure pertains to nucleic acid molecules comprising nucleic acid sequences that encode the antibody polypeptide or a functional fragment thereof, described herein or antigen-binding fragment thereof. In some embodiments, the isolated nucleic acid molecule comprises a nucleic acid sequence encoding a modified IgA heavy chain constant region. In some embodiments, the nucleic acid sequence encoding a modified IgA heavy chain constant region comprises a sequence selected from any one of SEQ ID NOs 25-32. In some embodiments, the nucleic acid sequence encoding a variable heavy chain polypeptide is selected from SEQ ID NOs.: 87-84. In some embodiments, the isolated nucleic acid molecule comprises a nucleic acid sequence encoding a light chain variable region polypeptide of an antibody. In some embodiments, the nucleic acid sequence encoding a light chain variable region polypeptide is selected from SEQ ID NOs.: 101-108.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame. The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgA1 or a IgA2 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH—and VL-encoding DNA fragments are operatively linked to another fragment encoding a flexible linker, e.g., encoding the amino acid sequence (Gly-4-Ser)3 (SEQ ID NO:122), such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., (1990) Nature 348:552-554).

Nucleic acid molecules isolated from the present disclosure can include nucleic acid molecules comprising an open reading frame (ORF), optionally with one or more introns, e.g., but not limited to, at least one specified portion of at least a CDR, as CDR1, CDR2 and/or CDR3 of at least one light chain; nucleic acid molecules comprising the coding sequence of a cancer associated antibody disclosed herein or variable region e.g., variable regions of the light chain; and nucleic acid molecules comprising a nucleotide sequence substantially different from those described above but which, due to the degeneracy of the genetic code, still encode at least antibody or antigen binding fragment thereof as described herein and/or as it is known in the art. Of course, the genetic code is well known in the art. Therefore, it would be routine for one skilled in the art to generate such degenerate nucleic acid variants encoding specific antibodies of the present disclosure. See for example, Ausubel et al., Supra, and such nucleic acid variants are included in the present invention.

Nucleic acid molecules comprising nucleic acid sequence that encode one or more chains of an antibody are provided herein. In some embodiments, a nucleic acid molecule comprises a nucleic acid sequence that encodes a heavy chain or a light chain of an antibody. In some embodiments, a nucleic acid molecule comprises both a nucleic acid sequence that encodes a heavy chain and a nucleic acid sequence that encodes a light chain, of an antibody. In some embodiments, a first nucleic acid molecule comprises a first nucleic acid sequence that encodes a heavy chain and a second nucleic acid molecule comprises a second nucleic acid sequence that encodes a light chain.

In some embodiments, the heavy chain and the light chain are expressed from one nucleic acid molecule, or from two separate nucleic acid molecules, as two separate polypeptides. In some embodiments, such as when an antibody is an scFv, a single nucleic acid sequence encodes a single polypeptide comprising both a heavy chain and a light chain linked together.

In some embodiments, a nucleic acid sequence encoding a heavy chain or light chain of an antibody disclosed herein comprises a nucleic acid sequence that encodes at least one of the CDRs provided herein. In some embodiments, a nucleic acid sequence encoding a heavy chain or light chain of an antibody disclosed herein comprises a sequence that encodes at least 3 of the CDRs provided herein. In some embodiments, a nucleic acid sequence encoding a heavy chain or light chain of an antibody comprises a sequence that encodes at least 6 of the CDRs provided herein. In some embodiments, a nucleic acid sequence encoding a heavy chain or light chain of an antibody comprises a nucleotide sequence that encodes a leader sequence, which, when translated, is located at the N terminus of the heavy chain or light chain. The leader sequence may be the native heavy or light chain leader sequence, or may be another heterologous leader sequence. The term "leader sequence" refers to a sequence of amino acid residues located at the N-terminus of a polypeptide that facilitates secretion of a polypeptide from a mammalian cell. A leader sequence can be cleaved upon export of the polypeptide from the mammalian cell, forming a mature protein. Leader sequences can be natural or synthetic, and they can be heterologous or homologous to the protein to which they are attached.

In some embodiments, the nucleic acid molecule is one that encodes for any of the amino acid sequences for the variable light chain and variable heavy chain in the Tables 7-8 herein. In some embodiments, the nucleic acid sequence is one that is at least 80% identical to a nucleic acid encoding any of the amino acid sequences variable light chain and variable heavy chain in the Tables 7-8 herein, for example, at least 80, 85, 90, 91, 92, 93, 94, 95, 96, 97, 98, or 99% identical. In some embodiments, the nucleic acid is one that hybridizes to any one or more of the nucleic acid sequences provided herein. In some of the embodiments, the hybridization is under moderate conditions. In some embodiments, the hybridization is under highly stringent conditions, such as: at least about 6×SSC and 1% SDS at 65° C., with a first wash for 10 minutes at about 42° C. with about 20% (v/v) formamide in 0.1×SSC, and with a subsequent wash with 0.2×SSC and 0.1% SDS at 65° C.

Nucleic acid molecules can be constructed using recombinant DNA techniques conventional in the art. In some embodiments, a nucleic acid molecule is placed in an expression vector that is suitable for expression in a selected host cell.

Vectors comprising nucleic acid molecules that encode the antibodies or antigen binding fragment herein are provided. Vectors comprising nucleic acid molecules that encode a heavy chains and/or a light chains are also provided. Such vectors include, but are not limited to, DNA vectors, phage vectors, viral vectors, retroviral vectors, etc. In one embodiment, the nucleic acid coding for the light chain and that coding for the heavy chain are isolated separately by the procedures outlined above. In one embodiment, the isolated nucleic acid encoding the light chain and that coding for the heavy chain may be inserted into separate expression plasmids, or together in the same plasmid, so long as each is under suitable promoter and translation control. In some embodiments, the heavy chain and light chain are expressed as part of a single polypeptide, such as, for example, when the antibody is an scFv.

In some embodiments, a first vector comprises a nucleic acid molecule that encodes a heavy chain and a second vector comprises a nucleic acid molecule that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used. In some embodiments, a vector is selected that is optimized for expression of polypeptides in CHO or CHO-derived cells, or in NSO cells. Exemplary such vectors are described, for example, in Running Deer et al., Biotechnol. Prog.20:880-889 (2004).

In one aspect, the present disclosure provides methods for treatment or prevention of cancer comprising administering nucleic acid molecules, wherein the nucleic acid molecules encode for a VH, VL, CDR3 region of VH or CDR 3 region of VL or antigen binding fragment thereof, wherein the nucleic acid molecule comprises a sequence disclosed herein (e.g. Table 3 or Table 4) by way of gene therapy. Gene therapy refers to therapy performed by the administration to a subject of an expressed or expressible nucleic acid. In this embodiment of the invention, the nucleic acids produce their encoded protein that mediates a prophylactic or therapeutic effect. Any of the methods for gene therapy available in the art can be used according to the embodiments herein.

For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5): 155-215 Methods. commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY. Delivery of a therapeutic antibody to appropriate cells can be effected via gene therapy ex vivo, in situ, or in vivo by use of any suitable approach known in the art, including by use of physical DNA transfer methods (e.g., liposomes or chemical treatments) or by use of viral vectors (e.g., adenovirus, adeno-associated virus, or a retrovirus). For example, for in vivo therapy, a nucleic acid encoding the desired antibody, either alone or in conjunction with a vector, liposome, or precipitate may be injected directly into the subject, and in some embodiments, may be injected at the site where the expression of the antibody compound is desired. For ex vivo treatment, the subject's cells are removed, the nucleic acid is introduced into these cells, and the modified cells are returned to the subject either directly or, for example, encapsulated within porous membranes which are implanted into the patient. See, e.g. U.S. Pat. Nos. 4,892,538 and 5,283,187. There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, and calcium phosphate precipitation. A commonly used vector for ex vivo delivery of a nucleic acid is a retrovirus.

The term "host cell" as used herein refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

Other in vivo nucleic acid transfer techniques include transfection with viral vectors (such as adenovirus, Herpes simplex I virus, or adeno-associated virus) and lipid-based systems. The nucleic acid and transfection agent are optionally associated with a microparticle. Exemplary transfection agents include I11 calcium phosphate or calcium chloride co-precipitation, DEAE-dextran-mediated transfection, quaternary ammonium amphiphile DOTMA ((dioleoyloxypropyl) trimethylammonium bromide, commercialized as Lipofectin™ by GIBCO-BRL))(Felgner et al, (1987) Proc. Natl. Acad. Sci. USA 84, 7413-7417; Malone et al. (1989) Proc. Natl Acad. Sci. USA 86 6077-6081); lipophilic glutamate diesters with pendent trimethylammonium heads (Ito et al. (1990) Biochem. Biophys. Acta 1023, 124-132); the metabolizable parent lipids such as the cationic lipid dioctadecylamido glycylspermine (DOGS, Transfectam™, Promega) and dipalmitoylphosphatidyl ethanolamylspermine (DPPES)(J. P. Behr (1986) Tetrahedron Lett. 27, 5861-5864; J. P. Behr et al. (1989) Proc. Natl. Acad. Sci. USA 86, 6982-6986); metabolizable quaternary ammonium salts (DOTB, N-(1-[2,3-dioleoyloxy]propyl)-N,N,N-trimethylammonium methylsulfate (DOTAP)(Boehringer Mannheim), polyethyleneimine (PEI), dioleoyl esters, ChoTB, ChoSC, DOSC)(Leventis et al. (1990) Biochim. Inter. 22, 235-241); 3beta[N—(N',N'-dimethylaminoethane)-carbamoyl]cholesterol (DC-Chol), dioleoylphosphatidyl ethanolamine (DOPE)/3beta[N—(N',N' dimethylaminoethane)-carbamoyl] cholesterolDC-Chol in one to one mixtures (Gao et al., (1991) Biochim. Biophys. Acta 1065, 8-14), spermine, spermidine, lipopolyamines (Behr et al., Bioconjugate Chem, 1994, 5: 382-389), lipophilic polylysines (LPLL) (Zhou et al., (1991) Biochim. Biophys. Acta 939, 8-18), [[(1, 1,3,3 tetramethylbutyl)cresoxy]ethoxy]ethyl]dimethylbnzylammonium hydroxide (DEBDA hydroxide) with excess phosphatidylcholine/cholesterol (Ballas et al., (1988) Biochim. Biophys. Acta 939, 8-18), cetyltrimethylammonium bromide (CTAB)/DOPE mixtures (Pinnaduwage et al, (1989) Biochim. Biophys. Acta 985, 33-37), lipophilic diester of glutamic acid (TMAG) with DOPE, CTAB, DEBDA, didodecylammonium bromide (DDAB), and stearylamine in admixture with phosphatidylethanolamine (Rose et al., (1991) Biotechnique 10, 520-525), DDAB/DOPE (TransfectACE, GIBCO BRL), and oligogalactose bearing lipids. Exemplary transfection enhancer agents that increase the efficiency of transfer include, for example, DEAE-dextran, polybrene, lysosome-disruptive peptide (Ohmori N I et al, Biochem Biophys Res Commun Jun. 27, 1997; 235(3):726-9), chondroitan-based proteoglycans, sulfated proteoglycans, polyethylenimine, polylysine (Pollard H et al. J Biol Chem, 1998 273 (13):7507-11), integrin-binding peptide CYGGRGDTP (SEQ ID NO:123), linear dextran nonasaccharide, glycerol, cholesteryl groups tethered at the 3'-terminal internucleoside link of an oligonucleotide (Letsinger, R. L. 1989 Proc Natl Acad Sci USA 86: (17):6553-6), lysophosphatide, lysophosphatidylcholine, lysophosphatidylethanolamine, and 1-oleoyl lysophosphatidylcholine.

In some situations, it may be desirable to deliver the nucleic acid with an agent that directs the nucleic acid containing vector to target cells. Such "targeting" molecules include antibodies specific for a cell-surface membrane protein on the target cell, or a ligand for a receptor on the target cell. Where liposomes are employed, proteins which bind to a cell-surface membrane protein associated with endocytosis may be used for targeting and/or to facilitate uptake. Examples of such proteins include capsid proteins and fragments thereof tropic for a particular cell type, antibodies for proteins which undergo internalization in cycling, and proteins that target intracellular localization and enhance intracellular half-life. In other embodiments, receptor-mediated endocytosis can be used. Such methods are described, for example, in Wu et al., 1987 or Wagner et al., 1990. For review of the currently known gene marking and gene therapy protocols, see Anderson 1992. See also WO 93/25673 and the references cited therein.

Chimeric Antigen Receptor

In one aspect, the disclosure herein, provides a chimeric antigen receptor comprising, an antigen binding fragment, disclosed herein, a transmembrane domain, and an intracellular signaling domain. The term "chimeric Antigen Receptor" (CAR), "artificial T cell receptor", "chimeric T cell receptor", or "chimeric immunoreceptor" as used herein refers to an engineered receptor, which grafts an arbitrary specificity onto an immune effector cell. CARs typically have an extracellular domain (ectodomain), which comprises an antigen-binding domain, a transmembrane domain, and an intracellular (endodomain) domain. The term "signaling domain" refers to the functional portion of a protein which acts by transmitting information within the cell to regulate cellular activity via defined signaling pathways by generating second messengers or functioning as effectors by responding to such messengers.

An "intracellular signaling domain," as the term is used herein, refers to an intracellular portion of a molecule. The intracellular signaling domain generates a signal that promotes an immune effector function of the CAR containing cell, e.g., a CART cell. Examples of immune effector function, e.g., in a CART cell, include cytolytic activity and helper activity, including the secretion of cytokines.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a CART, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, FcR gamma, FcR beta, CD3 gamma, CD3 delta, CD3 epsilon, CD5, CD22, CD79a, CD79b, and CD66d DAP10 and DAP12.

The term "zeta" or alternatively "zeta chain", "CD3-zeta" or "TCR-zeta" is defined as the protein provided as GenBan Acc. No. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain that are sufficient to functionally transmit an initial signal necessary for T cell activation. In one aspect the cytoplasmic domain of zeta comprises residues 52 through 164 of GenBank® Acc. No. BAG36664.1 or the equivalent residues from a non-human species, e.g., mouse, rodent, monkey, ape and the like, that are functional orthologs thereof.

The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to, an MHC class I molecule, BTLA and a Toll ligand receptor, as well as OX40, CD2, CD27, CD28, CD5, ICAM-1, LFA-1 (CD11a/CD18) and 4-1BB (CD137).

A costimulatory intracellular signaling domain can be derived from the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, lymphocyte function-associated antigen-1 (LFA-1), CD2, CD7, LIGHT, NKG2C, SLAMF7, NKp80, CD160, B7-H3, and a ligand that specifically binds with CD83, and the like.

The intracellular signaling domain can comprise the entire intracellular portion, or the entire native intracellular signaling domain, of the molecule from which it is derived, or a functional fragment thereof.

In another aspect, the antigen binding fragment comprises a humanized antibody or antibody fragment. In one embodiment, the antigen binding fragment comprises one or more (e.g., one, two, or all three) light chain complementary determining region 1 (LC-CDR1), light chain complementary determining region 2 (LC-CDR2), and light chain complementary determining region 3 (LC-CDR3) of an antibody described herein, and one or more (e.g., one, two, or all three) heavy chain complementary determining region 1 (HC-CDR1), heavy chain complementary determining region 2 (HC-CDR2), and heavy chain complementary determining region 3 (HC-CDR3) of an antibody described herein.

Transmembrane Domain

With respect to the transmembrane domain, in various embodiments, a CAR can be designed to comprise a transmembrane domain that is attached to the extracellular domain of the CAR A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the other domains of the CAR is used. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the CAR T-cell surface. In a different aspect, the amino acid sequence of the transmembrane domain may be modified or substituted so as to minimize interactions with the binding domains of the native binding partner present in the same CAR T-cell.

The transmembrane domain may be derived either from a natural or from a recombinant source. Where the source is natural, the domain may be derived from any membrane-bound or transmembrane protein. In one aspect the transmembrane domain is capable of signaling to the intracellular domain(s) whenever the CAR has bound to a target. A transmembrane domain, for example, can include at least the transmembrane region(s) of e.g., the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154.

In some instances, the transmembrane domain can be attached to the extracellular region of the CAR, e.g., the antigen-binding domain of the CAR, via a hinge, e.g., a hinge from a human protein. For example, in one embodiment, the hinge can be a human Ig (immunoglobulin) hinge, e.g., an IgG4 hinge, or a CD8a hinge. In one aspect, the hinge or spacer comprises an IgG4 hinge.

Cytoplasmic Domain

The cytoplasmic domain or region of the CAR includes an intracellular signaling domain. An intracellular signaling domain is generally responsible for activation of at least one of the normal effector functions of the immune cell in which the CAR has been introduced. The term "effector function" refers to a specialized function of a cell. Effector function of a T cell, for example, may be cytolytic activity or helper activity including the secretion of cytokines. The term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic signaling domain, e.g., a costimulatory domain).

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains that are of particular use in the invention include those of TCR zeta, FcR gamma, FcR beta, CD3 gamma, CD3 delta, CD3 epsilon, CD5, CD22, CD79a, CD79b, and CD66d. In one embodiment, a CAR of the invention, e.g., a CAR comprises a intracellular signaling domain, e.g., a primary signaling domain, of CD3-zeta. In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

The intracellular signaling domain of the CAR can comprise the CD3-zeta signaling domain by itself or it can be combined with any other desired intracellular signaling domain(s) useful in the context of a CAR of the invention. For example, the intracellular signaling domain of the CAR can comprise a CD3 zeta chain portion and a costimulatory signaling domain. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. For example, CD27 costimulation has been demonstrated to enhance expansion, effector function, and survival of human CART cells in vitro and augments human T cell persistence and antitumor activity in vivo (Song et al. Blood. 2012; 119(3):696-706).

The intracellular signaling sequences within the cytoplasmic portion of a CAR of the invention may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequence. In one embodiment, a glycine-serine doublet can be used as a suitable linker. In one embodiment, a single amino acid, e.g., an alanine, a glycine, can be used as a suitable linker.

In one aspect, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue.

In some embodiments, CAR does not actually recognize the entire antigen; instead it binds to only a portion of the antigen's surface, an area called the antigenic determinant or epitope.

In some embodiments, a CAR described herein include (including functional portions and functional variants thereof) glycosylated, amidated, carboxylated, phosphorylated, esterified, N-acylated, cyclized via, e.g., a disulfide bridge, or converted into an acid addition salt and/or optionally dimerized or polymerized, or conjugated.

Immunoconjugates

In one aspect of the present disclosure, the antibodies or antigen binding fragment thereof, disclosed herein, can initiate a potent immune response against the tumor and/or are capable of direct cytotoxicity. In this regard, the antibodies or antigen binding fragment thereof herein may elicit tumor cell lysis by either complement-mediated or antibody-dependent cell cytotoxicity (ADCC) mechanisms, both of which require an intact Fc portion of the immunoglobulin molecule for interaction with effector cell Fc receptor sites or complement proteins. In addition, antibodies that exert a direct biological effect on tumor growth are useful in the practice of the disclosure. Potential mechanisms by which such directly cytotoxic antibodies may act include inhibition of cell growth, modulation of cellular differentiation, modulation of tumor angiogenesis factor profiles, and the induction of apoptosis. The mechanism by which a particular antibody or an antigen binding fragment thereof, disclosed herein, exerts an anti-tumor effect may be evaluated using any number of in vitro assays designed to determine ADCC, ADMMC, complement-mediated cell lysis, and so forth, as is generally known in the art.

The antibodies or antigen binding fragment thereof, disclosed herein, may be administered in their "naked" or unconjugated form, or may have therapeutic agents conjugated to them. In one embodiment, antibodies or antigen binding fragment thereof are used as a radiosensitizer. In such embodiments, the antibodies or antigen binding fragment are conjugated to a radiosensitizing agent. The term "radiosensitizer," as used herein, is defined as a molecule, preferably a low molecular weight molecule, administered to animals in therapeutically effective amounts to increase the sensitivity of the cells to be radiosensitized to electromagnetic radiation and/or to promote the treatment of diseases that are treatable with electromagnetic radiation. Diseases that are treatable with electromagnetic radiation include neoplastic diseases, benign and malignant tumors, and cancerous cells.

The terms "electromagnetic radiation" and "radiation" as used herein include, but are not limited to, radiation having the wavelength of 10-20 to 100 meters. Preferred embodiments of the present disclosure can employ for example, the electro-magnetic radiation of: gamma-radiation c10-20 to 10-13 m), X-ray radiation (10-12 to 10-9 m), ultraviolet light (10 nm to 400 nm), visible light (400 nm to 700 nm), infrared radiation (700 nm to 1.0 mm), and microwave radiation (1 mm to 30 cm).

Radiosensitizers are known to increase the sensitivity of cancerous cells to the toxic effects of electromagnetic radiation. Many cancer treatment protocols currently employ radiosensitizers activated by the electromagnetic radiation of X-rays. Examples of X-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromode-oxyuridine (BUdR), 5-iododeoxyuridine (IUdR), bromode-oxycytidine, fluorodeoxyuridine (FUdR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

In another embodiment, the antibody may be conjugated to a receptor (such streptavidin) for utilization in tumor pretargeting wherein the antibody-receptor conjugate is administered to the patient, followed by removal of unbound conjugate from the circulation using a clearing agent and then administration of a ligand (e.g., avidin) which is conjugated to a cytotoxic agent (e.g., a radionuclide).

The present disclosure further provides the above-described antibodies or antigen binding thereof in detectably labeled form. Antibodies can be detectably labeled through the use of radioisotopes, affinity labels (such as biotin, avidin, etc.), enzymatic labels (such as horseradish peroxidase, alkaline phosphatase, etc.) fluorescent or luminescent or bioluminescent labels (such as FITC or rhodamine, etc.), paramagnetic atoms, and the like. Procedures for accomplishing such labeling are well known in the art; for example, see (Sternberger, L. A. et al., J. Histochem. Cytochem. 18:315 (1970); Bayer, E. A. et al., Meth. Enzym. 62:308 (1979); Engval, E. et al., Immunol. 109:129 (1972); Goding, J. W. J. Immunol. Meth. 13:215 (1976)).

"Label" refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable. Alternatively, the label may not be detectable on its own but may be an element that is bound by another agent that is detectable (e.g. an epitope tag or one of a binding partner pair such as biotin-avidin, etc.). Thus, the antibody may comprise a label or tag that facilitates its isolation, and methods of the invention to identify antibodies include a step of isolating the antigen/antibody through interaction with the label or tag.

Exemplary therapeutic immunoconjugates comprise the antibody described herein conjugated to a cytotoxic agent such as a chemotherapeutic agent, toxin (e.g., an enzymatically active toxin of bacterial, fungal, plant or animal origin, or fragments thereof), or a radioactive isotope (i.e., a radioconjugate). Fusion proteins are described in further detail below.

In some embodiments, antibodies and antigen binding fragments thereof disclosed herein can be conjugated to a therapeutic agent such as a chemotherapeutic cytotoxin, such as a cytostatic or cytocidal agent (e.g., paclitaxol, cytochalasin B or diphtheria toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracindione, mitoxantrone, mithramycin, actinomycin D, 1-dehydrotestosterone, glucocorticoids, procaine, tetracaine, lidocaine, propranolol, and puromycin and analogs or homologs thereof.), antimetabolites (e.g., methotrexate, 6-mercaptopurine, 6-thioguanine, cytarabine, fludarabin, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents, a thrombotic or anti-angiogenic agent or a radioactive label. Examples of suitable cytotoxic agents and chemotherapeutic agents for forming immunoconjugates are known in the art, see for example, WO 05/103081). In another embodiment, antibodies and antigen binding fragments thereof disclosed herein are conjugated to a detectable substrate such as, e.g., an enzyme, fluorescent marker, chemiluminescent marker, bioluminescent material, or radioactive material. In some embodiments of the aspects described herein, the antibody and antibody fragments thereof disclosed herein are conjugated to a toxin (e.g., an enzymatically active toxin of bacterial, fungal, plant or animal origin, or fragments thereof), a small molecule, an siRNA, a nanoparticle, a targeting agent (e.g., a microbubble), or a radioactive isotope (i.e., a radioconjugate). Such conjugates are referred to herein as "immunoconjugates". Such immunoconjugates can be used, for example, in diagnostic, theranostic, or targeting methods.

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. A variety of radioisotopes are available for the production of radioconjugate antibodies. Examples include, but are not limited to, 212 Bi, 131I, 131 In, 90Y and 186Re.

Conjugates of the antibodies or antigen binding fragments thereof described herein and a cytotoxic agent can be made using any of a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., 238 Science 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026.

In other embodiments, the antibody or portion thereof can be conjugated to a "receptor" (e.g., streptavidin) for utilization in tumor pretargeting wherein the antibody-receptor conjugate is administered to the subject, followed by removal of unbound conjugate from the circulation using a clearing agent and then administration of a "ligand" (e.g., avidin) which is conjugated to a cytotoxic agent (e.g. a radionucleotide). In some embodiments, the antibody or antibody fragment thereof can be conjugated to biotin, and the biotin conjugated antibody or antibody fragment thereof can be further conjugated or linked to a streptavidin-bound or -coated agent, such as a streptavidin-coated microbubble, for use in, for example, molecular imaging of angiogenesis.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62: 119-58 (1982).

Production of immunoconjugates is described in U.S. Pat. No. 6,306,393. Immunoconjugates can be pre-pared by indirectly conjugating a therapeutic agent to an antibody component. General techniques are described in Shih et al., Int. J. Cancer 41:832-839 (1988); Shih et al., Int.J. Cancer 46:1101-1106 (1990); and Shih et al., U.S. Pat. No. 5,057, 313. The general method involves reacting an antibody component having an oxidized carbohydrate portion with a carrier polymer that has at least one free amine function and that is loaded with a plurality of drug, toxin, chelator, boron addends, or other therapeutic agent. This reaction results in an initial Schiff base (imine) linkage, which can be stabilized by reduction to a secondary amine to form the final conjugate.

The carrier polymer is preferably an aminodextran or polypeptide of at least 50 amino acid residues, although other substantially equivalent polymer carriers can also be used. Preferably, the final immunoconjugate is soluble in an aqueous solution, such as mammalian serum, for ease of administration and effective targeting for use in therapy. Thus, solubilizing functions on the carrier polymer will enhance the serum solubility of the final immunoconjugate. In particular, an aminodextran will be preferred.

The process for preparing an immunoconjugate with an aminodextran carrier typically begins with a dextran polymer, advantageously a dextran of average molecular weight of about 10,000-100,000. The dextran is reacted with an oxidizing agent to affect a controlled oxidation of a portion of its carbohydrate rings to generate aldehyde groups. The oxidation is conveniently affected with glycolytic chemical reagents such as NaIO4, according to conventional procedures.

The oxidized dextran is then reacted with a polyamine, preferably a diamine, and more preferably, a mono- or polyhydroxy diamine. Suitable amines include ethylene diamine, propylene diamine, or other like polymethylene diamines, diethylene triamine or like polyamines, 1,3-diamino-2-hydroxypropane, or other like hydroxylated diamines or polyamines, and the like. An excess of the amine relative to the aldehyde groups of the dextran is used to ensure substantially complete conversion of the aldehyde functions to Schiff base groups.

A reducing agent, such as NaBH4, NaBH3CN or the like, is used to effect reductive stabilization of the resultant Schiff base intermediate. The resultant adduct can be purified by passage through a conventional sizing column to remove cross-linked dextrans. Other conventional methods of derivatizing a dextran to introduce amine functions can also be used, e.g., reaction with cyanogen bromide, followed by reaction with a diamine. The anminodextran is then reacted with a derivative of the particular drug, toxin, chelator, immunomodulator, boron addend, or other therapeutic agent to be loaded, in an activated form, preferably, a carboxyl-activated derivative, prepared by conventional means, e.g., using dicyclohexylcarbodiimide (DCC) or a water soluble variant thereof, to form an intermediate adduct.

Alternatively, polypeptide toxins such as poke-weed antiviral protein or ricin A-chain, and the like, can be coupled to aminodextran by glutaraldehyde condensation or by reaction of activated carboxyl groups on the protein with amines on the aminodextran. Chelators for radiometals or magnetic resonance enhancers are well-known in the art. Typical are derivatives of ethylenediaminetetraacetic acid (EDTA) and diethylen-etriaminepentaacetic acid (DTPA). These chelators typically have groups on the side chain by which the chelator can be attached to a carrier. Such groups include, e.g., benzylisothiocyanate, by which the DTPA or EDTA can be coupled to the amine group of a carrier. Alternatively, carboxyl groups or amine groups on a chelator can be coupled to a carrier by activation or prior derivatization and then coupling, all by well-known means.

Boron addends, such as carboranes, can be attached to antibody components by conventional methods. For example, carboranes can be prepared with carboxyl functions on pendant side chains, as is well known in the art. Attachment of such carboranes to a carrier, e.g., aminodextran, can be achieved by activation of the carboxyl groups of the carboranes and condensation with amines on the carrier to produce an intermediate conjugate. Such intermediate conjugates are then attached to antibody components to produce therapeutically useful immunoconjugates, as described below.

A polypeptide carrier can be used instead of aminodextran, but the polypeptide carrier should have at least 50 amino acid residues in the chain, preferably 100-5000 amino acid residues. At least some of the amino acids should be lysine residues or glutamate or aspartate residues. The pendant amines of lysine residues and pendant carboxylates of glutamine and aspartate are convenient for attaching a drug, toxin, immunomodulator, chelator, boron addend or other therapeutic agent. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier and immunoconjugate.

Conjugation of the intermediate conjugate with the antibody component is effected by oxidizing the carbohydrate portion of the antibody component and reacting the resulting aldehyde (and ketone) carbonyls with amine groups remaining on the carrier after loading with a drug, toxin, chelator, immunomodulator, boron addend, or other therapeutic agent. Alternatively, an intermediate conjugate can be attached to an oxidized antibody component via amine groups that have been introduced in the intermediate conjugate after loading with the therapeutic agent. Oxidation is conveniently effected either chemically, e.g., with NaI04 or other glycolytic reagent, or enzymatically, e.g., with neuraminidase and galactose oxidase. In the case of an aminodextran carrier, not all of the amines of the aminodextran are typically used for loading a therapeutic agent. The remaining amines of aminodextran condense with the oxidized antibody component to form Schiff base adducts, which are then reductively stabilized, normally with a borohydride reducing agent.

Analogous procedures are used to produce other immunoconjugates according to the invention. Loaded polypeptide carriers preferably have free lysine residues remaining for condensation with the oxidized carbohydrate portion of an antibody component. Carboxyls on the polypeptide carrier can, if necessary, be converted to amines by, e.g., activation with DCC and reaction with an excess of a diamine.

The final immunoconjugate is purified using conventional techniques, such as sizing chromatography on Sephacryl® S-300 or affinity chromatography using one or more CD84Hy epitopes. Alternatively, immunoconjugates can be prepared by directly conjugating an antibody component with a therapeutic agent. The general procedure is analogous to the indirect method of conjugation except that a therapeutic agent is directly attached to an oxidized antibody component. It will be appreciated that other therapeutic agents can be substituted for the chelators described herein. Those of skill in the art will be able to devise conjugation schemes without undue experimentation.

As a further illustration, a therapeutic agent can be attached at the hinge region of a reduced antibody component via disulfide bond formation. For example, the tetanus toxoid peptides can be constructed with a single cysteine residue that is used to attach the peptide to an antibody component. As an alternative, such peptides can be attached to the antibody component using a heterobifunctional cross-linker, such as N-succinyl 3-(2-pyridyldithio)proprionate (SPDP). Yu et al., Int. J. Cancer 56:244 (1994). General techniques for such conjugation are well-known in the art. See, for example, Wong, Chemistry Of Protein Conjugation and Cross-Linking (CRC Press 1991); Upeslacis et al., "Modification of Antibodies by Chemical Methods," in Monoclonal Antibodies: Principles and Applications, Birch et al. (eds.), pages 187-230 (Wiley-Liss, Inc. 1995); Price, "Production and Characterization of Synthetic Peptide-Derived Antibodies," in Monoclonal Antibodies: Production, Engineering and Clinical Application, Ritter et al. (eds.), pages 60-84 (Cambridge University Press 1995).

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azido-benzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionuclide to the antibody (see, e.g., WO94/11026).

As described above, carbohydrate moieties in the Fc region of an antibody can be used to conjugate a therapeutic agent. However, the Fc region may be absent if an antibody fragment is used as the antibody component of the immunoconjugate. Nevertheless, it is possible to introduce a carbohydrate moiety into the light chain variable region of an antibody or antibody fragment. See, for example, Leung et al., J. Immunol. 154:5919 (1995); Hansen et al., U.S. Pat. No. 5,443,953. The engineered carbohydrate moiety is then used to attach a therapeutic agent. [0404] In addition, those of skill in the art will recognize numerous possible variations of the conjugation methods. For example, the carbohydrate moiety can be used to attach polyethyleneglycol in order to extend the half-life of an intact antibody, or antigen-binding fragment thereof, in blood, lymph, or other extracellular fluids. Moreover, it is possible to construct a "divalent immunoconjugate" by attaching therapeutic agents to a carbohydrate moiety and to a free sulfhydryl group. Such a free sulfhydryl group may be located in the hinge region of the antibody component.

In some embodiments, provided herein is a method for diagnosing or treating a condition associated with a target antigen. In some embodiments, the condition associated with the antigen results due to an increase in the expression or biological activity of the antigen. In some embodiments, the condition associated with the antigen results due to a decrease in the expression or biological activity of the antigen.

In some embodiments, the antibody or antigen-binding fragment thereof disclosed herein binds an antigen and, thereby, partially or substantially inhibits the expression and/or at least one biological activity of the antigen. An antibody, or specified portion or variant thereof, that partially or preferably substantially inhibits the expression and/or at least one biological activity of an antigen disclosed herein can bind the protein antigen or fragment thereof and thereby inhibit activities mediated through the antigen e.g., binding of antigen to one or more receptor or ligand known in the art to bind a particular antigen. In some embodiments, the antibody can inhibit an antigen activity by about 20-120%, preferably by at least about 10, 20, 30, 40, 50, 55, 60, 65, 70, 75, 80, 85, 90, 91, 92, 93, 94, 95, 96, 97, 98, 99, 100% or more. An antibody, or specified portion or variant thereof, that partially or preferably substantially increases the expression and/or at least one biological activity of an antigen disclosed herein can bind the protein antigen or fragment thereof and thereby increase activities mediated through the antigen. In some embodiments, the antibody can increase an antigen activity by about 20-120/6, preferably by at least about 10, 20, 30, 40, 50, 55, 60, 65, 70, 75, 80, 85, 90, 91, 92, 93, 94, 95, 96, 97, 98, 99, 100% or more.

The capacity of an antibody to increase an antigen-dependent activity is preferably assessed by at least one suitable assay, as described herein and/or as known in the art. In some embodiments, the antigen related condition can be an immune related disease, a cardiovascular disease, an infectious disease, a malignant disease or a neurologic disease.

Methods of Treatment

Disclosed herein, in some embodiments, are methods of treating a subject in need thereof, comprising administering to the subject, a therapeutic dose of a therapeutic IgA antibody described herein or a pharmaceutical composition comprising said therapeutic IgA antibody described herein. In some embodiments, the subject has a cancer, an infectious disease, or an autoimmune disease.

In some embodiments, the subject has a cancer. In some embodiments, the subject has an inflammatory disorder. In some embodiments, the cancer is associated with expression of a tumor associated antigen described herein. In some embodiments, the cancer is associated with expression of CD47, CD20, GD2, CD38, CD19, EGFR, HER2, PD-L1, CD25, CD33, BCMA, CD44, α-Folate receptor, CAIX, CD30, ROR1, CEA, EGP-2, EGP-40, HER3, Folate-binding Protein, GD3, IL-13R-a2, KDR, EDB-F, mesothelin, CD22, EGFR, MUC-1, MAGE-A1, MUC16, h5T4, PSMA, TAG-72, EGFRvIII, CD123 or VEGF-R2.

In some embodiments, disclosed herein are methods of administering a therapeutic IgA antibody or pharmaceutical composition described herein, to a subject having a cancer associated with an overexpression of CD20. In some embodiments, disclosed herein are methods of administering a therapeutic IgA antibody or pharmaceutical composition described herein to a subject having a cancer associated with an overexpression of GD2. In some embodiments, disclosed herein are methods of administering a therapeutic IgA antibody or pharmaceutical composition described herein to a subject having a cancer associated with an overexpression of mesothelin. In some embodiments, disclosed herein are methods of administering a modified effector cell to a subject having a cancer associated with an overexpression of CD38, CD19, EGFR, HER2, PD-L1, CD25, CD33, BCMA, CD44, α-Folate receptor, CAIX, CD30, ROR1, CEA, EGP-2, EGP-40, HER3, Folate-binding Protein, GD2, GD3, IL-13R-a2, KDR, EDB-F, mesothelin, CD22, EGFR, MUC-1, MAGE-A1, MUC16, h5T4, PSMA, TAG-72, EGFRvIII, CD123 or VEGF-R2.

In some embodiments, the cancer is a metastatic cancer. In other embodiments, the cancer is a relapsed or refractory cancer. In some embodiments, a cancer is a solid tumor or a hematologic malignancy. In some embodiments, the cancer is a solid tumor. In other embodiments, the cancer is a hematologic malignancy. In some embodiments, the cancer is a metastatic cancer. In some embodiments, the cancer is a relapsed or refractory cancer.

In some embodiments, the cancer is a solid tumor. Exemplary solid tumors include, but are not limited to, anal cancer; appendix cancer; bile duct cancer (i.e., cholangiocarcinoma); bladder cancer; brain tumor; breast cancer; cervical cancer; colon cancer; cancer of Unknown Primary (CUP); esophageal cancer; eye cancer; fallopian tube cancer; gastroenterological cancer; kidney cancer; liver cancer; lung cancer; medulloblastoma; melanoma; oral cancer; ovarian cancer; pancreatic cancer; parathyroid disease; penile cancer; pituitary tumor; prostate cancer; rectal cancer; skin cancer; stomach cancer; testicular cancer; throat cancer; thyroid cancer; uterine cancer; vaginal cancer; vulvar cancer; or glioblastoma.

In some embodiments, the cancer is a hematologic malignancy. In some embodiments, a hematologic malignancy comprises a lymphoma, a leukemia, a myeloma, or a B-cell malignancy. In some embodiments, a hematologic malignancy comprises a lymphoma, a leukemia or a myeloma. In some embodiments, exemplary hematologic malignancies include chronic lymphocytic leukemia (CLL), small lymphocytic lymphoma (SLL), high risk CLL, non-CLL/SLL lymphoma, prolymphocytic leukemia (PLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some embodiments, the hematologic malignancy comprises a myeloid leukemia. In some embodiments, the hematologic malignancy comprises acute myeloid leukemia (AML) or chronic myeloid leukemia (CML).

In some embodiments, the antibody or fragment thereof binds one or more of $G_{D2}$, ALK, hNET, $G_{D3}$, and CD20. In some embodiments, the $G_{D2}$ positive tumor is neuroblastoma, retinoblastoma, melanoma, small cell lung cancer, glioblastoma, osteosarcoma, rhabdomyosarcoma, Ewing's sarcoma, liposarcoma, fibrosarcoma, leiomyosarcoma, and any combinations thereof. In an aspect, the antibody or fragment thereof binds a neuroblastoma cell. In some embodiments, the ALK (anaplastic lymphoma kinase) positive tumor is an anaplastic large-cell lymphoma, an adenocarcinoma of the lung, a neuroblastoma, an inflammatory myofibroblastic tumor, a renal cell carcinomas, esophageal squamous cell carcinoma, breast cancer, a colonic adenocarcinoma, a glioblastoma multiforme or an anaplastic thyroid cancer. In some embodiments, the hNET (human norepinephrine transporter) positive tumor is a bladder tumor, breast tumor, prostate tumor, carcinoma, leukemia, liver cancer, lung cancer, lymphoma, Hodgkin's lymphoma, Non-Hodgkin's lymphoma, melanoma, neuroblastoma, ovarian tumor, pancreatic tumor or a retinoblastoma. In some case, the $G_{D3}$ positive tumor is a neuroectodermal tumor of the center nervous system, glioma, neuroblastoma, retinoblastoma, ependymoma, sarcoma, melanoma, breast cancer, ovarian cancer, glioblastoma, Ewing's sarcoma, or small cell lung carcinoma. In some embodiments the CD20 positive tumor is a leukemia, a lymphoma or a neuroblastoma.

In other embodiments, disclosed herein are methods of administering to a subject having an infection due to an infectious disease. An infectious disease can be a disease resulting from a bacterial, viral or fungi infection. In other embodiments, exemplary viral pathogens include those of the families of Adenoviridae, Epstein-Barr virus (EBV), Cytomegalovirus (CMV), Respiratory Syncytial Virus (RSV), JC virus, BK virus, HSV, HHV family of viruses, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae. Exemplary pathogenic viruses cause smallpox, influenza, mumps, measles, chickenpox, ebola, and rubella. Exemplary pathogenic fungi include *Candida, Aspergillus, Cryptococcus, Histoplasma, Pneumocystis*, and Stachybotrys. Exemplary pathogenic bacteria include *Streptococcus, Pseudomonas, Shigella, Campylobacter, Staphylococcus, Helicobacter, E. coli, Rickettsia, Bacillus, Bordetella, Chlamydia*, Spirochetes, and *Salmonella*.

In some embodiments, the IgA antibody is administered with one or more additional therapeutic agents. In some embodiments, the IgA antibody and one or more additional therapeutic agents are co-administered. In some embodiments, the IgA antibody and one or more additional therapeutic agents are sequentially administered.

In some embodiments, the combination therapy can include one or more antibodies of the disclosure co-formulated with, and/or co-administered with, one or more additional therapeutic agents, e.g., chemotherapeutic or antineoplastic agents, such as cytokine and growth factor inhibitors, immunosuppressants, anti-inflammatory agents, metabolic inhibitors, enzyme inhibitors, and/or cytotoxic or cytostatic agents. The term "combination" in this context means that the agents are given substantially contemporaneously, either simultaneously or sequentially. Exemplary chemotherapeutic agents include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, duocarmycin, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol™), pilocarpine, prochloroperazine, saproin, tamoxifen, taxol, topotecan hydrochloride, vinblastine, vincristine and vinorelbine tartrate.

In some embodiments, the IgA antibodies described herein can be combined with an effective dose of other antibodies that have been used in treatment of cancer including, without limitation the following FDA approved monoclonal antibodies: rituximab (Rituxan®, CD20: chimeric IgG1), trastuzumab (Herceptin®, HER2: chimeric IgG1), alemtuzumab (Campath®, CD52: humanized IgG1), ibritumomab tiuxetan (Zevalin®, CD20: murine, IgG1, radiolabeled (Yttrium 90), tositumomab-I-131 (Bexxar®: CD20, murine, IgG2a, radiolabeled (Iodine 131)), cetuximab (Erbitux®, EGFR: cjimeric, IgG1), bevacizumab (VEGF: humanized, IgG4), panitumumab (Vectibix®, EGFR human IgG2), ofatumumab (Arzerra®, CD20: human IgG1), ipilimumab (Ypervoy®, CTLA-4: human IgG1), brentiuximab vedotin (Adectris®, CD30: chimeric, IgG1, drug-conjugate), pertuzumab (Perjecta®, HER2: humanized IgG1, drug conjugate), adotrastuzumab ematansine (Kadcyla®, HER2: humanized, IgG1, drug-conjugate), obinutuzumab (Gazyva®, CD20: humanized and glycolengineered), nivolumab and pembrolizumab (anti-PD-1s), etc. Trastuzumab targets the HER-2 antigen.

In some embodiments, the anti-CD47 IgA antibody is administered in combination with a HER2 inhibitor, an anti-HER2 antibody, an EGFR inhibitor, an anti-EGFR antibody. In some embodiments, the anti-CD47 IgA antibody is administered in combination with trastuzumab. In some embodiments, the anti-CD47 IgA antibody is administered in combination with a c-kit inhibitor. Dosages Provided herein are compositions comprising IgA antibodies or antigen binding fragment thereof for treatment (including prevention) of a disease (e.g., cancer). In some embodiments, the compositions are pharmaceutical compositions comprising a pharmaceutically acceptable carrier. The compositions are administered in an amount effective for treatment (including prophylaxis) of cancer. In some embodiments, the compositions (e.g., the antibodies or the antigen binding fragment thereof or the nucleic acid molecules encoding said antibody or antigen binding fragment thereof) are administered in an amount effective for enhancing an immune response and/or increasing T cell activation in a subject. The compositions are to be used for in vivo administration to a subject by any available means, such as parenteral administration. For administration to a subject, a composition or medicament comprising the antibodies or antigen binding fragment thereof described herein can be sterile, which can readily accomplished by filtration through sterile filtration membranes, or other methods known to those of skill in the art. In one embodiment, a composition or medicament has been treated to be free of pyrogens or endotoxins. Testing pharmaceutical compositions or medicaments for pyrogens or endotoxins and preparing pharmaceutical compositions or medicaments free of pyrogens or endotoxins or preparing pharmaceutical compositions or medicaments that have endotoxins at a clinically-acceptable level, are well understood to one of ordinary skill in the art. Commercial kits are available to test pharmaceutical compositions or medicaments for pyrogens or endotoxins.

The compositions to be used for in vivo administration, such as parenteral administration, in the methods described herein can be sterile, which is readily accomplished by filtration through sterile filtration membranes, or other methods known to those of skill in the art.

The IgA antibodies or antigen binding fragments thereof, describe herein, are formulated, dosed, and administered in a fashion consistent with good medical practice. Factors for consideration in this context include the particular disorder being treated, the particular subject being treated, the clinical condition of the individual subject, the cause of the disorder, the site of delivery of the agent, the method of administration, the scheduling of administration, and other factors known to medical practitioners. A "therapeutically effective amount" of a substance/molecule, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A therapeutically effective amount may be delivered in one or more administrations. A therapeutically effective amount refers to an amount effective, at dosages and for periods of time necessary, to achieve the desired therapeutic and/or prophylactic result. The "therapeutically effective amount" to be administered will be governed by such considerations, and refers to the minimum amount necessary to ameliorate, treat, or stabilize, the cancer; to increase the time until progression (duration of progression free survival) or to treat or prevent the occurrence or recurrence of a tumor, a dormant tumor, or a micrometastases. The antibodies or antigen binding fragment thereof, disclosed herein, is optionally formulated with one or more additional therapeutic agents currently used to prevent or treat cancer or a risk of developing a cancer. The effective amount of such other agents depends on the amount of antibody or antigen binding fragment thereof present in the formulation, the type of disorder or treatment, and other factors discussed above. These are generally used in the same dosages and with administration routes as used herein before or about from 1 to 99% of the heretofore employed dosage.

The dose of antibody may vary depending upon the age and the size of a subject to be administered, target disease, conditions, route of administration, and the like. The preferred dose is typically calculated according to body weight or body surface area. When an antibody or antigen binding fragment thereof disclosed herein is used for treating a condition or disease in an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg, about 5 mg/kg, about 7.5 mg/kg, about 10 mg/kg, or about 15 mg/kg body weight. Depending on the severity of the condition, the frequency and the duration of the treatment can be adjusted. Effective dosages and schedules for administering may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351).

In some embodiments, the compositions herein can comprise a prophylactically effective amount, eg., when administering to a subject at a risk of cancer or in earlier stages of a disease. A "prophylactically effective amount" refers to an amount effective, at dosages and for periods of time necessary, to achieve the desired prophylactic result. Typically, since a prophylactic dose is used in subjects prior to or at an earlier stage of disease, the prophylactic dose is lower than the therapeutic dose.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

The administration can be, for example, by one or more separate administrations, or by continuous infusion. For repeated administrations over several days or longer, depending on the condition, the treatment is sustained until, for example, the cancer is treated, as measured by the methods known in the art. However, other dosage regimens can be useful. In one non-limiting example, an antibody or antigen binding fragment thereof, disclosed herein is administered once every week, every two weeks, or every three weeks, at a dose range from about 5 mg/kg to about 15 mg/kg, including but not limited to 5 mg/kg, 7.5 mg/kg, 10 mg/kg or 15 mg/kg. The progress of using the methods described herein can be easily monitored by conventional techniques and assays. The duration of a therapy using the methods described herein will continue for as long as medically indicated or until a desired therapeutic effect (e.g., those described herein) is achieved. In certain embodiments, the administration of one or more antibodies or antigen binding fragment thereof, or compositions, described herein, is continued for 1 month, 2 months, 4 months, 6 months, 8 months, 10 months, 1 year, 2 years, 3 years, 4 years, 5 years, 10 years, 20 years, or for a period of years up to the lifetime of the subject.

Efficacy of Treatment

The efficacy of the treatment methods for example, for cancer, comprising administering the IgA antibodies or antigen binding fragment thereof, or pharmaceutical compositions of the present disclosure can be measured by various endpoints commonly used in evaluating cancer treatments, including but not limited to, tumor regression, tumor weight or size shrinkage, time to progression, duration of survival, progression free survival, overall response rate, duration of response, and quality of life. The antibodies or antigen binding fragments thereof disclosed herein can require unique measures and definitions of clinical responses to drugs. In the case of cancers, the therapeutically effective amount of the antibodies, antigen binding fragments thereof disclosed herein or compositions comprising the same can reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the antibodies or antigen binding fragment thereof, disclosed herein, act to prevent growth and/or kill existing cancer cells; it can be cytostatic and/or cytotoxic. For cancer therapy, efficacy in vivo can, for example, be measured by assessing the duration of survival, duration of progression free survival (PFS), the response rates (RR), duration of response, and/or quality of life. In some embodiments, the IgA antibodies or a functional fragment thereof disclosed herein inhibits tumor growth by at least about 2%, 3%, 5%, 6%, 10%, 15%, 20%, 25%, 30%, 35%, 40%, 45%, 50%, 60%, 70%, 80%, 90% or more relative to an untreated subject. In some embodiments, the IgA antibodies or a functional fragment thereof disclosed herein inhibits tumor engraftment by at least about 2%, 3%, 5%, 6%, 10%, 15%, 20%, 25%, 30%, 35%, 40%, 45%, 50%, 60%, 70%, 80%, 90% or more relative to an untreated subject. In some embodiments, the IgA antibodies or a functional fragment thereof disclosed herein induce cytolysis of tumor cell. In some embodiments, the IgA antibodies or a functional fragment thereof disclosed herein induce increased cytolysis of tumor cell by at least about 2%, 3%, 5%, 6%, 10%, 15%, 20%, 25%, 30%, 35%, 40%, 45%, 50%, 60%, 70%, 80/a, 90% or more relative to a corresponding WT IgA.

In other embodiments, described herein are methods for increasing progression free survival of a human subject susceptible to or diagnosed with a cancer, for example, skin cancer, such as cutaneous melanoma. Time to disease progression is defined as the time from administration of the drug until disease progression or death. In a preferred embodiment, the combination treatment of the invention using an antibody or antigen binding fragment thereof, disclosed herein, and one or more chemotherapeutic agents may significantly increase progression free survival by at least about 1 month, 1.2 months, 2 months, 2.4 months, 2.9 months, 3.5 months, such as by about 1 to about 5 months, when compared to a treatment with chemotherapy alone. In another embodiment, the methods described herein may significantly increase response rates in a group of human subjects susceptible to or diagnosed with a cancer that are treated with various therapeutics. Response rate is defined as the percentage of treated subjects who responded to the treatment. In one embodiment, the combination treatment described herein using an antibody or antigen binding fragment thereof, disclosed herein, such as a recombinant antibody or antigen binding fragment thereof, and one or more chemotherapeutic agents significantly increases response rate in the treated subject group compared to the group treated with chemotherapy alone.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with a chronic immune condition, such as, but not limited to, a chronic infection or a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

For example, in some embodiments, the methods described herein comprise administering an effective amount of the antibodies or antigen binding fragment thereof, described herein, to a subject in order to alleviate a symptom of a disease, for example, cancer. As used herein, "alleviating a symptom of a cancer" is ameliorating or reducing any condition or symptom associated with a disease. As compared with an equivalent untreated control, such reduction or degree of prevention is at least 5%, 10%, 20%, 40%, 50%, 60%, 80%, 90%, 95%, or 100% as measured by any standard technique. Ideally, the cancer is completely cleared as detected by any standard method known in the art, in which case the cancer is considered to have been treated. A patient who is being treated for a cancer is one who a medical practitioner has diagnosed as having such a condition. Diagnosis can be by any suitable means. Diagnosis and monitoring can involve, for example, detecting the level of cancer cells in a biological sample (for example, a tissue or lymph node biopsy, blood test, or urine test), detecting the level of a surrogate marker of the cancer in a biological sample, detecting symptoms associated with the specific cancer, or detecting immune cells involved in the immune response typical of such a cancer.

The term "effective amount" as used herein refers to the amount of an antibody or antigen binding fragment thereof or composition comprising the same needed to alleviate at least one or more symptom of the disease or disorder, and relates to a sufficient amount of pharmacological composition to provide the desired effect. The term "therapeutically effective amount" therefore refers to an amount of an antibody or antigen binding fragment thereof disclosed herein, that is sufficient to effect a particular effect when administered to a typical subject. An effective amount as used herein would also include an amount sufficient to delay the development of a symptom of the disease, alter the course of a symptom disease (for example but not limited to, slow the progression of a symptom of the disease), or reverse a symptom of the disease. Thus, it is not possible to specify the exact "effective amount". For any given case, however, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50-Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the antibody or antigen binding fragment thereof), which achieves a half-maximal inhibition of symptoms as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

The treatment and/or prevention of cancer includes, but is not limited to, alleviating symptoms associated with cancer, the inhibition of the progression of cancer, the promotion of the regression of cancer, the promotion of the immune response, inhibition of tumor growth, inhibition of tumor size, inhibition of metastasis, inhibition of cancer cell growth, inhibition of cancer cell proliferation, or cause cancer cell death.

Modes of Administration

The IgA antibodies or antigen binding fragment thereof, described herein, can be administered to a subject in need thereof by any appropriate route which results in an effective treatment in the subject. As used herein, the terms "administering," and "introducing" are used interchangeably and refer to the placement of an antibody or antibody portion thereof into a subject by a method or route which results in at least partial localization of such agents at a desired site, such as a site of inflammation or cancer, such that a desired effect(s) is produced.

In some embodiments, the antibodies or antigen binding fragment thereof, described herein, or compositions comprising the same is administered to a subject having a cancer, to be inhibited by any mode of administration that delivers the agent systemically or to a desired surface or target, and can include, but is not limited to, injection, infusion, instillation, and inhalation administration. Oral administration forms are also contemplated herein. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intracranial, intraspinal, intracerebro spinal, and intrasternal injection and infusion.

The phrases "parenteral administration" and "administered parenterally" as used herein, refer to modes of administration other than enteral and topical administration, usually by injection. The phrases "systemic administration," "administered systemically", "peripheral administration" and "administered peripherally" as used herein refer to the administration of the bispecific or multispecific polypeptide agent other than directly into a target site, tissue, or organ, such as a tumor site, such that it enters the subject's circulatory system and, thus, is subject to metabolism and other like processes.

In some embodiments, the antibodies, or antigen binding fragment thereof, described herein, or compositions comprising the same can be administered via intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Local administration, for example, to a tumor or cancer site where angiogenesis is occurring, is particularly desired if extensive side effects or toxicity is associated with the use of the antibodies, or antigen binding fragment thereof, described herein, or compositions comprising the same. An ex vivo strategy can also be used for therapeutic applications in some embodiments. Ex vivo strategies involve transfecting or transducing cells obtained from a subject with a nucleic acid sequence, disclosed herein. The transfected or transduced cells are then returned to the subject. The cells can be any of a wide range of types including, without limitation, hematopoietic cells (e.g., bone marrow cells, macrophages, monocytes, dendritic cells, T cells, or B cells), fibroblasts, epithelial cells, endothelial cells, keratinocytes, or muscle cells.

In some embodiments, an antibody or antigen binding fragment thereof, disclosed herein, or a composition comprising the same is administered by any suitable means, including parenteral, subcutaneous, intraperitoneal, intrapulmonary, and intranasal, and, if desired for local immunosuppressive treatment, intralesional administration.

Parenteral infusions include intramuscular, intravenous, intraarterial, intraperitoneal, or subcutaneous administration. In some embodiments, the antibody or antigen binding fragment thereof or compositions of the disclosure are suitably administered by pulse infusion, particularly with declining doses of the antibody. Preferably the dosing is given by injections, most preferably intravenous or subcutaneous injections, depending in part on whether the administration is brief or chronic. In some embodiments, the antibody or antigen binding fragment thereof or compositions of the disclosure are administered locally, e.g., by direct injections, when the disorder or location of the tumor permits, and the injections can be repeated periodically. In some embodiments, the antibody or antigen binding fragment thereof or compositions of the disclosure can also be delivered systemically to the subject or directly to the tumor cells, e.g., to a tumor or a tumor bed following surgical excision of the tumor, in order to prevent or reduce local recurrence or metastasis, for example of a dormant tumor or micrometastases.

Antibody-targeted sonoporation methods are contemplated for use in some embodiments of the methods for inhibiting tumors described herein, in order to enhance the efficacy and potency of the therapeutic compositions comprising antibodies and antigen binding fragment thereof provided herein. As used herein, "sonoporation" refers to the use of sound, preferably at ultrasonic frequencies, or the interaction of ultrasound with contrast agents (e.g., stabilized microbubbles) for temporarily modifying the permeability of cell plasma membranes, thus allowing uptake of large molecules, such as therapeutic agents. The membrane permeability caused by the sonoporation is transient, leaving the agents trapped inside the cell after the ultrasound exposure. Sonoporation employs acoustic cavitation of microbubbles to enhance delivery of large molecules.

Accordingly, in some embodiments of the methods, the antibody or antigen binding fragment thereof described herein, mixed with ultrasound contrast agents, such as microbubbles, can be injected locally or systemically into a subject in need of treatment for cancer, and ultrasound can be coupled and even focused into the defined area, e.g., tumor site, to achieve targeted delivery. In some embodiments, the methods use focused ultrasound methods to achieve targeted delivery. As used herein, HIFU or "High Intensity Focused Ultrasound" refers to a non-invasive therapeutic method using high-intensity ultrasound to heat and destroy malignant or pathogenic tissue without causing damage to overlying or surrounding health tissue. As described in Khaibullina et al., 49 J. Nucl. Med. 295 (2008), and WO 2010127369, HIFU can also be used as a means of delivery of therapeutic agents, such as antibodies or antibody fragments thereof.

Methods using contrast-enhanced ultrasound (CEUS) are also contemplated for use with an antibody or antigen binding fragment thereof, described herein. Contrast-enhanced ultrasound (CEUS) refers to the application of ultrasound contrast medium and ultrasound contrast agents to traditional medical sonography. Ultrasound contrast agents refer to agents that rely on the different ways in which sound waves are reflected from interfaces between substances. A variety of microbubble contrast agents are available for use with the compositions and methods described herein. Microbubbles can differ in their shell makeup, gas core makeup, and whether or not they are targeted. Targeting ligands that bind to receptors characteristic of angiogenic disorders, can be conjugated to microbubbles, enabling the microbubble complex to accumulate selectively in areas of interest, such as diseased or abnormal tissues. This form of molecular imaging, known as targeted contrast-enhanced ultrasound, will only generate a strong ultrasound signal if targeted microbubbles bind in the area of interest. Targeted contrast-enhanced ultrasound has many applications in both medical diagnostics and medical therapeutics. In some embodiments, an antibody or antigen binding fragment thereof, described herein, is administered to a subject in need of treatment for a cancer or a tumor, using a targeted ultrasound delivery.

Pharmaceutical Compositions and Dosage Forms

Disclosed herein, in certain embodiments, are pharmaceutical compositions comprising an IgA antibody or a functional fragment thereof disclosed herein for administration in a subject.

In some embodiments, pharmaceutical compositions comprising a IgA antibody described herein are formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Pharmaceutical compositions are optionally manufactured in a conventional manner, such as, by way of example only, by means of conventional mixing, dissolving, granulating, dragee-making, levigating, emulsifying, encapsulating, entrapping or compression processes.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The pharmaceutical compositions described herein are administered by any suitable administration route, including but not limited to, oral, parenteral (e.g., intravenous, subcutaneous, intramuscular, intracerebral, intracerebroventricular, intra-articular, intraperitoneal, or intracranial), intranasal, buccal, sublingual, or rectal administration routes. In some embodiments, the pharmaceutical composition is formulated for parenteral (e.g., intravenous, subcutaneous, intramuscular, intracerebral, intracerebroventricular, intra-articular, intraperitoneal, or intracranial) administration.

The pharmaceutical compositions described herein are formulated into any suitable dosage form, including but not limited to, aqueous oral dispersions, liquids, gels, syrups, elixirs, slurries, suspensions and the like, for oral ingestion by an individual to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

In some embodiments, the pharmaceutical compositions are formulated into capsules. In some embodiments, the pharmaceutical compositions are formulated into solutions (for example, for IV administration). In some embodiments, the pharmaceutical composition is formulated as an infusion. In some embodiments, the pharmaceutical composition is formulated as an injection.

The pharmaceutical solid dosage forms described herein optionally include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

In still other aspects, using standard coating procedures, such as those described in Remington's Pharmaceutical Sciences, 20th Edition (2000), a film coating is provided around the compositions. In some embodiments, the compositions are formulated into particles (for example for administration by capsule) and some or all of the particles are coated. In some embodiments, the compositions are formulated into particles (for example for administration by capsule) and some or all of the particles are microencapsulated.

In some embodiments, the compositions are formulated into particles (for example for administration by capsule) and some or all of the particles are not microencapsulated and are uncoated.

In certain embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

"Proliferative disease" as referred to herein means a unifying concept that excessive proliferation of cells and turnover of cellular matrix contribute significantly to the pathogenesis of several diseases, including cancer is presented.

"Patient" or "subject" as used herein refers to a mammalian subject diagnosed with or suspected of having or developing a physiological condition, for instance a cancer or an autoimmune condition or an infection. In some embodiments, the term "patient" refers to a mammalian subject with a higher than average likelihood of developing cancer. Exemplary patients may be humans, apes, dogs, pigs, cattle, cats, horses, goats, sheep, rodents and other mammalians that can benefit from the therapies disclosed herein. Exemplary human patients can be male and/or female. "Patient in need thereof" or "subject in need thereof" is referred to herein as a patient diagnosed with or suspected of having a disease or disorder, for instance, but not restricted to a proliferative disorder such as cancer. In some embodiments, a cancer is a solid tumor or a hematologic malignancy. In some embodiments, the cancer is a solid tumor. In other embodiments, the cancer is a hematologic malignancy. In some embodiments, the cancer is a metastatic cancer. In some embodiments, the cancer is a relapsed or refractory cancer. In some embodiments, the cancer is a solid tumor. Exemplary solid tumors include, but are not limited to, anal cancer; appendix cancer; bile duct cancer (i.e., cholangiocarcinoma); bladder cancer; brain tumor; breast cancer; cervical cancer; colon cancer; cancer of Unknown Primary (CUP); esophageal cancer; eye cancer; fallopian tube cancer; gastroenterological cancer; kidney cancer; liver cancer; lung cancer; medulloblastoma; melanoma; oral cancer; ovarian cancer; pancreatic cancer; parathyroid disease; penile cancer; pituitary tumor; prostate cancer; rectal cancer; skin cancer; stomach cancer; testicular cancer; throat cancer; thyroid cancer; uterine cancer; vaginal cancer; vulvar cancer; or glioblastoma. In some embodiments leukemia can be, for instance, acute lymphoblastic leukemia (ALL), acute myeloid leukemia (AML), chronic lymphocytic leukemia (CLL) and chronic myeloid leukemia (CML).

"Administering" is referred to herein as providing the compositions of the present disclosure to a patient. By way of example and not limitation, composition administration, e.g., injection, may be performed by intravenous (i.v.) injection, sub-cutaneous (s.c.) injection, intradermal (i.d.) injection, intraperitoneal (i.p.) injection, or intramuscular (i.m.) injection. One or more such routes may be employed. Parenteral administration can be, for example, by bolus injection or by gradual perfusion over time. Alternatively, or concurrently, administration may be by the oral route. Additionally, administration may also be by surgical deposition of a bolus or pellet of cells, or positioning of a medical device. In an embodiment, a composition of the present disclosure may comprise engineered cells or host cells expressing nucleic acid sequences described herein, or a vector comprising at least one nucleic acid sequence described herein, in an amount that is effective to treat or prevent proliferative disorders. A pharmaceutical composition may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

As used herein, the terms "treatment," "treating," and its grammatical equivalents refer to obtaining a desired pharmacologic and/or physiologic effect. In embodiments, the effect is therapeutic, i.e., the effect partially or completely cures a disease and/or adverse symptom attributable to the disease. To this end, the method described herein comprises administering a "therapeutically effective amount" of the composition comprising the host cells expressing the nucleic acid sequence described herein, or a vector comprising the nucleic acid sequences described herein.

The terms "therapeutically effective amount", "therapeutic amount", "immunologically effective amount", "anti-tumor effective amount", "tumor inhibiting effective amount" or their grammatical equivalents refers to an amount effective, at dosages and for periods of time necessary, to achieve a desired result. The therapeutically effective amount may vary according to factors such as the disease state, age, sex, and weight of the individual and the ability of a composition described herein to elicit a desired response in the individual. The precise amount of the compositions of the present disclosure to be administered can be determined by a physician with consideration of individual differences in age, weight, tumor size, extent of infection or metastasis, and condition of the patient (subject).

Alternatively, the pharmacologic and/or physiologic effect of administration of one or more compositions described herein to a patient or a subject may be "prophylactic," i.e., the effect completely or partially prevents a disease or symptom thereof.

A "prophylactically effective amount" refers to an amount effective, at dosages and for periods of time necessary, to achieve a desired prophylactic result (e.g., prevention of disease onset).

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

Antioxidants" include, for example, butylated hydroxytoluene (BHT), sodium ascorbate, ascorbic acid, sodium metabisulfite and tocopherol. In certain embodiments, antioxidants enhance chemical stability where required.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel), hydroxypropylmethylcellulose, hydroxyethylcellulose, hydroxypropylcellulose (e.g., Klucel®), ethylcellulose (e.g., Ethocel), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of ibrutinib and an anticancer agent, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, TWEEN® 60 (Polyethylene glycol sorbitan monostearate) or TWEEN® 80 (polyoxyethylene sorbitan monooleate), triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, TWEEN® 80 (polyoxyethylene sorbitan monooleate), vitamin E TPGS, ammonium salts and the like.

Optionally, the formulations comprising the compositions described herein contain a pharmaceutically acceptable salt, typically, e.g., sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are examples of preservatives. Optionally, the formulations of the invention can include a pharmaceutically acceptable surfactant at a concentration of 0.005 to 0.02%.

The compositions described herein can be specially formulated for administration of the antibody or antigen binding fragment thereof to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (7) nasally. Additionally, an antibody or antigen binding fragment thereof, or compositions of the present disclosure can be implanted into a patient or injected using a drug delivery system. See, e.g., Urquhart et al., 24 Ann. Rev. Pharmacol. Toxicol. 199 (1984); *Controlled Release of Pesticides & Pharmaceuticals* (Lewis, ed., Plenum Press, New York, 1981); U.S. Pat. Nos. 3,773,919, 3,270,960.

The compositions disclosed herein, comprising an antibody or antigen binding fragment, described herein, can also contain more than one active compound as necessary for the particular indication being treated, preferably those with complementary activities that do not adversely affect each other. For example, the composition can further comprise a cytotoxic agent, cytokine, growth inhibitory agent and/or an angiogenesis inhibitor such as a VEGFR antagonist. Such molecules are suitably present in combination in amounts that are effective for the purpose intended. The active ingredients of the compositions comprising an antibody or antigen binding fragment thereof described herein can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microparticle, microemulsions, nano-particles and nanocapsules) or in macroemulsions. Such techniques are disclosed in Remington's Pharmaceutical Sciences (16th ed., Osol, ed., 1980). The pharmaceutical composition can be also delivered in a vesicle, in particular a liposome (see Langer 1990 Science 249:1527-1533; Treat et al. (1989) in Liposomes in the Therapy of Infectious Disease and Cancer, Lopez-Berestein and Fidler (eds.), Liss, New York, pp. 353-365; Lopez-Berestein, ibid., pp. 317-327; see generally ibid.). Liposomes include emulsions, foams, micelles, insoluble monolayers, phospholipid dispersions, lamellar layers and the like, and can serve as vehicles to target the M-CSF antibodies to a particular tissue as well as to increase the half life of the composition. A variety of methods are available for preparing liposomes, as described in, e.g., U.S. Pat. Nos. 4,837,028 and 5,019,369, which patents are incorporated herein by reference.

Liposomes containing the antibody are prepared by methods known in the art, such as described in Epstein et al., Proc. Natl. Acad. Sci. USA 82: 3688 (1985); Hwang et al., Proc. Natl Acad. Sci. USA 77: 4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257: 286-288 (1982) via a disulfide interchange reaction. A chemotherapeutic agent (such as Doxorubicin) is optionally contained within the liposome [see, e.g., Gabizon et al., J. National Cancer Inst. 81(19): 1484 (1989)].

In some embodiments, sustained-release preparations can be used. Suitable examples of sustained-release preparations include semipermeable matrices of solid hydrophobic polymers containing an antibody or antigen binding fragment of the present disclosure, in which the matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they can denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thiodisulfide interchange, stabilization can be achieved by modifying sulfhydryl residues, lyophilizing from acidic solutions, controlling moisture content, using appropriate additives, and developing specific polymer matrix compositions. In certain situations, the pharmaceutical composition can be delivered in a controlled release system. In one embodiment, a pump may be used (see Langer, supra; Sefton 1987 CRC Crit. Ref. Biomed. Eng. 14:201). In another embodiment, polymeric materials can be used. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138).

A pharmaceutical composition of the present disclosure can be delivered, e.g., subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded. Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONICT™ pen (Disetronic Medical Systems, Burghdorf, Switzerland), HUMALOG MIX 75/25™ pen, HUMALOGT™ pen, HUMALIN70130™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition include, but certainly are not limited to the SOLOSTAR™ pen (Sanofi-Aventis), the FLEXPEN™ (Novo Nordisk), and the KWIKPEN™ (Eli Lilly).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Compositions of the present disclosure can be in the form of, for example, granules, powders, tablets, capsules, syrup, suppositories, injections, emulsions, elixirs, suspensions or solutions. The amount of the aforesaid antibody contained can be about 5 to about 500 mg per dosage form in a unit dose; especially in the form of injection, it is preferred that the aforesaid antibody is contained in about 5 to about 100 mg and in about 10 to about 250 mg for the other dosage forms.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. In some embodiments, pharmaceutical formulations and medicaments may be prepared as liquid suspensions or aqueous solutions, for example, using a sterile liquid, such as, but not limited to, an oil, water, an alcohol, and combinations of these. In some embodiments, pharmaceutical compositions can be prepared in a lyophilized form. The lyophilized preparations can comprise a cryoprotectant known in the art. The term "cryoprotectants" as used herein generally includes agents, which provide stability to the protein from freezing-induced stresses. Examples of cryoprotectants include polyols such as, for example, mannitol, and include saccharides such as, for example, sucrose, as well as including surfactants such as, for example, polysorbate, poloxamer or polyethylene glycol, and the like. Cryoprotectants also contribute to the tonicity of the formulations. Pharmaceutically suitable surfactants, suspending agents, emulsifying agents, may be added for oral or par-enteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, iso-propyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

For nasal administration, the pharmaceutical formulations and medicaments may be a spray or aerosol containing an appropriate solvent(s) and optionally other compounds such as, but not limited to, stabilizers, antimicrobial agents, antioxidants, pH modifiers, surfactants, bio-availability modifiers and combinations of these. A propellant for an aerosol formulation may include compressed air, nitrogen, carbon dioxide, or a hydrocarbon based low boiling solvent.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

For rectal administration, the pharmaceutical formulations and medicaments may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

The concentration of an antibody or an antigen binding fragment thereof in these compositions can vary widely, i.e., from less than about 10%, usually at least about 25% to as much as 75% or 90% by weight and will be selected primarily by fluid volumes, viscosities, etc., in accordance with the particular mode of administration selected. Actual methods for preparing orally, topically and parenterally administrable compositions will be known or apparent to those skilled in the art and are described in detail in, for example, Remington's Pharmaceutical Science, 19th ed., Mack Publishing Co., Easton, Pa. (1995), which is incorporated herein by reference.

In another embodiment of the invention, an article of manufacture containing materials useful for the treatment of the diseases, disorders or conditions described above is provided, including for treatment of cancer. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the antibody of the invention. The label on or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use. Pharmaceutical compositions and medicaments described herein are useful in treating a cancerous disease.

Diagnostic and Other Uses

Provided herein are methods of using the antibodies for detection, diagnosis and monitoring of a disease, disorder or condition associated with the antigen expression (either increased or decreased relative to a normal sample, and/or inappropriate expression, such as presence of expression in tissues(s) and/or cell(s) that normally lack the epitope expression). Provided herein are methods of determining whether a patient will respond to antibody therapy.

In some embodiments, the method comprises detecting whether the patient has cells that express target antigen using an antibody disclosed herein. In some embodiments, the method of detection comprises contacting the sample with an antibody or antigen binding fragment thereof of the disclosure, and determining whether the level of binding differs from that of a reference or comparison sample (such as a control). In some embodiments, the method may be useful to determine whether the antibodies or polypeptides described herein are an appropriate treatment for the subject.

In some embodiments, the cells or cell/tissue lysate are contacted with an antibody and the binding between the antibody and the cell is determined. When the test cells show binding activity as compared to a reference cell of the same tissue type, it may indicate that the subject would benefit from treatment with an antibody. In some embodiments, the test cells are from human tissues. In some embodiments, the test cells are from human blood.

Various methods known in the art for detecting specific antibody-antigen binding can be used. Exemplary immunoassays which can be conducted include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be attached to the subject antibodies and is selected so as to meet the needs of various uses of the method which are often dictated by the availability of assay equipment and compatible immunoassay procedures.

Appropriate labels include, without limitation, radionuclides (for example 125I, 131I, 35S, 3H, or 32P), enzymes (for example, alkaline phosphatase, horseradish peroxidase, luciferase, or β-glactosidase), fluorescent moieties or proteins (for example, fluorescein, rhodamine, phycoerythrin, GFP, or BFP), or luminescent moieties (for example, Qdot™ nanoparticles supplied by the Quantum Dot Corporation, Palo Alto, Calif.). General techniques to be used in performing the various immunoassays noted above are known to those of ordinary skill in the art.

For purposes of diagnosis, the antibodies or antigen binding fragment thereof can be labeled with a detectable moiety including but not limited to radioisotopes, fluorescent labels, and various enzyme-substrate labels know in the art. Methods of conjugating labels to an antibody are known in the art.

In some embodiments, the antibodies need not be labeled, and the presence thereof can be detected using a second labeled antibody which binds to the first antibody. The antibodies or antigen binding fragment thereof of the present invention may be used as affinity purification agents for a cancer associated antigen or in diagnostic assays for a cancer associated antigen protein, e.g., detecting its expression in specific cells, tissues, or serum. The antibodies or antigen binding fragment thereof, disclosed herein, may also be used for in vivo diagnostic assays. Generally, for these purposes the antibody is labeled with a radionuclide (such as u1In, 99Tc, 14C, 131I, 12sI, 3H, 32p or 3sS) so that the tumor can be localized using immunoscintiography.

The antibodies of the present invention may be employed in any known assay method, such as competitive binding assays, direct and indirect sandwich assays, such as ELISAs, and immunoprecipitation assays. Zola, Monoclonal Antibodies: A Manual of Techniques, pp. 147-158 (CRC Press, Inc. 1987). The antibodies may also be used for immunohistochemistry, to label tumor samples using methods known in the art. As a matter of convenience, the antibody of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Kits

Provided herein are also kits, medicines, compositions, and unit dosage forms for use in any of the methods described herein. Provided herein is a kit comprising a therapeutically effective amount of at least one of the IgA antibody or antigen binding fragment thereof disclosed herein. In some embodiments, the kit further comprises a second therapeutic agent (e.g., a chemotherapeutic agent). In some embodiments, the antibody or antigen binding fragment thereof is an aqueous form or a lyophilized form. The kit further comprises a diluent or a reconstitution solution.

Kits can include one or more containers comprising an antibody (or unit dosage forms and/or articles of manufacture). In some embodiments, a unit dosage is provided wherein the unit dosage contains a predetermined amount of a composition comprising an antibody (e.g., a therapeutically effective amount), with or without one or more additional agents. In some embodiments, such a unit dosage is supplied in single-use prefilled syringe for injection. In some embodiments, the composition comprising the antibody or antigen binding fragment thereof can comprise saline, sucrose, or the like; a buffer, such as phosphate, or the like; and/or be formulated within a stable and effective pH range. In some embodiments, the antibody or antigen binding fragment thereof can be provided as a lyophilized powder that may be reconstituted upon addition of an appropriate liquid, for example, sterile water. In some embodiments, the antibody or antigen binding fragment thereof further comprises one or more substances that inhibit protein aggregation, including, but not limited to, sucrose and arginine. In some embodiments, the antibody or antigen binding fragment thereof further comprises heparin and/or a proteoglycan.

In some embodiments, kits further comprise instructions for use in the treatment of cancer in accordance with any of the methods described herein. The kit may further comprise a description of selection an individual suitable or treatment. Instructions supplied in the kits are typically written instructions on a label or package insert (for example, a paper sheet included in the kit), but machine-readable instructions (for example, instructions carried on a magnetic or optical storage disk) are also acceptable. In some embodiments, the kit further comprises another therapeutic agent (e.g., an anti-cancer antibody or a chemotherapeutic agent)

The kits are in suitable packaging. Suitable packaging includes, but is not limited to, vials, bottles, jars, flexible packaging (for example, sealed Mylar® or plastic bags), and the like. Kits may optionally provide additional components such as buffers and interpretative information. The present application thus also provides articles of manufacture, which include vials (such as sealed vials), bottles, jars, flexible packaging, and the like.

EXAMPLES

Example 1. Engineered Therapeutic IgA Antibodies

A first wild type IgA2 antibody was engineered to incorporate the following amino acid substitutions and deletions: N45.2G, P124R, C86S, N114T, I115L, T116S, deletion of C147, and deletion of Y148, numbering according to IMG® scheme.

A second wild type IgA2 antibody was engineered to mutate the asparagine at position 135 to a glutamine. The N135Q mutation deletes an N-glycosylation site of the IgA2 antibody. The N135Q mutation can be combined with additional mutations of N45.2G, P124R, C86S, N114T, I115L, T116S, deletion of C147, and deletion of Y148, numbering according to IMG® scheme.

A third wild type IgA2 antibody was engineered to delete the entire tail piece, amino acids 131-148 (PTHINVSVVMAEADGTCY) (SEQ ID NO: 9). The N135 N-glycosylation site of the IgA2 antibody. The tail piece deletion can be combined with additional mutations of N45.2G, P124R, C86S, N114T, I115L, and T116S, numbering according to IMGT® scheme.

Table 1 details a comparison of the percent identity, percent positives, gaps, and total length of wild type IgA2 (IgA2_Valerius_hgnc_id=HGNC:5479); an engineered IgA2 antibody comprising the following amino acid substitutions and deletion: N45.2G, P124R, C86S, Ni 14T, I1115L, T1116S, deletion of C147, and deletion of Y48 (IgA2-2.0) (numbering according to IMGT® scheme); an engineered IgA2 antibody described herein comprising a N135Q mutation (IgA3.0 glycosylation mutated hgnc id=HGNC:5470); an engineered IgA2 antibody described herein comprising a deletion of the tail piece amino acids 131-148 (IgA2-3.0_tailpiece_del); IgA2 (tr|A0A0G2JMB2|A0A0G2JMB2 HUMAN); IgA2 (sp|P01877|IGHA2_HUMAN); and IgA2 (tr|A0A286YEY5|A0A286YEY5 HUMAN).

TABLE 1

Comparison of Engineered Antibody Amino Acid Sequences

| Name | Alternative name | Identities (%) | Positives (%) | Gaps | Total length |
|---|---|---|---|---|---|
| IgA2_Valerius_hgnc_id = HGNC:5479: | | 100 | 100 | 0 | 340 |
| IgA2 – 2.0 | | 332/338 (98%) | 334/338 (98%) | 0 | 338 |
| IgA2 – 3.0 glycosylation_mutated_ hgnc_id = HGNC:5479 | IgA3.0+ | 331/338 (98%) | 333/338 (98%) | 0 | 338 |
| IgA2 – 3.0_tailpiece_del_ | IgA3.0min | 316/322 (98%) | 318/322 (98%) | 0 | 322 |
| IgA4.0_NG | | 315/322 (98%) | 317/322 (98%) | 0 | 322 |
| IgA4.0_NQ | | 315/322 (98%) | 317/322 (98%) | 0 | 322 |
| IgA4.0_NT | | 315/322 (98%) | 317/322 (98%) | 0 | 322 |
| IgA4.0_NLI-TIS | | 313/322 (97%) | 317/322 (98%) | 0 | 322 |
| tr|A0A0G2JMB2|A0A0G 2JMB2_HUMAN | | 100 | 100 | 0 | 340 |
| sp|P01877|IGHA2_HUMAN | | 333/340 (98%) | 337/340 (99%) | 0 | 340 |
| tr|A0A286YEY5|A0A286 YEY5__HUMAN | | 316/321 (98%) | 319/321 (99%) | 0 | 391 |

Example 2 Engineered IgA Variants

Protein glycosylation plays a major role in function and serum half-life of an antibody in circulation. Incomplete glycosylation of IgA leads to clearance by dedicated receptors. The main receptor for the internalization of incompletely glycosylated proteins is the asialoglycoprotein receptor (ASGRP1). This receptor recognizes terminal galactose on N-glycosylated proteins, and is an important mediator of IgA clearance from serum. The IgA2(m1) antibody has a complicated N-linked glycosylation pattern formed by a total of 4 N-linked glycosylation sites (CH1-N45.2, CH2-N15.2, CH2-N114, CH3_CHS-N135). To enhance half-life of IgA2(m1) critical N-glycosylation motifs have been engineered to only contain either a single N-glycosylation motif or none at all. A single N-glycosylation site resulted in a more complete glycosylation profile increasing half-life and subsequently less antibody clearance. Yet, a fully aglycosylated IgA will not be subjected to glycosylation-dependent clearance at all, considerably augmenting half-life. Moreover, this aglycosylated variant will allow production in lower organisms, significantly increasing yields and reducing manufacturing costs. Hence, single- or non-glycosylated antibodies will simplify biopharmaceutical manufacturing and be an ideal candidate for therapeutic purposes.

Design of Engineered IgA Variants

The genetic sequence of the IgA2(m1) heavy chain was the backbone for IgA engineering and N-linked glycosylation motifs were silenced, and stabilizing mutations were introduced (Table 2; FIGS. 4A-4D). This resulted in a series of molecules: IgA3.0–(min), IgA3.0+(plus) and IgA4.0.

IgA3.0+Variants

The IgA3.0+ molecule was modified to allow for covalent binding between the heavy- and light-chain by the CH1-P124R mutation. Two Cysteine residues were modified or removed (CH2-C86S; CH3_CHS-C147del_Y148del) to prevent the formation of cysteine bridges with serum proteins, preventing dimeric aggregates and/or complex formation. Furthermore, three N-linked glycosylation motifs were silenced, by substitution of critical amino acids in these motifs (CH1-N45.2G; CH2-N114T; CH3_CHS-N135Q).

IgA3.0– or IgA3.0min Variants

The IgA3.0min molecule contains the same mutations as the CH1 and CH2 in IgA3.0+, but in contrast to IgA3.0+, in IgA3.0min almost the entire tailpiece was deleted (CH3_CHS-P131-Y148del).

IgA4.0 Variant or Aglycosylated Variant

The IgA4.0 molecules were created by silencing the only remaining N-linked glycosylation motif (CH2-N15.2) by 4 separate amino acid substitutions, thereby creating 4 fully aglycosylated IgA2 molecules.

Table 2 lists the mutations in engineered IgA variants; IgA3.0+, IgA3.0min, and IgA4.0 relative to the wild type (WT) IgA2(m1)

| Domain | Modification | Description | IgA2 (m1) | IgA 3.0+ | IgA3.0 min | IgA 4.0 |
|---|---|---|---|---|---|---|
| CH1 | N45.2G | Remove N-linked glycosylation motif | X | ✓ | ✓ | ✓ |
| | P124R | Covalent heavy-/light-chain interaction | X | ✓ | ✓ | ✓ |
| CH2 | N15.2G | Remove N-linked glycosylation motif | X | X | X | ✓ |
| | N15.2Q | Remove N-linked glycosylation motif | X | X | X | ✓ |
| | N15.2T | Remove N-linked glycosylation motif | X | X | X | ✓ |
| | L15.3I | Remove N-linked glycosylation motif | | | | |
| | T16S | Remove N-linked glycosylation motif | | | | |
| | C86S | Prevent cysteine bridging | X | ✓ | ✓ | ✓ |
| | N114T | Remove N-linked glycosylation motif | X | ✓ | ✓ | ✓ |
| | I115L | Remove N-linked glycosylation motif | | | | |
| | T116S | Remove N-linked glycosylation motif | | | | |
| CH3-CHS | N135Q | Remove N-linked glycosylation motif | X | ✓ | X | X |
| | C147del | Deletion preventing cysteine bridging | X | ✓ | X | X |
| | Y148del | Deletion | X | ✓ | X | X |
| | P131-Y148del | Deletion tailpiece | X | X | ✓ | ✓ |

Example 3

Methods

Cloning IgA3.0/IgA4.0

To clone the IgA3.0+ and IgA3.0min molecules, synthetic DNA covering the entire constant region of IgA3.0 (CH1-CH2-CH3-CHS) was ordered (Baseclear, Leiden NL) and cloned in the pEE14.4 vector, replacing the IgA2(m1) sequence. In some cases of IgA3.0min molecules, gBlocks® (IDT) covering both the variable and constant regions of IgA3.0min (VH-CH1-CH2-CH3-CHS) were cloned into the pcDNA3.4 vector. Based on the IgA3.0min vector, IgA4.0 molecules were cloned by replacing the CH1-CH2-CH3-CHS region of IgA3.0min in the pcDNA3.4 vector with gBlocks® (IDT) containing the proper mutations for IgA4.0.

Production

For the production of the IgA3.0+ and IgA3.0min HEK293F cells (Thermo Fisher) were used according to the manufacturer's instructions. For DNA complexing, separate vectors for IgA3.0+ or IgA3.0min heavy chain (HC), along with vectors for kappa light chain (LC) and pAdvantage™ (pAdv; Promega) were mixed in optimal HC:LC:pAdv ratios and complexed with 293fectin prior to transfection.

For the production of the IgA3.0min and IgA4.0 CHO-S cells (ExpiCHO-S™ cells (Thermo Fisher)) were used according to manufacturer's instructions. For DNA complexing, separate vectors for IgA3.0+ or IgA3.0min or IgA4.0 heavy chain, along with vectors for kappa light chain and pAdvantage™ (Promega) were mixed in optimal HC:LC:pAdv ratios and complexed with Expifectamine prior to transfection.

Purification

The procedure for the purification of IgA was identical for all IgA variants, and is performed by capturing kappa light chains from clarified and filtered cell culture supernatant using FPCL with a HiTrap® KappaSelect column (GE Healthcare), followed by a separation by a Size Exclusion Chromatography procedure using a HiPrep™ 26/60 Sephacryl® S-300 HR column.

Binding Assays

To determine binding of the engineered antibodies, both the binding of the variable portion and the Fc portion was assessed.

Clarified supernatants of IgA3.0min-Obinituzumab (IgA3.0min-Obi) or IgA3.0+-Obinituzumab (IgA3.0+-Obi) from HEK293F productions were tested on CD20-expressing Daudi cells in a FACS binding experiment. Clarified supernatants of Obinituzumab-IgA4.0 from CHO-S (ExpiCHO-S™) productions were used undiluted in a FACS binding experiment.

In short, supernatants were incubated with Daudi cells for 1 hour on ice. After washing, cells were incubated with PE-labeled anti-IgA antibody (Southern Biotech) for 45 minutes. After washing cells were fixed with PFA and measured on a Canto II (BD). CD20 recognizing control antibodies were added at concentration of 5-10 ug/mL.

To determine whether the antibody Fc-region is able to bind to FcαR, IgA2(m1) and IgA3.0min-Obi (25 µg/mL) were coated overnight in an ELISA plate in carbonate buffer pH9.0. Plates were blocked with 1% BSA after which CD89-expressing Calcein-labeled healthy donor polymorphonuclear neutrophils (PMN) were allowed to bind the plate for 45 minutes at 37° C. Subsequently, after every two washing steps, binding was determined by comparing the remaining signal to the input signal (no wash). An additional control to determine if coating concentrations were equal, was performed by staining an ELISA plate overnight with serially diluted IgA2(m1) and IgA3.0min antibody after which their presence was detected with anti-hIgA-HRP (Southern Biotech).

ADCC

Target cells were loaded with 51Cr (Perkin-Elmer), washed twice and incubated with serially diluted IgA antibodies and healthy donor PMN's for 4 hours. Chromium release was measured in the supernatant and specific lysis was calculated using following the formula: ((experimental cpm−basal cpm)/(maximal cpm−basal cpm))×100, with maximal lysis determined by incubating labelled cells with 1.25% TRITON™ (2-[4-(2,4,4-trimethylpentan-2-yl)phenoxy]ethanol) and minimal lysis in the absence of antibodies and effector cells. In the case of IgA4.0, undiluted supernatants of CHO-S (ExpiCHO-S™) productions were assessed.

Thermostability

Thermal stability was analyzed in thermal shift assay using Sypro® Orange (Life Technologies). A total of 12.5 µg of antibody diluted in 25 µL PBS and 3×SYPRO® Orange (final concentration) was transferred to a white 96-well thin-wall PCR plate (Roche) and sealed with Optical-Quality Sealing Tape (Roche). Plates were heated in a ViiA™ 7 (Roche) from 37° C. to 99° C. with a heat-rate of 1.6° C./second and 1 minute incubation at each degree. Fluorescence was recorded simultaneously using 490 and 575 nm as excitation and emission wavelengths, respectively.

To assess functionality of destabilized IgA molecules, antibodies in PBS were incubated at different temperatures (4° C., 23° C.-95° C. in incremental steps of 12° C.) for 5 minutes in a thermal cycler. After incubation complete medium was added and antibodies were used directly in an ADCC at a final concentration of 10 µg/mL.

Glycosylation Analysis

PNGase F treatments were performed according to manufacturer's instructions (NEB). In short, antibodies were first denatured for 10 minutes at 100° C., and subsequently NP-40, Glycobuffer and PNGase F enzyme were added and incubated for 1 hour at 37° C. Samples were taken in Laemmli buffer with 20 mM DTT and run on a 10% Mini-Protean® TGX™ SDS-PAGE (Bio-Rad). Gels were stained with InstantBlue (Expedeon) for 10 minutes, and rinsed with water.

Glycan identification and quantification was determined by mass spectrometry. For the Her2-IgA2(m1) a reflectron positive mode MALDI-TOF-MS analysis of the released N-glycosylation of IgA2 antibodies after linkage-specific sialic acid derivatization was performed as described before (Meyer, Nederend et al. 2015). For the IgA3.0min-Her2, IgA3.0min-Obi, and IgA4.0-Obi variants an LC/MS2 approach has been taken.

Antibodies were denatured, reduced, alkylated and proteolytically digested with GluC (Roche (Indianapolis, IN)) and trypsin (Sigma-Aldrich (Steinheim, Germany)). For this, 10 µg of antibody was brought to 100 mM Tris-HCl (pH 8.5) (Trizma® hydrochloride, Tris(hydroxymethyl)aminomethane hydrochloride), 5 mM Tris(2-carboxyethyl)-phosphine (TCEP, Sigma-Aldrich (Steinheim, Germany)), 30 mM chloroacetamide (CAA, Sigma-Aldrich (Steinheim, Germany)) and 1% sodium deoxychelate (SDC, Sigma-Aldrich (Steinheim, Germany)), water (MQ) (generated from a Q-POD® or Q-Gard® 1 system (Millipore), operated at ≥18.2 MΩ). This mixture was incubated for 4 h at 37° C. with GluC with an enzyme:protein ratio of 1:75 w/w, followed by an overnight incubation at 37° C. with trypsin (1:100 w/w). Hereafter, the SDC was precipitated by bringing the samples to 0.5% trifluoric acid (TFA, Sigma-Aldrich (Steinheim, Germany)) and centrifugation at maximum speed for 10 min. The supernatant was collected for solid-phase extraction (SPE).

For SPE, the use of an Oasis pElution HLB 96-well plate (Waters, Wexford, Ireland) positioned on a vacuum manifold was made. The plate was conditioned with acetonitrile (ACN, BioSolve Valkenswaard, The Netherlands) equilibrated with 0.5% TFA, loaded with the supernatant, washed with 0.5% TFA, and peptides were finally eluted with 50% ACN 0.5% TFA. The recovered eluate was dried by means of rotary evaporation, and reconstituted in 2% formic acid for subsequent LC-MS2 analysis.

For each of the digested and desalted samples, 100 ng was analyzed by use of an Agilent 1290 Infinity HPLC system (Agilent Technologies, Waldbronn, Germany), equipped with flow-splitter to achieve nanoflow, hyphenated to an Orbitrap Fusion™ Tribrid™ mass spectrometer (Thermo Fisher Scientific, Bremen, Germany). The samples were separated on a 2 cm trap column (100 µm inner diameter, packed with 3 µm ReproSil-Pur C18-AQ; Dr. Maisch GmbH, Ammerbuch-Entringen, German) coupled to a 50 cm analytical column (50 µm inner diameter, packed with 2.7 µm Poroshell 120 EC-C18; Agilent Technologies, Amstelveen, The Netherlands). Buffer A consisted of 0.1% formic acid, buffer B of 0.1% formic acid in 80% ACN. The LC gradient was as follows: 0-5 min: 100% A (the rest being B), 5-53 min: 87% A to 60% A, 53-58 min 0% A, 58-65 min 100% A.

Mass spectrometry was performed in positive ion mode, with electrospray ionization from a coated fused silica emitter at 2 kV spray voltage. Each sample was measured in triplicate, using the same MS1 acquisition methods, but different MS2 methods. For the MS1 scans, the mass range was set from m/z 350 to 2000 with a resolution of 60,000, an AGC target of 400,000 with maximum injection time of 50 ms. Each of the three MS2 methods initiated HCD fragmentation (30% normalized collision energy; NCE) on the highest charge state, lowest m/z signals within a 3 s cycle time, using an exclusion time of 30 s. MS2 by HCD was recorded with a resolution of 30,000 from m/z 120 to 4000, with an AGC target of 50,000 and a maximum injection time of 50 ms. For MS2 method 1, only HCD fragmentation was performed. For MS2 method 2, the detection of at least 3 oxonium ions (Hex: 127.0390, 145.0495, 163.0601; HexNAc: 138.0550, 168.0655, 186.0761, 204.0867; Phospho-Hex: 243.0264; NeuAc: 274.0921, 292.1027; Complex: 366.1395, 405.0793, 407.1660, 512.1974, 657.2349) within the HCD spectrum triggered stepping-HCD on the same precursor signal, combining the HCD fragments with NCEs of 10%, 25% and 40%. Stepping-HCD was recorded with a resolution of 30,000 from m/z 120 to 4000, with an AGC target of 200,000 and a maximum injection time of 250 ms For MS2 method 3, detection of the oxonium ions triggered EThcD (30% supplemental activation), which was recorded with a resolution of 30,000 from m/z 120 to 4000, with an AGC target of 200,000 and a maximum injection time of 250 ms.

Bottom-up data was interpreted with Byonic™ v3.3.11 (Protein Metrics Inc.). Raw data was searched with C-terminal cleavage sites at Arg and Lys (trypsin), and Glu and Asp (GluC). 3 missed cleavages were allowed, using a precursor mass tolerance of 10 ppm and fragment mass tolerance of 20 ppm. Cys carbamidomethylation was included as fixed modification and Met oxidation as variable modification. For N-glycosylation 279 compositions were included following the pathways for N-glycan biosynthesis.

Skyline (v3.7.0.11317) was used to perform relative quantification. For this, each of the peptides found glycosylated by Byonic™ were integrated, which included all major miscleavages and oxidation variants. For each of these, the aforementioned 279 glycan compositions were integrated from each LC-MS2 run. Integrations obtained as such were subsequently curated to adhere to the following criteria: 1):5 5 ppm error to the theoretical mass, 2) having an idotp of ≥0.85 with the theoretical isotopic pattern, 3) eluting within ±2 min of the mean retention time for that peptide, 4) having no apparent overlapping isotopic patterns. The resulting list of glycopeptides was in agreement with the annotation by Byonic™, and further used for relative quantification. For each of the curated peptide glycoforms, the MS1 areas were integrated and peptides informing on the same N-glycosylation site combined. As alternative way of quantification, the number of peptide spectrum matches (PSMs) was counted for each glycopeptide combination that informed on a given glycosylation site.

For visualization of glycan species, the recommendations of the Consortium for Functional Glycomics were followed. Glycan cartoons were constructed using GlycoWorkbench (v2.1 build 146). For native MS analysis antibodies were buffer exchanged to 150 mM ammonium acetate pH 7.5, using a Vivaspin 500 30 kDa molecular weight cut-off filter (Sartorius Stedim Biotech, Germany) by 10×15 min centrifugation at 15.000×g. Following buffer exchange, the antibodies were adjusted to an approximate concentration of 3 µM with 150 mM ammonium acetate pH 7.5.

Native MS was performed on a modified Exactive™ Plus Orbitrap™ instrument with extended mass range (EMR) (Thermo Fisher Scientific, Bremen), calibrated using a 25 mg/mL CsI solution. Voltage settings of the transport multipoles and ion lenses were manually optimized to provide good transmission at the required m/z range. Electrospray ionization was achieved from a gold-coated glass capillary, employing a capillary voltage of 1.2 kV, while the MS was operated with a source fragmentation of 80 V, a source temperature of 250° C., a collision energy of 80 V, and a resolution of 35000 at m/z 200. Desolvation of molecules was further achieved by addition of nitrogen to the HCD cell to reach a gas pressure of approximately 3.7×10-10 bar. Masses were calculated from the charge state distributions by fitting the charges to the lowest standard deviation on the mass (typically resulting in mass errors lower than 1 Da).

Pharmacokinetic/Pharmacodynamic Studies

For pharmacokinetics/pharmacodynamics of IgA BALB/cByJ mice (Jackson Laboratory) were injected i.v. with 100 µg (1 mg/mL) of antibody. Blood was collected at the indicated time points, centrifuged to separate and collect serum. ELISAs were performed on diluted serum.

Biodistribution

Antibodies were conjugated to a chelator prior to radiolabeling. Antibody was spun through a 30 kDa centrifugal filter at 12,000 g for 8 min. Subsequently, 500 µL of 0.1 M sodium bicarbonate (pH 8.2) was added to the centrifugal filter and spun again at 12,000 g for 8 min. The centrifugal filter was inverted into a new tube and centrifuged at 1,000 g for 2 min, yielding about 40 µL to which 60 µL of sodium bicarbonate buffer was added, resulting in 100 µL. A 20-fold molar excess of p-SCN-Bn-DTPA (2 mg/mL in dry DMSO (used 1 mg in 500 ul)) was added and vortexed for 30 sec, and incubated 1 hour at 37° C. Next, the BnDTPA-IgG1-dinutximab or BnDTPA-IgA3.0min-dinutximab conjugate was run through a G50 column, eluting with 0.5 M MES buffer (pH 5.4) in 100 μL fractions for 12 fractions. The 5 most concentrated fractions were pooled and spun through a 30 kDa centrifugal filter at 12,000 g for 8 mins. A volume of 500 μL 0.5 M MES buffer (pH 5.4) was added to the centrifugal filter and centrifuged for further 8 min at 12,300 g. The centrifugal filter was inverted into a new microcentrifuge tube and centrifuged at 1,000 g for 2 min. Protein concentration was measured by Nanodrop™.

To radiolabel the antibody 150 uL Indium solution (55.5 MBq) was added to 150 ug antibody in MES buffer in a microcentrifuge tube and incubated for 45 mins at room temperature. The reaction mixture was run through a G50 column, and eluted with PBS (pH 7.4). Sample is collected in a microcentrifuge tube in 100 μL fractions (3 drops) for 16 fractions, activity is checked and highest fractions were combined.

To check purity of the radiolabeled antibody by an iTLC strip, a total of 2 μL of the reaction mixture was pipetted onto the iTLC and dried for 2 minutes. A volume of 0.1 M citrate buffer was added to measurement cylinder covering the bottom. The iTLC strip was placed into measurement cylinder and allowed to draw the citrate buffer up until it is about 1 cm from the top. The strip was removed and scanned using radio-TLC.

In Vivo i.p Model

Mice were maintained in the animal facility of the University of Utrecht. Experiments were conducted using female hCD89 Tg or hCD89 NTg mice backcrossed on a CB17/lcr-Prkdcscid/lcrlcocrl (Charles river) background. Mice were housed in groups of 5 under a 12:12 light dark cycle, with food and water available ad libitum. All experiments were performed in accordance with international guidelines and approved by the national Central Authority for Scientific Procedures on Animals (CCD) and the local experimental animal welfare body.

An amount of 1×10e5 A431-Luc2-Her2 cells was injected i.p. on day 0 followed by a s.c. injection with 20 ug pegG-CSF (Amgen) on day 6. Bioluminescence (BLI) signal was measured on a U—OI system (MiLabs) 10 minutes after i.p. injection of 2.5 mg Luciferin (Promega) in PBS. On day 6 mice were randomized into the different treatment groups. Treatment started on day 7 with daily i.p. injections of 10 μg IgA3.0min-Her2 for 10 days. BLI signal was measured on the indicated time points.

Example 4

Results

Figure 5B:
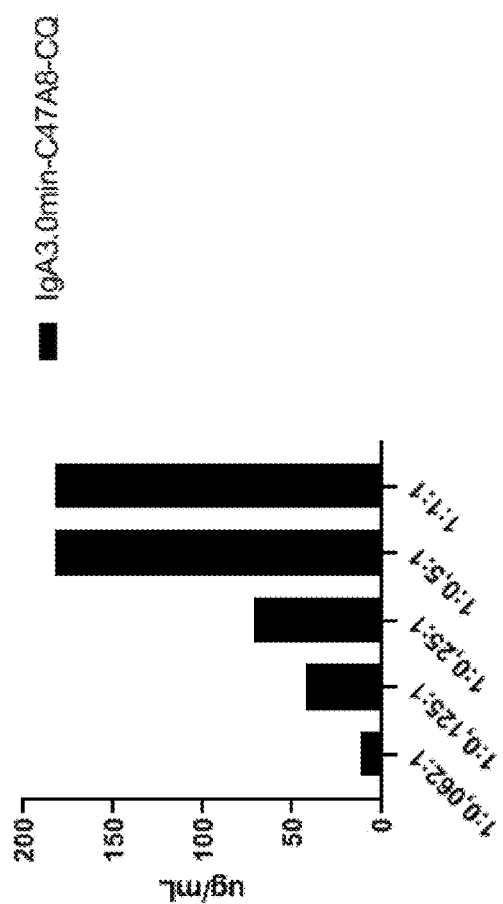
FIGS. 5A and 5B demonstrate yield of IgA3.0min antibody variants.
Figure 5A:
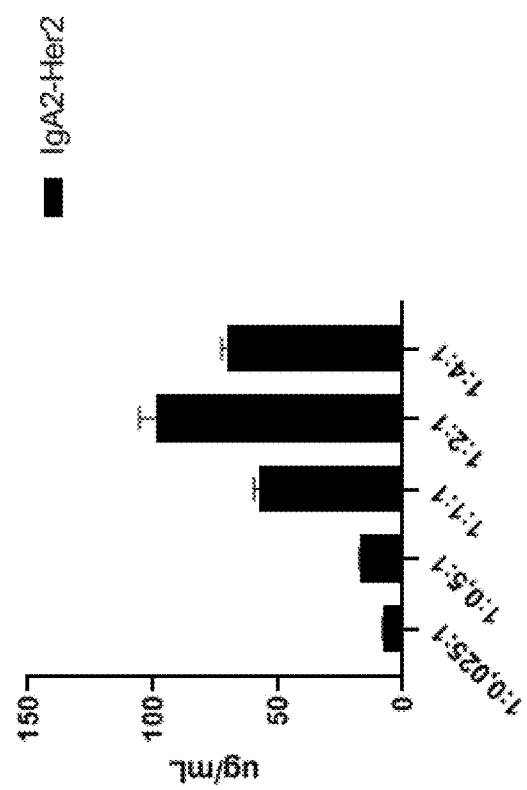

Plasmids encoding IgA2, IgA3.0min, IgA3.0+, and IgA4.0 molecules against various targets were transfected in HEK293F and/or CHO-S cells (ExpiCHO-S™ cells). The IgA3.0min-C47A8-CQ antibody was expressed to similar or better levels as wild type IgA2(m1)-Her2 as shown in FIGS. 5A-5B, where different HC:LC:pAdv ratios have been tested in HEK293F cells. This also holds true for IgA3.0+.

Figure 6C:
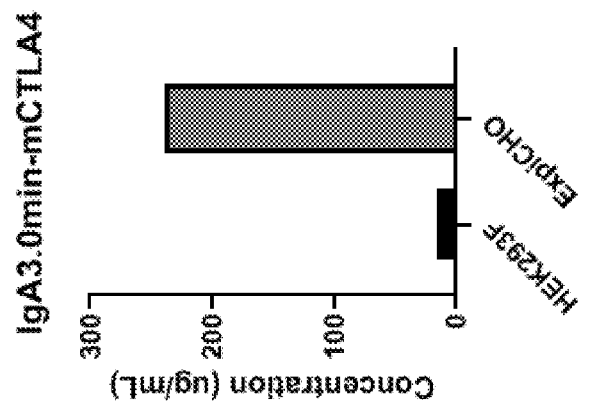
FIGS. 6A-6C show comparison of antibody yield of IgA3.0min antibody variants in HEK293F cells versus CHO-S cells (ExpiCHO-S™ cells) as determined in ELISA.
Figure 6B:
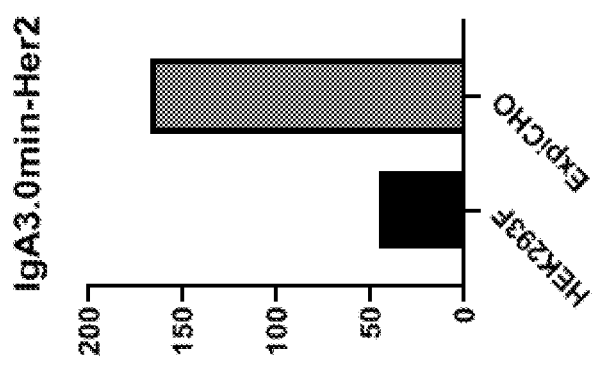
Figure 6A:
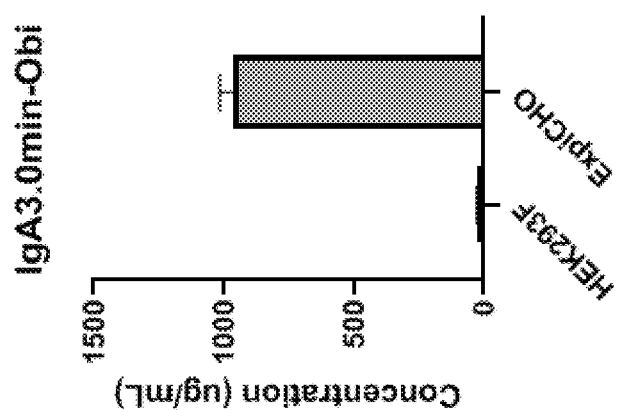
Figure 7A:
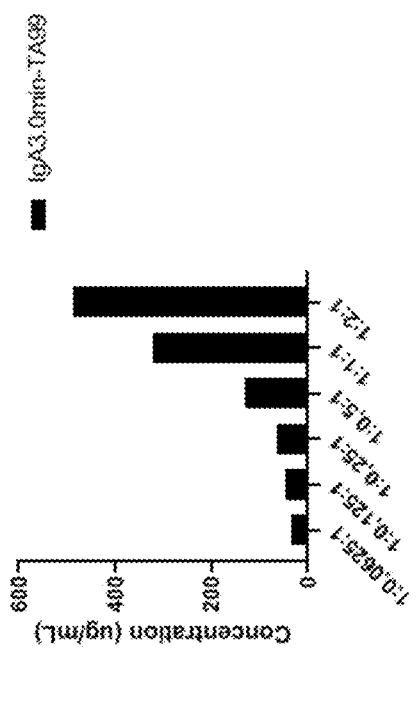
FIGS. 7A-7D demonstrate concentration of IgA3.0min antibody variants in CHO-S cells (ExpiCHO-S™ cells) transfected with different heavy chain (HC):light chain (LC):pAdvantage® ratios.
Figure 7B:
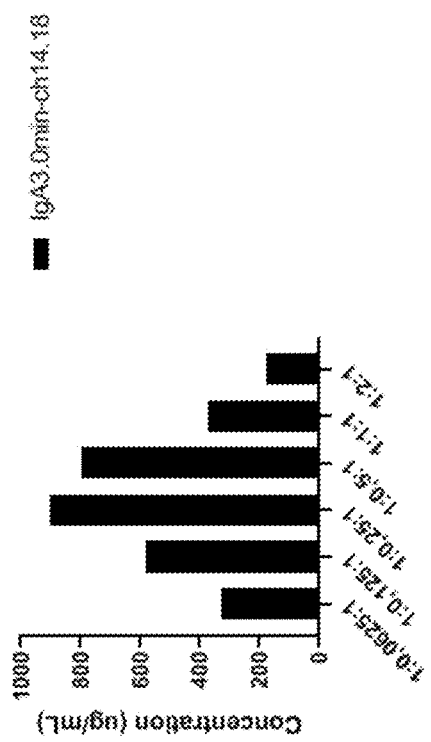
Figure 7C:
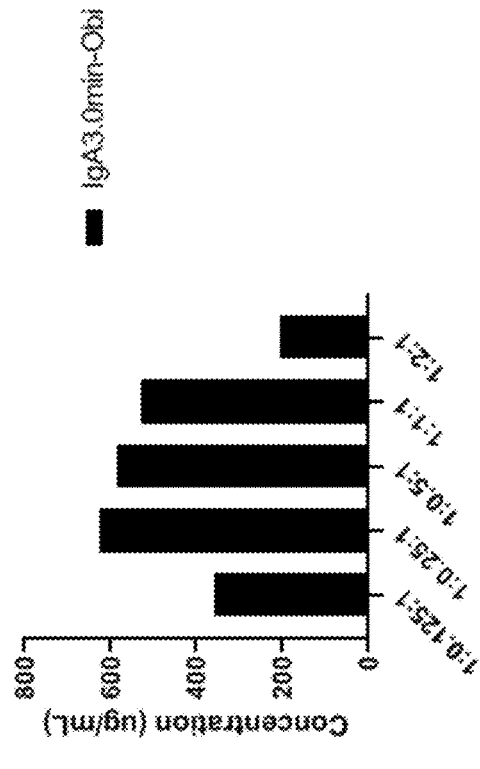
Figure 7D:
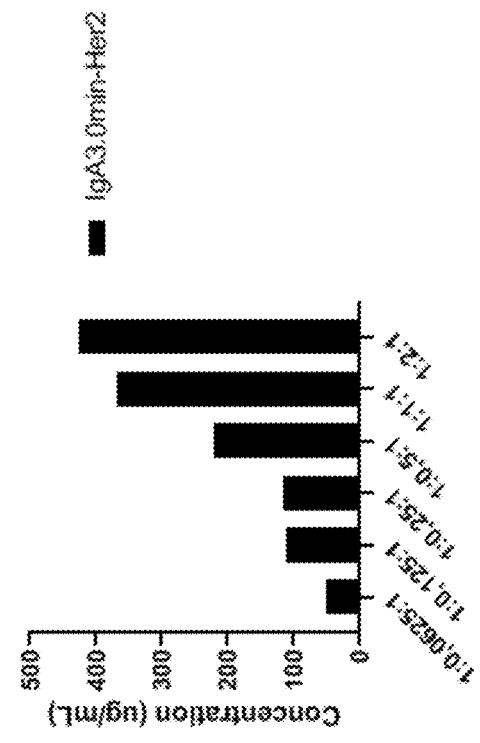
Figures 8A, 8B:
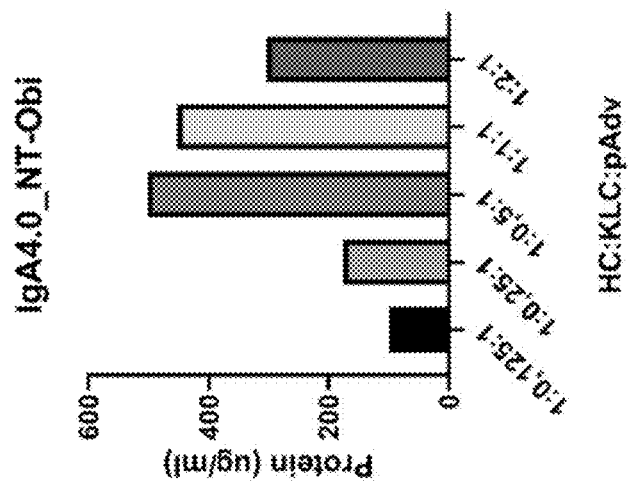
FIGS. 8A-8D show production rate of IgA4.0 antibody variants in CHO-S cells (ExpiCHO-S™ cells) transfected with different heavy chain (HC):light chain (LC):pAdvantage™ ratios.
Figure 8D:
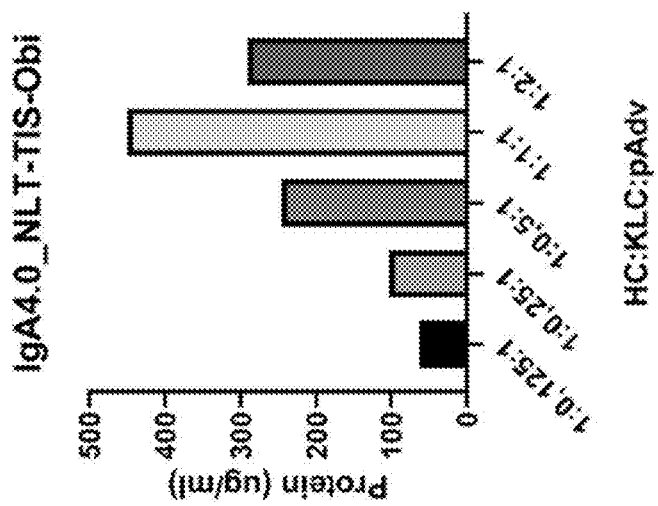
Figure 8C:
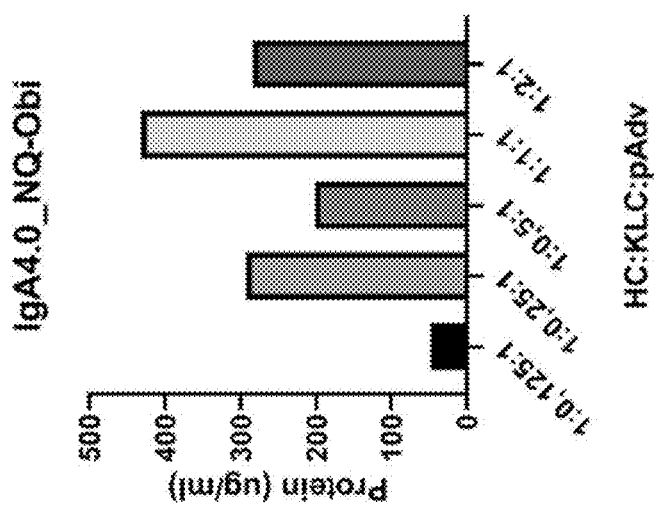

As a comparison between production cell lines, IgA3.0-molecules (e.g, IgA3.0min-Obi, IgA3.0min-Her2, IgA3.0min-mCTLA4, targeting three different antigens CD20, Her2, and mCTLA4 respectively) have been produced in both HEK293F and CHO-S (cells ExpiCHO-S™ cells) FIGS. 6A-6C. Expression levels of IgA3.0min molecules were higher in CHO-S cells (ExpiCHO-S™ cells), where they reached almost 1 g/L as determined by sandwich ELISA on supernatants. In addition, different IgA3.0min molecules (IgA3.0min-ch14.18, IgA3.0min-TA99, IgA3.0min-Her2, IgA3.0min-Obi, targeting various antigens GD2, gp75, Her2, CD20 respectively have been produced successfully in CHO-S cells (ExpiCHO-S™ cells) (FIGS. 7A-7D). These data indicate that engineered IgA3.0min and IgA3.0+ variants were expressed properly, independent of production system choice.

Also, all the four aglycosylated IgA4.0 variants expressed in CHO-S cells (ExpiCHO-S™ cells) showed similar expression levels as IgA3.0min antibodies (FIGS. 8A-8D). This indicates that none of the introduced mutations prevent expression of engineered IgA4.0 variants, and that a fully aglycosylated IgA antibody was properly expressed.

Figure 9A:
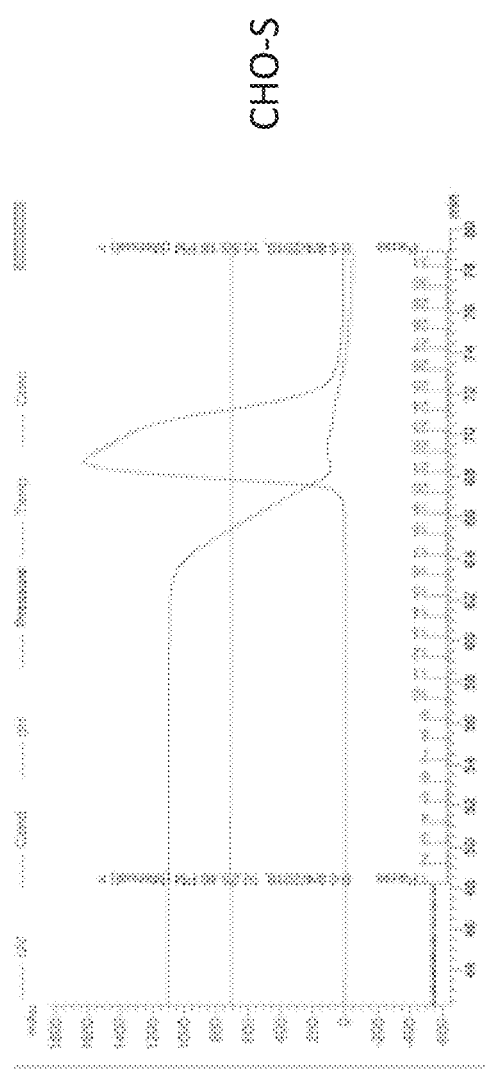
FIG. 9A-9B show elution profiles of IgA3.0min-Obi using a KappaSelect column (GE Healthcare) from supernatants from the producing CHO-S cell lines (ExpiCHO-S™ cell lines) (FIG. 9A) and HEK293F (FIG. 9B).
Figure 9B:
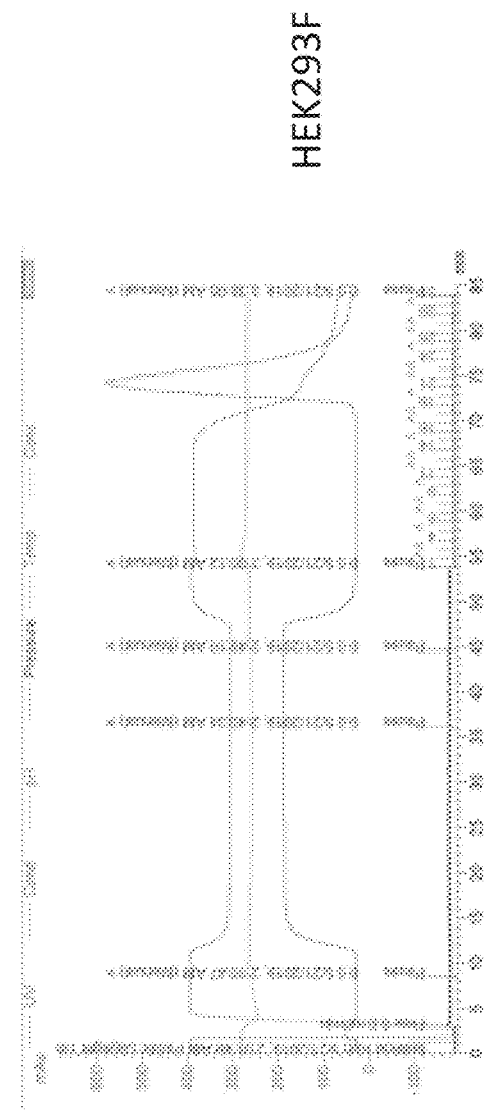
Figure 9C:
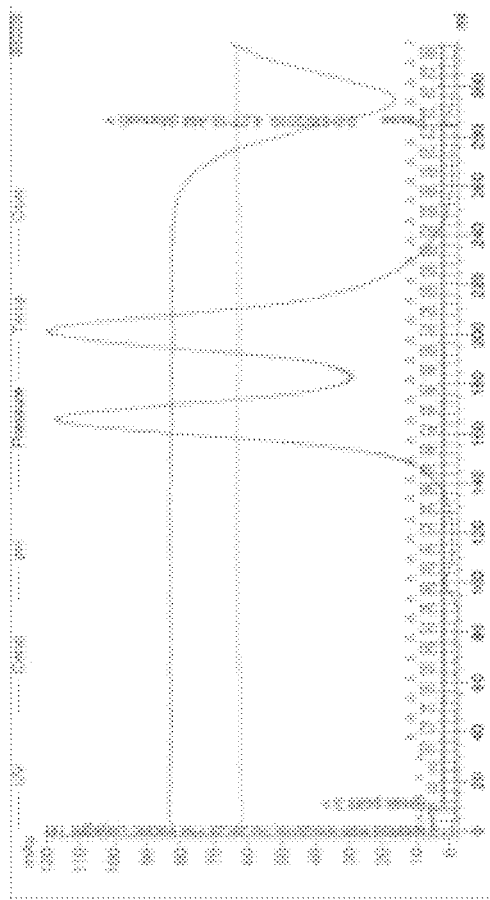
FIGS. 9C-9D show SEC separation profiles of IgA3.0min-Obi from the producing CHO-S cell lines (ExpiCHO-S™ cell lines ((FIG. 9C) and HEK293F (FIG. 9D), no aggregates are observed upon SEC separation.
Figure 9D:
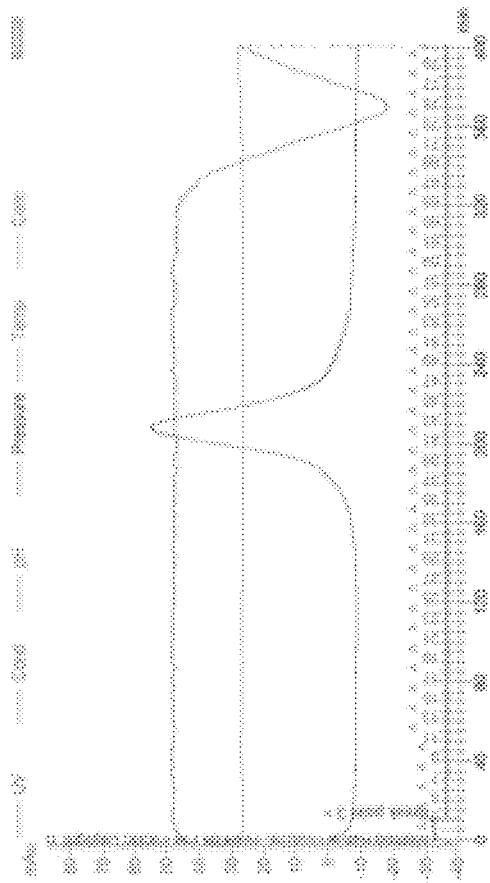
Figure 10A:
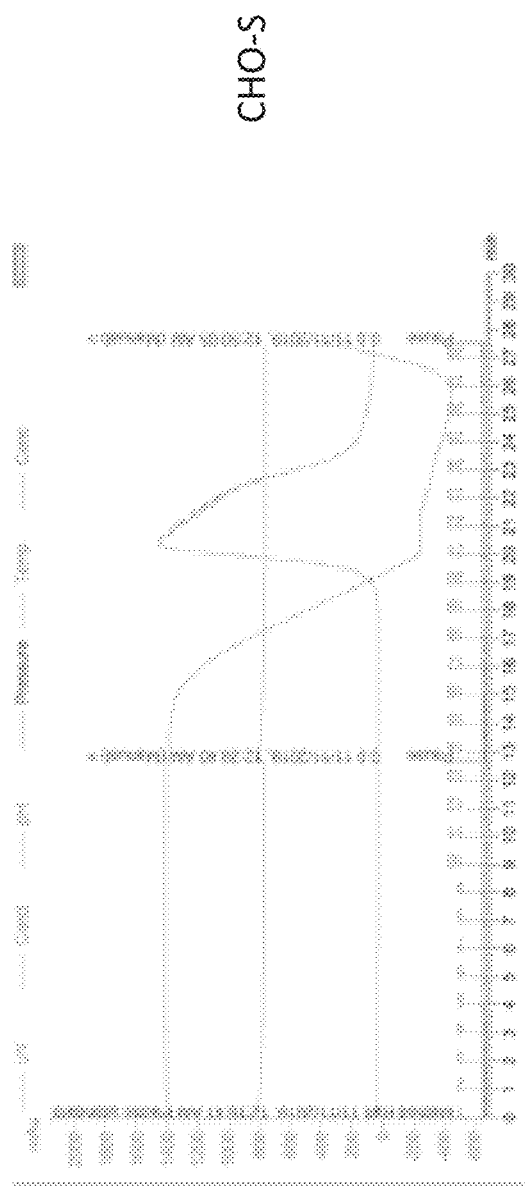
FIGS. 10A-10B show elution profiles of IgA3.0min-Her2 using a KappaSelect column (GE Healthcare) from supernatants from the producing CHO-S cell lines (ExpiCHO-S™ cell lines) (FIG. 10A) and HEK293F (FIG. 10B).
Figure 10B:
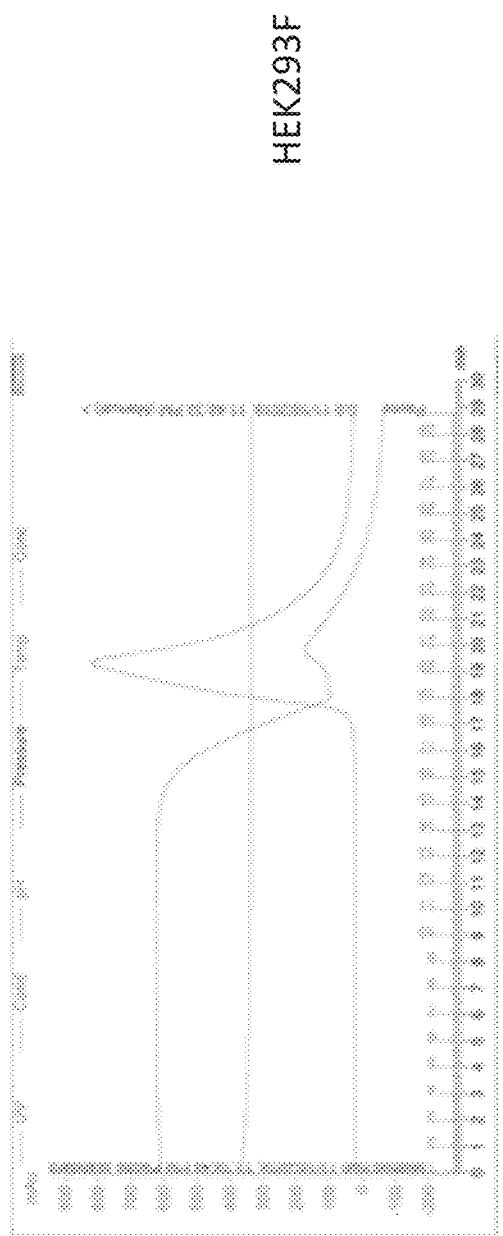
Figure 10C:
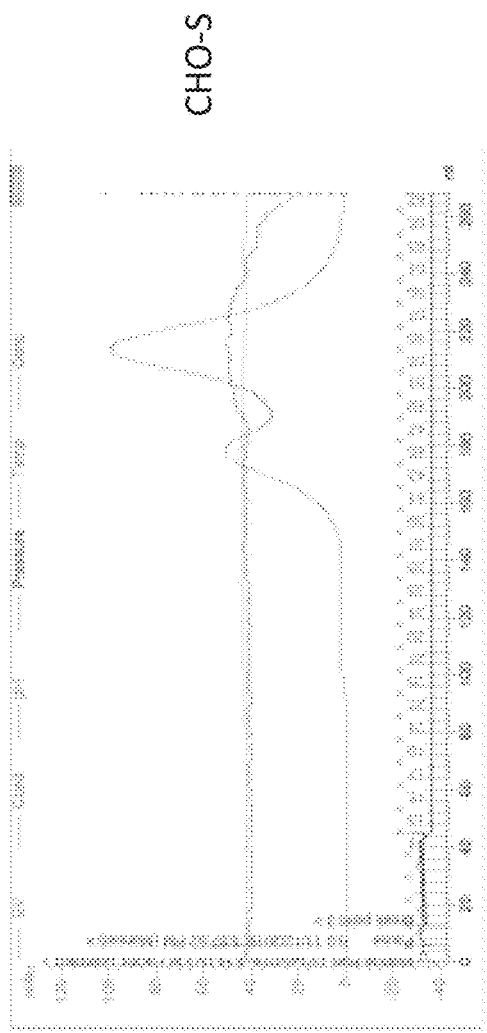
FIGS. 10C-10D show SEC elution profiles of IgA3.0min-Her2 from the producing CHO-S cell lines (ExpiCHO-S™ cell lines) (FIG. 10C) and HEK293F (FIG. 10D), no aggregates are observed upon SEC.
Figure 10D:
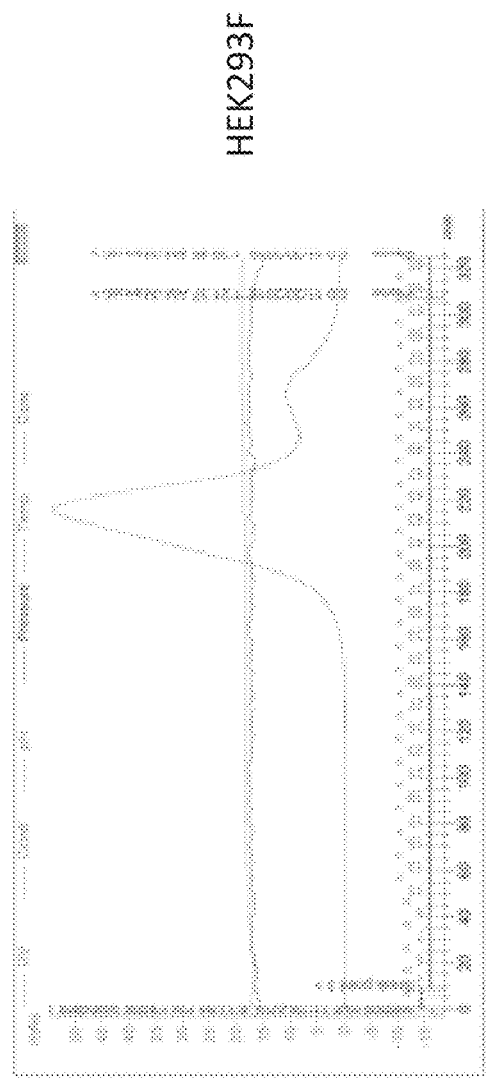
Figure 11A:
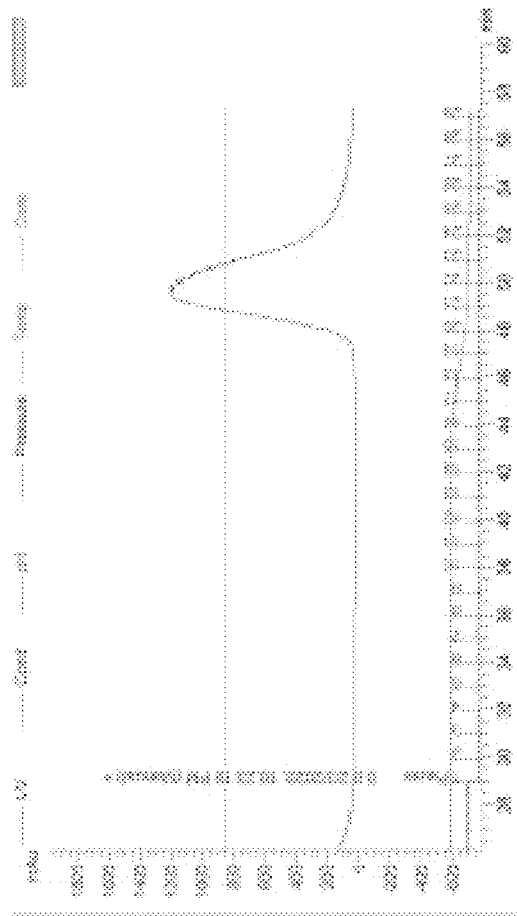
FIG. 11A shows typical elution profiles of IgA4.0-Obi using a KappaSelect column (GE Healthcare) from supernatants from the producing CHO-S cell line (ExpiCHO-S™ cell line).
Figure 11B:
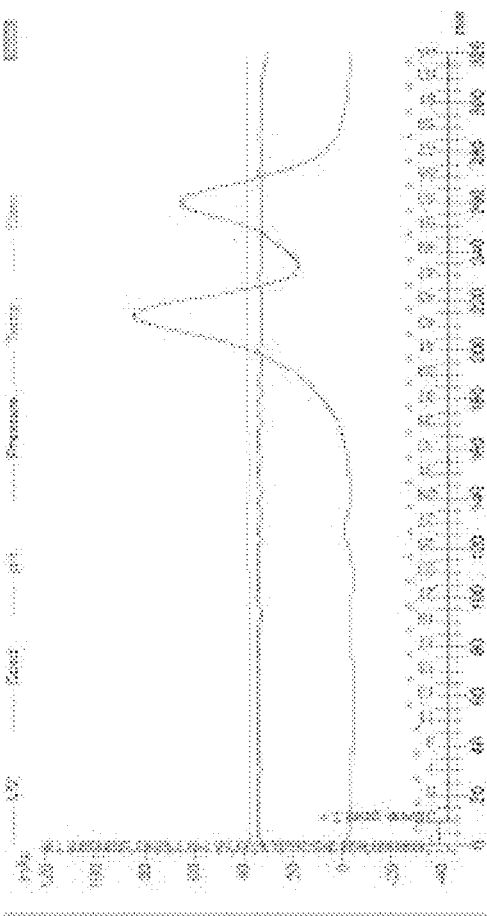
FIG. 11B shows SEC elution profile of IgA4.0-Obi from the producing CHO-S cell line (ExpiCHO-S™ cell line), no aggregates are observed upon SEC.
Figure 12A:
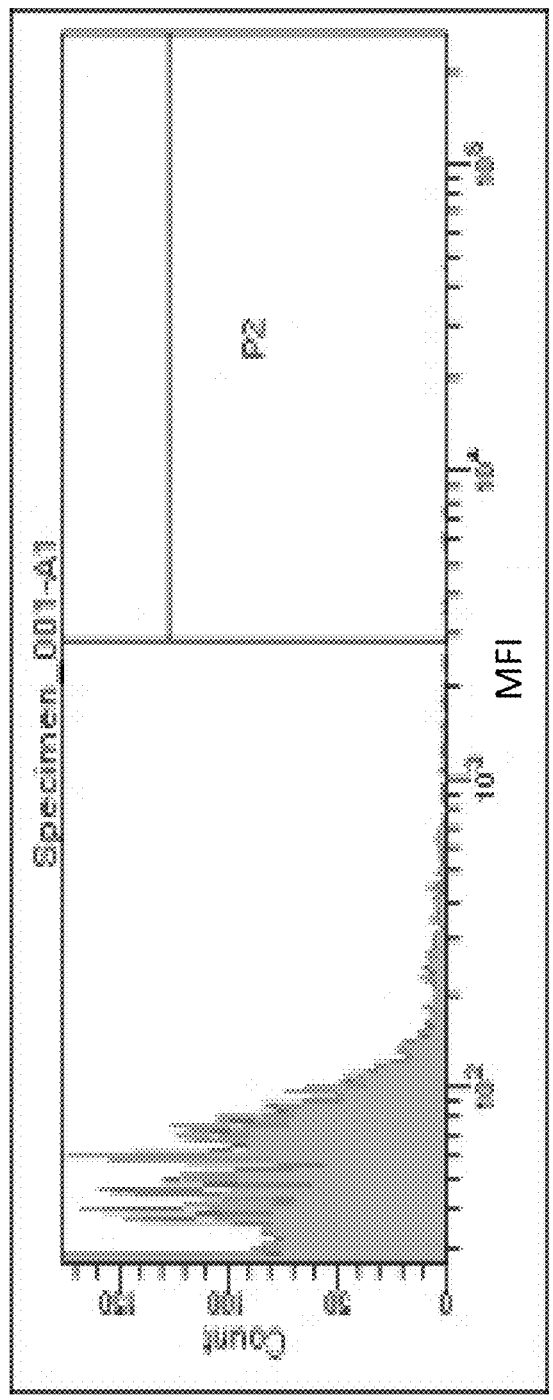
FIGS. 12A-12E shows binding of IgA3.0+-Obi and IgA3.0min-Obi to CD20 positive Daudi cells by flow cytometry.
Figure 12B:
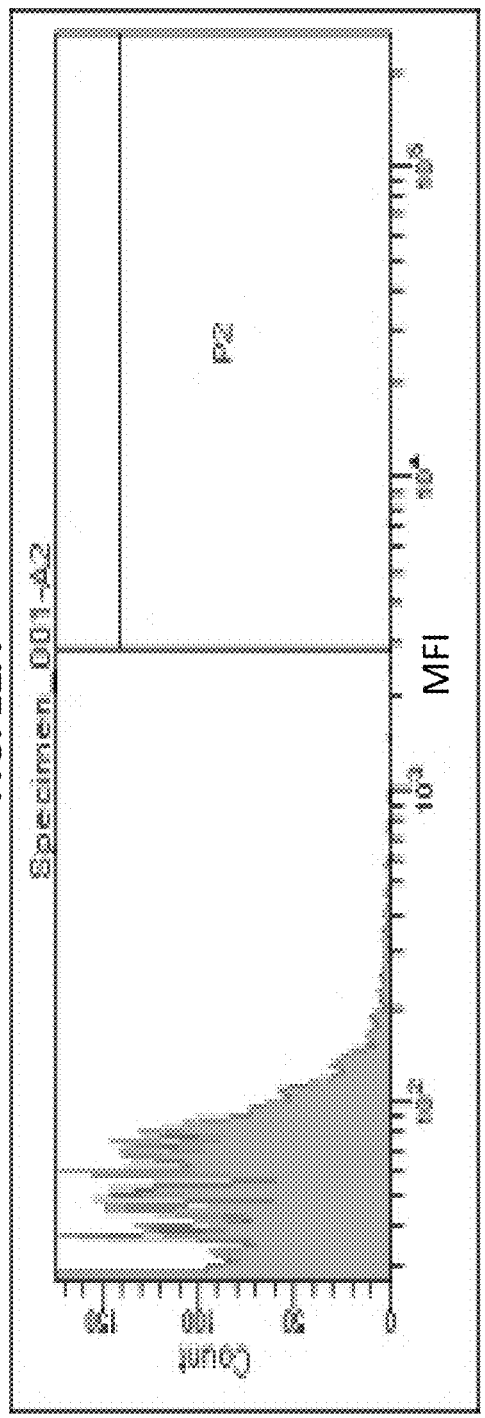
Figure 12C:
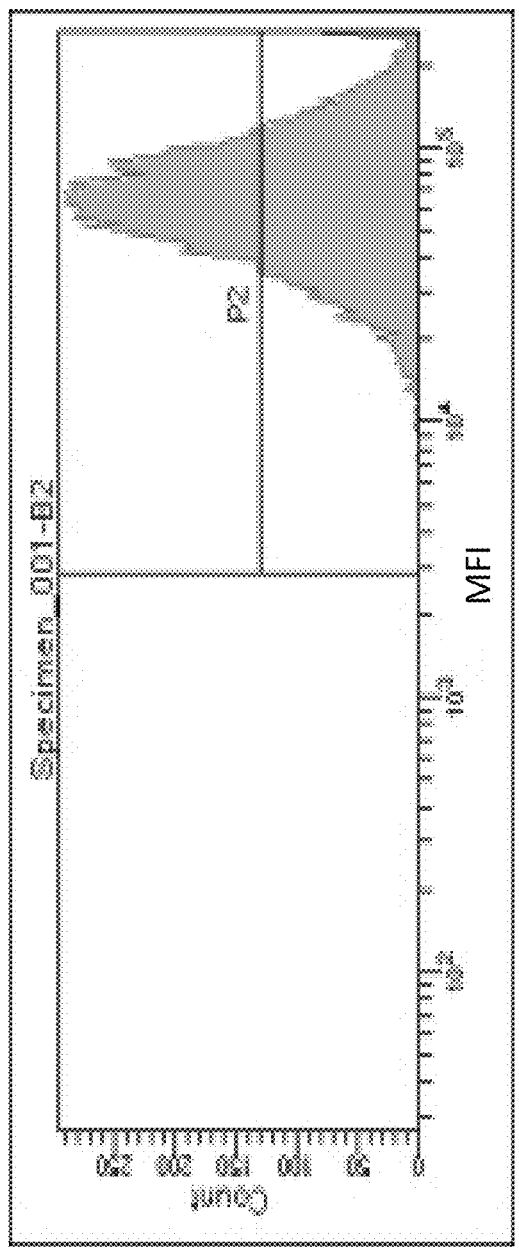
Figure 12D:
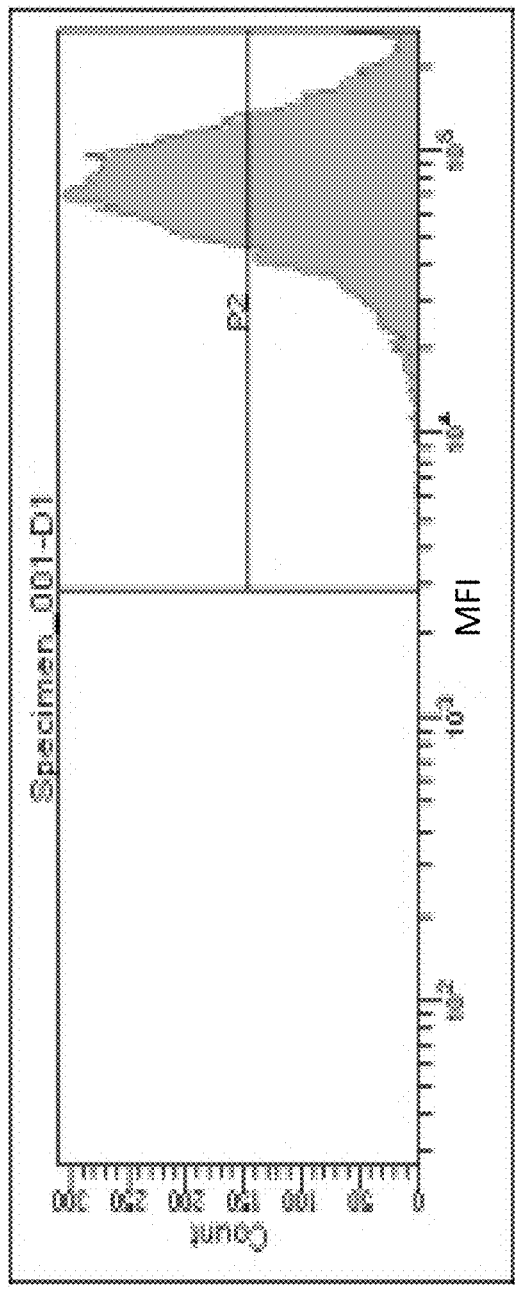
Figure 12E:
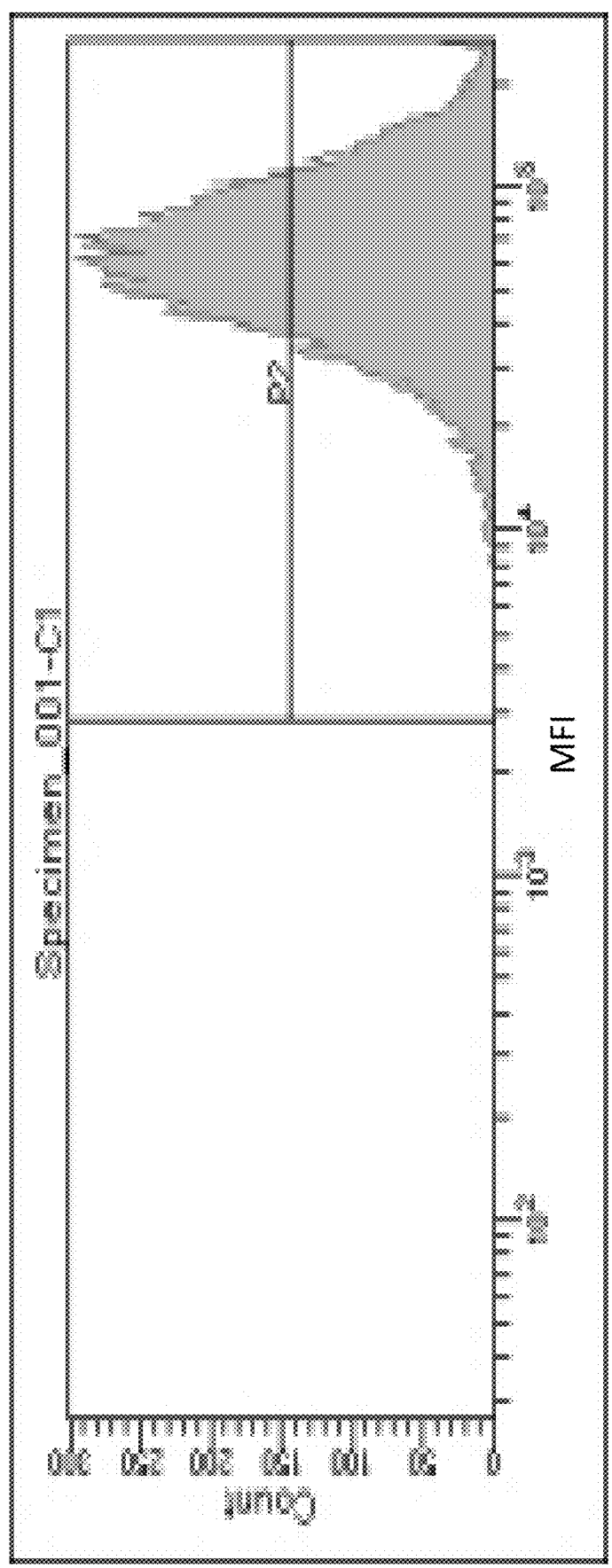

Subsequent kappa light chain dependent purification of IgA3.0min variants; IgA3.0min-Obi, (FIGS. 9A-9B)) and IgA3.0min-Her2 (FIGS. 10A-10B) followed by their respective SEC separation (FIGS. 9C-9D for IgA3.0min-Obi, and FIGS. 10C-10D demonstrating IgA3.0min-Her2, revealed no aggregates that are normally seen with wild type IgA2 (m1) due to cysteine in the tailpiece. By removing this cysteine (IgA3.0+) or the entire tailpiece (IgA3.0min) no aggregation occurred. Likewise, no aggregate formation was observed in the SEC separation of IgA4.0 variant; IgA4.0-Obi (FIGS. 11A-11B), which like IgA3.0min variants also lacks the tailpiece.

Figure 15:
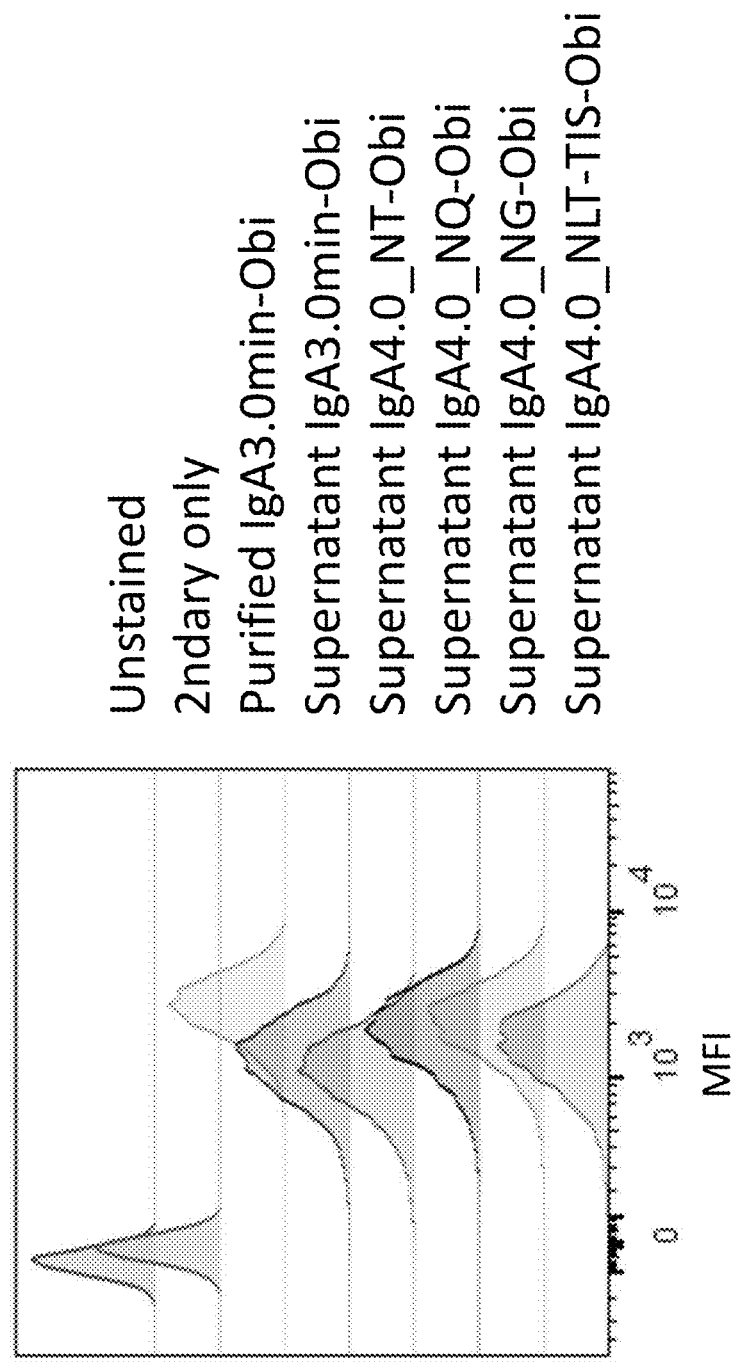
FIG. 15 shows binding analysis of IgA4.0 variants. Supernatants from CHO-S cells (ExpiCHO-Sm cells) transfected with IgA4.0 variants; IgA4.0_NT-Obi, IgA4.0_NQ-Obi, IgA4.0_NG-Obi, and IgA4.0_NLT-TIS-Obi, were assessed for binding on CD20 expressing SKBR3 cells. All variants of IgA4.0-Obi bind to SKBR3-CD20 to the same extent as supernatant from CHO-S cells (ExpiCHO-S™ cells) transfected with IgA3.0min-Obi or purified IgA3.0min-Obi.

Next, the binding capacities of the IgA3.0+−Obi and IgA3.0min-Obi molecules was determined by flow cytometry on Daudi cells. As expected, both the IgA3.0+−Obi as well as the IgA3.0min-Obi antibodies were able to bind to CD20 on Daudi cells, indicating their Fab fragments were properly folded (FIGS. 12A-12E). Next, to assess whether the fully aglycosylated IgA4.0 variants were also still able to bind target antigen, a flow cytometric assay was performed using CD20 complemented SKBR3 cells (FIG. 15). These FACS binding data indicated engineered IgA4.0 variants (IgA4.0_NT-Obi, IgA4.0_NQ-Obi, IgA4.0_NG-Obi, IgA4.0_NG-Obi, and IgA4.0_NLT-TIS-Obi) bind CD20 as well as the engineered IgA3.0min molecules, confirming the folding of the Fab regions are unaffected by the engineering.

Figure 13:
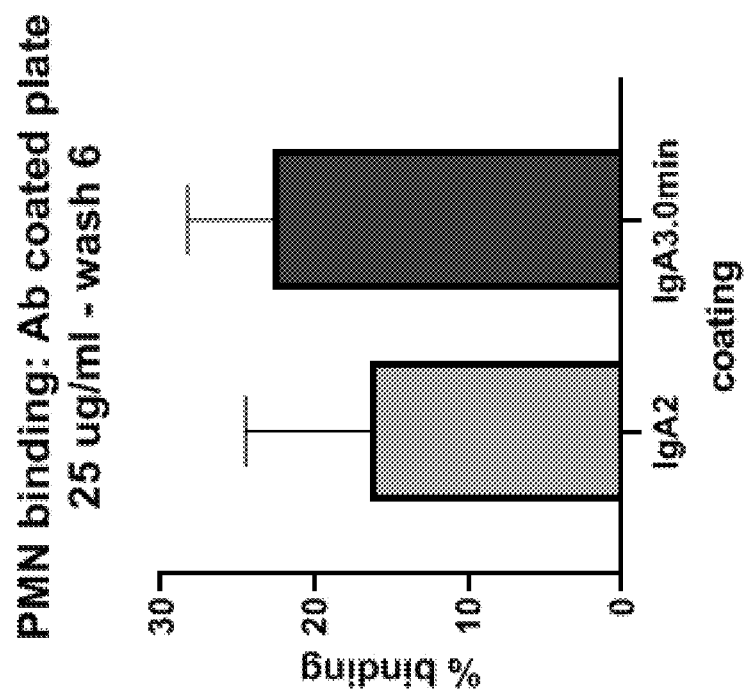
FIG. 13 shows the binding of the Fc-part to PMN by IgA3.0min-Obi as assessed by a PMN binding assay. PMNs were added to ELISA plate wells coated with antibody in different concentrations. A series of washing determines the binding strength of the Fc par to PMN of IgA3.0min-Obi and IgA2. After the 6th wash binding is plotted. IgA3.0min-Obi shows equal to better binding to PMNs as compared to wild type IgA2.
Figure 14:
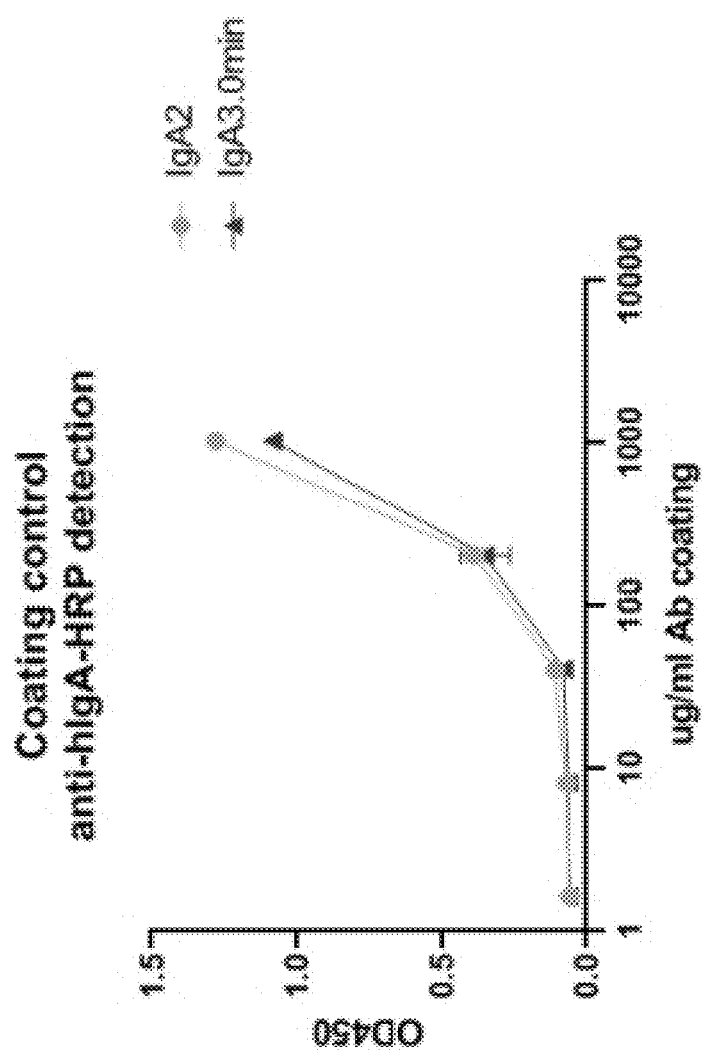
FIG. 14 shows equal coating concentrations of IgA3.0min compared to wild type IgA2.

To assess whether the Fc portion still retains the ability to bind FcαR, an IgA-FcαR binding assay has been performed where neutrophils were allowed to bind IgA coated plates followed by a series of washes. After a number of washes neutrophils were still capable of binding the IgA molecules, where IgA3.0min-Obi show similar or better binding profiles than IgA2(m1) (FIG. 13). To ensure the amount of IgA molecules presented to the neutrophils was equivalent, an IgA detection step was executed indicating equal concentrations of antibody of IgA2(m1) and IgA3.0min (FIG. 14).

Figure 16A:
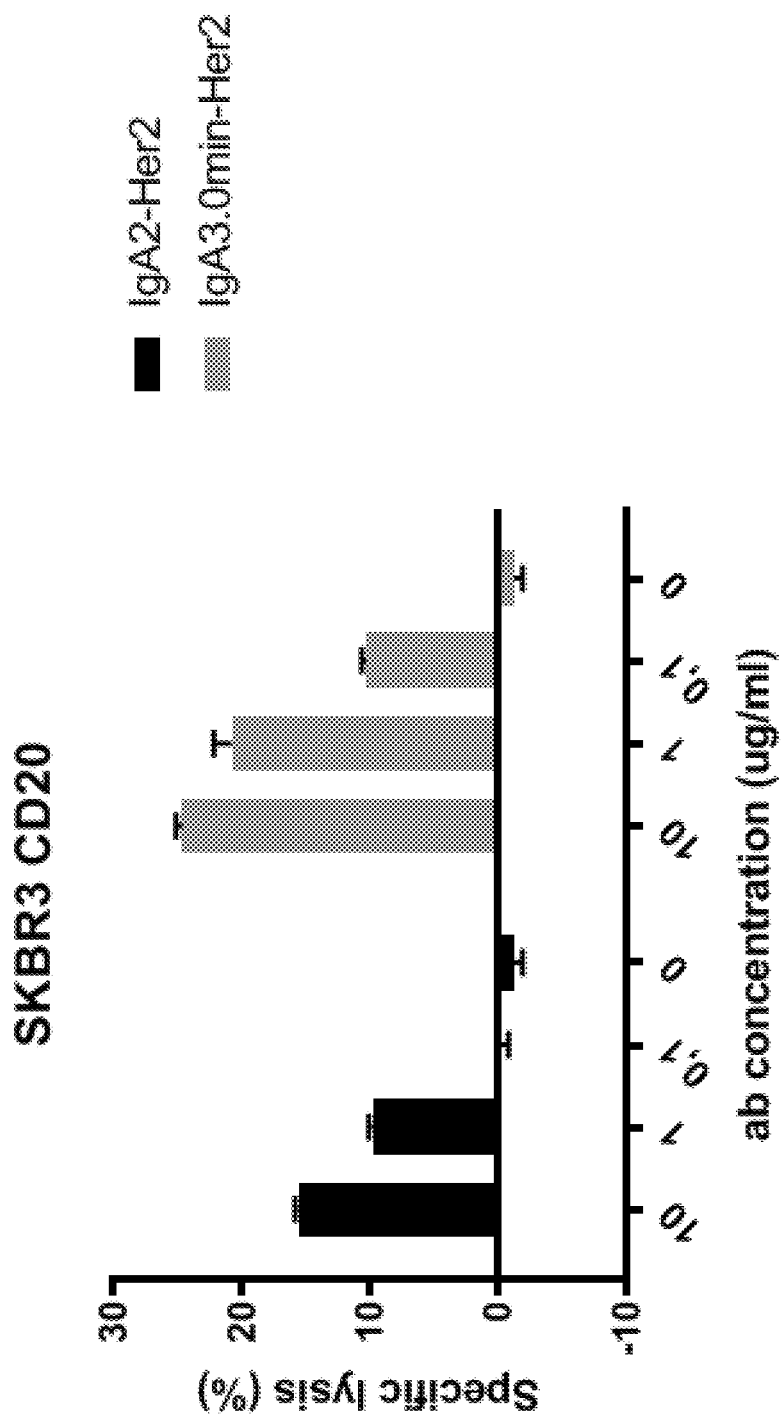
FIGS. 16A-16D shows IgA variants induce PMN-mediated ADCC against target cells.
Figures 16B, 16C:
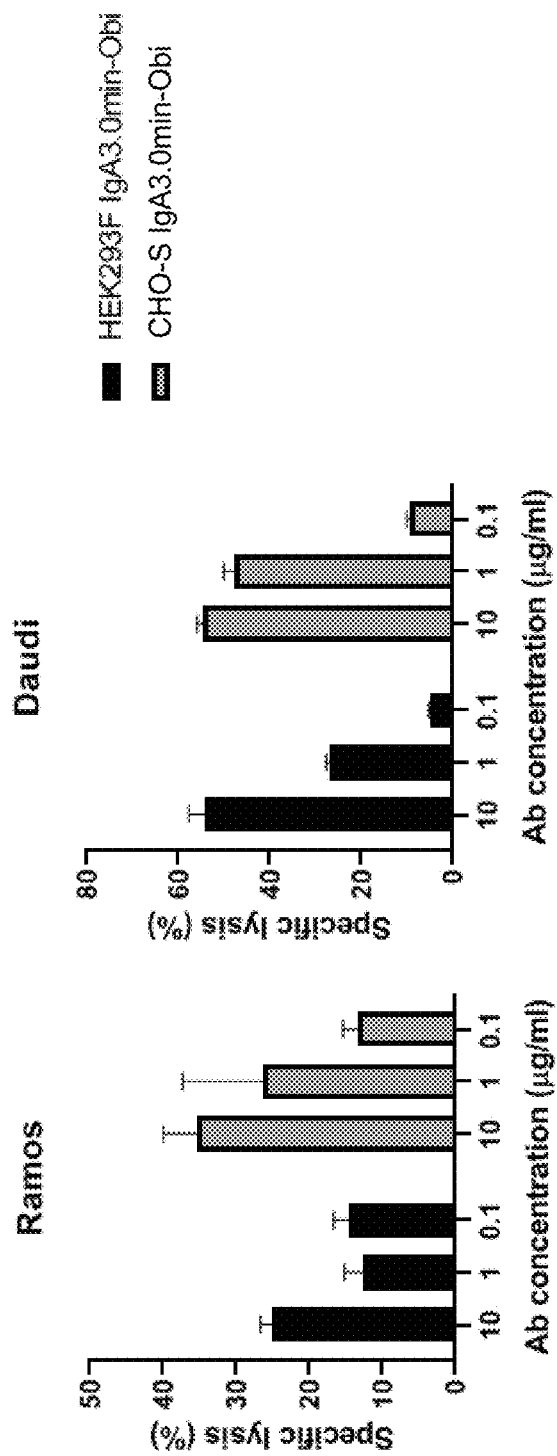
Figure 16D:
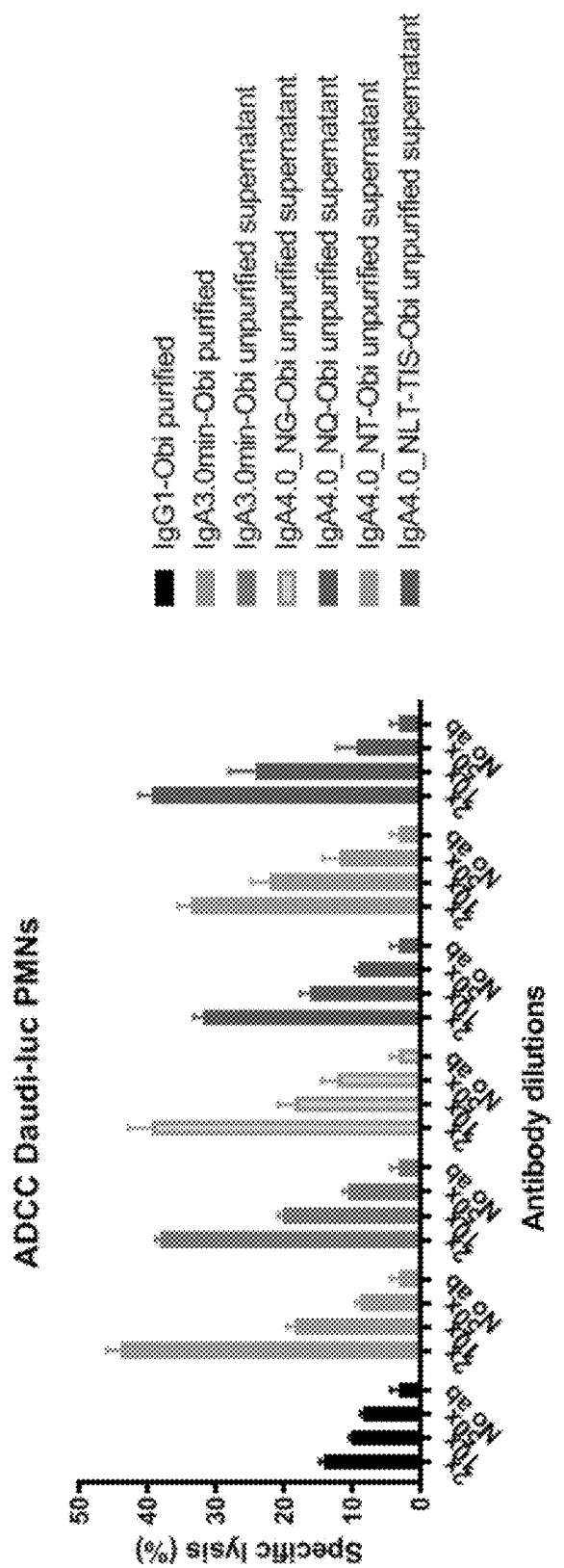

To demonstrate engineered IgA molecules are functional and are able to induce PMN-mediated ADCC, chromium release assays were performed. On SKBR3-CD20 cells the IgA3.0min-Her2 antibody was able to induce ADCC as good as, or better than IgA2(m1)-Her2 (FIG. 16A). Moreover, IgA3.0min-Obi antibodies produced in CHO-S cells (ExpiCHO-S™ cells) induced ADCC in both Daudi and Ramos cells as efficient as with HEK293F-produced antibodies (FIGS. 16B-16C). Furthermore, the fully aglycosylated IgA4.0 variants induced ADCC to similar levels as IgA3.0min-Obi (FIG. 16D), showing full functionality with regards to killing. This is in stark contrast to aglycosylated IgG1 which functionality is severely compromised or ablated (Jefferis 2009). These data indicate that, despite the modifications introduced for engineering IgA variants, both IgA3.0min as well as IgA4.0 still retained their function in inducing ADCC.

Figure 17B:
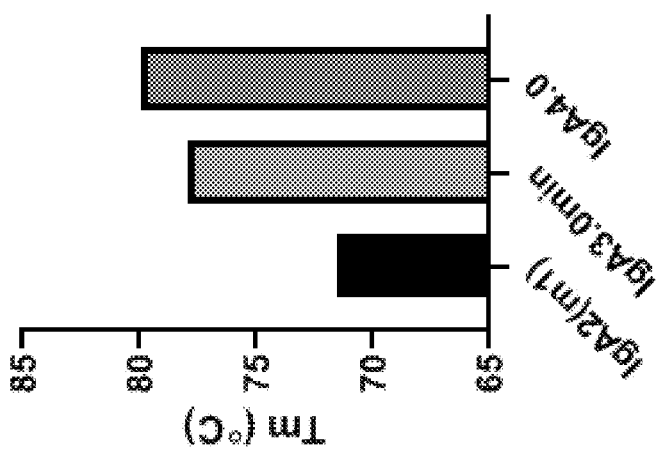
FIGS. 17A-17C show thermostability of IgA variants. Using a SYPRO™ Orange thermal shift assay the thermostability of IgA3.0min and IgA4.0 has been determined.
Figure 17A:
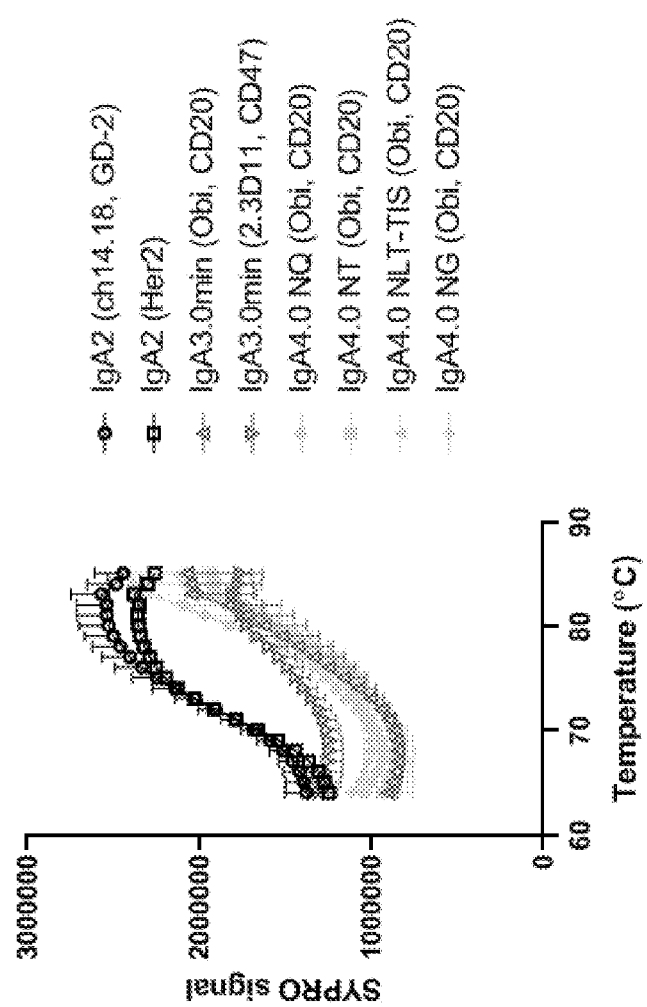

In order to see whether the engineered IgA3.0min and IgA4.0 variants were more thermally stable, a SYPRO™ thermal shift was executed. Antibodies were incubated in the presence of SYPRO™ Orange in a thermal cycler slowly raising its temperature. When the protein unfolds, SYPRO™ Orange is able to bind hydrophobic pockets and fluorescent signal can be detected. FIG. 17A shows the thermal stability profiles of two wild type IgA2(m1) antibodies versus two engineered IgA3.0min molecules and four engineered IgA4.0 antibodies. The shift in the curves indicate IgA3.0min variants and IgA4.0 variants were more stable at higher temperatures than wild type IgA2(m1). The Tm values calculated by a non-linear regression analysis have been averaged for the different IgA molecules assessed (FIG. 17B). Both types of engineered IgA variants (IgA3.0min and IgA4.0) show improved stability at higher temperatures compared to wild type IgA2(m1).

Figure 17C:
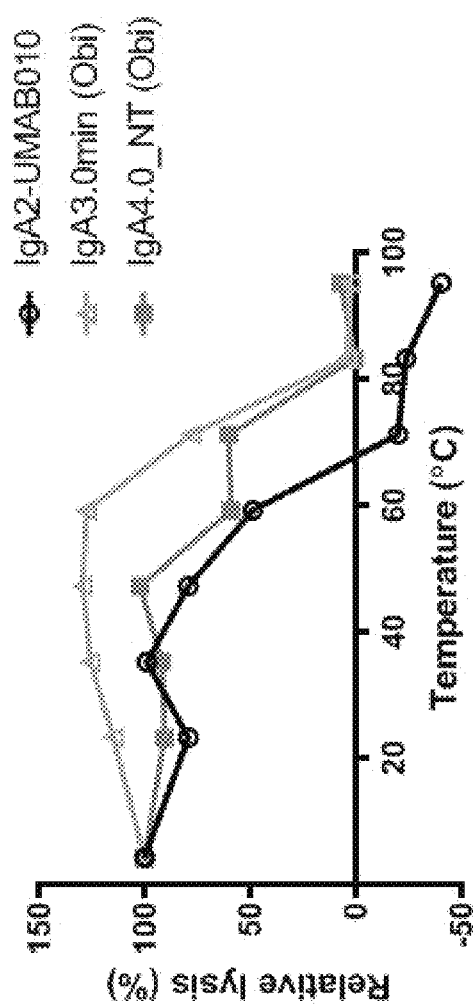

To translate the observed stability into functionality anti-CD20 IgA antibodies; wild type IgA2 and IgA3.0min-Obi were heated to certain temperatures and tested in a chromium release ADCC using Raji cells (FIG. 17C). Signals were normalized to the control which was antibody incubated at 4 C. The killing efficiency of thermally exposed antibodies differed between the wild type IgA2(m1) and engineered IgA3.0min/IgA4.0 molecules. The first showing a decremental profile at exposure at 47° C. or higher, while the latter still showed over 50% activity after exposure 71° C. All activity of the three antibodies tested was lost at temperatures higher than 83° C. This indicates that the stability of the antibodies is important in terms of functionality, and the improved thermostability of the engineered IgA variants relative to wild type is advantageous.

Figure 18:
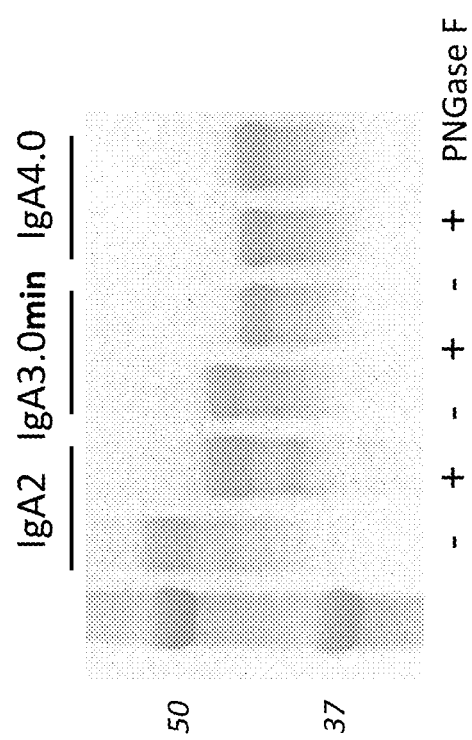
FIG. 18 shows effects of deglycosylation of engineered IgA3.0min variants and engineered IgA4.0 variant compared to wild type IgA2 by PNGase F treatment. Wild type IgA2; IgA2(m1)-UMAB10 shows the largest shift, whereas engineered IgA3.0min variant; IgA3.0min-Obi shows a minor shift indicating reduced glycosylation compared to wild type IgA2. Engineered IgA4.0 variant; IgA4.0_NG-Obi does not show a shift indicating reduced glycosylation compared to engineered IgA3.0min variant and wild type IgA2.

As the engineered IgA3.0min and IgA4.0 molecules have less or no sites for N-linked glycosylation in comparison to wild type IgA2(m1), a PNGase F assay has been performed to visualize remaining N-glycosylation (FIG. 18). For this, IgA molecules were treated with PNGase F which removes all N-linked glycosylation by cleaving between the innermost GlcNac and asparagine. Subsequently, samples were run on a reducing SDS-PAGE gel. As expected, the wild type IgA2(m1) (HEK293F-produced) shows a major shift in molecular weight, due to the presence of four N-linked glycans, while the shift of IgA3.0min-Obi (HEK293F-produced) is minor due to only as single glycosylation event. Yet, the aglycosylated IgA4.0 variants (CHO-S-produced (ExpiCHO-S™-produced)) does not show a shift at all, indicating this antibody is not glycosylated.

Figure 19A:
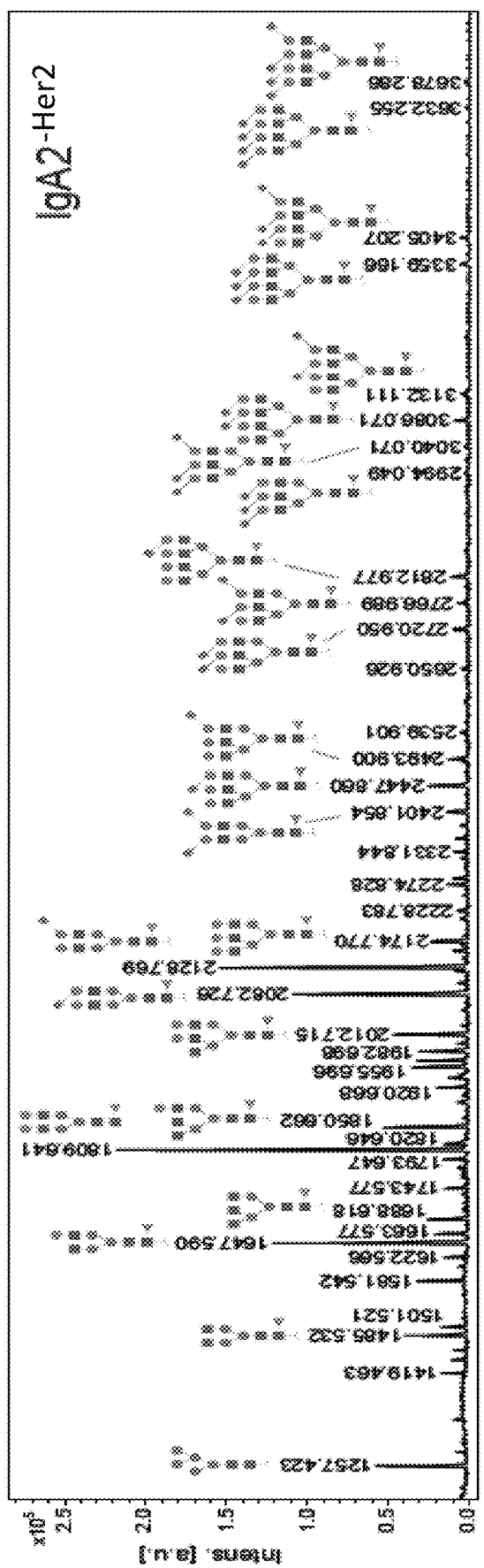
Figure 19B:
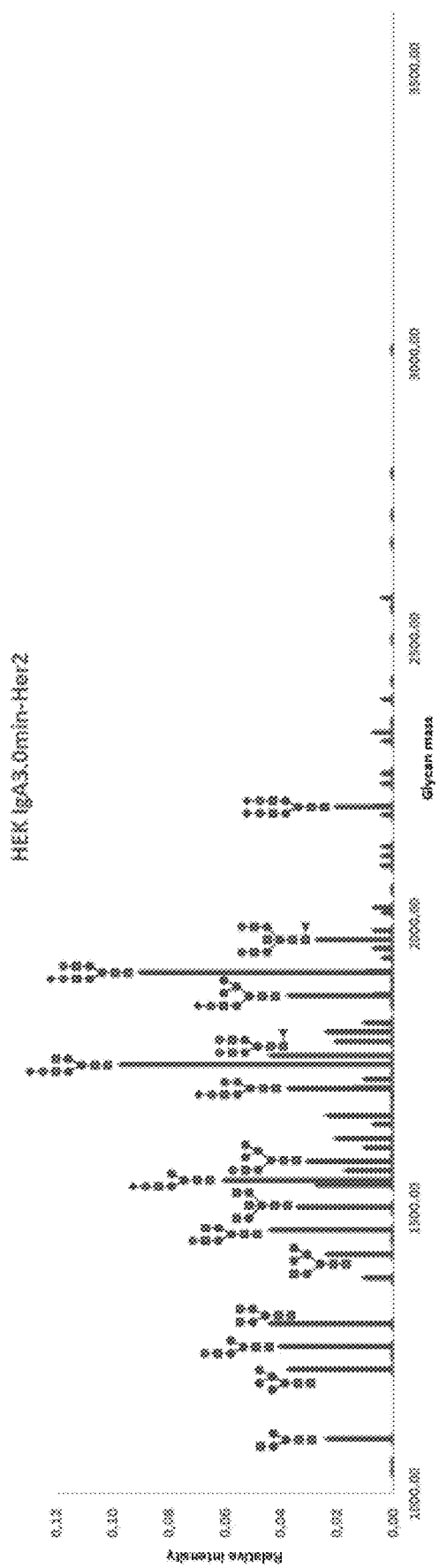
Figure 19C:
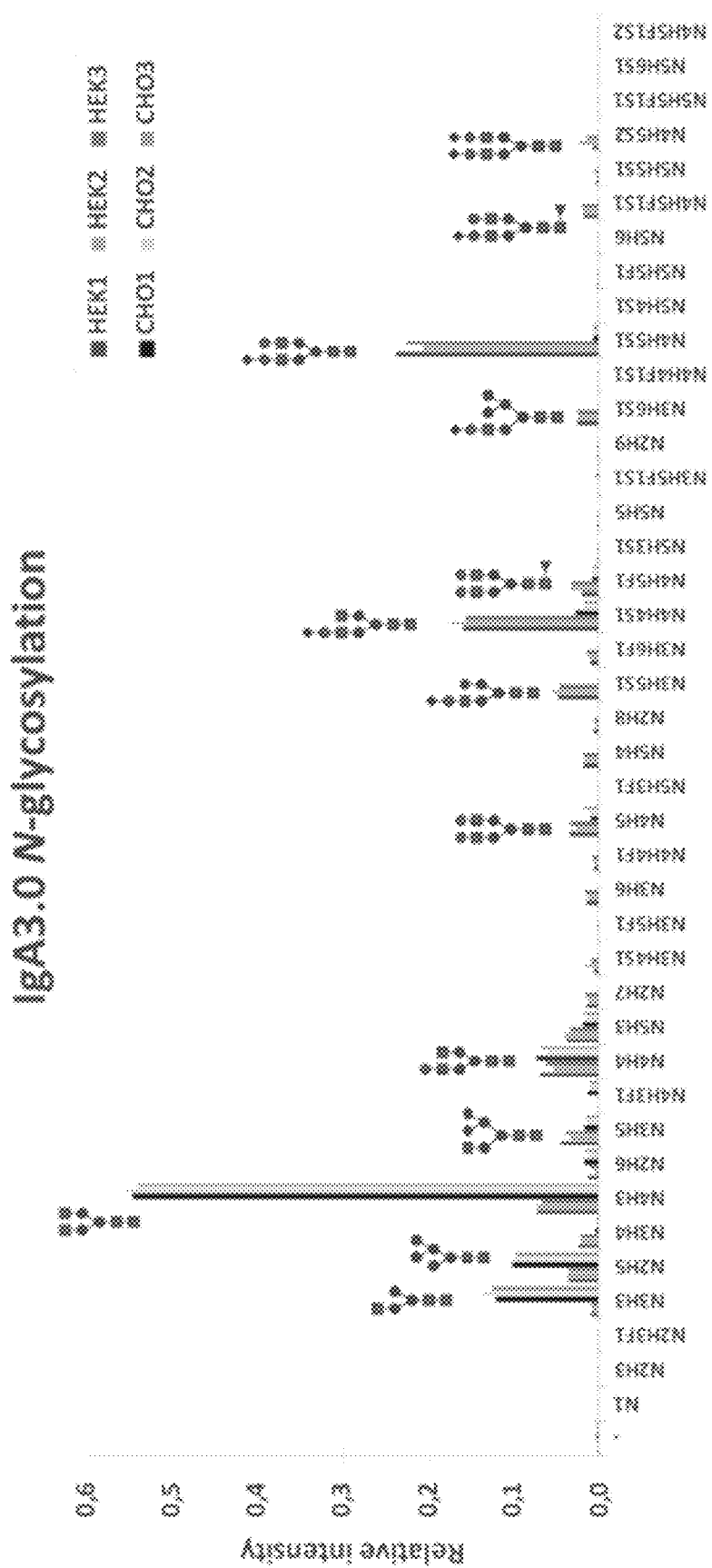

To assess the glycosylation profiles in more detail, antibodies were analyzed by mass spectrometry. The glycosylation profiles of Wild type IgA2(m1)-Her2 and IgA3.0min-Her2 (FIGS. 19A-19B) were analyzed. Several N-glycan species were detected by MALDI-TOF-MS analysis in IgA2(m1)-Her2 reflecting the overall glycosylation on the four N-linked glycosylation motifs. Yet, the peaks of the IgA3.0min-Her2 profile obtained from a LC/MS2 analysis only came from the single N-linked glycosylation motif left, thus also reflecting the overall glycosylation profile as no other sites have been modified. When comparing antibodies from the HEK293F and CHO-S (ExpiCHO-S™) antibody production systems by LC/MS2 a substantial difference in glycosylation profiles was observed (FIG. 19C). In CHO-S (ExpiCHO-S™) the majority (>50%) of the glycosylated antibodies were terminated on bi-antennary GlcNac while the HEK293F showed a more diverse array of glycosylation species of the hybrid or complex type. The unfavorable free galactoses were markedly more present in the HEK293F-produced antibodies than in CHO-S-produced antibodies (ExpiCHO-S™-produced antibodies). These results showed CHO-S-produced antibodies (ExpiCHO-S™-produced antibodies) showed less heterogeneic glycosylation and will have better half-life characteristics with regard to ASGPR-induced clearance. To determine whether glycosylation events occur in IgA4.0 molecules a native MS approach was taken, analyzing full, undigested antibodies. All four IgA4.0 variants the displayed a mass very close to the theoretical peptide backbone (FIGS. 19D-19G). There is a consistent loss of 36 Da amongst all four variants, which could not be attributed to N-glycan species, as these are typically 1500-2500 Da per glycan. The observed mass difference is likely to be formation of two pyroglutamates accounting for 36 Da. Thus, this analysis showed that the IgA4.0 antibody variants lack N-glycans on their backbone, demonstrating that aglycosylated IgA antibodies are fully functional in in vitro assays.

Figure 20A:
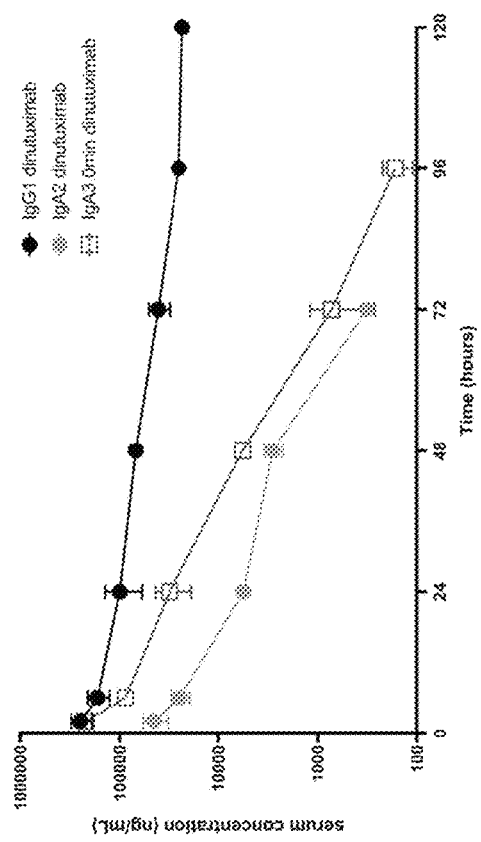
FIGS. 20A-20B show pharmacokinetics and pharmacodistribution analysis of engineered IgA variants. An amount of 100 μg of wild-type-IgG1-dinutuximab, wild type-IgA2-dinutuximab and IgA3.0min-dinutuximab, IgA3.0min-Obinutuzumab, IgA4.0-Obinutuzumab were injected into BALB/c mice and blood was analysed at indicated time points by ELISA.
Figure 20B:
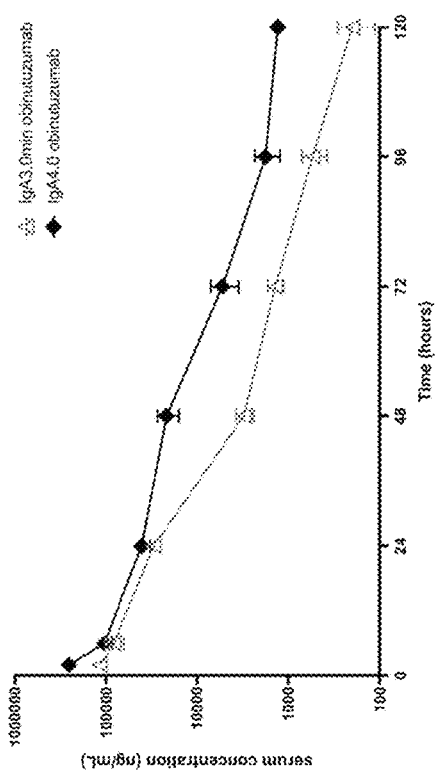

To determine whether the loss of glycosylation sites in engineered IgA3.0 variants and IgA4.0 variants lead to a better half-life in serum, a pharmacokinetics study was set-up. BALB/c mice were i.v. injected with 100 μg antibody and analysed serum samples at the indicated timepoints by ELISA. Two antibodies in different formats, dinutuximab and obinutzumab were assessed. Detected serum wild type IgG1-Dinutuximab levels were higher than wild type IgA2-Dinutuximab levels which was rapidly cleared (FIG. 20A). The difference in serum levels between IgA2 and IgA3.0min at 24 hours can be attributed to the clearance by the ASGPR within the first hours after injection. This demonstrated that the distribution phase is less pronounced in IgA3.0min, due to less N-glycosylation-dependent clearance by ASGPR. The data showed an increased serum half-life was observed with the IgA3.0min-Dinutuximab antibodies as compared to wild type IgA2-Dinutuximab. When assessing the serum half-life of Ig4.0-Obinutuzumab, a clear increase in serum half-life is observed compared to its IgA3.0min counterpart, IgA3.0min-Obinutuzumab (FIG. 20B). This demonstrates that engineered IgA variants has extended serum-half life relative to their wild type counterpart IgA and thus can leverage a similar effect on tumor using less antibody.

Figures 21A, 21B:
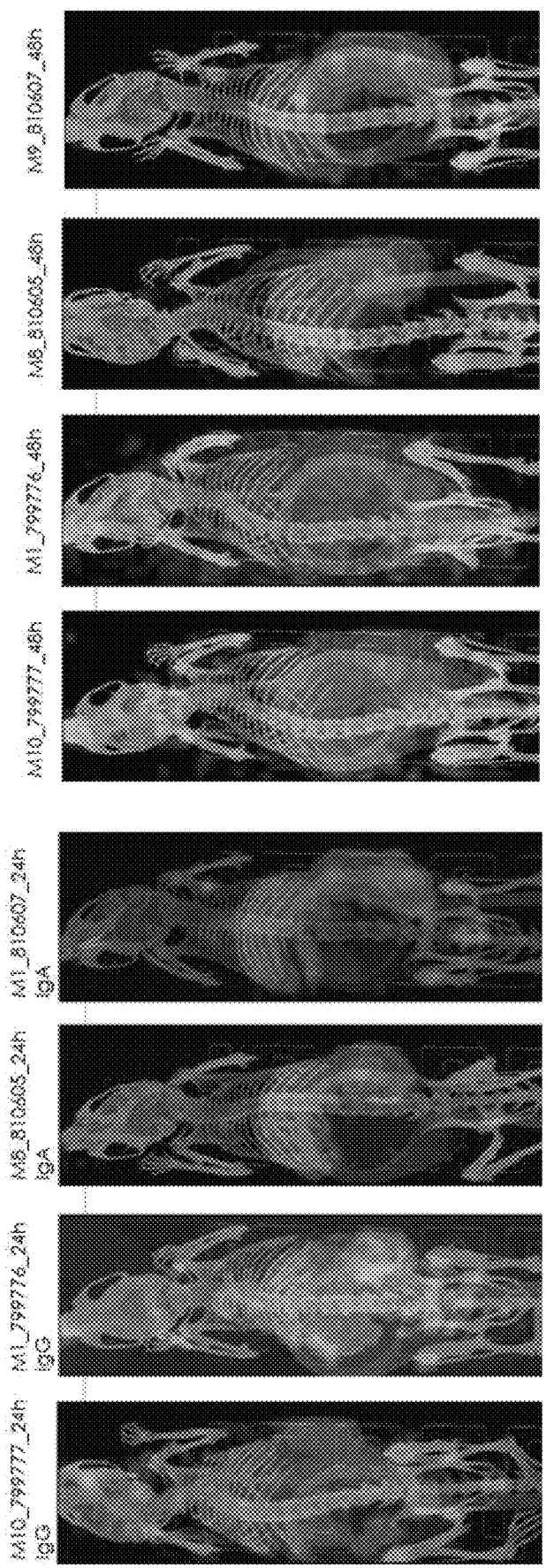
FIGS. 21A-21B shows biodistribution of IgG1 dinutuximab and engineered IgA3.0min variant, IgA3.0min dinutuximab that contains variable domains from dinutuximab. Indium-111 radiolabeled IgG1 dinutuximab and engineered IgA3.0min variant, IgA3.0min dinutuximab were i.v. injected into mice for biodistribution analysis. Mice were monitored to trace antibody distribution after 24 hours (FIG. 21A) and after 48 hours (FIG. 21B). A clear infiltration of both IgG1 and engineered IgA3.0min variants to the tumor is observed.
Figure 22:
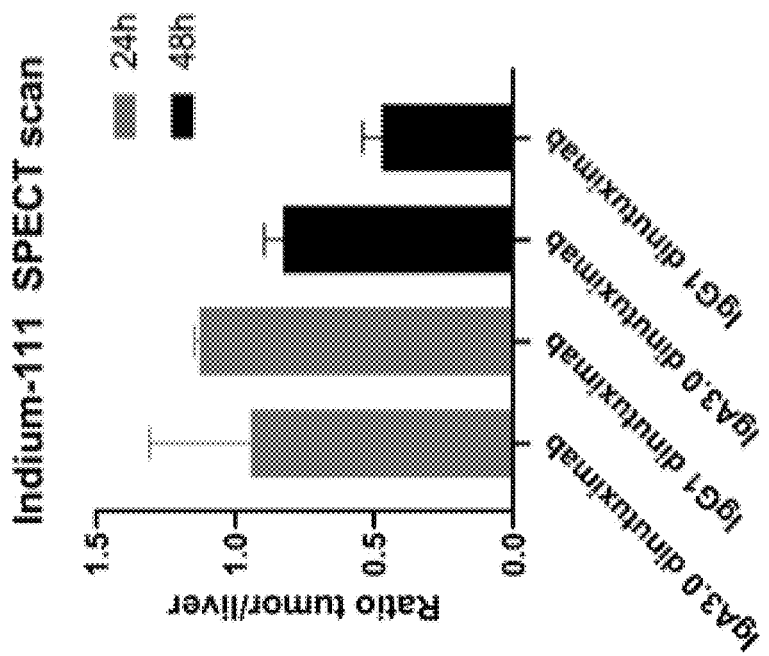
FIG. 22 shows quantification of the distribution of radiolabeled of IgG1 dinutuximab and engineered IgA3.0min variant, IgA3.0min dinutuximab distribution in mice from FIGS. 21A-21B. The ratio of tumor signal to liver signal has been determined to adjust for background signals. Plot shows engineered IgA3.0min variant, IgA3.0min dinutuximab showed increased tumor/liver ratio compared to the IgG1 dinutuximab.

To define if the IgA3.0min antibody distributes to tumors, a biodistribution experiment was performed where the antibodies were radiolabeled with 111Indium to monitor them in vivo. For this, GD2-expressing IMR-32 neuroblastoma cells were subcutaneously injected in NSG mice. After 42 days of outgrowth, mice were injected intravenously with radiolabeled wild type IgG1-dinutuximab and IgA3.0min-dinutuximab. Mice were screened 24 and 48 hours after injection (FIGS. 21A-21B). Radioactive signal was observed both in the liver and in the tumor, indicating antibodies infiltrate tumors. Liver signals represent accumulated antibodies from the bloodstream that are being catabolized. By determining the tumor/liver ratio the tumor-specific signal would be corrected for background. Initially after 24 hours the signals observed are similar, but at 48 hours the IgA3.0min-Dinutuximab signal is more tumor-specific than its IgG1 counterpart (FIG. 22).

Figure 23:
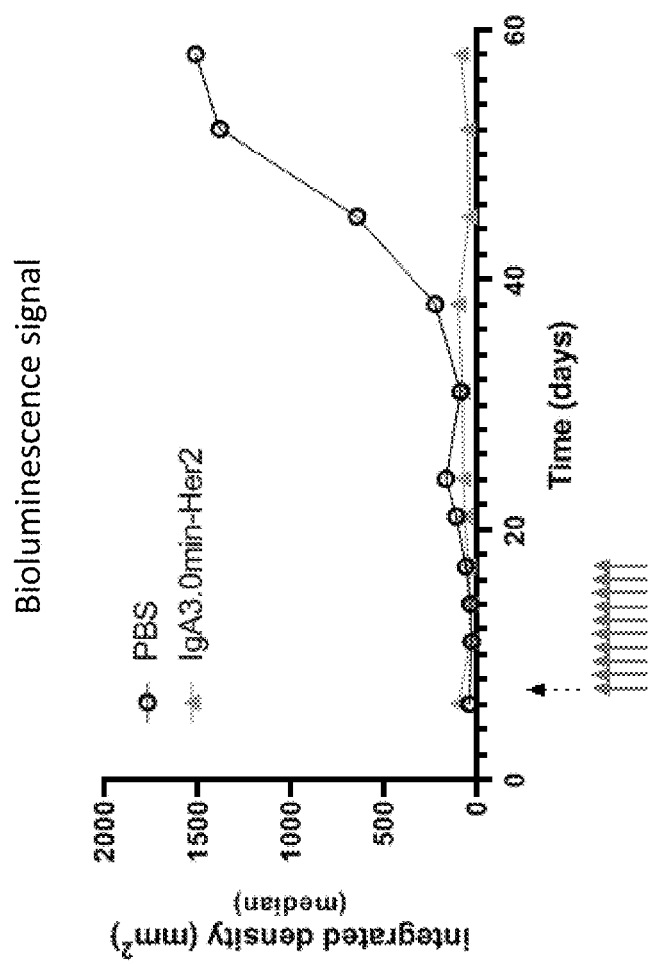
FIG. 23 shows inhibition of tumor growth in an established tumor model upon administration of engineered IgA3.0min variant; IgA3.0min-Her2. A431-Luc2-Her2 cells were injected intraperitoneally on day 0 in hCD89 Transgenic or non-transgenic SCID mice followed by a subcutaneous pegG-CSF injection on day 6. Bioluminescence signal was measured from day 6 onwards and mice were randomized into different treatment groups on this day, and significant signal was measured. Treatment started on day 7 with daily intraperitoneal injections of 10 ug IgA3.0min-Her2 for 10 days. Bioluminescence signal was measured on the indicated time points.

Next the efficacy of IgA3.0min in vivo was determined. For this an established tumor model with hCD89 transgenic and non-transgenic SCID was used (Brandsma, Ten Broeke et al. 2015). Mice were injected i.p. with A431-luc2-Her2 cells. Once tumors were established, mice were treated by administering either PBS or IgA3.0min-Her2 i.v. (FIG. 23). Tumor growth was monitored by BLI on the indicated time points. Tumors showed exponential outgrowth in the PBS group. However, mice treated with IgA3.0min-Her2 showed no outgrowth of tumor and control the cancer after 58 days, demonstrating the efficacy of engineered IgA variants.

The results demonstrated that compared to wild type IgA2(m1) all engineered IgA variants; IgA3.0+, IgA3.0min, and IgA4.0 show improved biopharmaceutical properties while still retaining their functionality. Engineered IgA variants are expressed to high levels, and can be purified without aggregates, resulting in a pure and more stable IgA antibody that still displays robust binding to target antigen and efficient killing of target cells both in vitro as well as in vivo.

Table 3 lists exemplary amino acid sequences and nucleic acid sequences of the heavy chain constant region of the engineered IgA variants

| IgA constant chain | SEQ ID NO: | Amino acid sequence | SEQ ID NO: | Nucleic acid sequence |
|---|---|---|---|---|
| IgA2m1 | 1 | ASPTSPKVFPLSLDSTPQDGNVV VACLVQGFFPQEPLSVTWSESG QNVTARNFPPSQDASGDLYTTSS QLTLPATQCPDGKSVTCHVKHY TNPSQDVTVPCPVPPPPPCCHPR LSLHRPALEDLLLGSEANLTCTL TGLRDASGATFTWTPSSGKSAV QGPPERDLCGCYSVSSVLPGCA QPWNHGETFTCTAAHPELKTPL TANITKSGNTFRPEVHLLPPPSEE LALNELVTLTCLARGFSPKDVL VRWLQGSQELPREKYLTWASR QEPSQGTTTFAVTSILRVAAEDW KKGDTFSCMVGHEALPLAFTQK TIDRLAGKPTHVNVSVVMAEVD GTCY | 22 | gccagccccaccagccccaaggtgttcccctgagc ctggacagcacccccaggacggcaacgtggtggt ggcctgcctggtgcagggcttcttccccaggagcc cctgagcgtgacctggagcgagagcggccagaac gtgaccgccaggaacttccccccagccaggacgc cagcggcgacctgtacaccaccagcagccagctga ccctgcccgccacccagtgccccgacggcaagagc gtgacctgccacgtgaagcactacaccaaccccagc caggacgtgaccgtgccctgcccgtgccccccc cccccctgctgccacccaggctgagcctgcacag gcccgccctggaggacctgctgctgggcagcgagg ccaacctgacctgcaccctgaccggcctgagggac gccagcggcgccaccttcacctggaccccagcag cggcaagagcgccgtgcagggcccccccgagagg gacctgtgcggctgctacagcgtgagcagcgtgctg cccggctgcgcccagccctggaaccacggcgaga ccttcacctgcaccgccgccaccccgagctgaaga ccccctgaccgccaacatcaccaagagcggcaac accttcaggcccgaggtgcacctgctgcccccccc agcgaggagctggccctgaacgagctggtgaccct gacctgcctggccaggggcttcagccccaaggacg tgctggtgaggtggctgcagggcagcaggagctg cccaggagaagtacctgacctgggcagcaggca ggagcccagccagggcaccaccaccttcgccgtga ccagcatcctgagggtggccgccgaggactggaag aagggcgacaccttcagctgcatggtgggccacga ggccctgcccctggccttcacccagaagaccatcga caggctggccggcaagcccacccacgtgaacgtga gcgtggtgatggccgaggtggacggcacctgctac |
| IgA2m2 | 2 | ASPTSPKVFPLSLDSTPQDGNVV VACLVQGFFPQEPLSVTWSESG QNVTARNFPPSQDASGDLYTTSS QLTLPATQCPDGKSVTCHVKHY TNSSQDVTVPCRVPPPPPCCHPR LSLHRPALEDLLLGSEANLTCTL TGLRDASGATFTWTPSSGKSAV QGPPERDLCGCYSVSSVLPGCA QPWNHGETFTCTAAHPELKTPL TANITKSGNTFRPEVHLLPPPSEE LALNELVTLTCLARGFSPKDVL VRWLQGSQELPREKYLTWASR QEPSQGTTTYAVTSILRVAAED WKKGETFSCMVGHEALPLAFTQ KTIDRMAGKPTHINVSVVMAEA DGTCY | 23 | gccagccccaccagccccaaggtgttcccctgagc ctggacagcacccccaggacggcaacgtggtggt ggcctgcctggtgcagggcttcttccccaggagcc cctgagcgtgacctggagcgagagcggccagaac gtgaccgccaggaacttccccccagccaggacgc cagcggcgacctgtacaccaccagcagccagctga ccctgcccgccacccagtgccccgacggcaagagc gtgacctgccacgtgaagcactacaccaacagcagc caggacgtgaccgtgccctgcagggtgccccccc cccccctgctgccacccaggctgagcctgcacag gcccgccctggaggacctgctgctgggcagcgagg ccaacctgacctgcaccctgaccggcctgagggac gccagcggcgccaccttcacctggaccccagcag cggcaagagcgccgtgcagggcccccccgagagg gacctgtgcggctgctacagcgtgagcagcgtgctg cccggctgcgcccagccctggaaccacggcgaga ccttcacctgcaccgccgccaccccgagctgaaga ccccctgaccgccaacatcaccaagagcggcaac accttcaggcccgaggtgcacctgctgcccccccc agcgaggagctggccctgaacgagctggtgaccct gacctgcctggccaggggcttcagccccaaggacg tgctggtgaggtggctgcagggcagcaggagctg cccaggagaagtacctgacctgggcagcaggca ggagcccagccagggcaccaccacctacgccgtga ccagcatcctgagggtggccgccgaggactggaag aagggcgagaccttcagctgcatggtgggccacga ggccctgcccctggccttcacccagaagaccatcga caggatggccggcaagcccacccacatcaacgtga gcgtggtgatggccgaggccgacggcacctgctac |
| IgA2_A0A286YEY5 | 3 | ASPTSPKVFPLSLDSTPQDGNVV VACLVQGFFPQEPLSVTWSESG QNVTARNFPPSQDASGDLYTTSS QLTLPATQCPDGKSVTCHVKHY TNSSQDVTVPCRVPPPPPCCHPR LSLHRPALEDLLLGSEANLTCTL TGLRDASGATFTWTPSSGKSAV | 24 | gccagccccaccagccccaaggtgttcccctgagc ctggacagcacccccaggacggcaacgtggtggt ggcctgcctggtgcagggcttcttccccaggagcc cctgagcgtgacctggagcgagagcggccagaac gtgaccgccaggaacttccccccagccaggacgc cagcggcgacctgtacaccaccagcagccagctga ccctgcccgccacccagtgccccgacggcaagagc |

| IgA constant chain | SEQ ID NO: | Amino acid sequence | SEQ ID NO: | Nucleic acid sequence |
|---|---|---|---|---|
| | | QGPPERDLCGCYSVSSVLPGCA QPWNHGETFTCTAAHPELKTPL TANITKSGNTFRPEVHLLPPPSEE LALNELVTLTCLARGFSPKDVL VRWLQGSQELPREKYLTWASR QEPSQGTTTYAVTSILRVAAED WKKGETFSCMVGHEALPLAFTQ KTIDRMAGSCCVADWQMPPPY VVLDLPQETLEEETPGANLWPT TITFLTLFLLSLFYSTALTVTSVR GPSGKREGPQY | | gtgacctgccacgtgaagcactacaccaacagcagc caggacgtgaccgtgccctgcagggtgccccccc cccccctgctgccacccaggctgagcctgcacag gcccgccctggaggacctgctgctgggcagcgagg ccaacctgacctgcacccctgaccggcctgagggac tgcgcgatgcctccggcgccaccttcacctggaccccagcag cggcaagagcgccgtgcagggcccccccgagagg gacctgtgcggctgctacagcgtgagcagcgtgctg cccggctgcgcccagccctggaaccacggcgaga cctt cacctgcaccgccgccccacccccgagctgaaga cccccctgaccgccaacatcaccaagagcggcaac accttcaggcccgaggtgcacctgctgccccccc agcgaggagctggccctgaacgagctggtgaccct gacctgcctggcagggggcttcagccccaaggacg tgctggtgaggtggctgcagggcagccaggagctg cccagggagaagtacctgacctgggccagcaggca ggagcccagccagggcaccaccacctacgccgtga ccagcatcctgagggtggccgccgaggactggaag aagggcgagaccttcagctgcatggtgggccacga ggccctgcccctggccttcacccagaagaccatcga caggatggccggcagctgctgcgtggccgactggc agatgccccccccctacgtggtgctggacctgccc aggagaccctggaggaggagacccccggcgccaa cctgtggcccaccaccatcaccttcctgaccctgttcc tgctgagcctgttctacagcaccgccctgaccgtgac cagcgtgaggggccccagcggcaagagggaggg cccccagtac |
| IgA3.0+ | 16 | ASPTSPKVFPLSLDSTPQDGNVV VACLVQGFFPQEPLSVTWSESG QGVTARNFPPSQDASGDLYTTSS QLTLPATQCPDGKSVTCHVKHY TNPSQDVTVPCRVPPPPPCCHPR LSLHRPALEDLLLGSEANLTCTL TGLRDASGATFTWTPSSGKSAV QGPPERDLCGCYSVSSVLPGSAQ PWNHGETFTCTAAHPELKTPLT ATLSKSGNTFRPEVHLLPPPSEEL ALNELVTLTCLARGFSPKDVLV RWLQGSQELPREKYLTWASRQE PSQGTTTFAVTSILRVAAEDWK KGDTFSCMVGHEALPLAFTQKT IDRLAGKPTHVQVSVVMAEVDG T | 25 | gctagcccaacctctcctaaggtgttccctctgagcct ggacagcacccctcaggatggaaatgtggtggtgg cctgtctggtgcagggattcttcccacaagagccct gtccgtgacttggagcgaatctggacagggcgtgac cgccagaaacttcccaccttctcaggacgcctctggc gacctgtacaccacctcttctcagctgacctgcct gcacagtgcctgatggcaagtctgtgacctgccac gtgaagcactacaccaatcctagccaggacgtgacc gtgccttgcagagttcctcctcctccaccttgctgtcac cctcggctgtctctgcacagacccgctctggaagatc tgctgctgggctctgaggccaacctgacatgtaccct gaccggcctgagagatgcctggcgccacctttacc tggacaccttccagcggaaagtccgctgttcaggga cctcctgagagggacctgtgcggctgttactctgtgtc tagtgtgctgcctggcagcgcccagccttggaatcat ggcgagacattcacctgtaccgctgctcaccccgag ctgaaaacccctctgaccgccacactgtccaagtccg gcaacaccttccggcctgaagtgcatctgctgcctcc acctagcgaggaactggccctgaatgagctggtcac cctgacctgtctggcagggggctagccctaaggac gtgctcgttagatggctgcagggctcccaagagctg cccagagagaagtatctgacctgggcctctcggcaa gagccatctcagggcaccacaacctttgccgtgacc agcatcctgagagtggccgccgaagattggaagaa gggcgacaccttcagctgcatggtcggacatgaagc cctgcctctggctttcacccagaaaaccatcgacaga ctggccggcaagcccacccatgtccaagtgtctgttg tcatggcggaggtggacggcacc |
| IgA3.0min | 17 | ASPTSPKVFPLSLDSTPQDGNVV VACLVQGFFPQEPLSVTWSESG QGVTARNFPPSQDASGDLYTTSS QLTLPATQCPDGKSVTCHVKHY TNPSQDVTVPCRVPPPPPCCHPR LSLHRPALEDLLLGSEANLTCTL TGLRDASGATFTWTPSSGKSAV QGPPERDLCGCYSVSSVLPGSAQ PWNHGETFTCTAAHPELKTPLT ATLSKSGNTFRPEVHLLPPPSEEL ALNELVTLTCLARGFSPKDVLV RWLQGSQELPREKYLTWASRQE PSQGTTTFAVTSILRVAAEDWK KGDTFSCMVGHEALPLAFTQKT IDRLAGK | 26 | gctagcccaacctctcctaaggtgttccctctgagcct ggacagcacccctcaggatggaaatgtggtggtgg cctgtctggtgcagggattcttcccacaagagccct gtccgtgacttggagcgaatctggacagggcgtgac cgccagaaacttcccaccttctcaggacgcctctggc gacctgtacaccacctcttctcagctgacctgcctgc cacagtgcctgatggcaagtctgtgacctgccac gtgaagcactacaccaatcctagccaggacgtgacc gtgccttgcagagttcctcctcctccaccttgctgtcac cctcggctgtctctgcacagacccgctctggaagatc tgctgctgggctctgaggccaacctgacatgtaccct gaccggcctgagagatgcctggcgccacctttacc tggacaccttccagcggaaagtccgctgttcaggga cctcctgagagggacctgtgcggctgttactctgtgtc tagtgtgctgcctggcagcgcccagccttggaatcat ggcgagacattcacctgtaccgctgctcaccccgag ctgaaaacccctctgaccgccacactgtccaagtccg gcaacaccttccggcctgaagtgcatctgctgcctcc |

-continued

| IgA constant chain | SEQ ID NO: | Amino acid sequence | SEQ ID NO: | Nucleic acid sequence |
|---|---|---|---|---|
| | | | | acctagcgaggaactggccctgaatgagctggtcac<br>cctgacctgtctggccaggggctnagccctaaggac<br>gtgctcgttagatggctgcagggctcccaagagctg<br>cccagagagaagtatctgacctgggcctctcggcaa<br>gagccatctcagggcaccacaacctttgccgtgacc<br>agcatcctgagagtggccgccgaagattggaagaa<br>gggcgacaccttcagctgcatggtcggacatgaagc<br>cctgcctctggcttttcacccagaaaaccatcgacaga<br>ctggccggcaag |
| IgA4.0_<br>NG | 18 | ASPTSPKVFPLSLDSTPQDGNVV<br>VACLVQGFFPQEPLSVTWSESG<br>QGVTARNFPPSQDASGDLYTTSS<br>QLTLPATQCPDGKSVTCHVKHY<br>TNPSQDVTVPCRVPPPPPCCHPR<br>LSLHRPALEDLLLGSEAGLTCTL<br>TGLRDASGATFTWTPSSGKSAV<br>QGPPERDLCGCYSVSSVLPGSAQ<br>PWNHGETFTCTAAHPELKTPLT<br>ATLSKSGNTFRPEVHLLPPPSEEL<br>ALNELVTLTCLARGFSPKDVLV<br>RWLQGSQELPREKYLTWASRQE<br>PSQGTTTFAVTSILRVAAEDWK<br>KGDTFSCMVGHEALPLAFTQKT<br>IDRLAGK | 27 | gctagcccaacctctcctaaggtgttccctctgagcct<br>ggacagcacccctcaggatggaaatgtggtggtgg<br>cctgtctggtgcagggattcttcccacaagagcccct<br>gtccgtgacttggagcgaatctggacagggcgtgac<br>cgccagaaacttcccaccttctcaggacgcctctggc<br>gacctgtacaccacctcttctcagctgaccctgcctgc<br>cacacagtgccctgatggcaagtctgtgacctgccac<br>gtgaagcactacaccaatcctagccaggacgtgacc<br>gtgccttgcagagttcctcctcctccaccttgctgtcac<br>cctcggctgtctctgcacagacccgctctggaagatc<br>tgctgctgggctctgaggccggcctgacatgtaccct<br>gaccggcctgagagatgcttctggcgccaccttttacc<br>tggacaccttccagcggaaagtccgctgttcaggga<br>cctcctgagagggacctgtgcggctgttactctgtgtc<br>tagtgtgctgcctggcagcgcccagccttggaatcat<br>ggcgagacattcacctgtaccgctgctcaccccgag<br>ctgaaaacccctctgaccgccacactgtccaagtccg<br>gcaacaccttccggcctgaagtgcatctgctgcctcc<br>acctagcgaggaactggccctgaatgagctggtcac<br>cctgacctgtctggccaggggctttagccctaaggac<br>gtgctcgttagatggctgcagggctcccaagagctg<br>cccagagagaagtatctgacctgggcctctcggcaa<br>gagccatctcagggcaccacaacctttgccgtgacc<br>agcatcctgagagtggccgccgaagattggaagaa<br>gggcgacaccttcagctgcatggtcggacatgaagc<br>cctgcctctggcttttcacccagaaaaccatcgacaga<br>ctggccggcaag |
| IgA4.0_<br>NQ | 19 | ASPTSPKVFPLSLDSTPQDGNVV<br>VACLVQGFFPQEPLSVTWSESG<br>QGVTARNFPPSQDASGDLYTTSS<br>QLTLPATQCPDGKSVTCHVKHY<br>TNPSQDVTVPCRVPPPPPCCHPR<br>LSLHRPALEDLLLGSEAQLTCTL<br>TGLRDASGATFTWTPSSGKSAV<br>QGPPERDLCGCYSVSSVLPGSAQ<br>PWNHGETFTCTAAHPELKTPLT<br>ATLSKSGNTFRPEVHLLPPPSEEL<br>ALNELVTLTCLARGFSPKDVLV<br>RWLQGSQELPREKYLTWASRQE<br>PSQGTTTFAVTSILRVAAEDWK<br>KGDTFSCMVGHEALPLAFTQKT<br>IDRLAGK | 28 | gctagcccaacctctcctaaggtgttccctctgagcct<br>ggacagcacccctcaggatggaaatgtggtggtgg<br>cctgtctggtgcagggattcttcccacaagagcccct<br>gtccgtgacttggagcgaatctggacagggcgtgac<br>cgccagaaacttcccaccttctcaggacgcctctggc<br>gacctgtacaccacctcttctcagctgaccctgcctgc<br>cacacagtgccctgatggcaagtctgtgacctgccac<br>gtgaagcactacaccaatcctagccaggacgtgacc<br>gtgccttgcagagttcctcctcctccaccttgctgtcac<br>cctcggctgtctctgcacagacccgctctggaagatc<br>tgctgctgggctctgaggcccagctgacatgtaccct<br>gaccggcctgagagatgcttctggcgccaccttttacc<br>tggacaccttccagcggaaagtccgctgttcaggga<br>cctcctgagagggacctgtgcggctgttactctgtgtc<br>tagtgtgctgcctggcagcgcccagccttggaatcat<br>ggcgagacattcacctgtaccgctgctcaccccgag<br>ctgaaaacccctctgaccgccacactgtccaagtccg<br>gcaacaccttccggcctgaagtgcatctgctgcctcc<br>acctagcgaggaactggccctgaatgagctggtcac<br>cctgacctgtctggccaggggctttagccctaaggac<br>gtgctcgttagatggctgcagggctcccaagagctg<br>cccagagagaagtatctgacctgggcctctcggcaa<br>gagccatctcagggcaccacaacctttgccgtgacc<br>agcatcctgagagtggccgccgaagattggaagaa<br>gggcgacaccttcagctgcatggtcggacatgaagc<br>cctgcctctggcttttcacccagaaaaccatcgacaga<br>ctggccggcaag |
| IgA4.0_<br>NT | 20 | ASPTSPKVFPLSLDSTPQDGNVV<br>VACLVQGFFPQEPLSVTWSESG<br>QGVTARNFPPSQDASGDLYTTSS<br>QLTLPATQCPDGKSVTCHVKHY<br>TNPSQDVTVPCRVPPPPPCCHPR<br>LSLHRPALEDLLLGSEATLTCTL<br>TGLRDASGATFTWTPSSGKSAV<br>QGPPERDLCGCYSVSSVLPGSAQ<br>PWNHGETFTCTAAHPELKTPLT | 29 | gctagcccaacctctcctaaggtgttccctctgagcct<br>ggacagcacccctcaggatggaaatgtggtggtgg<br>cctgtctggtgcagggattcttcccacaagagcccct<br>gtccgtgacttggagcgaatctggacagggcgtgac<br>cgccagaaacttcccaccttctcaggacgcctctggc<br>gacctgtacaccacctcttctcagctgaccctgcctgc<br>cacacagtgccctgatggcaagtctgtgacctgccac<br>gtgaagcactacaccaatcctagccaggacgtgacc<br>gtgccttgcagagttcctcctcctccaccttgctgtcac |

| IgA constant chain | SEQ ID NO: | Amino acid sequence | SEQ ID NO: | Nucleic acid sequence |
|---|---|---|---|---|
| | | ATLSKSGNTFRPEVHLLPPPSEEL ALNELVTLTCLARGFSPKDVLV RWLQGSQELPREKYLTWASRQE PSQGTTTFAVTSILRVAAEDWK KGDTFSCMVGHEALPLAFTQKT IDRLAGK | | cctcggctgtctctgcacagacccgctctggaagatc tgctgctgggctctgaggccaccctgacatgtaccct gaccggcctgagagatgcttctggcgccacctttacc tggacaccttccagcggaaagtccgctgttcaggga cctcctgagagggacctgtgcggctgttactctgtgtc tagtgtgctgcctggcagcgcccagccttggaatcat ggcgagacattcacctgtaccgctgctcaccccgag ctgaaaaccctctgaccgccacactgtccaagtccg gcaacaccttccggcctgaagtgcatctgctgcctcc acctagcgaggaactggccctgaatgagctggtcac cctgacctgtctggccaggggctttagccctaaggac gtgctcgttagatggctgcagggctcccaagagctg cccagagagaagtatctgacctgggcctctcggcaa gagccatctcagggcaccacaaccttggcgtgacc agcatcctgagagtggccgccgaagattggaagaa gggcgacaccttcagctgcatggtcggacatgaagc cctgcctctggctttcacccagaaaaccatcgacaga ctggccggcaag |
| IgA4.0_NLT-TIS | 21 | ASPTSPKVFPLSLDSTPQDGNVV VACLVQGFFPQEPLSVTWSESG QGVTARNFPPSQDASGDLYTTSS QLTLPATQCPDGKSVTCHVKHY TNPSQDVTVPCRVPPPPPCCHPR LSLHRPALEDLLLGSEATISCTLT GLRDASGATFTWTPSSGKSAVQ GPPPERDLCGCYSVSSVLPGSAQP WNHGETFTCTAAHPELKTPLTA TLSKSGNTFRPEVHLLPPPSEELA LNELVTLTCLARGFSPKDVLVR WLQGSQELPREKYLTWASRQEP SQGTTTFAVTSILRVAAEDWKK GDTFSCMVGHEALPLAFTQKTI DRLAGK | 30 | gctagcccaacctctcctaaggtgttccctctgagcct ggacagcacccctcaggatggaaatgtggtggtgg cctgtctggtgcagggattcttcccacaagagcccct gtccgtgacttggagcgaatctggacagggcgtgac cgccagaaacttcccaccttctcaggacgcctctggc gacctgtacaccacctcttctcagctgaccctgcctgc cacacagtgccctgatggcaagtctgtgacctgccac gtgaagcactacaccaatcctagccaggacgtgacc gtgccttgcagagttcctcctcctccaccttgctgtcac cctcggctgtctctgcacagacccgctctggaagatc tgctgctgggctctgaggccaccatcagctgtaccct gaccggcctgagagatgcttctggcgccacctttacc tggacaccttccagcggaaagtccgctgttcaggga cctcctgagagggacctgtgcggctgttactctgtgtc tagtgtgctgcctggcagcgcccagccttggaatcat ggcgagacattcacctgtaccgctgctcaccccgag ctgaaaaccctctgaccgccacactgtccaagtccg gcaacaccttccggcctgaagtgcatctgctgcctcc acctagcgaggaactggccctgaatgagctggtcac cctgacctgtctggccaggggctttagccctaaggac gtgctcgttagatggctgcagggctcccaagagctg cccagagagaagtatctgacctgggcctctcggcaa gagccatctcagggcaccacaaccttggcgtgacc agcatcctgagagtggccgccgaagattggaagaa gggcgacaccttcagctgcatggtcggacatgaagc cctgcctctggctttcacccagaaaaccatcgacaga ctggccggcaag |

Table 4 lists exemplary amino acid sequences and nucleic acid sequences of a kappa light chain constant domain of the engineered IgA variants.

Table 5 lists exemplary lists amino acid sequences of complementarity determining regions of the variable heavy chain of engineered IgA variants

| Name | SEQ ID NO | Amino acid sequences | SEQ ID NO | Nucleic acid sequences |
|---|---|---|---|---|
| kappa light chain constant domain | 31 | RTVAAPSVFIFPPSDEQLKSGTASV VCLLNNFYPREAKVQWKVDNAL QSGNSQESVTEQDSKDSTYSLSST LTLSKADYEKHKVYACEVTHQGL SSPVTKSFNRGEC | 32 | cggacagtggccgctccttccgtgttcatcttcc caccttccgacgagcagctgaagtccggcaca gctagcgtggtctgcctgctgaacaacttctacc ctcgggaagccaaggtgcagtggaaggtgga caatgccctgcagtccggcaactccaagagt ctgtgaccgagcaggactccaaggacagcac ctacagcctgtcctccacactgaccctgtccaa ggccgactacgagaagcacaaggtgtacgcct gcgaagtgacccatcagggcctgtctagccct gtgaccaagtctttcaaccggggcgagtgt |

| Antigen | Variable heavy chain of Antigen binding domain | SEQ ID NO | HC-CDR1 | SEQ ID NO | HC-CDR2 | SEQ ID NO | HC-CDR3 |
|---|---|---|---|---|---|---|---|
| CD20 | Obinutuzumab | 33 | GYAFSYSWIN | 41 | RIFPGDGDTDYNGKFKG | 49 | NVFDGYWLVY |
| GD2 Disialo-ganglioside expressed on tumors of neuroectodermal origin | Dinutuximab (also called Ch14.18 or Unituxin) | 34 | GSSFTGYNMN | 42 | AIDPYYGGTSYNQKFKG | 50 | GMEY |
| Her2 | Trastuzumab | 35 | GFNIKDTYIH | 43 | RIYPTNGYTRYADSVKG | 51 | WGGDGFYAMDY |
| Tyrosinase-related protein-1 or gp75 Glycoprotein produced by pigmented melanocytes and melanomas | TA99 | 36 | GFNIKDYFLH | 44 | WINPDNGNTVYDPKFQG | 52 | RDYTYEKAALDY |
| cytotoxic T-lymphocyte-associated protein 4 (mCTLA-4) | | 37 | GYSITSGYGWN | 45 | FIYYEGSTYYNPSIKS | 53 | QTGYFDY |
| CD47 | 2.3D11 | 38 | SGVSIRSINWWN | 46 | EIYHSGSTNYNPSLKS | 54 | DGGIAVTDYYYYGLDV |
| CD47 | C47A8-CQ | 39 | SGYTFTSYYMH | 47 | IINPSGGSTSYAQKFQG | 55 | STLWFSEFDY |
| CD20 | UMAB10 | 40 | GFTFPSYNLH | 48 | AIYPGNGDTSYNQKFKG | 56 | SAYYGSNVWFFDV |

Table 6 lists exemplary lists amino acid sequences of complementarity determining regions of the variable light chain of engineered IgA variant

| Antigen | Variable light chain of Antigen binding domain | SEQ ID NO | LC-CDR1 | SEQ ID NO | LC-CDR2 | SEQ ID NO | LC-CDR3 |
|---|---|---|---|---|---|---|---|
| CD20 | Obinutuzumab | 57 | RSSKSLLHSNGITYLY | 65 | QMSNLVS | 73 | AQNLELPYT |
| GD2 | Dinutuximab (also called Ch14.18 or Unituxin ®) | 58 | RSSQSLVHRNGNTYLH | 66 | KVSNRFS | 74 | SQSTHVPPLT |
| Her2 | Trastuzumab | 59 | RASQDVNTAVA | 67 | SASFLYS | 75 | QQHYTTPPT |
| Tyrosinase-related protein-1 or gp75 | TA99 | 60 | RASGNIYNYLA | 68 | DAKTLAD | 76 | QHFWSLP |

-continued

| Antigen | Variable light chain of Antigen binding domain | SEQ ID NO | LC-CDR1 | SEQ ID NO | LC-CDR2 | SEQ ID NO | LC-CDR3 |
|---|---|---|---|---|---|---|---|
| cytotoxic T-lymphocyte-associated protein 4 (mCTLA-4) | | 61 | KSSQSLFNSNAKTNYLN | 69 | YASTRHT | 77 | QQWYDYPYT |
| CD47 | 2.3D11 | 62 | RASESVSSNLA | 70 | GAFNRAT | 78 | QQRSDWFT |
| CD47 | C47A8-CQ | 63 | SGTSSDVGGHNYVS | 71 | DVTKRPS | 79 | QSYAGSRVYV |
| CD20 | UMAB10 | 64 | RASSSVSYMD | 72 | ATSNLAS | 80 | QQWISNPPT |

Table 7 lists exemplary amino acid sequences and nucleic acid sequences of the variable heavy chain of engineered IgA variant. The CDR regions are depicted in bold font

| Antigen | Antigen binding domain | SEQ ID NO | Amino acid sequence | SEQ ID NO | Nucleic acid sequence |
|---|---|---|---|---|---|
| CD20 | Obinutuzumab | 81 | QVQLVQSGAEVKKPGSSVKVSCKASGYAFSYSWI NWVRQAPGQGLEWMGRIFPGDGDTDYNGKFKGRVTITADKSTSTAYMELSSLRSEDTAVYYCARNVFDGYWLVYWGQGTLVTVSS | 87 | caggtgcaattggtgcagtctggcgctg aagttaagaagcctgggagttcagtgaa ggtctcctgcaaggcttccggatacgcc ttcagctattcttggatcaattgggtgcgg caggcgcctggacaagggctcgagtg gatgggacggatctacccggcgatggg gatactgactacaatgggaaattcaagg gcagagtcacaattaccgccgacaaatc cactagcacagcctatatggagctgagc agcctgagatctgaggacacggccgtg tattactgtgcaagaaatgtctttgatggtt actggcttgatactggggccagggaac cctggtcaccgtctcgaca |
| GD2 | Dinutuximab (also called Ch14.18 or Unituxin ®) | 4 | EVQLLQSGPELEKPGASVMISCKASGSSFTGYNMNWVRQNIGKSLEWIGAIDPYYGGTSYNQKFKGRATLTVDKSSSTAYMHLKSLTSEDSAVYYCVSGMEYWGQGTSVTVSS | 88 | gaagtgcagctggtgcagagcggcgc ggaagtggaaaaaccgggcgcgagcg tgaaaattagctgcaaagcgagcggca gcagctttaccggctataacatgaactgg gtgcgccagaacattggcaaaagcctg gaatggattggcgcgattgatccgtatta tggcggcaccagctataaccagaaattt aaaggccgcgcgaccctgaccgtggat aaaagcaccagcaccgcgtatatgcatc tgaaaagcctgcgcagcgaagataccg cggtgtattattgcgtgagcggcatgga atattggggccagggcaccagcgtgac cgtgagcagc |
| Her2 | Trastuzumab | 82 | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSS | 89 | Gaggtgcagctggtcgagagcggcgg agggctggtgcagccaggcggcagcc tgaggctgtcctgcgccgccagcggctt caacatcaaggacacctacatccactgg gtgcggcaggccccaggcaagggcct ggagtgggtggccaggatctaccccac caacggctacaccagatacgccgacag cgtgaagggcaggttcaccatcagcgc cgacaccagcaagaacaccgcctacct gcagatgaacagcctgagggccgagg acaccgccgtgtactactgcagcagatg gggcggggacggcttctacgctatgga ctactggggccagggcacccctggtgac cgtgagcagc |

-continued

| Antigen | Antigen binding domain | SEQ ID NO | Amino acid sequence | SEQ ID NO | Nucleic acid sequence |
|---|---|---|---|---|---|
| Tyrosinase-related protein-1 or gp75 | TA99 | 83 | EVQLQQSGAELVRPGALV KLSCKTSGFNIKDYFLH WVRQRPDQGLEWIGWIN PDNGNTVYDPKFQGTAS LTADTSSNTVYLQLSGLT SEDTAVYFCTRRDYTYE KAALDYWGQGTTVTVST | 90 | gaggttcagttgcagcagtctggcgccg aactcgttagacctggcgctctggttaag ctgtcctgcaagacctccggcttcaatat caaggactacttcctgcactgggtccga cagaggcctgaccaaggactggaatgg atcggctggatcaaccccgacaacggc aacaccgtgtacgaccctaagttccagg gcaccgcttctctgaccgccgacacctc ttccaataccgtgtacctgcagctgtccg gcctgacctctgaggataccgccgtgta cttctgcaccagacgggactacacctac gagaaggccgctctggattattggggcc agggcacaaccgtgaccgtgtctaca |
| cytotoxic T-lymphocyte-associated protein 4 (mCTLA-4) | | 84 | QVKLEESGPGLVNPSQSL SLSCSVTGYSITSGYGWN WIRQFPGQKVEWMGFIY YEGSTYYNPSIKSRISITR DTSKNQFFLQVNSVTTED TATYYCARQTGYFDYW GQGTMVTVSS | 91 | caggtgaaactggaagaaagcggccc gggcctggtgaacccgagccagagcct gagcctgagctgcagcgtgaccggcta tagcattaccagcggctatggctggaac tggattcgccagtttccgggccagaaag tggaatggatgggctttatttattatgaag gcagcacctattataacccgagcattaaa agccgcattagcattacccgcgatacca agcgtgaccaccgaagataccgcgacc tattattgcgcgcgccagaccggctatttt gattattggggccagggcaccatggtga ccgtgagcagcggtgagtgc |
| CD47 | 2.3D11 | 85 | QVQLQESGPGLVKPSGTL SLTCAVSGVSIRSINWWN WVRQPPGKGLEWIGEIY HSGSTNYNPSLKSRVTIS VDKSKNQFSLKLNSVTAA DTAVYYCARDGGIAVTD YYYYGLDVWGQGTTVT VSS | 92 | caggtgcagctgcaggaaagcggccc gggcctggtgaaaccgagcggcaccct gagcctgacctgcgcggtgagcggcgt gagcattcgcagcattaactggtggaac tgggtgcgccagccgccgggcaaagg cctggaatggattggcgaaatttatcata gcggcagcaccaactataacccgagcc tgaaaagccgcgtgaccattagcgtgga taaaagcaaaaaccagtttagcctgaaa ctgaacagcgtgaccgcggcggatacc gcggtgtattattgcgcgcgcgatggcg gcattgcggtgaccgattattattattatg gcctggatgtgtggggccagggcacca ccgtgaccgtgagcagc |
| CD47 | C47A8-CQ | 86 | QVQLVQSGAEVKKPGAS VKVSCKASGYTFTSYYM HWVRQAPGQGLEWMGII NPSGGSTSYAQKFQGRV TMTRDTSTSTVYMELSSL RSEDTAVYYCARSTLWF SEFDYWGQGTLVTVSS | 93 | caggtgcagctggtgcagagcggcgc ggaagtgaaaaaaccgggcgcgagcg tgaaagtgagctgcaaagcgagcggct ataccttaccagctattatatgcattgggt gcgccaggcgccgggccagggcctgg aatggatgggcattattaacccgagcgg cggcagcaccagctatgcgcagaaattt cagggccgcgtgaccatgacccgcgat accagcaccagcaccgtgtatatggaac tgagcagcctgcgcagcgaagataccg cggtgtattattgcgcgcgcagcaccct gtggtttagcgaatttgattattggggcca gggcaccctggtgaccgtgagcagc |
| CD20 | UMAB10 | 7 | QAYLQQSGADLVRPGAS VKMSCKASGFTFPSYNL HWVKQTPRQGLEWIGAI YPGNGDTSYNQKFKGK ATLTVDKSSSTAYMQLSS LTSEDSAVYFCARSAYYG SNVWFFDVWGTGTTVTV SS | 94 | caagcctacctgcagcagtctggcgcc gatctcgtgcggcctggcgcctctgtga agatgagctgtaaagccagcggcttcac cttcccagctacaacctgcactgggtc aagcagaccccagacagggcctgga atggatcggagccatctaccccggcaa cggcgacacctcctacaaccagaagttc aagggcaaggccaccctgaccgtggac aagagcagcagcaccgcctacatgca gctgagcagcctgaccagcgaggaca gcgccgtgtacttctgtgccagaagcgc ctactacggcagcaacgtgtggttcttcg acgtgtggggcaccggcaccaccgtga cagtgtcatct |

Table 8 lists exemplary amino acid sequences and nucleic acid sequences of the variable light chain of engineered IgA variant. The CDR regions are depicted in bold font

| Antigen | Antigen binding domain | SEQ ID NO | Amino acid sequence | SEQ ID NO | Nucleic acid sequence |
|---|---|---|---|---|---|
| CD20 | Obinutuzu-mab | 95 | DIVMTQTPLSLPVT PGEPASISCRSSKS LLHSNGITYLYW YLQKPGQSPQLLI YQMSNLVSGVPD RFSGSGSGTDFTL KISRVEAEDVGVY YCAQNLELPYTF GGGTKVEIK | 101 | gatatcgtgatgacccagacacctctgagcctgcct gtgacacctggcgagcctgcttccatctcctgccgg tcctctaagtccctgctgcactctaacggcatcacct acctgtactggtatctgcagaagcccggccagtctc ctcagctgctgatctaccagatgtccaacctggtgtc tggcgtgcccgacagattttccggctctggctctgg caccgacttcacccctgaagatctccagagtggaag ccgaggacgtgggcgtgtactattgtgcccagaac ctggaactgcctacacctttggcggaggcaccaa ggtggaaatcaag |
| GD2 | Dinutuximab (also called Ch14.18 or Unituxin ®) | 5 | EIVMTQSPATLSVS PGERATLSCRSSQ SLVHRNGNTYLH WYLQKPGQSPKLL IHKVSNRFSGVPD RFSGSGSGTDFTL KISRVEAEDLGVY FCSQSTHVPPLTF GAGTKLELK | 102 | gaaattgtgatgacccagagcccggcgaccctgag cgtgagcccgggcgaacgcgcgaccctgagctgc cgcagcagccagagcctggtgcatcgcaacggca acacctatctgcattggtatctgcagaaaccgggcc agagcccgaaactgctgattcataaagtgagcaac cgctnagcggcgtgccggatcgcntagcggcag cggcagcggcaccgattttaccctgaaaattagccg cgtggaagcggaagatctgggcgtgtatttttgcag ccagagcacccatgtgccgccgctgacctttggcg cgggcaccaaactggaactgaaa |
| Her2 | Trastuzumab | 96 | DIQMTQSPSSLSAS VGDRVTITCRASQ DVNTAVAWYQQK PGKAPKLLIYSASF LYSGVPSRFSGSRS GTDFTLTISSLQPE DFATYYCQQHYT TPPTFGQGTKVEI K | 103 | gacatccagatgacccagtctccatcctctctgtccg cctctgtgggcgacagagtgaccatcacctgtaga gccagccaggacgtgaacaccgccgtggcttggt atcagcagaagcctggcaaggcccctaagctgctg atctactcccgcctccttcctgtactctggcgtgccctc cagattctccggcagcagatctggcaccgactttac cctgacaatctccagcctgcagcctgaggacttcgc cacctactactgccagcagcactacaccacacctcc aacctaggccagggcaccaaggtggaaatcaag |
| Tyrosinase-related protein-1 or gp75 | TA99 | 97 | IQMSQSPASLSASV GETVTITCRASGNI YNYLAWYQQKQG KSPEILLVYDAKTL ADGVPSRFSGSGS GTQYSLKISSLQTE DSGNYYCQHFWS LPFTFGSGTKLEIK | 104 | atccagatgagtcagtctccggcctccctatctgcat ctgtgggagaaactgtcaccatcacatgtcgagcaa gtggaaatatttacaattatttagcatggtatcagcag aaacagggaaaatctcctcacctcctggtctatgatg caaaaaccttagcagatggtgtgccatcaaggttca gtggcagtggctcagggacaatattctctcaaga ttagcagccttcagactgaagattctgggaattattac tgtcaacatttttggagtcttccattcacgttcggctcg gggaccaagctggaaataaaa |
| cytotoxic T-lymphocyte-associated protein 4 (mCTLA-4) | | 98 | DVMMTQSPSSMS VSAGEKATISCKSS QSLFNSNAKTNY LNWYMQKPGQSP KLLTYYASTRHTG VPDRFRGSGSGTD FTLTISSVQDEDQA FYYCQQWYDYPY TFGAGTKLEIK | 105 | gatgtgatgatgacccagagcccgagcagcatga gcgtgagcgcgggcgaaaaagcgaccattagctg caaaagcagccagagcctgtttaacagcaacgcga aaaccaactatctgaactggtatatgcagaaaccgg gccagagcccgaaactgctgacctattatgcgagc acccgccataccggcgtgccggatcgctttcgcgg cagcggcagcggcaccgattttaccctgaccattag cagcgtgcaggatgaagatcaggcgttttattattgc cagcagtggtatgattatccgtatacctaggcgcgg gcaccaaactggaaattaaa |
| CD47 | 2.3D11 | 99 | EIVLTQSPATLSLS PGERATLSCRASE SVSSNLAWYQQK PGQAPRLLIYGAF NRATGIPARFSGS GSGTDFTLTISSLE PEDFAVYYCQQRS DWFTFGGGTKVEI K | 106 | gaaattgtgctgacccagagcccggcgaccctgag cctgagcccgggcgaacgcgcgaccctgagctgc cgcgcgagcgaaagcgtgagcagcaacctggcgt ggtatcagcagaaaccgggccaggcgccgcgcct gctgatttatggcgcgtttaaccgcgcgaccggcat tccggcgcgctttagcggcagcggcagcggcacc gattttaccctgaccattagcagcctggaaccggaa gattttgcggtgtattattgccagcagcgcagcgatt ggtaacctaggcggcggcaccaaagtggaatta aa |
| CD47 | C47A8-CQ | 100 | QSVLTQPSSVSASP GQSITISCSGTSSD VGGHNYVSWYQ QHPGKAPKLMIYD VTKRPSGVPDRFS | 107 | cagagcgtgctgacccagccgagcagcgtgagcg cgagcccgggccagagcattaccattagctgcagc ggcaccagcagcgatgtgggcggccataactatgt gagctggtatcagcagcatccgggcaaagcgccg aaactgatgatttatgatgtgaccaaacgcccgagc |

-continued

| Antigen | Antigen binding domain | SEQ ID NO | Amino acid sequence | SEQ ID NO | Nucleic acid sequence |
|---|---|---|---|---|---|
| | | | GSKSGNTASLTVS GLQAEDEADYYC QSYAGSRVYVFG TGTKLTVL | | ggcgtgccggatcgctttagcggcagcaaaagcg gcaacaccgcgagcctgaccgtgagcggcctgca ggcggaagatgaagcggattattattgccagagcta tgcgggcagccgcgtgtatgtgtaggcaccggca ccaaactgaccgtgctg |
| CD20 | UMAB10 | 8 | QIVLSQSPAILSASP GEKVTMTCRASSS VSYMDWYQQKPG SSPKPWIYATSNL ASGVPTRFSGSGS GTSYSLTISRVEAE DAATYYCQQWIS NPPTFGAGTKLDL K | 108 | cagatcgtgctgagccagagccccgccatcctgag tgctagccctggcgagaaagtgaccatgacctgca gagccagcagcagcgtgtcctacatggactggtat cagcagaagcccggcagcagccccaagccctgg atctacgccacaagcaatctggccagcggcgtgcc cacaagatttccggcagcggctctggcaccagcta cagcctgaccatcagccgggtggaagccgaagat gccgccacctactactgccagcagtggatcagcaa ccccccacctttggagccggcaccaagctggatc tgaag |

Table 9 lists exemplary IgA variant antibodies capable of binding different antigen. The table shows exemplary pairings of sequences of the variable light chain, variable heavy chain, IgA heavy chain constant region and kappa light chain constant region for the IgA variant antibodies.

| Exemplary engineered IgA antibody | Antigen | HC-CDR 1 of SEQ ID NO: | HC-CDR 2 of SEQ ID NO: | HC-CDR 3 of SEQ ID NO: | Variable heavy chain of SEQ ID NO: | LC-CDR 1 of SEQ ID NO: | LC-CDR 2 of SEQ ID NO: | LC-CDR 3 of SEQ ID NO: | Variable light chain of SEQ ID NO: | IgA heavy chain constant region of SEQ ID NO: | Kappa light chain constant region of SEQ ID NO: |
|---|---|---|---|---|---|---|---|---|---|---|---|
| IgA3.0+-Obi | CD20 | 33 | 41 | 49 | 81 | 57 | 65 | 73 | 95 | 16 | 31 |
| IgA3.0+-ch14.18 | GD2 | 34 | 42 | 50 | 4 | 58 | 66 | 74 | 5 | 16 | 31 |
| IgA3.0+-Her2 | Her2 | 35 | 43 | 51 | 82 | 59 | 67 | 75 | 96 | 16 | 31 |
| IgA3.0+-TA99 | gp75 | 36 | 44 | 52 | 83 | 60 | 68 | 76 | 97 | 16 | 31 |
| IgA3.0+-mCTLA4 | CTLA4 | 37 | 45 | 53 | 84 | 61 | 69 | 77 | 98 | 16 | 31 |
| IgA.3.0+-2.3D11 | CD47 | 38 | 46 | 54 | 85 | 62 | 70 | 78 | 99 | 16 | 31 |
| IgA3.0+-C47A8-CQ | CD47 | 39 | 47 | 55 | 86 | 63 | 71 | 79 | 100 | 16 | 31 |
| IgA3.0+-UMAB10 | CD20 | 40 | 48 | 56 | 7 | 64 | 72 | 80 | 8 | 16 | 31 |
| IgA3.0min-Obi | CD20 | 33 | 41 | 49 | 81 | 57 | 65 | 73 | 95 | 17 | 31 |
| IgA3.0min-ch14.18 | GD2 | 34 | 42 | 50 | 4 | 58 | 66 | 74 | 5 | 17 | 31 |
| IgA3.0min-Her2 | Her2 | 35 | 43 | 51 | 82 | 59 | 67 | 75 | 96 | 17 | 31 |
| IgA3.0min-TA99 | gp75 | 36 | 44 | 52 | 83 | 60 | 68 | 76 | 97 | 17 | 31 |
| IgA3.0min-mCTLA4 | CTLA4 | 37 | 45 | 53 | 84 | 61 | 69 | 77 | 98 | 17 | 31 |
| IgA.3.0min-2.3D11 | CD47 | 38 | 46 | 54 | 85 | 62 | 70 | 78 | 99 | 17 | 31 |
| IgA3.0min-C47A8-CQ | CD47 | 39 | 47 | 55 | 86 | 63 | 71 | 79 | 100 | 17 | 31 |
| IgA3.0min-UMAB10 | CD20 | 40 | 48 | 56 | 7 | 64 | 72 | 80 | 8 | 17 | 31 |
| IgA4.0_NG-Obi | CD20 | 33 | 41 | 49 | 81 | 57 | 65 | 73 | 95 | 18 | 31 |
| IgA4.0_NT-Obi | CD20 | 33 | 41 | 49 | 81 | 57 | 65 | 73 | 95 | 20 | 31 |
| IgA4.0_NQ-Obi | CD20 | 33 | 41 | 49 | 81 | 57 | 65 | 73 | 95 | 19 | 31 |

-continued

| Exemplary engineered IgA antibody | Antigen | HC-CDR 1 of SEQ ID NO: | HC-CDR 2 of SEQ ID NO: | HC-CDR 3 of SEQ ID NO: | Variable heavy chain of SEQ ID NO: | LC-CDR 1 of SEQ ID NO: | LC-CDR 2 of SEQ ID NO: | LC-CDR 3 of SEQ ID NO: | Variable light chain of SEQ ID NO: | IgA heavy chain constant region of SEQ ID NO: | Kappa light chain constant region of SEQ ID NO: |
|---|---|---|---|---|---|---|---|---|---|---|---|
| IgA4.0_NLT-TIS-Obi | CD20 | 33 | 41 | 49 | 81 | 57 | 65 | 73 | 95 | 21 | 31 |
| IgA4.0_NG-ch14.18 | GD2 | 34 | 42 | 50 | 4 | 58 | 66 | 74 | 5 | 18 | 31 |
| IgA4.0_NT-ch14.18 | GD2 | 34 | 42 | 50 | 4 | 58 | 66 | 74 | 5 | 20 | 31 |
| IgA4.0_NQ-ch14.18 | GD2 | 34 | 42 | 50 | 4 | 58 | 66 | 74 | 5 | 19 | 31 |
| IgA4.0_NLT-TIS-ch14.18 | GD2 | 34 | 42 | 50 | 4 | 58 | 66 | 74 | 5 | 21 | 31 |
| IgA4.0_NG-Her2 | Her2 | 35 | 43 | 51 | 82 | 59 | 67 | 75 | 96 | 18 | 31 |
| IgA4.0_NT-Her2 | Her2 | 35 | 43 | 51 | 82 | 59 | 67 | 75 | 96 | 20 | 31 |
| IgA4.0_NQ-Her2 | Her2 | 35 | 43 | 51 | 82 | 59 | 67 | 75 | 96 | 19 | 31 |
| IgA4.0_NLT-TIS-Her2 | Her2 | 35 | 43 | 51 | 82 | 59 | 67 | 75 | 96 | 21 | 31 |
| IgA4.0_NG-TA99 | gp75 | 36 | 44 | 52 | 83 | 60 | 68 | 76 | 97 | 18 | 31 |
| IgA4.0_NT-TA99 | gp75 | 36 | 44 | 52 | 83 | 60 | 68 | 76 | 97 | 20 | 31 |
| IgA4.0_NQ-TA99 | gp75 | 36 | 44 | 52 | 83 | 60 | 68 | 76 | 97 | 19 | 31 |
| IgA4.0_NLT-TIS-TA99 | gp75 | 36 | 44 | 52 | 83 | 60 | 68 | 76 | 97 | 21 | 31 |
| IgA4.0_NG-mCTLA4 | CTLA4 | 37 | 45 | 53 | 84 | 61 | 69 | 77 | 98 | 18 | 31 |
| IgA4.0_NT-mCTLA4 | CTLA4 | 37 | 45 | 53 | 84 | 61 | 69 | 77 | 98 | 20 | 31 |
| IgA4.0_NQ-mCTLA4 | CTLA4 | 37 | 45 | 53 | 84 | 61 | 69 | 77 | 98 | 19 | 31 |
| IgA4.0_NLT-TIS-mCTLA4 | CTLA4 | 37 | 45 | 53 | 84 | 61 | 69 | 77 | 98 | 21 | 31 |
| IgA4.0_NG-2.3D11 | CD47 | 38 | 46 | 54 | 85 | 62 | 70 | 78 | 99 | 18 | 31 |
| IgA4.0_NT-2.3D11 | CD47 | 38 | 46 | 54 | 85 | 62 | 70 | 78 | 99 | 20 | 31 |
| IgA4.0_NQ-2.3D11 | CD47 | 38 | 46 | 54 | 85 | 62 | 70 | 78 | 99 | 19 | 31 |
| IgA4.0_NLT-TIS-2.3D11 | CD47 | 38 | 46 | 54 | 85 | 62 | 70 | 78 | 99 | 21 | 31 |
| IgA4.0_NG-C47A8-CQ | CD47 | 39 | 47 | 55 | 86 | 63 | 71 | 79 | 100 | 18 | 31 |
| IgA4.0_NT-C47A8-CQ | CD47 | 39 | 47 | 55 | 86 | 63 | 71 | 79 | 100 | 20 | 31 |
| IgA4.0_NQ-C47A8-CQ | CD47 | 39 | 47 | 55 | 86 | 63 | 71 | 79 | 100 | 19 | 31 |
| IgA4.0_NLT-TIS-C47A8-CQ | CD47 | 39 | 47 | 55 | 86 | 63 | 71 | 79 | 100 | 21 | 31 |

-continued

| Exemplary engineered IgA antibody | Anti-gen | HC-CDR 1 of SEQ ID NO: | HC-CDR 2 of SEQ ID NO: | HC-CDR 3 of SEQ ID NO: | Variable heavy chain of SEQ ID NO: | LC-CDR 1 of SEQ ID NO: | LC-CDR 2 of SEQ ID NO: | LC-CDR 3 of SEQ ID NO: | Variable light chain of SEQ ID NO: | IgA heavy chain constant region of SEQ ID NO: | Kappa light chain constant region of SEQ ID NO: |
|---|---|---|---|---|---|---|---|---|---|---|---|
| IgA4.0_NG-UMAB10 | CD20 | 40 | 48 | 56 | 7 | 64 | 72 | 80 | 8 | 18 | 31 |
| IgA4.0_NT-UMAB10 | CD20 | 40 | 48 | 56 | 7 | 64 | 72 | 80 | 8 | 20 | 31 |
| IgA4.0_NQ-UMAB10 | CD20 | 40 | 48 | 56 | 7 | 64 | 72 | 80 | 8 | 19 | 31 |
| IgA4.0_NLT-TIS-UMAB10 | CD20 | 40 | 48 | 56 | 7 | 64 | 72 | 80 | 8 | 21 | 31 |

20

Table 10 lists exemplar sequence of CH1. CH2 and CH3 domains of WT IgA heavy chain constant region

| Name | SEQ ID NO: | Amino acid sequence |
|---|---|---|
| CH1 domain of WT IgA2 heavy chain constant region | 109 | ASPTSPKVFPLSLDSTPQDGNVVVACLVQGFFPQEPLSVTWSESGQNVTARNFPPSQDASGDLYTTSSQLTLPATQCPDGKSVTCHVKHYTNPSQDVTVPCP |
| CH2 domain of WT IgA2 heavy chain constant region | 110 | CCHPRLSLHRPALEDLLLGSEANLTCTLTGLRDASGATFTWTPSSGKSAVQGPPERDLCGCYSVSSVLPGCAQPWNHGETFTCTAAHPELKTPLTANITKS |
| CH3 domain of WT IgA2 heavy chain constant region including C-terminal Tail-piece | 111 | GNTFRPEVHLLPPPSEELALNELVTLTCLARGFSPKDVLVRWLQGSQELPREKYLTWASRQEPSQGTTTFAVTSILRVAAEDWKKGDTFSCMVGHEALPLAFTQKTIDRLAGKPTHVNVSVVMAEVDGTCY |

TABLE 11

IMGT numbering table
IMGT accession number J00221

| | 1.8 | 1.7 | 1.6 | 1.5 | 1.4 | 1.3 | 1.2 | 1.1 | 1 | 2 | 3 | 4 | 5 | 6 | 7 | 8 | 9 | 10 | 11 | 12 |
|---|---|---|---|---|---|---|---|---|---|---|---|---|---|---|---|---|---|---|---|---|
| | | | | | | | | | A | S | P | T | S | P | L | S | L | D | S | T |
| J00221 IGHA2*01 F CH1 gDNA | | | | | | | | | gca | tcc | ccg | acc | agc | ccc | ctg | agc | ctc | gac | agc | acc |

| | 13 | 14 | 15 | 15.1 | 15.2 | 15.3 | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|---|---|---|---|
| | P | Q | | | | | D | G | N | V | V | V | A | C | L | V | Q | G | F | F |
| J00221 IGHA2*01 F CH1 gDNA | ccc | caa | ... | | | | gat | ggg | aac | gtg | gtc | gtc | gca | tgc | ctg | gtc | cag | ggc | ttc | ttc |

| | 30 | 31 | | | 34 | 35 | 36 | 37 | 38 | 39 | 40 | 41 | 42 | 43 | 45.7 | 45 | 45.1 | 45.2 | 45.3 | 45.4 | 45.5 | 45.6 |
|---|---|---|---|---|---|---|---|---|---|---|---|---|---|---|---|---|---|---|---|---|---|---|
| | P | Q | | | E | P | L | S | V | T | W | S | E | S | | G | Q | N | V | | | |
| J00221 IGHA2*01 F CH1 gDNA | ccc | cag | ... | ... | gag | cca | ctc | agt | gtg | acc | tgg | agc | gaa | agc | | gga | cag | aac | gtg | ... | ... | ... |

| | 45.7 | | | | | | | 84 | 84.1 | 84.2 | 84.3 | 84.4 | 84.5 | 84.6 | 84.7 | 85.6 | 85.5 | 85.4 |
|---|---|---|---|---|---|---|---|---|---|---|---|---|---|---|---|---|---|---|
| | | T | A | R | N | F | P | S | Q | D | A | S | G | | | | | D |
| J00221 IGHA2*01 F CH1 gDNA | ... | acc | gcc | aga | aac | ttc | cca | cct | agc | cag | gat | gcc | tcc | ggg | ... | ... | ... | gac |

| | 85.3 | 85.1 | | 85 | 86 | 87 | 88 | 89 | 90 | 91 | 92 | 93 | 94 | 95 | 96 | 96.1 | 96.2 | 97 | 98 | 99 |
|---|---|---|---|---|---|---|---|---|---|---|---|---|---|---|---|---|---|---|---|---|
| | L | Y | T | T | S | S | Q | L | T | L | P | A | T | Q | C | | | P | D | G |
| J00221 IGHA2*01 F CH1 gDNA | ctg | tac | acc | acg | agc | agc | cag | ctg | acc | ctg | ccg | aca | cag | tgc | ... | ... | cca | gac | ggc |

| | 100 | 101 | 102 | 103 | 104 | 105 | 106 | 107 | 108 | 109 | 110 | 111 | 112 | 113 | 114 | 115 | 116 | 117 | 118 | 119 |
|---|---|---|---|---|---|---|---|---|---|---|---|---|---|---|---|---|---|---|---|---|
| | K | S | V | T | C | H | V | K | H | Y | | | | T | N | P | S | Q | D | V |
| J00221 IGHA2*01 F CH1 gDNA | aag | tcc | gtg | aca | tgc | cac | gtg | aag | cac | tac | ... | ... | ... | acg | aat | ccc | agc | cag | gat | gtg |

| | 120 | 121 | 122 | 123 | 124 |
|---|---|---|---|---|---|
| | T | V | P | C | P |
| J00221 IGHA2*01 F CH1 gDNA | act | gtg | ccc | tgc | cca |

| | 1 | 2 | 3 | 4 | 5 | 6 | 7 | 8 | 9 | 10 | 11 | 12 |
|---|---|---|---|---|---|---|---|---|---|---|---|---|
| | V | P | P | P | P | P | | | | | | |
| J00221 IGHA2*01 F H gDNA | gtt | ccc | cca | cct | ccc | cca | | | | | | |

TABLE 11-continued

IMGT numbering table
IMGT accession number J00221

| | | | | | | | | | | | | | | | | | |
|---|---|---|---|---|---|---|---|---|---|---|---|---|---|---|---|---|---|
| | | 1.8 | 1.7 | 1.6 | 1.5 | 1.4 | 1.3 | 1.2 | 1.1 | 1 | 2 | 3 | 4 | 5 | 6 | 7 | 8 | 9 | 10 | 11 | 12 |
| | | C | C | H | P | R | L | S | L | H | R | P | A | L | E | D | L | L | L | |
| J00221 | IGHA2*01 F CH2 gDNA | tgc | tgc | cac | ccc | cga | ctg | tcg | ctg | cac | cga | ccg | gcc | ctc | gag | gac | ctg | cta | ... | ... |

| | | | AB | | 15.3 | | | | | | | | | | | | | | | |
| | | 13 | 14 | 15 | 15.1 | 15.2 | 16 | 17 | 18 | 19 | 20 | 21 | 22 | 23 | 24 | 25 | 26 | 27 | 28 | 29 |
| | | G | S | E | A | N | C | T | L | T | G | L | R | D | A | S | G | A |
| J00221 | IGHA2*01 F CH2 gDNA | ggt | tca | gaa | gcg | aac | tgc | aca | ctg | acc | ggc | ctg | aga | gat | gcc | ... | tct | ggt | gcc |

| | | | | | BC | | | | | | | | | | CD | | | |
| | | 30 | 31 | 34 | 35 | 36 | 37 | 38 | 39 | 40 | 41 | 42 | 43 | 44 | 45 | 45.1 | 45.2 | 45.3 | 45.4 | 45.5 | 45.6 |
| | | T | F | T | W | T | P | S | S | G | K | S | | | | | | A | V | Q | G |
| J00221 | IGHA2*01 F CH2 gDNA | acc | ttc | acg | tgg | acg | ccc | tca | agt | ggg | aag | agc | ... | ... | ... | | | gct | gtt | caa | gga |

| | | 45.7 | | | | | | | | | 84.1 | | 84.2 | 84.3 | 84.4 | 84.5 | 84.6 | 84.7 | DE | 85.5 | 85.6 |
| | | P | P | E | R | D | L | C | G | | | | | | C | Y | S | V | S |
| J00221 | IGHA2*01 F CH2 gDNA | cca | cct | gag | cgt | gac | ctc | tgt | ggc | ... | ... | ... | ... | ... | tgc | tac | agc | gtg | tcc | agt |

| | | 85.3 | 85.2 | 85.1 | 85 | 86 | 87 | 88 | 89 | 90 | 91 | 92 | 93 | 94 | 95 | 96 | 96.1 EF | 96.2 | 97 | 98 | 99 |
| | | V | L | P | G | C | A | Q | P | W | N | | | N | H | G | E | T | F | T | C | T |
| J00221 | IGHA2*01 F CH2 gDNA | gtc | ctg | cct | ggc | tgt | gcc | cag | cca | tgg | aac | ... | ... | cat | ggg | gag | acc | ttc | acc | tgc | act |

| | | 100 | 101 | 102 | 103 | 104 | 105 | 106 | 107 | 108 | 109 | 110 | 111 FG | 112 | 113 | 114 | 115 | 116 | 117 | 118 |
| | | A | A | H | P | E | | | L | K | T | P | L | T | A | N | I | K | S |
| J00221 | IGHA2*01 F CH2 gDNA | gct | gcc | cac | ccc | gag | ... | ... | ttg | aag | acc | cca | cta | acc | gcc | aac | atc | aaa | tcc |

| | | 1.8 | 1.7 | 1.6 | 1.5 | 1.4 | 1.3 | 1.2 | 1.1 | 1 | 2 | 3 | 4 | 5 | 6 | 7 | 8 | 9 | 10 | 11 | 12 |
| | | | | | | | G | N | T | F | R | P | E | V | H | L | L | P | P | S | E |
| J00221 | IGHA2*01 F CH3-CHS gDNA | gga | aac | aca | ttc | cgg | cct | gag | gtc | cac | ctg | ctg | ccg | ccg | tcg | gag |

| | | | AB | | 15.3 | | | | | | | | | | | | | | | |
| | | 13 | 14 | 15 | 15.1 | 15.2 | 16 | 17 | 18 | 19 | 20 | 21 | 22 | 23 | 24 | 25 | 26 | 27 | 28 | 29 |
| | | E | L | A | L | | | N | E | L | V | T | L | T | C | L | A | R | G | F | S |
| J00221 | IGHA2*01 F CH3-CHS gDNA | gag | ctg | gcc | ctg | ... | ... | aac | gag | ctg | gtg | acg | ctg | acg | tgc | ctg | gca | cgt | ggc | ttc | agc |

| | | | | | BC | | | | | | | | | | CD | | | |
| | | 30 | 31 | 34 | 35 | 36 | 37 | 38 | 39 | 40 | 41 | 42 | 43 | 44 | 45 | 45.1 | 45.2 | 45.3 | 45.4 | 45.5 | 45.6 |
| | | P | | | K | D | V | L | V | R | W | L | Q | G | S | Q | E | L | P | R | E |
| J00221 | IGHA2*01 F CH3-CHS gDNA | ccc | ... | ... | aag | gat | gtg | ctg | gtt | cgc | tgg | ctg | cag | ggg | tca | cag | gag | ctg | ccc | cgc | gag |

TABLE 11-continued

IMGT numbering table
IMGT accession number J00221

```
                    45.7
                         77   78   79   80   81   82   83   84   84.1 84.2 84.3 84.4 84.5 84.6 84.7 85.7 85.6 85.5 85.4
                         K    Y    L    T    W    A    S    R    Q    E    P    S    Q    G              T    T    T
J00221  IGHA2*01 F CH3-CHS gDNA  ... aag tac ctg act tgg gca tcc cgg cag gag ccc agc cag ggc ... ... ... acc acc acc DE
                         85.3 85.2 85.1 85   86   87   88   89   90   91   92   93   94   95   96  96.2 97   98   99
                         T    F    A    V    T    S    I    L    R    V    A    A    E    D    W   K    K    K    G
J00221  IGHA2*01 F CH3-CHS gDNA  act ttc gct gtg acc agc ata ctg cgc gtg gca gcc gag gac tgg ... aag aag aag ggg EF
                                                                                              96.1
                         100  101  102  103  104  105  106  107  108  109  110  111  112  113  114  115  116  117  118  119
                         D    T    F    S    C    M    V    G    H    E    A    L    P    L    A    F    T    Q    K
J00221  IGHA2*01 F CH3-CHS gDNA  gac acc ttc tcc tgc atg gtg ggc cac gag gcc ... ctg ccg ctg gcc ttc aca cag aag
                                                                    FG                                                    CHS
                         120  121  122  123  124  125  126  127  128  129  130  131  132  133  134  135  136  137  138  139
                         T    I    D    R    L    A                   G    K    P    T    H    V    N    V    S    V    V
J00221  IGHA2*01 F CH3-CHS gDNA  acc atc gac cgc ttg gcg ... ... ... ggt aaa ccc acc cat gtc aat gtg tct gtt gtc 140  141  142  143  144  145  146  147  148
                         M    A    E    V    D    G    T    C    Y
J00221  IGHA2*01 F CH3-CHS gDNA  atg gcg gag gtg gac ggc acc tgc tac
```

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments described herein, or combinations of one or more of these embodiments or aspects described therein may be employed in practicing the present disclosure. It is intended that the following claims define the scope of the present disclosure and that methods and structures within the scope of these claims and their equivalents be covered thereby.

What is claimed is:

1. A pharmaceutical composition comprising an engineered immunoglobulin A subclass 2 (IgA2) antibody or a functional fragment thereof and a pharmaceutically acceptable carrier, diluent or excipient, wherein the engineered IgA2 antibody or a functional fragment thereof comprises an antibody antigen binding domain; and a constant domain, wherein the constant domain comprises an IgA2 heavy chain constant region, wherein the IgA2 heavy chain constant region comprises an IgA2 CH1 region, an IgA2 CH2 region, and an IgA2 CH3 region, wherein the IgA2 CH3 region comprises:
   (a) an amino acid substitution at N135, and
   (b) a deletion of C147 and Y148,
each relative to a wildtype (WT) IgA heavy chain constant region comprising the amino acid sequence of SEQ ID NO: 1 according to the IMGT numbering scheme.

2. The pharmaceutical composition of claim 1, wherein the IgA2 CH1 region comprises an amino acid substitution at P124, relative to the WT IgA heavy chain constant region comprising the amino acid sequence of SEQ ID NO: 1 according to the IMGT numbering scheme.

3. The pharmaceutical composition of claim 2, wherein the amino acid substitution at P124 is P124R, relative to the WT IgA heavy chain constant region comprising the amino acid sequence of SEQ ID NO: 1 according to the IMGT numbering scheme.

4. The pharmaceutical composition of claim 1, wherein the IgA2 CH1 region comprises an amino acid substitution at N45.2, relative to the WT IgA heavy chain constant region comprising the amino acid sequence of SEQ ID NO: 1 according to the IMGT numbering scheme.

5. The pharmaceutical composition of claim 4, wherein the amino acid substitution at N45.2 is N45.2G or N45.2A, relative to the WT IgA heavy chain constant region comprising the amino acid sequence of SEQ ID NO: 1 according to the IMGT numbering scheme.

6. The pharmaceutical composition of claim 1, wherein the amino acid substitution at N135 is N135Q, relative to the WT IgA heavy chain constant region comprising the amino acid sequence of SEQ ID NO: 1 according to the IMGT numbering scheme.

7. The pharmaceutical composition of claim 1, wherein the IgA2 heavy chain constant region comprises an amino acid sequence selected from the group consisting of SEQ ID NOs: 18-21.

8. The pharmaceutical composition of claim 1, wherein the IgA2 CH2 region comprises an Asn to Gly, an Asn to Gln, or an Asn to Thr amino acid substitution corresponding to amino acid residue 23 of SEQ ID NO: 110.

9. The pharmaceutical composition of claim 1, wherein the IgA2 CH2 region comprises at least one amino acid substitution of a residue corresponding to any one of amino acid residues 97, 98, and 99 of SEQ ID NO: 110.

10. The pharmaceutical composition of claim 1, wherein the IgA2 CH2 region comprises at least one amino acid substitution of a residue corresponding to amino acid residue 24 or 25 of SEQ ID NO: 110.

11. A pharmaceutical composition comprising an engineered immunoglobulin A subclass 2 (IgA2) antibody or a functional fragment thereof and a pharmaceutically acceptable carrier, diluent or excipient, wherein the engineered IgA2 antibody or functional fragment thereof comprises an antibody antigen binding domain; and a constant domain, wherein the constant domain comprises an IgA2 heavy chain constant region, wherein the IgA2 heavy chain constant region comprises an IgA2 CH1 region, an IgA2 CH2 region, and an IgA2 CH3 region, wherein (a) the IgA2 CH1 region comprises an amino acid substitution of N45.2, and
(b) the IgA2 CH3 region comprises a deletion of residues P131 to Y148, each relative to a wildtype (WT) IgA heavy chain constant region comprising the amino acid sequence of SEQ ID NO: 1 according to the IMGT numbering scheme.

12. The pharmaceutical composition of claim 11, wherein the IgA2 CH1 region comprises an amino acid substitution at P124, relative to a wildtype (WT) IgA heavy chain constant region comprising the amino acid sequence of SEQ ID NO: 1 according to the IMGT numbering scheme.

13. The pharmaceutical composition of claim 12, wherein the amino acid substitution at P124 is P124R, relative to the WT IgA heavy chain constant region comprising the amino acid sequence of SEQ ID NO: 1 according to the IMGT numbering scheme.

14. The pharmaceutical composition of claim 11, wherein the IgA2 CH2 region comprises an Asn to Gly, an Asn to Gln, or an Asn to Thr amino acid substitution corresponding to amino acid residue 23 of SEQ ID NO: 110.

15. The pharmaceutical composition of claim 11, wherein the IgA2 CH2 region comprises at least one amino acid substitution of a residue corresponding to any one of amino acid residues 97, 98, and 99 of SEQ ID NO: 110.

16. The pharmaceutical composition of claim 11, wherein the IgA2 CH2 region comprises at least one amino acid substitution of a residue corresponding to amino acid residue 24 or 25 of SEQ ID NO: 110.

17. The pharmaceutical composition of claim 11, wherein the amino acid substitution of N45.2 in the IgA2 CH1 region is N45.2G or N45.2A, relative to the WT IgA heavy chain constant region comprising the amino acid sequence of SEQ ID NO: 1 according to the IMGT numbering scheme.

* * * * *